United States Patent
Tasker et al.

[11] Patent Number: 6,124,341
[45] Date of Patent: Sep. 26, 2000

[54] ENDOTHELIN ANTAGONISTS

[75] Inventors: Andrew S. Tasker, Gurnee; Martin Winn, Deerfield; Steven A. Boyd, Mundelein; Hwan-Soo Jae, Glencoe; Thomas W. von Geldern, Richmond; Bryan K. Sorensen, Waukegan, all of Ill.; Kenneth J. Henry, Fishers, Ind.

[73] Assignee: Abbott Laboratories, Abbott Park, Ill.

[21] Appl. No.: 09/087,178

[22] Filed: May 29, 1998

Related U.S. Application Data

[63] Continuation-in-part of application No. 08/877,187, Jun. 17, 1997, which is a continuation-in-part of application No. 08/794,505, Feb. 4, 1997, abandoned, which is a continuation-in-part of application No. 08/600,724, Feb. 13, 1996, abandoned.

[51] Int. Cl.⁷ .......................... A61K 31/4025; A61P 9/00; C07D 403/10
[52] U.S. Cl. .................... 514/422; 548/311.7; 548/518; 548/526; 548/531
[58] Field of Search ................................. 548/412, 518, 548/526; 514/422

[56] References Cited

U.S. PATENT DOCUMENTS 3,342,833  9/1967  Fremery .
4,132,709  1/1979  Santrouch et al. .
4,216,218  8/1980  Ehrgott et al. .
4,340,715  7/1982  Grounder et al. .
5,296,494  3/1994  Lavielle et al. .
5,482,960  1/1996  Berryman et al. .
5,767,144  6/1998  Winn et al. .............................. 514/422

FOREIGN PATENT DOCUMENTS 9730046  8/1997  WIPO .

*Primary Examiner*—Robert W. Ramsuer
*Attorney, Agent, or Firm*—Janelle D. Strode

[57] ABSTRACT

A compound of the formula (I):

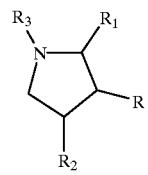

or a pharmaceutically acceptable salt thereof is disclosed, as well as processes for and intermediates in the preparation thereof, and a method of antagonizing endothelin.

36 Claims, No Drawings

ENDOTHELIN ANTAGONISTS

This is a continuation-in-part application of U.S. Ser. No. 08/877,187 filed Jun. 17, 1997 which is a continuation-in-part of Ser. No. 08/794,505 filed Feb. 4, 1997, abandoned, which is a continuation-in-part of Ser. No. 08/660,724 filed Feb. 13, 1996, abandoned.

TECHNICAL FILED

The present invention relates to compounds which are endothelin antagonists, processes for making such compounds, synthetic intermediates employed in these processes and methods and compositions for antagonizing endothelin.

BACKGROUND OF THE INVENTION

Endothelin (ET) is a 21 amino acid peptide that is produced by endothelial cells. ET is produced by enzymatic cleavage of a Trp-Val bond in the precursor peptide big endothelin (Big ET). This cleavage is caused by an endothelin converting enzyme (ECE). Endothelin has been shown to constrict arteries and veins, increase mean arterial blood pressure, decrease cardiac output, increase cardiac contractility in vitro, stimulate mitogenesis in vascular smooth muscle cells in vitro, contract non-vascular smooth muscle including guinea pig trachea, human urinary bladder strips and rat uterus in vitro, increase airway resistance in vivo, induce formation of gastric ulcers, stimulate release of atrial natriuretic factor in vitro and in vivo, increase plasma levels of vasopressin, aldosterone and catecholamines, inhibit release of renin in vitro and stimulate release of gonadotropins in vitro.

It has been shown that vasoconstriction is caused by binding of endothelin to its receptors on vascular smooth muscle (Nature 332 411 (1988), FEBS Letters 231 440 (1988) and Biochem. Biophys. Res. Commun. 154 868 (1988)). An agent which suppresses endothelin production or an agent which binds to endothelin or which inhibits the binding of endothelin to an endothelin receptor will produce beneficial effects in a variety of therapeutic areas. In fact, an anti-endothelin antibody has been shown, upon intrarenal infusion, to ameliorate the adverse effects of renal ischemia on renal vascular resistance and glomerular filtration rate (Kon, et al., J. Clin. Invest. 1762 (1989)). In addition, an anti-endothelin antibody attenuated the nephrotoxic effects of intravenously administered cyclosporin (Kon, et al., Kidney Int. 37 1487 (1990)) and attenuated infarct size in a coronary artery Clozel et al. (Nature 365: 759–761 (1993)) report that Ro 46-2005, a nonpeptide ET-A/B antagonist, prevents postischaemic renal vasoconstriction in rats, prevents the decrease in cerebral blood flow due to subarachnoid hemorrhage (SAH) in rats, and decreases MAP in sodium-depleted squirrel monkeys when dosed orally. A similar effect of a linear tripeptide-like ET-A antagonist, BQ-485, on arterial caliber after SAH has also been recently reported (S. Itoh, T. Sasaki, K. Ide, K. Ishikawa, M. Nishikibe, and M. Yano, Biochem. Biophys. Res. Comm., 195: 969–75 (1993). These results indicate that agents which antagonize ET/ET receptor binding will provide therapeutic benefit in the indicated disease states.

Two structurally related endothelin receptors have been cloned, sequenced and characterized (Hosada, K.; Nakao, K.; Arai, H.; Suga, S.; Ogawa, Y.; Mukoyama, M.; Shirakami, G.; Saito, Y.; Nakanishi, S.; Imura, H. FEBS Left. 1991, 187, 23–26: Sakamoto, A.; Yanagisawa, M.; Sakurai, T.; Takuwa, Y.; Yanagisawa, H.; Masaki, T. Biochem. Biophys. Res. Commun. 1991,178, 656–663). Each binds the three endothelin isopeptides with differing affinities; the $ET_A$ receptor displays affinity for ET-1 and ET-2 over ET-3, while the $ET_B$ receptor is non-isopeptide selective. Originally described as a vasodilatory receptor due to its mediation of nitric oxide release (DeNucci,G.; Thomas, R.; D'Orleans-Juste, P.; Antunes, E.; Walder, C.; Warner, T. D.; Vane, J. R. Proc. Natl. Acad. Sci. U.S.A. 1988, 85, 9797–9800), it is now apparent that the $ET_B$ receptor is responsible for a greater diversity of physiologic function. Current research suggests a role for $ET_B$ mediated responses in certain disease states including established pulmonary hypertension (McCulloch, K. M.; MacLean, M. R.; J. Cardiovasc. Pharmacol. 1995, 26(Suppl. 3), S169–S176), contractile dysfunction associated with benign prostatic hyperplasia (Webb, M. L.; Chao, C.-C.; Rizzo, M.; Shapiro, R. A.; Neubauer, M.; Liu, E. C. K.; Aversa, C. R.; Brittain, R. J.; Treiger, B. Mol. Pharmacol. 1995, 47, 730–737; Webb, M. L.; Meek, T. D. Med. Res. Rev. 1997,17,17–67), myocardial infarction (Vitola, J. V.; Forman, M. B.; Holsinger, J. P.; Kawana, M.; Atkinson, J. B.;

Quertermous, T.; Jackson, E. K.; Murray, J. J. J. Cardiovasc. Pharmacol. 1996, 28, 774–783), and atherosclerosis (Dagassan, P. H.; Breu, V.; Clozel, M.; Kunzli, A.; Vogt, P, Turina, M.; Kiowski, Clozel, J. -P. J. Cardiovasc. Pharmacol. 1996, 27, 147–153). Our group has previously reported the discovery of a series of pyrrolidine-3-carboxylic acids which which bind potently and selectively to the ETA receptor subtype (Winn, M.; von Geldern, T. W.; Opgenorth, T. J.; Jae, H. -S.; Tasker, A. S.; Boyd, S. A.; Kester, J. A.; Mantei, R. A.; Bal, R. B.; Sorensen, B. K.; Wu-Wong, J. R.; Chiou, W. J.; Dixon, D. B.; Novosad, E. I.; Hernandez, L.; Marsh, K. C. J. Med. Chem. 1996, 39,1039–1048). The compounds claimed in the current invention differ from those previously described and are unique in that they bind potently and selectively to the $ET_B$ subtype, blocking the actions of the endothelins on these receptors. As such, they may find utility in the treatment of diseases that are mediated by the $ET_B$ receptor.

DISCLOSURE OF THE INVENTION

In accordance with the present invention there are compounds of the formula (I)

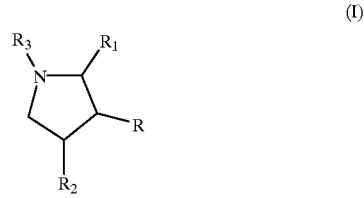

wherein
R is —$(CH_2)_m$—W wherein m is an integer from 0 to 6 and W is
(a) —$C(O)_2$—G wherein G is hydrogen or a carboxy protecting group,
(b) —$PO_3H_2$,
(c) —P(O)(OH)E wherein E is hydrogen, loweralkyl or arylalkyl,
(d) —CN,
(e) —C(O)$NHR_{17}$ wherein $R_{17}$ is loweralkyl,
(f) alkylaminocarbonyl, (g) dialkylaminocarbonyl,
(h) tetrazolyl,
(i) hydroxy,
(j) alkoxy,
(k) sulfonamido,
(l) —C(O)NHS(O)$_2$R$_{16}$ wherein R$_{16}$ is loweralkyl, haloalkyl, aryl or dialkylamino,
(m) —S(O)$_2$NHC(O)R$_{16}$ wherein R$_{16}$ is defined as above, (n)
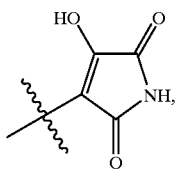

(o)
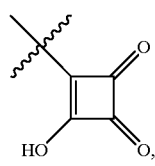

(p)
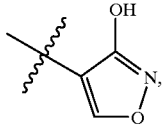

(q)
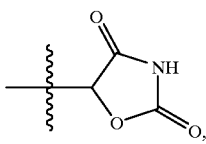

(r)
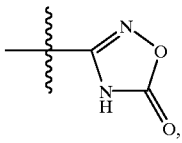

(s)
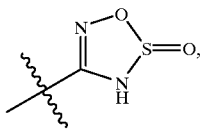

(t)
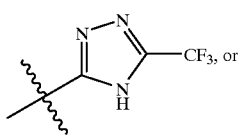

(u)
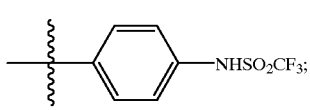

R$_1$ and R$_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, heterocyclic, (heterocyclic)alkyl and (R$_{aa}$)(R$_{bb}$)N—R$_{cc}$— wherein R$_{aa}$ is aryl or arylalkyl, R$_{bb}$ is hydrogen or alkanoyl and R$_{cc}$ is alkylene, with the proviso that one or both of R$_1$ and R$_2$ is other than hydrogen;

R$_3$ is R$_4$—C(O)—R$_5$— or R$_6$—S(O)$_2$—R$_7$- wherein R$_5$ is (i) a covalent bond, (ii) alkylene, (iii) alkenylene, (iv) —N(R$_{20}$)—R$_8$— or —R$_{8a}$—N(R$_{20}$)—R$_8$- wherein R$_8$ and R$_{8a}$ are independently selected from the group consisting of alkylene and alkenylene; and R$_{20}$ is hydrogen, loweralkyl, alkenyl, haloalkyl, alkoxyalkyl, haloalkoxyalkyl, cylcoalkyl or cycloalkylalkyl or (v) —O—R$_9$— or —R$_{9a}$—O—R$_9$— wherein R$_9$ and R$_{9a}$ are independently selected from alkylene;

R$_7$ is (i) a covalent bond, (ii) alkylene, (iii) alkenylene or (iv) —N(R$_{21}$)—R$_{10}$— or —R$_{10a}$—N(R$_{21}$)—R$_{10}$— wherein R$_{10}$ and R$_{10a}$ are independently selected from the group consisting of alkylene and alkenylene and R$_{21}$ is hydrogen, loweralkyl, alkenyl, haloalkyl, alkoxyalkyl, haloalkoxyalkyl, aryl or arylalkyl;

wherein R$_4$ and R$_6$ are (i)
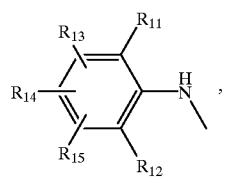

wherein R$_{11}$ and R$_{12}$ are independently selected from the group consisting of loweralkyl, cyano, alkoxy, halo, haloalkyl and phenyl and R$_{13}$, R$_{14}$, and R$_{15}$ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano; or (ii) heterocyclic(amino), or a pharmaceutically acceptable salt thereof.

A preferred embodiment of the invention is a compound of formula (II)

(II)
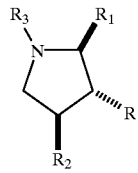

wherein the substituents —R$_2$, —R and —R$_1$ exist in a trans,trans relationship and R, R$_1$, R$_2$, and R$_3$ are as defined above.

A more preferred embodiment of the invention is a compound of formula (I) or (II) wherein R$_3$ is R$_4$—C(O)—R$_5$— wherein R$_4$ is as defined above and R$_5$ is alkylene or R$_3$ is R$_6$—S(O)$_2$—R$_7$— wherein R$_7$ is alkylene and R$_6$ is defined as above.

An even more preferred embodiment of the invention is a compound of formula (I) or (II) wherein R is —C(O)$_2$—G wherein G is hydrogen or a carboxy protecting group or R is tetrazolyl or R is —C(O)—NHS(O)$_2$R$_{16}$ wherein R$_{16}$ is loweralkyl, haloalkyl or aryl, R$_1$ and R$_2$ are independently selected from (i) loweralkyl, (ii) cycloalkyl, (iii) substituted and unsubstituted aryl, and (iv) substituted or unsubstituted heterocyclic, and R$_3$ is R$_4$—C(O)—R$_5$— wherein R$_4$ is as defined above and R$_5$ is alkylene or R$_3$ is R$_6$—S(O)$_2$—R$_7$— wherein R$_7$ is alkylene and R$_6$ is defined as above.

A yet more preferred embodiment of the invention is a compound of formula (I) or (II) wherein R is —C(O)$_2$—G wherein G is hydrogen or a carboxy protecting group, tetrazolyl or —C(O)—NHS(O)$_2$R$_{16}$ wherein R$_{16}$ is loweralkyl, haloalkyl or aryl, R$_1$ is (i) alkoxyalkyl, (ii) cycloalkyl, (iii) phenyl, (iv) pyridyl, (v) furanyl or (vi) substituted or unsubstituted 4-methoxyphenyl, 4-fluorophenyl, 3-fluorophenyl, 4-ethoxyphenyl, 4-propoxyphenyl, 4-isopropoxyphenyl, 4-trifluoromethylphenyl, 4-pentafluoroethylphenyl, 2-fluoro-4-ethoxyphenyl, 3-fluoro-4-methoxyphenyl, 3-fluoro-4-ethoxyphenyl, 3-fluoro-4-propoxyphenyl, 3-methoxy-4-propoxyphenyl, 2-fluorophenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, R$_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofuranyl; 4-methoxyphenyl, dimethoxyphenyl, fluorophenyl or difluorophenyl and R$_3$ is R$_4$—C(O)—R$_5$— wherein R$_4$ is as defined above and R$_5$ is alkylene or R$_3$ is R$_6$—S(O)$_2$—R$_7$— wherein R$_7$ is alkylene and R$_6$ is defined as above.

Another yet more preferred embodiment of the invention is a compound of formula (I) or (II) wherein R is —C(O)$_2$—G wherein G is hydrogen or a carboxy protecting group, tetrazolyl or —C(O)—NHS(O)$_2$R$_{16}$ wherein R$_{16}$ is loweralkyl, haloalkyl or aryl, R$_1$ is (i) alkoxyalkyl, (ii) cycloalkyl, (iii) phenyl, (iv) pyridyl, (v) furanyl or (vi) substituted or unsubstituted 4-methoxyphenyl, 4-fluorophenyl, 3-fluorophenyl, 4-ethoxyphenyl, 4-propoxyphenyl, 4-isopropoxyphenyl, 4-trifluoromethylphenyl, 4-pentafluoroethylphenyl, 2-fluoro-4-ethoxyphenyl, 3-fluoro-4-methoxyphenyl, 3-fluoro-4-ethoxyphenyl, 3-fluoro-4-propoxyphenyl, 3-methoxy-4-propoxyphenyl, 2-fluorophenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, R$_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofuranyl, 4-methoxyphenyl, dimethoxyphenyl, fluorophenyl or difluorophenyl and R$_3$ is R$_4$—C(O)—R$_5$— wherein R$_4$ is as defined above and R$_5$ is alkylene.

A still more preferred embodiment of the invention is a compound of formula (I) or (II) wherein R is —C(O)$_2$—G wherein G is hydrogen or a carboxy protecting group, tetrazolyl or —C(O)—NHS(O)$_2$R$_{16}$ wherein R$_{16}$ is loweralkyl or haloalkyl, R$_1$ is substituted or unsubstituted 4-methoxyphenyl, 4-fluorophenyl, 2-fluorophenyl, 4-ethoxyphenyl, 4-propoxyphenyl, 4-isopropoxyphenyl, 3-fluoro-4-methoxyphenyl, 3-fluoro-4-ethoxyphenyl, 2-fluoro-4-ethoxyphenyl, 3-fluoro-4-propoxyphenyl, 3-methoxy-4-propoxyphenyl, 4-trifluoromethylphenyl, 4-pentafluoroethylphenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, R$_2$ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and R$_3$ is R$_4$—C(O)—R$_5$— wherein R$_4$ is as defined above and R$_5$ is alkylene.

A most highly preferred embodiment of the invention is a compound of formula (I) or (II) wherein R is —C(O)$_2$—G wherein G is hydrogen or a carboxy protecting group, R$_1$ is substituted or unsubstituted 4-methoxyphenyl, 4-fluorophenyl, 2-fluorophenyl, 3-fluoro-4-ethoxyphenyl, 3-fluoro-4-methoxyphenyl, 4-ethoxyphenyl, 4-propoxyphenyl, 4-isopropoxyphenyl, 2-fluoro-4-ethoxyphenyl, 3-fluoro-4-propoxyphenyl, 3-methoxy-4-propoxyphenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, R$_2$ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and R$_3$ is R$_4$—C(O)—R$_5$— wherein R$_4$ is

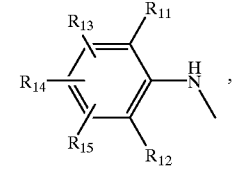

wherein R$_{11}$ and R$_{12}$ are independently selected from loweralkyl, and R$_{13}$, R$_{14}$, and R$_{15}$ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano and R$_5$ is alkylene.

A most highly preferred embodiment of the invention is a compound of formula (I) or (II) wherein R is —C(O)$_2$—G wherein G is hydrogen or a carboxy protecting group, R$_1$ is substituted or unsubstituted 4-methoxyphenyl, 4-fluorophenyl, 2-fluorophenyl, 3-fluoro-4-ethoxyphenyl, 3-fluoro-4-methoxyphenyl, 4-ethoxyphenyl, 4-propoxyphenyl, 4-isopropoxyphenyl, 2-fluoro-4-ethoxyphenyl, 3-fluoro-4-propoxyphenyl, 3-methoxy-4-propoxyphenyl, 4methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, R$_2$ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and R$_3$ is R$_4$—C(O)—R$_5$— wherein R$_4$ is

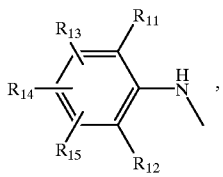

wherein $R_{11}$ and $R_{12}$ are independently selected from the group consisting of lower alkyl, alkoxy and halo, and $R_{13}$, $R_{14}$, and $R_{15}$ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano and $R_5$ is alkylene.

Another most highly preferred embodiment of the invention is a compound of formula (I) or (II) wherein R is $-C(O)_2-G$ wherein G is hydrogen or a carboxy protecting group, $R_1$ is substituted or unsubstituted 4-methoxyphenyl, 4-fluorophenyl, 2-fluorophenyl, 3-fluoro-4-ethoxyphenyl, 3-fluoro-4-methoxyphenyl, 4-ethoxyphenyl, 4-propoxyphenyl, 4-isopropoxyphenyl, 2-fluoro-4-ethoxyphenyl, 3-fluoro-4-propoxyphenyl, 3-methoxy-4-propoxyphenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and $R_3$ is $R_4-C(O)-R_5-$ wherein $R_4$ is

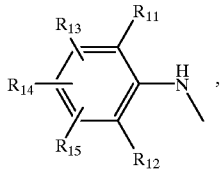

wherein $R_{11}$ and $R_{12}$ are independently selected from the group consisting of methyl, ethyl, and isopropyl, and $R_{13}$, $R_{14}$, and $R_{15}$ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano and $R_5$ is alkylene.

Another most highly preferred embodiment of the invention is a compound of formula (I) or (II) wherein R is $-C(O)_2-G$ wherein G is hydrogen or a carboxy protecting group, $R_1$ is substituted or unsubstituted 4-methoxyphenyl, 4-fluorophenyl, 2-fluorophenyl, 3-fluoro-4-ethoxyphenyl, 3-fluoro-4-methoxyphenyl, 4-ethoxyphenyl, 4-propoxyphenyl, 4-isopropoxyphenyl, 2-fluoro-4-ethoxyphenyl, 3-fluoro-4-propoxyphenyl, 3-methoxy-4-propoxyphenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and $R_3$ is $R_4-C(O)-R_5-$ wherein $R_4$ is

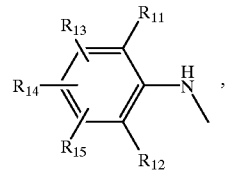

wherein $R_{11}$ and $R_{12}$ are independently selected from the group consisting of methyl, ethyl, and isopropyl, and $R_{13}$, $R_{14}$, and $R_{15}$ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano and $R_5$ is methylene.

The present invention also relates to processes for preparing the compounds of formula (I) and (II) and to the synthetic intermediates employed in these processes.

The present invention also relates to a method of antagonizing endothelin in a mammal (preferably a human) in need of such treatment, comprising administering to the mammal a therapeutically effective amount of a compound of formula (I) or (II).

The invention further relates to endothelin antagonizing compositions comprising a pharmaceutical carrier and a therapeutically effective amount of a compound of formula (I) or (II).

The compounds of the invention comprise two or more asymmetrically substituted carbon atoms. As a result, racemic mixtures, mixtures of diastereomers, as well as single diastereomers of the compounds of the invention are included in the present invention. The terms "S" and "R" configuration are as defined by the IUPAC 1974 Recommendations for Section E, Fundamental Stereochemistry, Pure Appl. Chem. (1976) 45,13–30.

The term "carboxy protecting group" as used herein refers to a carboxylic acid protecting ester group employed to block or protect the carboxylic acid functionality while the reactions involving other functional sites of the compound are carried out. Carboxy protecting groups are disclosed in Greene, "Protective Groups in Organic Synthesis" pp. 152–186 (1981), which is hereby incorporated herein by reference. In addition, a carboxy protecting group can be used as a prodrug whereby the carboxy protecting group can be readily cleaved in vivo for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields, as described in U.S. Pat. Nos. 3,840,556 and 3,719,667, the disclosures of which are hereby incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy protecting groups are $C_1$ to $C_8$ alkyl (e.g., methyl, ethyl or tertiary butyl and the like); haloalkyl; alkenyl; cycloalkyl and substituted derivatives thereof such as cyclohexyl, cyclopentyl and the like; cycloalkylalkyl and substituted derivatives thereof such as cyclohexylmethyl, cyclopentylmethyl and the like; arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like);

alkanoyloxyalkyl groups such as acetoxymethyl, butyryloxymethyl, valerytoxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-di methyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "alkanoyl" as used herein refers to an alkyl group as defined herein appended to the parent molecular moiety through a carbonyl (—C(O)—) group. Examples of alkanoyl include acetyl, propionyl and the like.

The term "alkanoylamino" as used herein refers to an alkanoyl group as previously defined appended to an amino group. Examples alkanoylamino include acetamido, propionamido and the like.

The term "alkanoylaminoalkyl" as used herein refers to $R_{43}$—NH—$R_{44}$— wherein $R_{43}$ is an alkanoyl group and $R_{44}$ is an alkylene group.

The term "alkanoyloxyalkyl" as used herein refers to $R_{30}$—O—$R_{31}$— wherein $R_{30}$ is an alkanoyl group and $R_{31}$ is an alkylene group. Examples of alkanoyloxyalkyl include acetoxymethyl, acetoxyethyl and the like.

The term "alkenyl" as used herein refers to a straight or branched chain. hydrocarbon radical containing from 2 to 15 carbon atoms and also containing at least one carbon-carbon double bond. Alkenyl groups include, for example, vinyl (ethenyl), allyl (propenyl), butenyl, 1-methyl-2-buten-1-yl and the like.

The term "alkenylene" denotes a divalent group derived from a straight or branched chain hydrocarbon containing from 2 to 15 carbon atoms and also containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkenyloxy" as used herein refers to an alkenyl group, as previously defined, connected to the parent molecular moiety through an oxygen (—O—) linkage. Examples of alkenyloxy include allyloxy, butenyloxy and the like.

The term "alkoxy" as used herein refers to $R_{42}$O— wherein $R_{42}$ is a loweralkyl group, as defined herein. Examples of alkoxy include, but are not limited to, methoxy, ethoxy, propoxy, iso-butoxy, tert-butoxy, and the like.

The term "alkoxyalkoxy" as used herein refers to $R_{80}$O—$R_{81}$O— wherein $R_{80}$ is loweralkyl as defined above and $R_{81}$ is alkylene. Representative examples of alkoxyalkoxy groups include methoxymethoxy, ethoxymethoxy, t-butoxymethoxy and the like.

The term "alkoxyalkoxyalkoxy" as used herein refers to $R_{82}$O—$R_{83}$O—$R_{84}$O— wherein $R_{82}$ is loweralkyl as defined above and $R_{83}$ and $R_{84}$ are alkylene. Representative examples of alkoxyalkoxyalkoxy groups include methoxyethoxymethoxy, ethoxymethoxymethoxy, t-butoxymethoxymethoxy and the like.

The term "(alkoxyalkyl)sulfonyl" as used herein refers to $R_{85}$—O—$R_{86}$—S(O)$_2$—, wherein $R_{85}$ is loweralkyl and $R_{86}$ is alkylene.

The term "alkoxyalkoxyalkyl" as used herein refers to an alkoxyalkoxy group as previously defined appended to an alkyl radical. Representative examples of alkoxyalkoxyalkyl groups include methoxyethoxyethyl, methoxymethoxymethyl, and the like.

The term "alkoxyalkyl" as used herein refers to an alkoxy group as previously defined appended to an alkyl radical as previously defined. Examples of alkoxyalkyl include, but are not limited to, methoxymethyl, methoxyethyl, isopropoxymethyl and the like.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, isopropoxycarbonyl and the like.

The term "alkoxycarbonylalkenyl" as used herein refers to an alkoxycarbonyl group as previously defined appended to an alkenyl radical. Examples of alkoxycarbonylalkenyl include methoxycarbonylethenyl, ethoxycarbonylethenyl and the like.

The term "alkoxycarbonylalkyl" as used herein refers to $R_{34}$—C(O)—$R_{35}$— wherein $R_{34}$ is an alkoxy group and $R_{35}$ is an alkylene group. Examples of alkoxycarbonylalkyl include methoxycarbonyl methyl, methoxycarbonylethyl, ethoxycarbonylmethyl and the like.

The term "alkoxycarbonylaminoalkyl" as used herein refers to $R_{38}$—C(O)—NH—$R_{39}$— wherein $R_{38}$ is an alkoxy group and $R_{39}$ is an alkylene group. Examples of alkoxycarbonylaminoalkyl include methoxycarbonylaminoethyl and the like.

The term "alkoxycarbonyloxyalkyl" as used herein refers to $R_{36}$—C(O)—O—$R_{37}$— wherein $R_{36}$ is an alkoxy group and $R_{37}$ is an alkylene group. Examples of alkoxycarbonyloxyalkyl include (ethoxycarbonyloxy)methyl and the like.

The term "(alkoxycarbonyl)thioalkoxy" as used herein refers to an alkoxycarbonyl group as previously defined appended to a thioalkoxy radical. Examples of (alkoxycarbonyl)thioalkoxy include methoxycarbonylthiomethoxy, ethoxycarbonylthiomethoxy and the like.

The terms "alkyl" and "loweralkyl" as used herein refer to straight or branched chain alkyl radicals containing from 1 to 15 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkylamino" as used herein refers to $R_{51}$ NH— wherein $R_{51}$ is a loweralkyl group, for example, ethylamino, butylamino, and the like.

The term "(alkylamino)alkoxy" as used herein refers $R_{52}$NH—$R_{53}$—O— wherein $R_{52}$ is loweralkyl and $R_{53}$ is alkylene.

The term "alkylaminocarbonyl" as used herein refers to an alkylamino group, as previously defined, appended to the parent molecular moiety through a carbonyl (—C(O)—) linkage. Examples of alkylaminocarbonyl include methylaminocarbonyl, ethylaminocarbonyl, isopropylaminocarbonyl and the like.

The term "alkylaminocarbonylalkenyl" as used herein refers to an alkenyl radical to which is appended an alkylaminocarbonyl group.

The term "alkylaminocarbonylalkyl" as used herein refers to a loweralkyl radical to which is appended an alkylaminocarbonyl group.

The term "alkylaminocarbonylaminoalkyl" as used herein refers to $R_{40}$—C(O)—NH—$R_{41}$— wherein $R_{40}$ is an alkylamino group and $R_{41}$ is an alkylene group.

The term "alkylene" denotes a divalent group derived from a straight or branched chain saturated hydrocarbon having from 1 to 15 carbon atoms by the removal of two hydrogen atoms, for example —CH$_2$—, —CH$_2$CH$_2$—, —CH(CH$_3$)—, —CH$_2$CH$_2$CH$_2$—, —CH$_2$C(CH$_3$)$_2$CH$_2$— and the like.

The term "alkylsulfonyl" refers to an alkyl group appended to the parent molecular moiety through a sulfonyl group —S(O)2—. Examples of alkylsulfonyl include methylsulfonyl, ethylsulfonyl, isopropylsulfonyl and the like.

The term "(alkylsulfonyl)amino" as used herein refers to an alkyl group as previously defined appended to the parent molecular moiety through a sulfonylamino (—S(O)$_2$—NH—) group. Examples of (alkylsulfonyl)amino include methylsulfonylamino, ethylsulfonylamino, isopropylsulfonylamino and the like.

The term "(alkylsulfonyl)alkoxy" as used herein refers to an alkylsuffonyl group as previously defined appended to the parent molecular moiety through a alkoxy group. Examples of (alkylsulfonyl)alkoxy include methylsulfonylmethoxy, ethylsulfonylethoxy, isopropylsulfonylisopropoxy and the like.

The term "(alkylthio)alkoxy" as used herein refers to $R_{54}$—S—$R_{55}$—O—, wherein $R_{54}$ is loweralkyl and $R_{55}$ is alkylene.

The term "alkynyl" as used herein refers to a straight or branched chain hydrocarbon radical containing from 2 to 15 carbon atoms and also containing at least one carbon-carbon triple bond. Examples of alkynyl include —C≡C—H, H—C≡C—CH$_2$—, H—C≡C—CH(CH$_3$)—, CH$_3$—C≡C—CH$_2$—, and the like.

The term "aminocarbonyl" as used herein refers to H$_2$N—C(O)—.

The term "aminocarbonylalkenyl" as used herein refers to an alkenyl radical to which is appended an aminocarbonyl (NH$_2$C(O)—) group.

The term "aminocarbonylalkoxy" as used herein refers to H$_2$N—C(O)— appended to an alkoxy group as previously defined. Examples of aminocarbonylalkoxy include aminocarbonylmethoxy, aminocarbonylethoxy and the like.

The term "aminocarbonylalkyl" as used herein refers to a loweralkyl radical to which is appended an aminocarbonyl (NH$_2$C(O(—) group.

The term "aroyloxyalkyl" as used herein refers to $R_{32}$—C(O)—O—$R_{33}$— wherein $R_{32}$ is an aryl group and $R_{33}$ is an alkylene group. Examples of aroyloxyalkyl include benzoyloxymethyl, benzoyloxyethyl and the like.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups can be unsubstituted or substituted with one, two or three substituents independently selected from loweralkyl, halo, haloalkyl, haloalkoxy, hydroxyalkyl, alkenyloxy, alkoxy, alkoxyalkoxy, alkoxycarbonyl, alkoxyalkoxyalkoxy, (cycloalkyl)alkoxy, cycloalkoxy, (alkylamino)alkoxy, (alkylthio)alkoxy, alkoxycarbonylalkenyl, (alkoxycarbonyl) thioalkoxy, thioalkoxy, amino, alkylamino, dialkylamino, (dialkylamino)alkyl, (dialkylamino)alkoxy, aminocarbonyl, aminocarbonylalkoxy, alkanoylamino, arylalkoxy, aryloxy, mercapto, cyano, nitro, carboxaldehyde, carboxy, carboxyalkenyl, carboxyalkoxy, carboxamide, alkylsulfonyl, (alkylsulfonyl)amino, (alkylsulfonyl)alkoxy, (alkoxyalkyl)sulfonyl, cyanoalkoxy, (heterocyclic)alkoxy, hydroxy, hydroxalkoxy, phenyl and tetrazolylalkoxy. In addition, substituted aryl groups include tetrafluorophenyl and pentafluorophenyl.

The term "arylalkenyl" as used herein refers to an alkenyl radical to which is appended an aryl group, for example, phenylethenyl and the like.

The term "arylalkoxy" as used herein refers to $R_{45}$O— wherein $R_{45}$ is an arylalkyl group, for example, benzyloxy, and the like.

The term "arylalkoxyalkyl" as used herein refers to a loweralkyl radical to which is appended an arylalkoxy group, for example, benzyloxymethyl and the like.

The term "arylalkyl" as used herein refers to an aryl group as previously defined, appended to a loweralkyl radical, for example, benzyl and the like.

The term "aryloxy" as used herein refers to $R_{46}O$— wherein $R_{46}$ is an aryl group, for example, phenoxy, and the like.

The term "arylalkylcarbonyloxy" as used herein refers to a $R_{62}C(O)O$— wherein $R_{62}$ is an arylalkyl group.

The term "arylalkylcarbonyloxyalkyl" as used herein refers to a loweralkyl radical to which is appended an arylalkylcarbonyloxy group.

The term "aryloxyalkyl" refers to an aryloxy group as previously defined appended-to an alkyl radical. Examples of aryloxyalkyl include phenoxymethyl, 2-phenoxyethyl and the like.

The term "carboxaldehyde" as used herein refers to a formaldehyde radical, —C(O)H.

The term "carboxamide" as used herein refers to $NH_2$—C(O)—.

The term "carboxy" as used herein refers to a carboxylic acid radical, —C(O)OH.

The term "carboxyalkenyl" as used herein refers to a carboxy group as previously defined appended to an alkenyl radical as previously defined. Examples of carboxyalkenyl include 2-carboxyethenyl, 3-carboxy-1-propenyl and the like.

The term "carboxyalkoxy" as used herein refers to a carboxy group as previously defined appended to an alkoxy radical as previously defined. Examples of carboxyalkoxy include carboxymethoxy, carboxyethoxy and the like.

The term "cyanoalkoxy" as used herein refers to an alkoxy radical as previously defined to which is appended a cyano (—CN) group. Examples of cyanoalkoxy include 3-cyanopropoxy, 4-cyanobutoxy and the like.

The term "cycloalkanoyloxy" as used herein refers to $R_{60}$—C(O)—O— wherein $R_{60}$ is a cycloalkyl group.

The term "cycloalkanoyloxyalkyl" as used herein refers to a loweralkyl radical to which is appended a cycloalkanoyloxy group.

The term "cycloalkyl" as used herein refers to an aliphatic ring system having 3 to 10 carbon atoms and 1 to 3 rings including, but not limited to, cyclopropyl, cyclopentyl, cyclohexyl, norbornyl, adamantyl, and the like. Cycloalkyl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "cycloalkyloxy" herein refers $R_{61}$—O— wherein $R_{61}$ is a cycloalkyl group. Examples of cycloalkyloxy include cyclohexyloxy and the like.

The term "(cycloalkyl)alkoxy" herein $R_{63}$—$R_{64}O$— wherein $R_{63}$ is a cycloalkyl as defined above and is appended to the parent molecular moiety through an alkoxy radical wherein $R_{64}$ is an alkylene group. Examples of (cycloalkyl)alkoxy include (cyclopropyl)ethoxy and the like.

The term "cycloalkylalkyl" as used herein refers to a cycloalkyl group appended to a loweralkyl radical, including but not limited to cyclohexylmethyl.

The term "dialkylamino" as used herein refers to $(R_{56})(R_{57})N$— wherein $R_{56}$ and $R_{57}$ are independently selected from loweralkyl, for example diethylamino, methyl propylamino, and the like.

The term "(dialkylamino)alkyl" as used herein refers to a loweralkyl radical to which is appended a dialkylamino group.

The term "(dialkylamino)alkoxy" as used herein refers to an alkoxy radical to which is appended a dialkylamino group.

The term "dialkylaminocarbonyl" as used herein refers to a dialkylamino group, as previously defined, appended to the parent molecular moiety through a carbonyl (—C(O(—) linkage. Examples of dialkylaminocarbonyl include dimethylaminocarbonyl, diethylaminocarbonyl and the like.

The term "dialkylaminocarbonylalkenyl" as used herein refers to an alkenyl radical to which is appended a dialkylaminocarbonyl group.

The term "dialkylaminocarbonylalkyl" as used herein refers to $R_{58}$—C(O)—$R_{59}$— wherein $R_{58}$ is a dialkylamino group and $R_{59}$ is an alkylene group.

The term "halo" or "halogen" as used herein refers to I, Br, Cl or F.

The term "haloalkenyl" as used herein refers to an alkenyl radical to which is appended at least one halogen substituent.

The term "haloalkoxy" as used herein refers to an alkoxy radical as defined above, bearing at least one halogen substituent, for example, 2-fluoroethoxy, 2,2,2-trifluoroethoxy, trifluoromethoxy, 2,2,3,3,3-pentafluoropropoxy and the like.

The term "haloalkoxyalkyl" as used herein refers to a loweralkyl radical to which is appended a haloalkoxy group.

The term "haloalkyl" as used herein refers to a lower alkyl radical, as defined above, to which is appended at least one halogen substituent, for example, chloromethyl, fluoroethyl, trifluoromethyl or pentafluoroethyl and the like.

The term "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; or two sulfur atoms in non-adjacent positions. The 5-membered ring has 0–2 double bonds and the 6- and 7-membered rings have 0–3 double bonds. The nitrogen heteroatoms can be optionally quaternized. The terms "heterocyclic" or "heterocycle" also includes bicyclic groups in which any of the above heterocyclic rings is fused to a benzene ring or a cycloalkane ring or another heterocyclic ring (for example, indolyl, dihydroindolyl, quinolyl, isoquinolyl, tetrahydroquinolyl, tetrahydroisoquinolyl, decahydroquinolyl, decahydroisoquinolyl, benzofuryl, dihydrobenzofuryl or benzothienyl and the like). Heterocyclics include: aziridinyl, azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, oxetanyl, furyl, tetrahydrofuranyl, thienyl, thiazolidinyl, isothiazolyl, triazolyl, tetrazolyl, isoxazolyl, oxadiazolyl, thiadiazolyl, pyrrolyl, pyrimidyl and benzothienyl.

Heterocyclics also include compounds of the formula

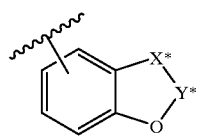

where X* is —CH₂— or —O— and Y* is —C(O)— or [—C(R")₂—]ᵥ where R" is hydrogen or $C_1$–$C_4$-alkyl and v is 1, 2 or 3 such as 1,3-benzodioxolyl, 1,4-benzodioxanyl and the like. Heterocyclics also include bicyclic rings such as quinuclidinyl and the like.

Heterocyclics can be unsubstituted, monosubstituted, disubstituted, or trisubstituted with substituents independently selected from hydroxy, halo, oxo (=O), alkylimino (R*N=wherein R* is a loweralkyl group), amino, alkylamino, dialkylamino, alkoxy, alkoxyalkoxy, haloalkyl, cycloalkyl, aryl, phenyl, arylalkyl, —COOH, —SO₃H, alkoxycarbonyl, nitro, cyano and loweralkyl. In addition, nitrogen containing heterocycles can be N-protected.

The term "(heterocyclic)alkoxy" as used herein refers to a heterocyclic group as defined above appended to an alkoxy radical as defined above. Examples of (heterocyclic)alkoxy include 4-pyridylmethoxy, 2-pyridylmethoxy and the like.

The term "(heterocyclic)alkyl" as used herein refers to a heterocyclic group as defined above appended to a loweralkyl radical as defined above. Examples of (heterocyclic)alkyl include 2-pyridylmethyl and the like.

The term "heterocyclic(amino)" refers to $R_{77}$—NH— wherein $R_{77}$ is an aromatic heterocyclic group as defined above which is appended to an amino group. The aromatic heterocycle is substituted with substituents $R_{75}$ and $R_{76}$ which are both bonded to the atoms of the aromatic heterocycle which are directly adjacent to the nitrogen. $R_{75}$ and $R_{76}$ are substituents independently selected from hydroxy, halo, oxo (=O), alkylimino (R*N=wherein R* is a loweralkyl group), amino, alkylamino, dialkylamino, alkoxy, alkoxyalkoxy, haloalkyl, cycloalkyl, aryl, phenyl, arylalkyl, —COOH, —SO₃H, alkoxycarbonyl, nitro, cyano and loweralkyl. The aromatic heterocycle may also be optionally substituted with a third substituent which is selected from the group hydroxy, halo, oxo (=O), alkylimino (R*N= wherein R* is a loweralkyl group), amino, alkylamino, dialkylamino, alkoxy, alkoxyalkoxy, haloalkyl, cycloalkyl, aryl, phenyl, arylalkyl, —COOH, —SO₃H, alkoxycarbonyl, nitro, cyano and loweralkyl. Examples of heterocyclic (amino) include 2,4-diethylpyridine-3-amino, 2,4-diethylthiophene-3-amino, 2,4-diethylpyridine-2-amino, and the like.

The term "heterocycliccarbonyloxyalkyl" as used herein refers to $R_{47}$—C(O)—O—$R_{48}$— wherein $R_{47}$ is a heterocyclic group and $R_{48}$ is an alkylene group.

The term "hydroxy" as used herein refers to —OH.

The term "hydroxyalkenyl" as used herein refers to an alkenyl radical to which is appended a hydroxy group.

The term "hydroxyalkoxy" as used herein refers to an alkoxy radical as previously defined to which is appended a hydroxy (—OH) group. Examples of hydroxyalkoxy include 3-hydroxypropoxy, 4-hydroxybutoxy and the like.

The term "hydroxyalkyl" as used herein refers to a loweralkyl radical to which is appended a hydroxy group.

The term "mercapto" as used herein refers to —SH.

The terms "methylenedioxy" and "ethylenedioxy" refer to one or two carbon chains respectively attached to the parent molecular moiety through two oxygen atoms. In the case of methylenedioxy, a fused 5 membered ring is formed. In the case of ethylenedioxy, a fused 6 membered ring is formed. Methylenedioxy substituted on a phenyl ring results in the formation of a benzodioxolyl radical.

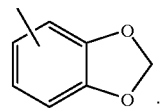

Ethylenedioxy substituted on a phenyl ring results in the formation of a benzodioxanyl radical

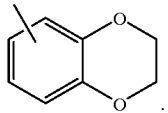

The term "substantially pure" as used herein means 90% or more of the specified compound.

The term "tetrazolyl" as used herein refers to a radical of the formula

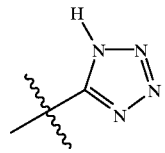

or a tautomer thereof.

The term "tetrazolylalkoxy" as used herein refers to a tetrazolyl radical as defined above appended to an alkoxy group as defined above. Examples of tetrazolylalkoxy include tetrazolylmethoxy, tetrazolylethoxy and the like.

The term "thioalkoxy" as used herein refers to $R_{70}$S— wherein $R_{70}$ is loweralkyl. Examples of thioalkoxy include, but are not limited to, methylthio, ethylthio and the like.

The term "thioalkoxyalkoxy" as used herein refers to $R_{71}$S—$R_{72}$O— wherein $R_{71}$ is loweralkyl as defined above and $R_{72}$ is alkylene. Representative examples of thioalkoxyalkoxy groups include CH₃SCH₂O—, CH₃CH₂SCH₂O—, t-BuSCH₂O— and the like.

The term "thioalkoxyalkoxyalkyl" as used herein refers to a thioalkoxyalkoxy group appended to an alkyl radical. Representative examples of thioalkoxyalkoxyalkyl groups include CH₃SCH₂CH₂OCH₂CH₂—, CH₃SCH₂OCH₂—, and the like. The term "trans,trans" as used herein refers to the orientation of substituents ($R_1$ and $R_2$) relative to the central substituent R as shown

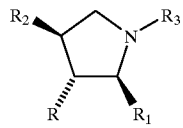

The term "trans,cis" as used herein refers to the orientation of substituents ($R_1$ and $R_2$) relative to the central substituent R as shown This definition encompasses both the case where R and R$_2$ are cis and R and R$_1$ are trans and the case where R$_2$ and R are trans and R and R$_1$ are cis.

The term "cis,cis" as used herein refers to the orientation of substituents (R$_1$ and R$_2$) relative to the central substituent R as shown Representative compounds of the invention include:

trans,trans-2-(4-Methoxyphenyl)-4-(1,3-benzodioxol-5-yl)-1-((2,4,6-trimethyl)phenylaminocarbonylmethyl)-pyrrolidine-3-carboxylic acid, trans,trans-2-(3-Fluoro-4-methoxyphenyl)-4-(1,3-benzodioxol-5-yl)-1-((2,4,6-trimethyl)phenylaminocarbonylmethyl)-pyrrolidine-3-carboxylic acid, trans, trans-2-(4-Propoxyphenyl)-4-(1,3-benzodioxol-5-yl)-1-((2,4,6-trimethyl)phenylaminocarbonylmethyl)-pyrrolidine-3-carboxylic acid, trans,trans-2-(4-Methoxyphenyl)-4-(1,3-benzodioxol-5-yl)-1-((2,6-diethyl)phenylaminocarbonylmethyl)-pyrrolidine-3-carboxylic acid, trans,trans-2-(4-Propoxyphenyl)-4-(1,3-benzodioxol-5-yl)-1-((2,6-diethyl)phenylaminocarbonylmethyl)-pyrrolidine-3-carboxylic acid, trans,trans-2-(3-Fluoro-4-methoxyphenyl)-4-(1,3-benzodioxol-5-yl)-1-((2,6-diethyl)phenylaminocarbonylmethyl)-pyrrolidine-3-carboxylic acid, trans, trans-2-(3-Fluoro-4-ethoxyphenyl)-4-(1,3-benzodioxol-5-yl)-1-((2,6-diethyl)phenylaminocarbonylmethyl)-pyrrolidine-3-carboxylic acid, trans,trans-2-(3-Fluoro-4-methoxyphenyl)-4-(7-methoxy-1,3-benzodioxol-5-yl)-1-((2,6-diethyl)phenylaminocarbonylmethyl)-pyrrolidine-3-carboxylic acid, trans,trans-2-(3-methoxy-4-propoxyphenyl)-4-(1,3-benzodioxol-5-yl)-1-((2,6-diethylphenyl)aminocarbonylmethyl)-pyrrolidine-3-carboxylic acid, trans,trans-2-(4-ethoxyphenyl)-4-(1,3-benzodioxol-5-yl)-1-((2,6-diethylphenyl)aminocarbonylmethyl)-pyrrolidine-3-carboxylic acid, trans,trans-2-(4-methoxyphenyl)-4-(1,3-benzodioxol-5-yl)-1-((2,6-dimethylphenyl)aminocarbonylmethyl)-pyrrolidine-3-carboxylic acid, trans,trans-2-(4-propoxyphenyl)-4-(7-methoxy-1,3-benzodioxol-5-yl)-1-((2,6-diethylphenyl)aminocarbonylmethyl)-pyrrolidine-3-carboxylic acid, trans, trans-2-(3-methoxy-4-propoxyphenyl)-4-(7-methoxy-1,3-benzodioxol-5-yl)-1-((2,6-diethylphenyl)aminocarbonylmethyl)-pyrrolidine-3-carboxylic acid, trans,trans-2-(4-methoxyphenyl)-4-(1,3-benzodioxol-5-yl)-1-((2,6-dibromo)phenylaminocarbonylmethyl)-pyrrolidine-3-carboxylic acid,

[2R,3R,4S]2-(4-Methoxyphenyl)-4-(1,3-benzodioxol-5-yl)-1-(N—(2,6-diethyl)phenylaminocarbonylmethyl)-pyrrolidine-3-carboxylic acid, trans,trans-2-(4-methoxyphenyl)-4-(1,3-benzodioxol-5-yl)-1-((2,6-dimethoxy)phenylaminocarbonylmethyl)-pyrrolidine-3-carboxylic acid, trans,trans-2-(4-methoxyphenyl)-4-(1,3-benzodioxol-5-yl)-1-((4-bromo-2,6-diethyl)phenylaminocarbonylmethyl)-pyrrolidine-3-carboxylic acid, trans,trans-2-(4-methoxyphenyl)-4-(1,3-benzodioxol-5-yl)-1-((2-ethyl-6-methyl)phenylaminocarbonylmethyl)-pyrrolidine-3-carboxylic acid, trans,trans-2-(4-methoxyphenyl)-4-(1,3-benzodioxol-5-yl)-1-((2,4,6-triethyl)phenylaminocarbonylmethyl)-pyrrolidine-3-carboxylic acid,

[2R,3R,4S]-2-(4-Propoxyphenyl)-4-(1,3-benzodioxol-5-yl)-1-(N—(2,6-diethyl)phenylaminocarbonylmethyl)-pyrrolidine-3-carboxylic acid, trans,trans-2-(4-methoxyphenyl)-4-(1,3-benzodioxol-5-yl)-1-((2,6-diisopropyl)phenylaminocarbonylmethyl)-pyrrolidine-3-carboxylic acid, trans,trans-2-(4-methoxyphenyl)-4-(1,3-benzodioxol-5-yl)-1-((2,6-diethyl-4-methyl)phenylaminocarbonylmethyl)-pyrrolidine-3-carboxylic acid,

[2R,3R,4S]-2-(4-ethoxyphenyl)-4-(1,3-benzodioxol-5-yl)-1-((2,6-diethyl)phenylaminocarbonylmethyl)-pyrrolidine-3-carboxylic acid, trans, trans-2-(4-methoxyphenyl)-4-(1,3-benzodioxol-5-yl)-1-((4-carboxy-2,6-diethyl)phenylaminocarbonylmethyl)-pyrrolidine-3-carboxylic acid, trans,trans-2-(4-methoxyphenyl)-4-(1,3-benzodioxol-5-yl)-1-((4-nitro-2,6-diethyl)phenylaminocarbonylmethyl)-pyrrolidine-3-carboxylic acid, trans, trans-2-(4-methoxyphenyl)-4-(1,3-benzodioxol-5-yl)-1-((2-isopropyl-6-methyl)phenylaminocarbonylmethyl)-pyrrolidine-3-carboxylic acid, trans,trans-2-(4-Methoxyphenyl)-4-(1,3-benzodioxol-5-yl)-1-(N—(2-ethyl-6-methoxy)phenylaminocarbonylmethyl)-pyrrolidine-3-carboxylic acid, trans,trans-2-(4-isopropoxyphenyl)-4-(1,3-benzodioxol-5-yl)-1-(2,6-diethylphenylaminocarbonylmethyl)-pyrrolidine-3-carboxylic acid, trans,trans-2-(2-fluoro-4-propoxyphenyl)-4-(1,3-benzodioxol-5-yl)-1-(2,6-diethylphenylaminocarbonylmethyl)-pyrrolidine-3-carboxylic acid, trans,trans-2-(4-(2-Methoxyethoxy)phenyl)-4-(1,3-benzodioxol-5-yl)-1-(2,6-diethylphenylaminocarbonylmethyl)-pyrrolidine-3-carboxylic acid, trans,trans-2-(4-(2-Ethoxyethoxy)phenyl)-4-(1,3-benzodioxol-5-yl)-1-(2,6-diethylphenylaminocarbonylmethyl)-pyrrolidine-3-carboxylic acid,

[2R,3R,4S]-2-(4-(2-Methoxyethoxy)phenyl)-4-(1,3-benzodioxol-5-yl)-1-(2,6-diethylphenylaminocarbonylmethyl)-pyrrolidine-3-carboxylic acid,

[2R,3R,4S]-2-(4-(2-Ethoxyethoxy)phenyl)-4-(1,3-benzodioxol-5-yl)-1-(2,6-diethylphenylaminocarbonylmethyl)-pyrrolidine-3-carboxylic acid, trans,trans-2-(4-(2-isopropoxyethoxy)phenyl)-4-(1,3-benzodioxol-5-yl)-1-(2,6-diethylphenylaminocarbonylmethyl)-pyrrolidine-3-carboxylic acid, or a pharmaceutically acceptable salt thereof.

Preferred compounds of the invention are selected from the group consisting of:

trans,trans-2-(4-Methoxyphenyl)-4-(1,3-benzodioxol-5-yl)-1-((2,6-diethyl)phenylaminocarbonylmethyl)-pyrrolidine-3-carboxylic acid;

trans,trans-2-(4-Propoxyphenyl)-4-(1,3-benzodioxol-5-yl)-1-((2,6-diethyl)phenylaminocarbonylmethyl)-pyrrolidi ne-3-carboxylic acid;

trans,trans-2-(3-Fluoro-4-methoxyphenyl)-4-(1,3-benzodioxol-5-yl)-1-((2,6-diethyl)phenylaminocarbonylmethyl)-pyrrolidine-3-carboxylic acid;

trans,trans-2-(3-Fluoro-4-ethoxyphenyl)-4-(1,3-benzodioxol-5-yl)-1-((2,6-diethyl)phenylaminocarbonylmethyl)-pyrrolidine-3-carboxylic acid;

trans,trans-2-(3-Fluoro-4-methoxyphenyl)-4-(7-methoxy-1,3-benzodioxol-5-yl)-1-((2,6-diethyl)phenylaminocarbonylmethyl)-pyrrolidine-3-carboxylic acid;

trans,trans-2-(3-methoxy-4-propoxyphenyl)-4-(1,3-benzodioxol-5-yl)-1-((2,6-diethyl)phenylaminocarbonylmethyl)-pyrrolidine-3-carboxylic acid;

trans,trans-2-(4-ethoxyphenyl)-4-(1,3-benzodioxol-5-yl)-1-((2,6-diethyl)phenylaminocarbonylmethyl)-pyrrolidine-3-carboxylic acid;

trans,trans-2-(4-propoxyphenyl)-4-(7-methoxy-1,3-benzodioxol-5-yl)-1-((2,6-diethyl)phenylaminocarbonylmethyl)-pyrrolidine-3-carboxylic acid trans,trans-2-(3-methoxy-4-propoxyphenyl)-4-(7-methoxy-1,3-benzodioxol-5-yl)- 1-((2,6-diethyl)phenylaminocarbonylmethyl)-pyrrolidine-3-carboxylic acid;

[2R,3R,4S]2-(4-Methoxyphenyl)-4-(1,3-benzodioxol-5-yl)-1-(N—(2,6-diethyl)phenylaminocarbonylmethyl)-pyrrolidine-3-carboxylic acid,

[2R,3R,4S]2-(4-Propoxyphenyl)-4-(1,3-benzodioxol-5-yl)-1-(N—(2,6-diethyl)phenylaminocarbonylmethyl)-pyrrolidine-3-carboxylic acid; and

[2R,3R,4S]-2-(4-ethoxyphenyl)-4-(1,3-benzodioxol-5-yl)-1-((2,6-diethyl)phenylaminocarbonylmethyl)-pyrrolidine-3-carboxylic acid, trans,trans-2-(4-isopropoxyphenyl)-4-(1,3-benzodioxol-5-yl)-1-(2,6-diethylphenylaminocarbonylmethyl)-pyrrolidine-3-carboxylic acid, trans,trans-2-(2-fluoro-4-propoxyphenyl)-4-(1,3-benzodioxol-5-yl)-1-(2,6-diethylphenylaminocarbonylmethyl)-pyrrolidine-3-carboxylic acid, trans,trans-2-(4-(2-Methoxyethoxy)phenyl)-4-(1,3-benzodioxol-5-yl)-1-(2,6-diethylphenylaminocarbonylmethyl)-pyrrolidine-3-carboxylic acid, trans,trans-2-(4-(2-Ethoxyethoxy)phenyl)-4-(1,3-benzodioxol-5-yl)-1-(2,6-diethylphenylaminocarbonylmethyl)-pyrrolidine-3-carboxylic acid,

[2R,3R,4S]-2-(4-(2-Methoxyethoxy)phenyl)-4-(1,3-benzodioxol-5-yl)-1-(2,6-diethylphenylaminocarbonylmethyl)-pyrrolidine-3-carboxylic acid,

[2R,3R,4S]-2-(4-(2-Ethoxyethoxy)phenyl)-4-(1,3-benzodioxol-5-yl)-1-(2,6-diethylphenylaminocarbonylmethyl)-pyrrolidine-3-carboxylic acid, trans,trans-2-(4-(2-isopropoxyethoxy)phenyl)-4-(1,3-benzodioxol-5-yl)-1-(2,6-diethylphenylaminocarbonylmethyl)-pyrrolidine-3-carboxylic acid, or a pharmaceutically acceptable salt thereof.

Most preferred are the compounds:

trans,trans-2-(4-Propoxyphenyl)-4-(1,3-benzodioxol-5-yl)-1-((2,6-diethyl)phenylaminocarbonylmethyl)-pyrrolidine-3-carboxylic acid;

[2R,3R,4S]2-(4-Methoxyphenyl)-4-(1,3-benzodioxol-5-yl)-1-(N—(2,6-diethyl)phenylaminocarbonylmethyl)-pyrrolidine-3-carboxylic acid;

[2R,3R,4S]2-(4-Propoxyphenyl)-4-(1,3-benzodioxol-5-yl)-1-(N—(2,6-diethyl)phenylaminocarbonylmethyl)-pyrrolidine-3-carboxylic acid; and

[2R,3R,4S]-2-(4-ethoxyphenyl)-4-(1,3-benzodioxol-5-yl)-1-((2,6-diethyl)phenylaminocarbonylmethyl)-pyrrolidine-3-carboxylic acid;

trans,trans-2-(4-(2-Methoxyethoxy))-4-(1,3-benzodioxol-5-yl)-1-(2,6-diethylphenylaminocarbonylmethyl)-pyrrolidine-3-carboxylic acid, trans,trans-2-(4-(2-Methoxyethoxy)phenyl)-4-(1,3-benzodioxol-5-yl)-1-(2,6-diethylphenylaminocarbonylmethyl)-pyrrolidine-3-carboxylic acid, trans,trans-2-(4-(2-Ethoxyethoxy)phenyl)-4-(1,3-benzodioxol-5-yl)-1-(2,6-diethylphenylaminocarbonylmethyl)-pyrrolidine-3-carboxylic acid,

[2R,3R,4S]-2-(4-(2-Methoxyethoxy)phenyl)-4-(1,3-benzodioxol-5-yl)-1-(2,6-diethylphenylaminocarbonylmethyl)-pyrrolidine-3-carboxylic acid,

[2R,3 R,4S]-2-(4-(2-Ethoxyethoxy)phenyl)-4-(1,3-benzodioxol-5-yl)-1-(2,6-diethylphenylaminocarbonylmethyl)-pyrrolidine-3-carboxylic acid, trans,trans-2-(4-(2-isopropoxyethoxy)phenyl)-4-(1,3-benzodioxol-5-yl)-1-(2,6-diethylphenylaminocarbonylmethyl)-pyrrolidine-3-carboxylic acid, or a pharmaceutically acceptable salt thereof.

Methods for preparing the compounds of the invention are shown in Schemes I–VII.

Scheme I illustrates the general procedure for preparing the compounds of the invention when m is 0 and W is —$CO_2H$. A β-ketoester 1, where E is loweralkyl or a carboxy protecting group, is reacted with a nitro vinyl compound 2, in the presence of a base (for example, 1,8-diazabicyclo[5.4.0]undec-7-ene (DBU) or sodium ethoxide or sodium hydride and the like) in an inert solvent such as toluene, berizene, tetrahydrofuran or ethanol and the like. The condensation product 3 is reduced (for example, by hydrogenation using a Raney nickel or platinum catalyst). The resulting amine cyclizes to give the dihydro pyrrole 4. Reduction of 4 (for example, sodium cyanoborohydride or catalytic hydrogenation and the like) in THF solvent or the like gives the pyrrolidine compound 5 as a mixture of cis-cis, trans,trans and cis,trans products. Chromatographic separation removes the cis-cis isomer leaving a mixture of the trans,trans and cis,trans isomers which is further elaborated. The cis-cis isomer can be epimerized (for example, using sodium ethoxide in ethanol or DBU in toluene) to give the trans,trans isomer and then carried on as described below. The pyrrolidine nitrogen is (1) acylated or sulfonylated with $R_3$—X ($R_3$ is $R_4$—C(O)— or $R_6$—S(O)$_2$— and X is a leaving group such as a halide (Cl is preferred) or X taken together with $R_4$—C(O)— or $R_6$—S(O)$_2$— forms an activated ester including esters or anhydrides derived from formic acid, acetic acid and the like, alkoxycarbonyl halides, N-hydroxysuccinimide, N-hydroxyphthalimide, N-hydroxybenzotriazole, N-hydroxy-5-norbornene-2,3-dicarboxamide, 2,4,5-trichlorophenol and the like) or (2) alkylated with $R_3$—X where X is a leaving group (for example, X is a halide (for example, Cl, Br or I) or X is a leaving group such as a sulfonate (for example, mesylate, tosylate, triflate and the like)) in the presence of a base such as diisopropyl ethylamine or triethylamine and the like to give the N-derivatized pyrrolidine 6 which is still a mixture of trans,trans and cis,trans isomers. Hydrolysis of the ester 6 (for example, using a base such a sodium hydroxide in EtOH/$H_2O$) selectively hydrolyzes the trans,trans ester to give a mixture of 7 and 8, which are readily separated.

Many of the β-ketoester starting materials employed in the preparation of the compounds of the present invention are commercially available. They may also be prepared using the methods indicated in Scheme VII. In the method of Scheme VIII(a), an aromatic, heteroaromatic, or α-quaternary methyl ketone is deprotonated (e.g., with sodium hydride or lithium diisopropylamide) and treated with a reagent capable of transferring a carboalkoxy group (e.g., diethyl carbonate, methyl chloroformate, or di-tert-butyldicarbonate). Alternatively, as shown in Scheme VIII (b), a carboxylic acid may be activated (e.g., with carbonyldiimidazole or oxalyl chloride) and treated with an acetate equivalent (e.g., ethyl lithioacetate, magnesium methylmalonate, or Meldrum's acid followed by thermal alcoholysis).

A preferred embodiment is shown in Schemes II and III. A benzoyl acetate such as 26 or 4-(2-methoxyethoxy) benzoyl acetate is reacted with a nitro vinyl benzodioxolyl compound 27 using 1,8-diazabicyclo[5.4.0]undec-7-ene (DBU) as the base in toluene to give compound 28. Catalytic hydrogenation using Raney nickel leads to reduction of the nitro group to an amine and subsequent cyclization to give the dihydropyrrole 29. The double bond is reduced with sodium cyanoborohydride to give the pyrrolidine compound 30 as a mixture of cis-cis, trans,trans and cis,trans isomers. Chromatography separates the cis-cis isomer, leaving a mixture of the trans,trans and cis,trans isomers (31).

Scheme III illustrates the further elaboration of the trans, trans isomer. The mixture (31) of trans,trans and cis,trans pyrrolidines described in Scheme IV is reacted with Br—$CH_2C(O)NHR_4$ in acetonitrile in the presence of ethyldiisopropylamine to give the alkylated pyrrolidine compound 32, still as a mixture of trans,trans and cis,trans isomers. Sodium hydroxide in ethanol-water hydrolyzes the ethyl ester of the trans,trans compound but leaves the ethyl ester of the cis,trans compound untouched, thus allowing separation of the trans,trans carboxylic acid 33 from the cis,trans ester 34.

Scheme IV illustrates the preparation of compounds where W is other than carboxylic acid. Compound 55, which can be prepared by the procedures described in Scheme I, is converted (for example, using peptide coupling condition, e.g. N-methylmorpholine, EDCl and HOBt, in the presence of ammonia or other amide forming reactions) to give carboxamide 56. The carboxamide is dehydrated (for example, using phosphorus oxychloride in pyridine) to give nitrile 57. Nitrile 57 under standard tetrazole-forming conditions (sodium azide and triethylamine hydrochloride or trimethylsilylazide and tin oxide) is reacted to give tetrazole 58. Alternatively nitrile 57 is reacted with hydroxylamine hydrochloride in the presence of a base (for example, potassium carbonate, sodium carbonate, sodium hydroxide, triethylamine, sodium methoxide or NaH) in a solvent such as DMF, DMSO, or dimethylacetamide to give amidoxime 59. The amidoxime 59 is allowed to react with a methyl or ethyl chloroformate in a conventional organic solvent (such as, chloroform, methylene chloride, dioxane, THF, acetonitrile or pyridine) in the presence of a base (for example, triethylamine, pyridine, potassium carbonate and sodium carbonate) to give an 0-acyl compound. Heating of the O-acyl amidoxime in an inert solvent (such as benzene, toluene, xylene, dioxane, THF, dichloroethane, or chloroform and the like) results in cyclization to compound 60. Alternatively reacting the amidoxime 59 with thionyl chloride in an inert solvent (for example, chloroform, dichloromethane, dioxane and THF and the like) affords the oxathiadiazole 61.

Scheme V illustrates a method for synthesizing pyrrolidines by an azomethine ylide type [3+2]-cycloaddition to an acrylate. General structures such as compound 70 are known to add to unsaturated esters such as 71 to provide pyrrolidines such as compound 72 (O. Tsuge, S. Kanemasa, K. Matsuda, Chem. Lett. 1131–4 (1983), O. Tsuge, S. Kanemasa, T. Yamada, K. Matsuda, J. Org. Chem. 52 2523–30 (1987), and S. Kanemasa, K. Skamoto, O. Tsuge, Bull. Chem. Soc. Jpn. 62 1960–68 (1989)). Silylimine 73 is reacted with acrylate 74 in the presence of trimethylsilyl triflate and tetrabutylammonium fluoride to give the desired pyrrolidine 75 as a mixture of isomers. This method can be modified to provide the N-acetamido derivatives directly by reacting 73 and 74 with the appropriate bromoacetamide (for example, dibutyl bromoacetamide) in the presence of tetrabutylammonium iodide and cesium fluoride to give compound 76.

Scheme VI illustrates a method for producing an enantiomerically pure pyrrolidine 80, which can be further elaborated on the pyrrolidine nitrogen.

Intermediate racemic pyrrolidine ester 77 (for example, prepared by the procedure described in Scheme V) is Boc-nitrogen protected (for example, by treatment with $Boc_2O$) and then the ester is hydrolyzed (for example, using sodium or lithium hydroxide in ethanol and water) to give t-butyl carbamoyl pyrrolidine carboxylic acid 78. The carboxylic acid is converted to its (+)-α-methylbenzylamine salt, which can be recrystallized (for example from ethyl acetate and hexane or chloroform and hexane) to afford the diastereomerically pure salt. This diastereomerically pure salt can be neutralized (for example, with sodium carbonate or citric acid) to afford enantiomerically pure carboxylic acid 79. The pyrrolidine nitrogen can be deprotected (for example, using trifluoroacetic acid) and the ester reformed by the use of ethanolic hydrochloric acid to give salt 80. Alternatively one can use ethanolic HCl to cleave the protecting group and form the ester in one step. The pyrrolidine nitrogen can be further elaborated (for example, by treatment with the 2,6-diethylbenzamide of bromoacetic acid in acetonitrile in the presence of diisopropylethylamine) to give optically active compound 81. The use of (−)-α-methylbenzylamine will give the opposite enantiomer. Other optically active amines may also be employed.

A preferred process is shown in Scheme VII. Nitro vinyl compound (88) is reacted with β-keto ester 89 in the presence of a base such as sodium ethoxide and the like or a trialkylamine such as triethylamine or diisopropylethylamine and the like or an amidine such as DBU and the like in an inert solvent such as THF, toluene, DMF, acetonitrile, ethyl acetate, isopropyl acetate or methylene chloride and the like at a temperature of from about 0° C. to about 100° C. for a period of time from about 15 minutes to overnight to give compound 90. Reduction of the nitro group followed by cyclization was effected for example by catalytic hydrogenation with a hydrogen pressure of from about atmospheric pressure to 300 p.s.i. over from about 1 hour to about 1 day of compound 90 in an inert solvent such as THF, ethyl acetate, toluene, ethanol, isopropanol, DMF or acetonitrile and the like, using a hydrogenation catalyst such as Raney nickel, palladium on carbon, a platinum catalyst, such as platinum oxide, platinum on carbon or platinum on alumina and the like, or a rhodium catalyst, such as rhodium on carbon or rhodium on alumina and the like, and the like affords intermediate nitrone 91a or a mixture of nitrone 91a and imine 91b. The reaction mixture comprising the nitrone or nitrone/imine mixture is treated with an acid such as trifluoroacetic acid or acetic acid or sulfuric acid or phosphoric acid or methanesulfonic acid and the like, and the hydrogenation is continued to give pyrrolidine compound 92 as the cis,cis-isomer. Epimerization at C-3 is effected by treatment of compound 92 with a base such as sodium ethoxide, potassium t-butoxide, lithium t-butoxide or potassium t-amyloxide and the like or a trialkylamine such as triethylamine or diisopropylethylamine and the like or an amidine such as DBU and the like in an inert solvent such as ethanol, ethyl acetate, isopropyl acetate, THF, toluene or DMF and the like at a temperature of from about −20° C. to about 120° C. to give the trans,trans compound 93. Compound 93 itself can optionally be resolved into enantiomers prior to reacting with X—R$_3$. The substantially pure (i.e., at least 95% of the desired isomer) optically active (+)-isomer of compound 93 is obtained by treatment of a mixture of the (+)-isomer and the (−)-isomer of 93 with S-(+)-mandelic acid, D-tartaric acid or D-dibenzoyl tartaric acid or the like in a solvent such as acetonitrile, ethyl acetate, isopropyl acetate, ethanol or isopropanol and the like. The (+)-isomer of 93 selectively crystallizes as the salt, leaving the (−)-isomer of 93 in solution. Alternatively, the substantially pure (i.e., at least 95% of the desired isomer) optically active (−)-isomer of compound 93 can be selectively crystallized by reaction of a mixture of the (+)-isomer and the (−)-isomer of 93 with L-tartaric acid, L-dibenzoyl tartaric acid or L-pyroglutamic acid and the like, leaving the desired (+)-isomer of compound 93 in solution.

Compound 93 (racemic or optically active) is reacted with X—R$_3$ (where X is a leaving group (for example, a halide or a sulfonate) and R$_3$ is as previously defined) using a base such as diisopropylethylamine, triethylamine, sodium bicarbonate or potassium carbonate and the like in an inert solvent such as acetonitrile, THF, toluene, DMF or ethanol and the like at a temperature of from about 0° C. to about 100° C. to give the intermediate ester 94. The ester can be isolated or converted in situ to the carboxylic acid (95) using hydrolysis conditions such as a base such as sodium hydroxide or lithium hydroxide or potassium hydroxide and the like in a solvent such as ethanol-water or THF-ethanol and the like.

Scheme I

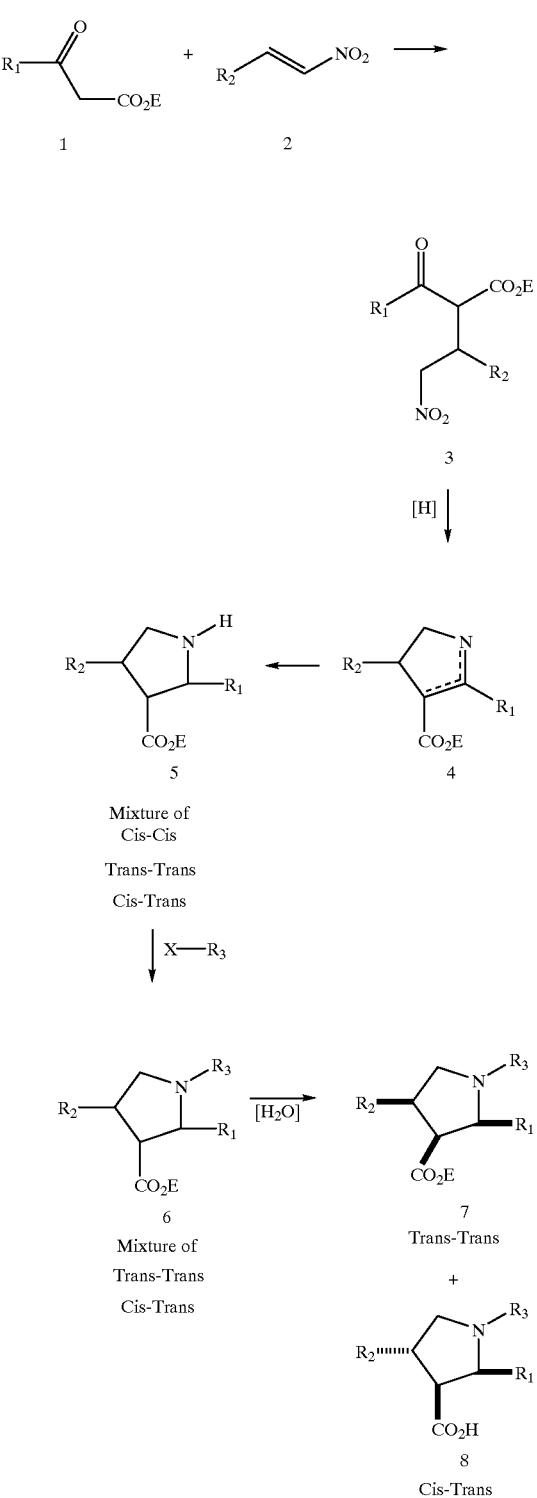

Scheme II
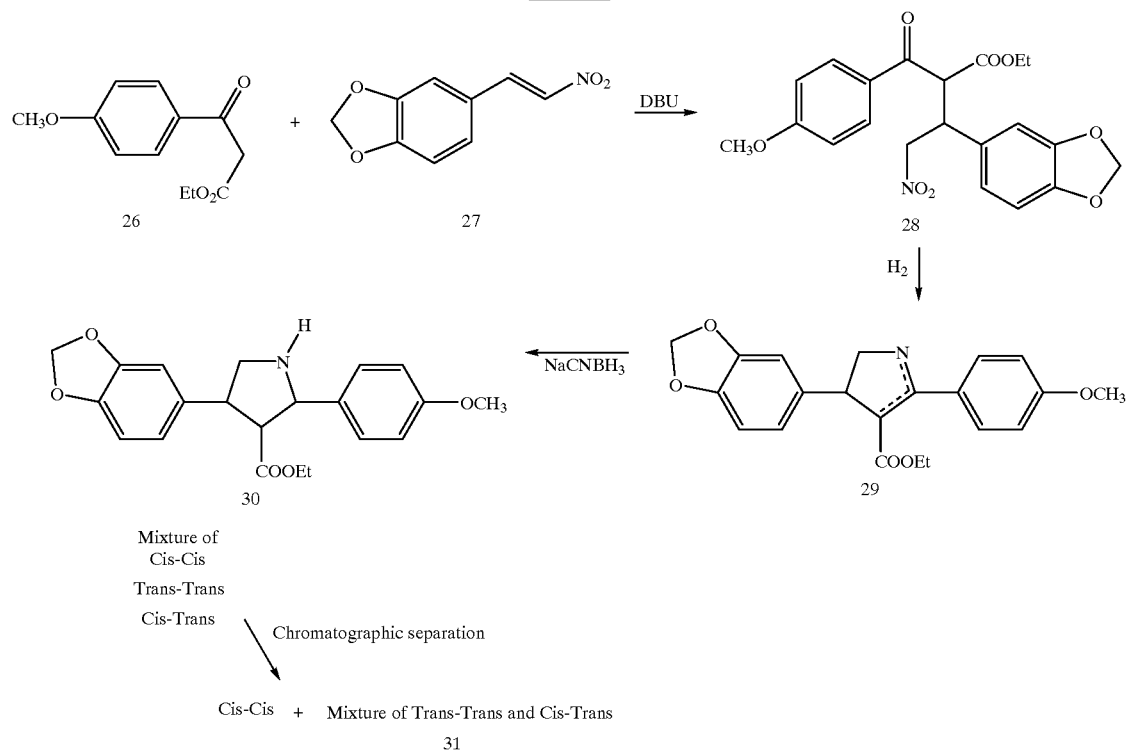
Scheme III
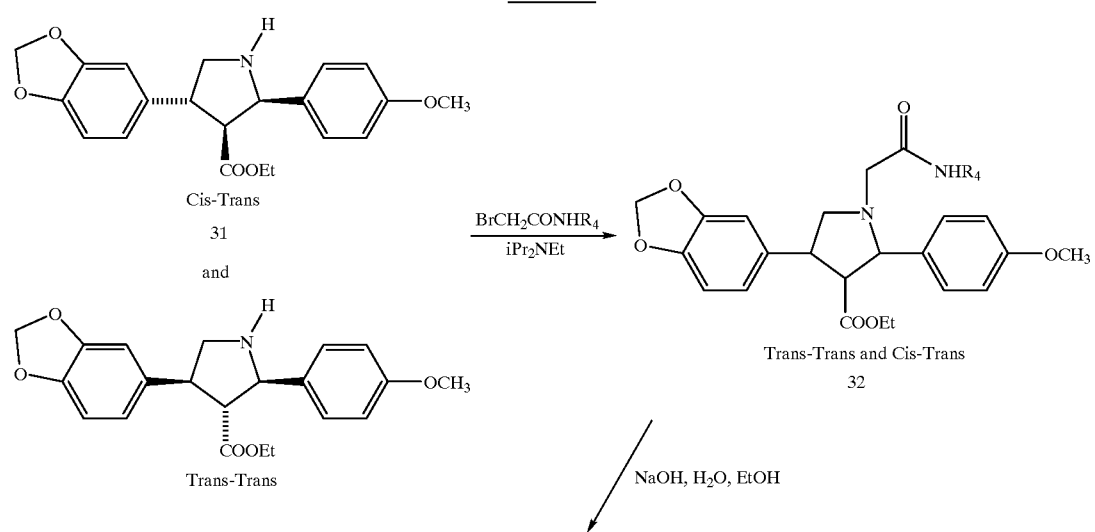

27
28
-continued
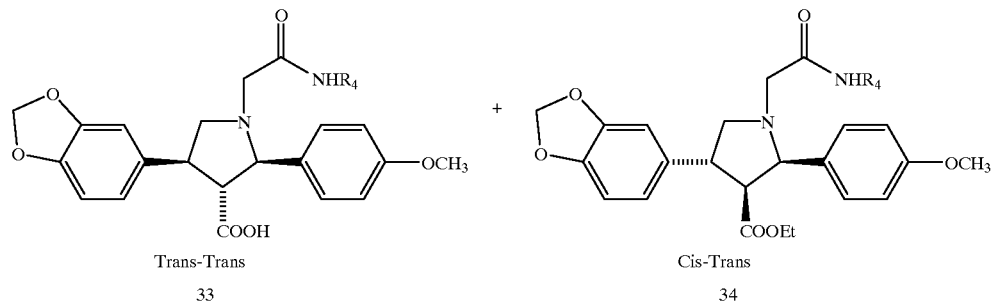
Trans-Trans
33
Cis-Trans
34
Scheme IV
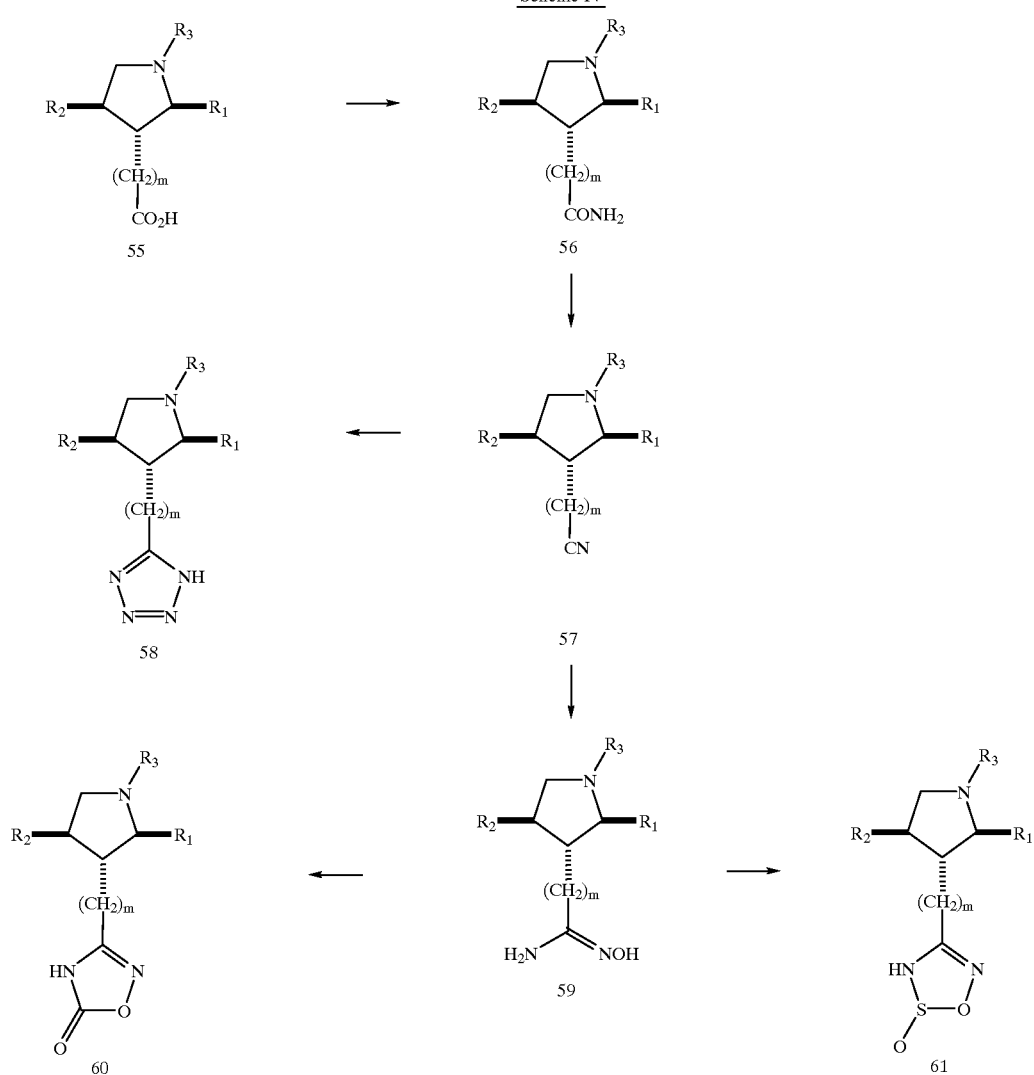

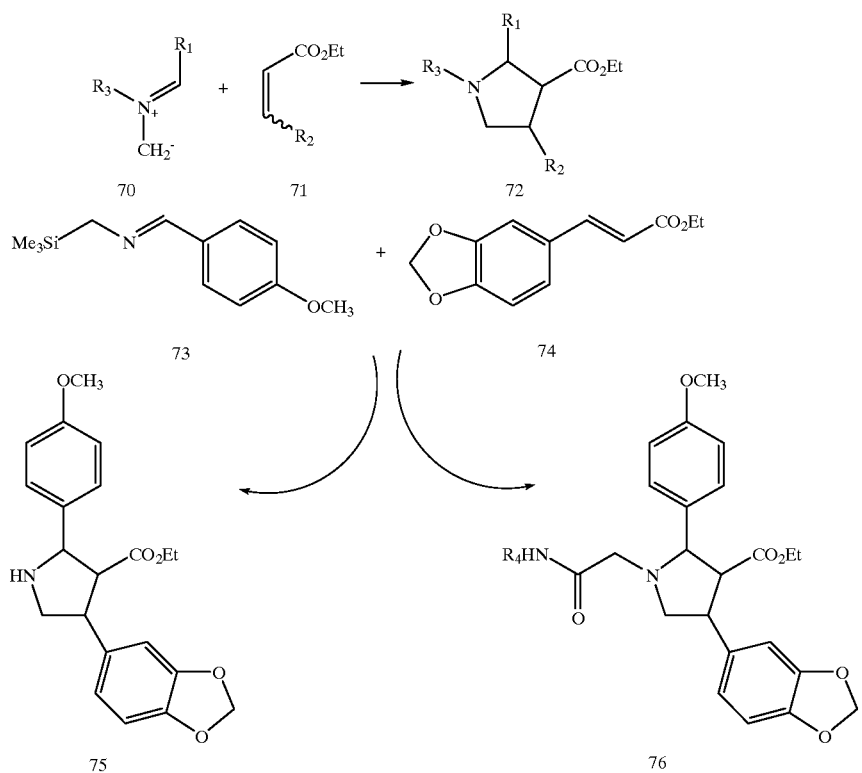
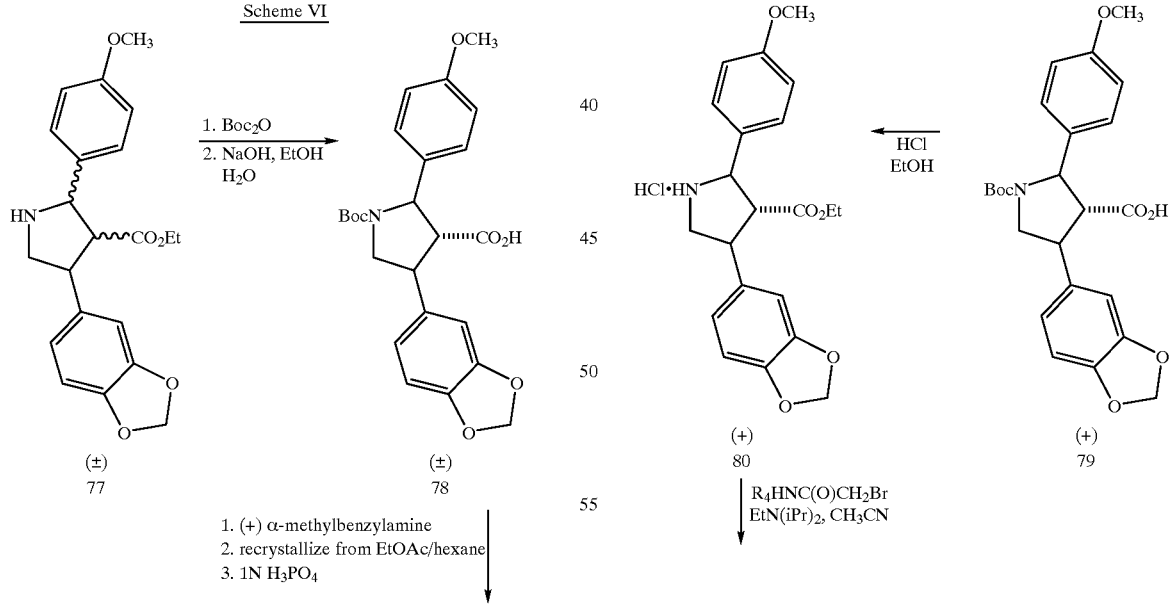

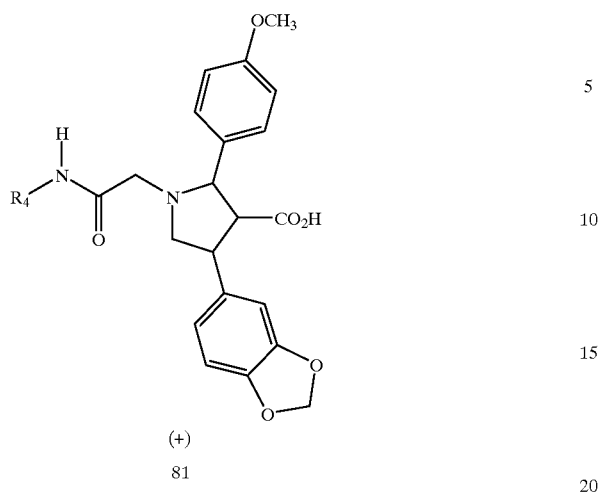
81
Scheme VII
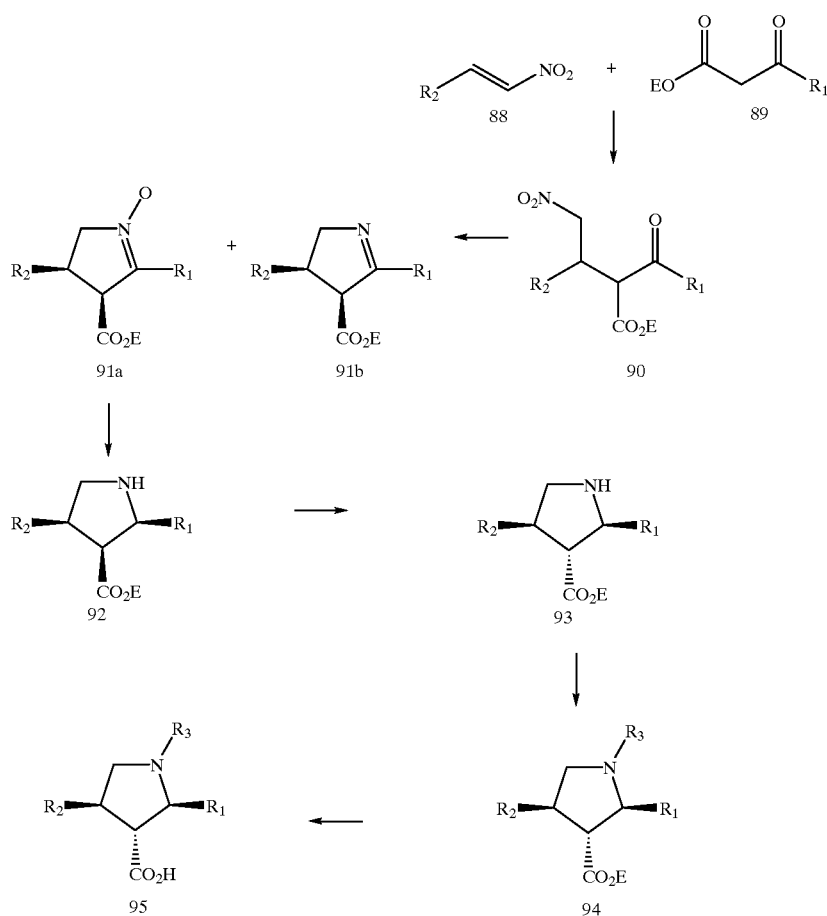

SCHEME VIII

Scheme VIIIa

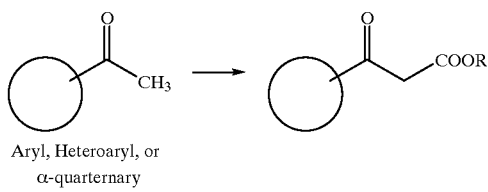

Aryl, Heteroaryl, or
α-quarternary

Scheme VIIIb

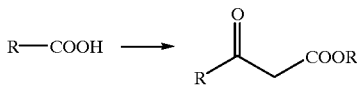

Compounds which are useful as intermediates for the preparation of compounds of the invention are:

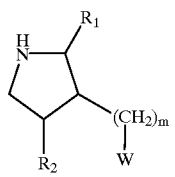
(III)

wherein m is 0 to 6;

W is (a) —C(O)₂—G where G is hydrogen or a carboxy protecting group,
(b) —PO₃H₂,
(c) —P(O)(OH)E where E is hydrogen, loweralkyl or arylalkyl,
(d) —CN,
(e) —C(O)NHR₁₇ where R₁₇ is loweralkyl,
(f) alkylaminocarbonyl,
(g) dialkylaminocarbonyl,
(h) tetrazolyl,
(i) hydroxy,
(j) alkoxy,
(k) sulfonamido,
(l) —C(O)NHS(O)₂R₁₆ where R₁₆ is loweralkyl, haloalkyl, phenyl or dialkylamino,
(m) —S(O)₂NHC(O)R₁₆, (n)

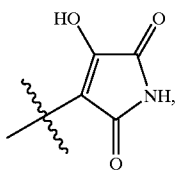

(o)

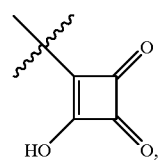

(p)

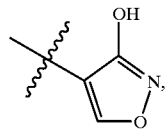

(q)

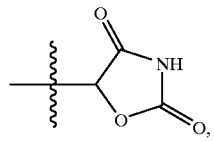

(r)

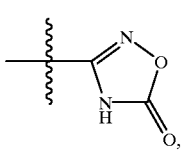

(s)

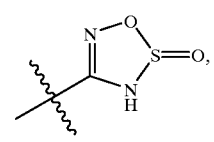

(t)

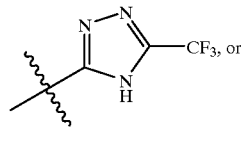
—CF₃, or (u)

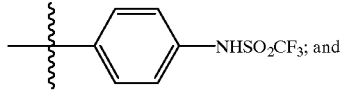
—NHSO₂CF₃; and

R₁ and R₂ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, heterocyclic, (heterocyclic)alkyl and (R$_{aa}$)(R$_{bb}$)N—R$_{cc}$— wherein R$_{aa}$ is aryl or aryfalkyl, R$_{bb}$ is hydrogen or alkanoyl and R$_{cc}$ is alkylene, with the proviso that one or both of R₁ and R₂ is other than hydrogen; or a salt thereof;

and a compound of the formula:

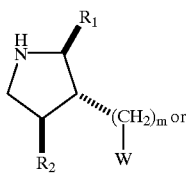
(IV)

-continued (V)

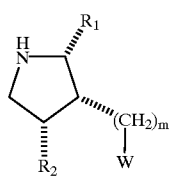

wherein n is 0 or 1;
m is 0 to 6;
W is
(a) —C(O)₂—G where G is hydrogen or a carboxy protecting group,
(b) —PO₃H₂,
(c) —P(O)(OH)E where E is hydrogen, loweralkyl or arylalkyl,
(d) —CN,
(e) —C(O)NHR₁₇ where R₁₇ is loweralkyl,
(f) alkylaminocarbonyl,
(g) dialkylaminocarbonyl,
(h) tetrazolyl,
(i) hydroxy,
(j) alkoxy,
(k) sulfonamido,
(l) —C(O)NHS(O)₂R₁₆ where R₁₆ is loweralkyl, haloalkyl, phenyl or dialkylamino,
(m) —S(O)₂NHC(O)R₁₆, (n)

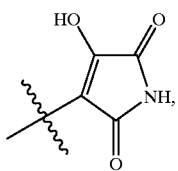

(o)

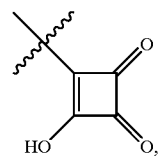

(p)

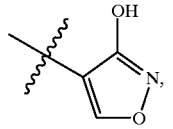

(q)

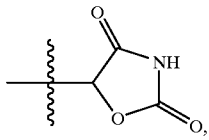

(r)

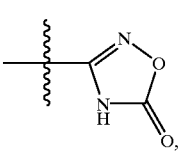

(s)

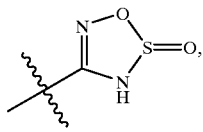

(t)

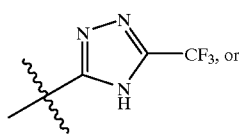

(u)

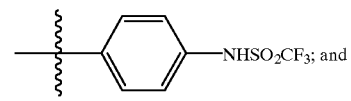

$R_1$ and $R_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbony lalkenyl, hydroxyalkenyl, aryl, arylalkyl, aryloxyalkyl, arylalkoxyalkyl, heterocyclic, (heterocyclic)alkyl and $(R_{aa})(R_{bb})N$—$R_{cc}$—wherein $R_{aa}$ is aryl or arylalkyl, $R_{bb}$ is hydrogen or alkanoyl and $R_{cc}$ is alkylene, with the proviso that one or both of $R_1$ and $R_2$ is other than hydrogen; or a salt thereof.

Preferred intermediates include compounds of formula (III), (IV) and (V) wherein
m is zero or 1;
W is —CO₂—G wherein G is hydrogen or a carboxy protecting group, and $R_1$ and $R_2$ are as defined above; or
the substantially pure (+)- or (−)-isomer thereof.

Particularly preferred intermediates are compounds of formula (III), (IV) and (V) wherein
m is 0;
W is —CO₂—G wherein G is hydrogen or a carboxy protecting group; and $R_1$ is (i) alkoxyalkylalkyl, (ii) cycloalkyl, (iii) phenyl, (iv) pyridyl, (v) furanyl or (vi) substituted or unsubstituted 4-methoxyphenyl, 4-fluorophenyl, 2-fluorophenyl, 4-trifluoromethylphenyl, 4-ethoxyphenyl, 3-fluoro-4-methoxyphenyl, 3-fluoro-4-ethoxyphenyl, 4-propoxyphenyl, 4-isopropoxyphenyl, 2-fluoro-4-ethoxyphenyl, 4-(2-methoxyethoxy)phenyl, 4-(2-ethoxyethoxy)phenyl, 4-(2-isopropoxyethoxy)phenyl, 3-fluoro-4-propoxyphenyl, 3-methoxy-4-propoxyphenyl, 4-pentafluoroethylphenyl, 4-methoxymethoxyphenyl, 4-hydroxyphenyl, 1,3-benzodioxolyl, 7-methoxy-1,3-benzodioxolyl, 1,4-benzodioxanyl or dihydrobenzofuranyl wherein the substituent is selected from alkoxy, alkoxyalkoxy and carboxyalkoxy and $R_2$ is 1,3-benzodioxolyl, 1,4-benzodioxanyl, dihydrobenzofuranyl, benzofuranyl, 4-methoxyphenyl, dimethoxyphenyl, fluorophenyl or difluorophenyl; or
the substantially pure (+)- or (−)-isomer thereof.

The foregoing may be better understood by reference to the following examples which are provided for illustration and not intended to limit the scope of the inventive concept. The following abbreviations are used: Boc for tert-butyloxycarbonyl, Cbz for benzyloxycarbonyl, DBU for 1,8-diazabicyclo[5.4.0]undec-7-ene, EDCl for 1-(3-dimethylaminopropyl-3-ethylcarbodiimide hydrochloride, EtOAc for ethyl acetate, EtOH for ethanol, HOBt for 1-hydroxybenzotriazole, Et$_3$N for triethylamine, TFA for trifluoroacetic acid and THF for tetrahydrofuran.

EXAMPLE 1 trans,trans-2-(4-Methoxyphenyl)-4-(1,3-benzodioxol-5-yl)-1-((2,4,6-trimethyl) phenylaminocarbonylmethyl)-pyrrolidine-3-carboxylic acid

Example 1A

Ethyl 2-(4-methoxybenzoyl)-4-nitromethyl-3-(1.3-benzodioxole-5-yl)butyrate

To ethyl (4-methoxybenzoyl)acetate (23.0 g, 0.104 mol), prepared by the method of Krapcho et aL, Org. Syn. 47, 20 (1967), and 5-(2-nitrovinyl)-1,3-benzodioxole (17.0 g, 0.088 mol) dissolved in 180 mL of toluene and heated to 80° C. was added 1,8-diazabicyclo[5,4,0] undec-7-ene (DBU, 0.65 g) with stirring. The mixture was heated until all the nitro starting material dissolved. The solution was stirred without heating for 30 minutes and then an additional 0.65 g of DBU was added. After stirring an additional 45 minutes, thin layer chromatography (5% ethyl acetate in methylene chloride) indicated the absence of nitro starting material. Toluene (200 mL) was added, and the organic phase was washed with dilute hydrochloric acid and NaCl solution. The organic phase was dried over sodium sulfate and then concentrated under reduced pressure. The residue obtained was chromatographed on silica gel eluting with 3:1 hexane-ethyl acetate to give 21.22 g of the desired product as a mixture of isomers and 9.98 g. of recovered ethyl (4-methoxybenzoyl)acetate.

Example 1B

Ethyl 2-(4-methoxyphenyl)-4-(1,3-benzodioxol-5-yl)-4.5-dihydro-3H-pyrrole-3-carboxylate The compound resulting from Example 1A (21 g) in 500 mL of ethanol was hydrogenated under 4 atmospheres of hydrogen pressure using a Raney nickel 2800 catalyst (51 g). (The Raney nickel was washed with ethanol three times before use.) The catalyst was removed by filtration, and the solution was concentrated under reduced pressure. The residue obtained was chromatographed on silica gel eluting with 8.5% ethyl acetate in methylene chloride to give 12.34 g of the desired product.

Example 1C

Ethyl 2-(4-methoxyphenyl-4-(1,3-benzodioxol-5-yl)-pyrrolidine-3-carboxylate) as a mixture of cis-cis; trans,trans; and cis,trans-isomers The compound resulting from Example 1B (11.89 g, 0.324 mol) was dissolved in 27 mL of tetrahydrofuran and 54 mL of ethanol. Sodium cyanoborohydride (2.35 g, 0.374 mol) and 5 mg bromocresol green were added. To this blue solution was added dropwise a solution of 1:2 concentrated HCl in ethanol at such a rate that the color was kept at light yellow-green. After the yellow color persisted without additional HCl, the solution was stirred an additional 20 minutes. The solution was concentrated in vacuo and then partitioned between chloroform and an aqueous potassium bicarbonate solution. The organic phase was separated, dried over sodium sulfate, and concentrated under reduced pressure. The residue was chromatographed on silica gel eluting with 85:15 ethyl acetate-hexane to give 5.96 g. of a mixture of 64% trans,trans-compound and 34% cis,trans-compound. Further elution with pure ethyl acetate gave 0.505 g of an unknown solid followed by 3.044 g of pure cis,cis-compound.

Example 1D

N-(2,4.6-Trimethylphenyl) bromoacetamide

To a stirred solution of 2,4,6-trimethylaniline (1 g, 7.40 mmol) in methylene chloride (25 mL) at −50° C. was added successively N,N-diisopropylethylamine (1.58 mL, 8.14 mmol, 1.1 eq) and bromoacetyl bromide (0.72 mL, 7.40 mmol, 1 eq) such that the temperature did not exceed −40° C. On completion of the addition, the cooling bath was removed, and the reaction mixture was allowed to warm to room temperature. After stirring for a further 30 minutes, the mixture was diluted with ether (70 mL) and poured into 1N sodium bisulfate solution. The phases were separated, and the upper layer was washed successively with water and brine. The organic phase was dried (Na$_2$SO$_4$) and the solvent evaporated to half volume, at which point the product crystallized. The crystals were removed by vacuum filtration to afford the title compound (1.51 g, 80%).

Example 1E trans,trans-2-(4-Methoxyphenyl)-4-(1,3-benzodioxol-5-yl)-1-((2,4,6-trimethyl) phenylaminocarbonylmethyl)-pyrrolidine-3-carboxylic acid The mixture of 64% trans,trans- and 34% cis,trans-pyrrolidines (the mixture resulting from Example 1C) (5.72 g, 15.50 mmol), ethyldiisopropylamine (4.20 g, 32.56 mmol), and the compound resulting from Example 1D (19.0 mmol) in 30 mL of acetonitrile was heated at 50° C. for 1 hour. The solution was concentrated in vacuo. The residue was dissolved in toluene, shaken with potassium bicarbonate solution, dried over sodium sulfate and concentrated in vacuo to give the product as a mixture of trans,trans- and cis,trans- ethyl esters.

This mixture was dissolved in a solution of 50 mL of ethanol and 15 mL of water containing 5.00 g of sodium hydroxide and stirred for 3 hours at room temperature. The solution was concentrated in vacuo and 60 mL of water added. The mixture was extracted with ether to remove the unreacted cis,trans- ethyl ester. The aqueous phase was treated with hydrochloric acid until slightly cloudy. It was then further neutralized with acetic acid to give the crude acid product. The crude product was filtered and purified by dissolving it in tetrahydrofuran, drying over sodium sulfate, concentrating in vacuo, and crystallizing from ether to give the title compound. $^1$H NMR (300 MHz, CDCl$_3$) 88.22 (1H, bs), 7.78 (2H, d, J=8 Hz), 6.95 (5H, m), 6.82 (1H, bd, J=8 Hz), 6.77 (1H, d, J=8 Hz), 5.96 (2H, s), 3.97 (1H, bd, J=10 Hz), 3.81 (3H, s), 3.70 (1H, ddd, 6, 5 & 3 Hz), 3.57 (bdd, 10&3 Hz), 3.45 (1H, d, J=16 Hz), 3.13 (2H, m), 2.24 (3H, s), 2.06 (6H, s). MS (DCl, NH$_3$) m/e 517 (M+H+). Anal. Calc for C$_{30}$H$_{32}$N$_2$O$_6$. 0.5H$_2$O: C, 68.56, H, 6.33, N 5.33. Found: C, 68.84, H, 6.20, N, 5.31

EXAMPLE 2 trans,trans-2-(3-Fluoro-4-methoxyphenyl)-4-(1.3-benzodioxol-5-yl)-1-((2,4,6-trimethyl)phenylaminocarbonylmethyl)-pyrrolidine-3-carboxylic acid The title compound was prepared by the procedures described in Example 1. $^1$H NMR (300 MHz, CDCl$_3$) δ 8.22 (1H, bs), 7.21 (1H, dd, J=12 & 2 Hz), 7.12 (1H, bd, J=8 Hz), 6.95 (1H, t, 8 Hz), 6.90 (2H, bs), 6.84 (1H, d, J=2 Hz), 6.80 (1H, dd, J=8 & 3 Hz), 6.76 (1H, d, J=8 Hz), 5.93 (2H, s), 3.96 (1H, d, J=1 OHz), 3.89 (3H, s), 3.70 (1H, ddd, 6, 5 & 3 Hz), 3.56 (1H, dd, 11 &5 Hz), 3.45 (1H, d, J=16 Hz), 3.10 (1H, t, J=10 Hz), 3.07 (1H, dd, 8 & 6 Hz), 3.02 (1H, d, J=16 Hz), 2.17 (3H, s), 2.07 (6H, s). MS (DCl, NH$_3$) m/e 535 (M+H$^+$). Anal. Calc for C$_{30}$H$_{31}$FN$_2$O$_6$.0.75H2O : C, 65.74, H, 5.98, N 5.11. Found: C, 65.96, H, 5.88, N, 5.16

EXAMPLE 3 trans,trans-2-(4-Propoxyphenyl)-4-(1,3-benzodioxol-5-yl)-1-((2,4,6-trimethyl)phenylaminocarbonylmethyl)-pyrrolidine-3-carboxylic acid The title compound was prepared by the procedures described in Example 1. $^1$H NMR (300 MHz, CDCl$_3$) δ 8.21 (1H, bs), 7.38 (2H, d, J=8 Hz), 6.90 (2H, d, J=8 Hz), 6.89 (2H, d, 3 Hz), 7.83 (1H, dd, J=8 & 2 Hz), 6.75 (1H, d, J=8 Hz), 5.94 (1H, d, J=3 Hz), 5.93 (1H, d, J=3 Hz), 3.96 (1H, d, J=10 Hz), 3.85 (2H, q, J=7 Hz), 3.70 (1H, ddd, 6, 5 & 3 Hz), 3.58 (1H, dd, 11 & 5 Hz), 3.48 (1H, d, J=16 Hz), 3.15 (1H, dd, 8 & 6 Hz), 3.13 (1H, t, J=10 Hz), 2.99 (1H, d, J=1 6 Hz), 2.25 (3H, s), 2.05 (6H, s), 1.81 (2H, sext, J=7 Hz), 1.04 (3H, t, J=7 Hz). MS (DCl, NH$_3$) m/e 545 (M+H+). Anal. Calc for C$_{32}$H$_{36}$N$_2$O$_6$.0.33H$_2$O: C, 69.79, H, 6.71, N 5.09, Found: C, 69.78, H, 6.73, N, 4.81

EXAMPLE 4 trans,trans-2-(4-Methoxyphenyl)-4-(1,3-benzodioxol-5-yl)-1-((26-diethyl)phenylaminocarbonylmethyl)-pyrrolidine-3-carboxylic acid The title compound was prepared by the procedures described in Example 1. $^1$H NMR (300 MHz, CDCl$_3$) δ 8.24 (1H, bs), 7.39 (2H, d, J=8 Hz), 7.21 (1H, dd, 8 & 6 Hz), 7.11 (2H, d, J=8 Hz), 6.92 (2H, d, 8 Hz), 7.89 (1H, d, J=3 Hz), 7.82 (1H, dd, J=8 & 2 Hz), 6.75 (1H, d, J=8 Hz), 5.94 (1H, d, J=3 Hz), 5.93 (1H, d, J=3 Hz), 3.96 (1H, d, J=10 Hz), 3.82 (3H, s), 3.70 (1H, ddd, 6, 5 & 3 Hz), 3:56 (1H, dd, 11 & 5 Hz), 3.45 (1H, d, J=16 Hz), 3.15 (1H, dd, 8 & 6 Hz), 3.13 (1H, t, J=1 OHz), 3.01 (1H, d, J=16 Hz), 2.42 (4H, q, J=7 Hz), 1.08 (6H, t, J=7 Hz). MS (DCl, NH$_3$) m/e 559 (M+H$_4$+), 531 (M+H$^+$). Anal. Calc for C$_{31}$H$_{34}$N$_2$O$_6$: C, 70.17, H, 6.46, N 5.28. Found: C, 69.88, H, 6.42, N, 5.09.

EXAMPLE 5 trans,trans-2-(4-Propoxyphenyl)-4-(1,3-benzodioxol-5-yl)-1 -((2,6-diethyl)phenylaminocarbonylmethyl)-pyrrolidine-3-carboxylic acid The title compound was prepared by the procedures described in Example 1. $^1$H NMR (300 MHz, CDCl$_3$) δ 8.27 (1H, bs), 7.37 (2H, d, J=8 Hz), 7.21 (1H, dd, 8 & 6 Hz), 7.11 (2H, d, J=8 Hz), 6.90 (2H, d, 8 Hz), 7.86 (1H, d, J=3 Hz), 7.83 (1H, dd, J=8 & 2 Hz), 6.75 (1H, d, J=8 Hz), 5.93 (1H, d, J=3 Hz), 5.92 (1H, d, J=3 Hz), 3.96 (1H, d, J=10 Hz), 3.85 (2H, q, J=7 Hz), 3.70 (1H, ddd, 6, 5 & 3 Hz), 3.55 (1H, dd, 11 & 5 Hz), 3.48 (1H, d, J=l6 Hz), 3.15 (1H, dd, 8 & 6 Hz), 3.13 (1H, t, J=1 OHz), 3.01 (1H, d, J=16 Hz), 2.43 (4H, q, J=7 Hz), 1.82 (2H, sext, J=7 Hz), 1.08 (6H, t, J=7 Hz) 1.04 (3H, t, J=7 Hz). MS (DCl, NH$_3$) m/e 559 (M+H$^+$). Anal. Calc for C$_{33}$H$_{38}$N206 - 0.25H20: C, 70.38, H, 6.89, N 4.97. Found: C, 70.49, H, 6.85, N, 4.68.

EXAMPLE 6 trans,trans-2-(3-Fluoro-4-methoxyphenyl)-4-(1,3-benzodioxol-5-yl)-1-((2,6-diethyl)phenylaminocarbonylmethyl)-pyrrolidine-3-carboxylic acid The title compound was prepared by the procedures described in Example 1. $^1$H NMR (300 MHz, CDCl$_3$) δ 8.21 (1H, bs), 7.22 (1H, dt, J=8 & 2 Hz), 7.20 (1H, d, J=8 Hz), 7.17 (1H, dt, J=8 & 2 Hz), 7.10 (2H, d, J=8 Hz), 6.96 (1H, t, J=8 Hz), 6.83 (1H, dd, J=8 & 2 Hz), 6.80 (1H, d, J=3 Hz), 6.76 (1H, d, J=8 Hz), 5.94 (1H, d, J=3 Hz), 5.93 (1H, d, J=3 Hz), 3.97 (1H, d, J=10 Hz), 3.90 (3H, s), 3.72 (1H, ddd, 6, 5 & 3 Hz), 3.58 (1H, dd, 11 & 5 Hz), 3.46 (1H, d, J=16 Hz), 3.14 (1H, t, J=lOHz), 3.12 (1H, dd, 8 & 6 Hz), 3.05 (1H, d, J=16 Hz), 2.45 (4H, q, J=7 Hz), 1.09 (6H, t, J=7 Hz). MS (DCl, NH$_3$) m/e 549 (M+H$^+$). Anal. Calc for C$_{31}$H$_{33}$FN$_2$O$_6$.0.5H$_2$0: C, 66.78, H, 6.15, N 5.02. Found: C, 66.81, H, 5.89, N, 4.87.

EXAMPLE 7 trans,trans-2-(3-Fluoro-4-ethoxyphenyl)-4-(1,3-benzodioxol-5-yl)-1-((2,6-diethyl)phenylaminocarbonylmethyl)-pyrrolidine-3-carboxylic acid The title compound was prepared by the procedures described in Example 1. $^1$H NMR (300 MHz, CDCl$_3$) δ 8.23 (1H, bs), 7.23 (1H, d, J=2 Hz), 7.20 (1H, dd, J=8 & 3 Hz), 7.11 (3H, m), 6.96 (1H, t, J=8 Hz), 6.83 (1H, dd, J=8 & 2 Hz), 6.80 (1H, d, J=3 Hz), 6.76 (1H, d, J=8 Hz), 5.93 (1H, d, J=3 Hz), 5.92 (1H, d, J=3 Hz), 4.11 (2H, t. J=7 Hz), 3.97 (1H, d, J=10 Hz), 3.72 (1H, ddd, 6, 5 & 3 Hz), 3.55 (1H, dd, 11 & 5 Hz), 3.47 (1H, d, J=1 6 Hz), 3.14 (1H, t, J=1 OHz), 3.12 (1H, dd, 8 & 6 Hz), 3.04 (1H, d, J=16 Hz), 2.45 (4H, q, J=7 Hz), 1.47 (3H, t, J=7 Hz), 1.09 (6H, t, J=7 Hz). MS (DCl, NH$_3$) m/e 563 (M+H$^+$). Anal. Calc for C$_{32}$H$_{35}$FN$_2$O$_6$.0.15TFA: C, 66.92, H, 6.11, N 4.83. Found: C, 67.19, H, 5.75, N, 4.69.

EXAMPLE 8 trans,trans-2-(3-Fluoro-4-methoxyphenyl)-4-(7-methoxy-1,3-benzodioxol-5-yl)-1-((2,6-diethyl)phenylaminocarbonylmethyl)-pyrrolidine-3-carboxylic acid The title compound was prepared by the procedures described in Example 1. $^1$H NMR (300 MHz, CDCl$_3$) δ 8.24 (1H, s), 7.25 (1H, t, J=3 Hz), 7.21 (1H, bd), 7.14 (1H, m), 7.08 (2H, d, J=8 Hz), 6.96 (1H, t, J=8 Hz), 6.56 (1H, d, J=3 Hz), 6.50 (1H, d, J=3 Hz), 5.93 (1H, d, J=2 Hz), 5.91 (1H, d, J=2 Hz), 3.97 (1H, d, J=10 Hz), 3.90 (3H, s), 3.72 (1H, ddd, 6, 5 & 3 Hz), 3.58 (1H, dd, 11 & 5 Hz), 3.46 (1H, d, J=1 6 Hz), 3.14 (1H, t, J=10 Hz), 3.12 (1H, dd, 8 & 6 Hz), 3.05 (1H, d, J=1 6 Hz), 2.45 (4H, q, J=7 Hz), 1.09 (6H, t, J=7 Hz). MS (DCl, NH$_3$) m/e 579 (M+H$^+$). Anal. calcd for C$_{32}$H$_{35}$FN$_2$O$_7$ 1.5H$_2$0: C, 63.65, H, 6.31, N 4.64. Found: C, 64.00, H, 6.29, N, 4.26.

EXAMPLE 9 trans,trans-2-(3-methoxy-4-propoxyphenyl)-4-(1,3-benzodioxol-5-yl)-1-((2,6-diethyl)phenylaminocarbonylmethyl)-pyrrolidine-3-carboxylic acid The title compound was prepared by the procedures described in Example 1. $^1$H NMR (300 MHz, CDCl$_3$) δ 8.22 (1H, s), 7.21 (1H, m), 7.12 (2H, d, J=10 Hz), 7.02 (1H, dd, J=9 & 3 Hz), 6.93 (1H, d, J=2 Hz), 6.88 (1H, d, J=2 Hz), 6.85 (1H, m), 6.82 (1H, d, J=2 Hz), 6.75 (1H, d, J=9 Hz), 5.95 (1H, d, J=2 Hz), 5.93 (1H, d, J=2 Hz), 3.97 (2H, q, J=9 Hz), 3.84 (3H, s), 3.72 (2H, m), 3.60-3.45 (2H, m), 3.15 (2H, m), 3.03 (1H, d J=18 Hz), 2.43 (4H, q, J=9 Hz), 1.87 (2H, m), 1.08 (6H, t, J=9 Hz), 1.04 (3H, t, J=9 Hz). MS (DCl, NH$_3$) m/e 589 (MH+). Anal.calcd. for C$_{34}$H$_{40}$N$_2$O$_7$ 0.45.H$_2$O: C, 68.43, H, 6.91, N, 4.69. Found: C, 68.45, H, 6.91, N, 4.62.

EXAMPLE 10 trans,trans-2-(4-ethoxphenyl)-4-(1,3-benzodioxol-5-yl)-1-((2,6-diethyl)phenylaminocarbonylmethyl)-pyrrolidine-3-carboxylic acid The title compound was prepared by the procedures described in Example 1. $^1$H NMR (300 MHz, CDCl$_3$) δ 8.26 (1H, bs), 7.36 (2H, d, J=9 Hz), 7.21 (1H, m), 7.11 (2H, d, J=10 Hz), 6.90 (2H, d, J=9 Hz), 6.86 (1H, d, J=2 Hz), 6.83 (1H, dd, J=8 & 2 Hz), 6.73 (1H, d, J=9 Hz), 5.94 (1H, d, J=2 Hz), 5.92 (1H, d, J=2 Hz), 4.10-3.90 (3H, m), 3.71 (1H, m), 3.60-3.40 (2H, m), 3.15 (2H, m), 3.02 (1H, d J=18 Hz), 2.43 (4H, q, J=9 Hz), 1.42 (3H, t, J=9 Hz), 1.08 (6H, t, J=9 Hz). MS (DCl, NH$_3$) m/e 545 (MH+). Anal. calcd. for C$_{32}$H$_{36}$N$_2$O$_6$. 0.5 H$_2$O: C, 69.42, H, 6.74, N, 5.06. Found: C, 69.52, H, 6.52, N, 4.89.

EXAMPLE 11 trans,trans-2-(4-methoxyphenyl)-4-(1,3-benzodioxol-5-yl)-1-((2,6-dimethyl)phenylaminocarbonylmethyl)-pyrrolidine-3-carboxylic acid The title compound was prepared by the procedures described in Example 1. $^1$H NMR (300 MHz, CDCl$_3$) δ 8.32 (1H, bs), 7.37 (2H, d, J=9 Hz), 7.08 (3H, m), 6.91 (2H, d, J=9 Hz), 6.88 (1H, d, J=2 Hz), 6.82 (1H, dd, J=8 & 2 Hz), 6.75 (1H, d, J=9 Hz), 5.95 (1H, d, J=2 Hz), 5.93 (1H, d, J=2 Hz), 3.95 (1H, d, J=10 Hz), 3.81 (3H, s), 3.72 (1H, m), 3.55 (1H, dd, J=10 & 5 Hz), 3.46 (1H, d J=18 Hz), 3.13 (2H, m), 3.00 (1H, d, J=18 Hz), 2.10 (6H, s). MS (DCl, NH$_3$) mle 502 (MH+). Anal. calcd. for C$_{29}$H$_{30}$N$_2$O$_6$. 0.5 H$_2$O: C ,68.09, H, 6.11, N, 5.48. Found: C, 67.98, H, 6.02, N, 5.33.

EXAMPLE 12 trans,trans-2-(4-propoxyphenyl)-4-(7-methoxy-1,3-benzodioxol-5-yl)-1-((2,6-diethyl)phenylaminocarbonylmethyl)-pyrrolidine-3-carboxylic acid The title compound was prepared by the procedures described in Example 1. $^1$H NMR (300 MHz, CDCl$_3$) δ 8.30 (1H, bs), 7.36 (2H, d, J=9 Hz), 7.21 (1H, m), 7.09 (2H, d, J=10 Hz), 6.91 (2H, d, J=9 Hz), 6.59 (1H, d, J=2 Hz), 6.51 (1H, d, J=2 Hz), 5.93 (1H, d, J=2 Hz), 5.91 (1H, d, J=2 Hz), 3.93 (3H, m), 3.80 (3H, s), 3.72 (1H, m), 3.60-3.50 (2H, m), 3.15 (2H, m), 3.02 (1H, d J=18 Hz), 2.43 (4H, q, J=9 Hz), 1.82 (2H, m), 1.08 (6H, t, J=9 Hz), 1.05 (3H, t, J=9 Hz). MS (DCl, NH$_3$) mle 589 (MH+). Anal. calcd. for C$_{34}$H$_{40}$N$_2$O$_7$.0.25 H$_2$O: C, 68.84, H, 6.88, N, 4.72. Found: C, 68.80, H, 6.59, N, 4.52.

EXAMPLE 13 trans,trans-2-(3-methoxy-4-propoxyphenyl)-4-(7-methoxy-1,3-benzodioxol-5-yl)-1-((2,6-diethyl)phenylaminocarbonylmethyl)-pyrrolidine-3-carboxylic acid The title compound was prepared by the procedures described in Example 1. $^1$H NMR (300 MHz, CDCl$_3$) δ 8.22 (1H, s), 7.21 (1H, m), 7.09 (2H, d, J=10 Hz), 7.02 (1H, dd, J=9 & 3 Hz), 6.93 (1H, d, J=2 Hz), 6.87 (1H, d, J=9 Hz), 6.61 (1H, d, J=2 Hz), 6.53 (1H, d, J=2 Hz), 5.93 (1H, d, J=2 Hz), 5.91 (1H, d, J=2 Hz), 3.97 (3H, q, J=9 Hz), 3.84 (3H, s), 3.82 (3H, s), 3.70 (1H, m), 3.60-3.45 (2H, m), 3.15 (2H, m), 3.02 (1H, d J=18 Hz), 2.42 (4H, q, J=9 Hz), 1.85 (2H, m), 1.08 (6H, t, J=9 Hz), 1.05 (3H, t, J=9 Hz). MS (DCl, NH$_3$) m/e 619 (MH+). Anal. calcd. for C$_{35}$H$_{42}$N$_2$O$_8$: C, 67.94, H, 6.84, N, 5 4.53. Found: C, 67.65, H, 6.98, N, 4.44.

EXAMPLE 14 trans,trans-2-(4-methoxyphenyl)-4-(1,3-benzodioxol-5-yl)-1-((2,6-dibromo)phenylaminocarbonylmethyl)-pyrrolidine-3-carboxylic acid The title compound was prepared by the procedures described in Example 1. $^1$H NMR (300 MHz, CDCl$_3$) δ 8.58 (1H, bs), 7.58 (2H, d, J=9 Hz), 7.40 (2H, bd, J=10 Hz), 7.02 (1H, t, J=9 Hz), 6.91 (2H, d, J=9 Hz), 6.86 (1H, m), 6.76 (1H, d, J=9 Hz), 5.93 (2H, s), 3.98 (1H, bd, J=10 Hz), 3.81 (3H, s), 3.73 (2H, m), 3.55 (1H, bd, J=15 Hz), 3.13 (2H, m), 3.01 (1H, bd, J=18 Hz). MS (DCl, NH$_3$) m/e 633 (MH+). Anal. calcd. for C$_{27}$H$_{24}$Br$_2$N$_2$O$_6$.0.3 H$_2$O: C, 50.85, H, 3.89,. N, 4.39. Found: C, 50.45, H, 3.48, N, 4.22.

EXAMPLE 15

[2R,3R,4S]2-(4-Methoxyphenyl)-4-(1 .3-benzodioxol-5-yl)-1-(N-(2,6-diethyl)phenylaminocarbonylmethyl)-pyrrolidine-3-carboxylic acid, hydrochloride salt

Example 15A–E

Alternative preparation of Ethyl trans-trans-2-(4-methoxyphenyl)-4-(1,3-benzodioxol-5-yl)-pyrrolidine-3-carboxylate

Example 15A 5-(2-Nitrovinyl)-1,3-benzodioxole

To piperonal (15.55 kg, 103.5 mol) under mechanical stirring and under nitrogen was added ammonium acetate (13.4 kg, 173.8 mol), acetic acid (45.2 kg), and nitromethane (18.4 kg, 301.4 mol) sequentially. The mixture was warmed to 70° C. After about 30 minutes, the yellow product began to crystallize. The reaction temperature was raised to 80° C. and stirred for about 10 hours until minimal piperonal remains. The somewhat thick reaction mixture was cooled to 10° C. and filtered. The precipitate was washed with acetic acid (2×8 kg) and then water (2×90 kg). The product was dried under a nitrogen purge and then in a vacuum oven at 50° C. for 2 days to afford 15.94 kg (80%) of the title compound as a bright yellow solid.

Example 15B

Ethyl (4-methoxybenzoyl)acetate

To potassium t-amylate (25 wt %, 50.8 kg, 99.26 mol) in toluene (15.2 kg) cooled to 5° C. under mechanical stirring and under nitrogen was added a mixture of 4-methoxyacetophenone (6.755 kg, 44.98 mol) and diethyl carbonate (6.40 kg, 54.18 mol) in toluene over 1 hour maintaining the temperature below 10° C. The reaction mixture was heated to 60° C. for 8 hours until no 4-methoxyacetophenone was detected by HPLC. The mixture was cooled to 20° C. and quenched by adding to a mixture of acetic acid (8 kg) and water (90 kg) over 30 minutes while maintaining the temperature at <20° C. The layers were separated, and the organic layer was washed with 5% sodium bicarbonate solution (41 kg) and concentrated to 14.65 kg. The temperature is maintained below 50° C. during the distillation. The yellow product concentrate was assayed by HPLC against an external standard and the yield was found to be 9.40 kg (94%).

Example 15C

Ethyl 2-(4-methoxybenzoyl)-4-nitromethyl-3-(1,3-benzodioxole-5-yl)butyrate

To the compound resulting from Example 15A (7.5 kg, 37.9 mol) suspended in THF (56 kg) with mechanical stirring under nitrogen was added the compound resulting from Example 15B (8.4 kg, 37.9 mol). The mixture was cooled to 17° C., sodium ethoxide (6.4 g, 0.095 mol) was added, and the reaction was stirred for 30 minutes. After about 15 minutes, the nitrostyrene was completely dissolved. Sodium ethoxide (6.4 g, 0.095 mol) was added, and the mixture was stirred at 25° C. until HPLC shows less than 1 area % ketoester remaining. The reaction was concentrated to 32.2 kg which was determined by HPLC assay to be ~14.9 kg (95%).

Example 15D

Ethyl cis,cis-2-(4-methoxyphenyl)-4-(1,3-benzodioxol-5-yl)-pyrrolidine-3-carboxylate Raney nickel (20.0 g), from which the water had been decanted, was charged to a stirred hydrogenator equipped with a thermocouple. THF (20 mL), the crude compound resulting from Example 15C (40.82 g, 0.0482 mol), and acetic acid (2.75 mL, 0.0482 mol) were added sequentially. The mixture was put under a hydrogen atmosphere at 60 psi until the hydrogen uptake slowed dramatically. TFA was added, and the mixture was hydrogenated at 200 psi until HPLC shows no residual imine and <2 area % nitrone. The catalyst was filtered away and washed with 100 mL of methanol. The filtrate was assayed by HPLC and found to contain 13.3 g (75% yield) of the cis, cis-pyrrolidine compound. The filtrate was concentrated and chased with additional THF (200 mL) to give a final volume of 100 mL. The mixture was neutralized with 2N NaOH solution (50 mL), diluted with water (200 mL), and extracted with ethyl acetate (2×100 mL). The combined nearly colorless ethyl acetate layers were assayed against an external standard by HPLC to be 13.0 g (73%) of the title compound.

Example 15E

Ethyl trans,trans-2-(4-methoxyphenyl)-4-(1,3-benzodioxol-5-yl)-pyrrolidine-3-carboxylate The solution of the compound resulting from Example 15D (38.1 g, 0.103 mol) was chased with ethanol (200 mL) to a final volume of 100 mL and sodium ethoxide (3.40 g, 0.050 mol) was added. The mixture was heated to 75° C. When HPLC shows <3% of the cis,cis isomer remaining, the mixture was cooled to room temperature. The product was assayed by HPLC against an external standard and found to contain 34.4 g (90% yield) of the title compound. The crude compound solution was concentrated and the residue taken up in isopropyl acetate (400 mL). The organic layer was washed with water (2×150 mL) and then extracted with 0.25M phosphoric acid solution (2×400 mL). The combined phosphate layers were stirred with ethyl acetate (200 mL) and neutralized to pH 7 with solid sodium bicarbonate (21 g). The organic layer was separated and found to contain 32.9 g (87%) of the title compound.

Example 15F

Ethyl [2R,3R,4S]2-(4-Methoxyphenyl)-4-(1,3-benzodioxol-5-yl)-pyrrolidine-3-carboxylate The racemic amino ester from Example 1 (32.9 g) was dissolved in 50 mL of acetonitrile. (S)-(+)-Mandelic acid (2.06 g, 0.0136 mmol) was added and allowed to dissolve. The mixture was seeded with the product and allowed to stir at room temperature for 16 hours. The reaction mixture was cooled to 0° C. and stirred for 5 hours. The product was filtered and dried in a vacuum oven with a nitrogen purge for 1 day at 50° C. The resultant salt (20.0 g, 0.0383 mol) was suspended in ethyl acetate (150 mL) and 5% sodium bicarbonate solution (150 mL). The mixture was stirred at room temperature until the salt dissolved and carbon dioxide evolution had ceased. The organic layer was separated and concentrated.

Example 15G

[2R,3R,4S]2-(4-Methoxyphenyl)-4-(1.3-benzodioxol-5-yl)-1-(N-(2,6-diethyl) phenylaminocarbonylmethyl)-pyrrolidine-3-carboxylic acid The title compound was prepared from the compound of Example 15F according to the procedures of Example 1E.

Example 15H

[2R,3R,4S]2-(4-Methoxyphenyl)-4-(1,3-benzodioxol-5-yl)-1-(N-(2,6-diethyl) phenylaminocarbonylmethyl)-pyrrolidine-3-carboxylic acid, hydrochloride salt The compound of Example 15G (450 mg) was dissolved in 10 mL of isopropanol. A slight excess of saturated HCl in ethanol was added, and the resultant solution was stirred for 10 min. The solvents were removed in vacuo, and the excess HCl was chased with isopropanol. The residue was taken up in ether and filtered, leaving 448 mg of the title compound as a white solid. MS (DCl/NH$_3$) m/e 531 (M+H)$^+$. Anal calcd for C$_{31}$H35N$_2$O$_6$Cl: C, 65.66 H, 6.22; N, 4.94. Found: C, 65.72; H, 6.39; N, 4.65.

EXAMPLE 16 trans,trans-2-(4-methoxyphenyl)-4-(1,3-benzodioxol-5-yl)-1-((2,6-dimethoxy) phenylaminocarbonylmethyl)-pyrrolidine-3-carboxylic acid

Example 16A

2,6-Dimethoxyaniline

To a stirred solution of 2,6-dimethoxybenzoic acid (2.00 g, 11.0 mmol) in 1,2-dichloroethane (45 mL) at ambient temperature was successively added N-methylmorpholine (1.45 mL, 13.2 mmol) and diphenylphosphoryl azide (2,60 mL, 12.1 mmol). After heating the mixture for 2 hours at 75° C., cuprous iodide (150 mg) and benzyl alcohol (2.27 mL, 22.0 mmol) were added and heating was continued overnight. Solvents were removed in vacuo and the residue was chromatographed on silica gel, eluting with 4:1 hexane-ethyl acetate to give the intermediate carbamate (1.50 g, 48 % yield) as a white, crystalline solid. The solid was dissolved in methanol (15 mL) and added to a flask purged with nitrogen containing 10% palladium-on-charcoal (500 mg). The mixture was placed under a balloon of hydrogen and stirred 4 hours at ambient temperature. The mixture was filtered through a pad of Celite and solvents were removed in vacuo to give the title compound (800 mg, 48% yield).

Example 16B trans trans-2-(4-methoxyphenyl)-4-(1,3-benzodioxol-5-yl)-1-((2,6-dimethoxy) phenylaminocarbonylmethyl)-pyrrolidine-3-carboxylic acid The title compound was prepared by the procedures described in Example 1, substituting the compound of Example 16A for 2,4,6-trimethylaniline in Example 1 D. $^1$H NMR (300 MHz, CDCl$_3$) δ 8.18 (1H, bs), 7.39 (2H, bd, J=9 Hz), 7.17 (1H, t, J=9 Hz), 6.99 (1H, d, J=2 Hz), 6.90 (2H, d, J=9 Hz), 6.86 (1H, d, J=2 Hz), 6.75 (1H, d, J=9 Hz), 6.56 (2H, d, J=9 Hz), 5.93 (2H, s), 3.88 (1H, bd, J=10 Hz), 3.81 (3H, s), 3.71 (6H, s), 3.70 (2H, m), 3.49 (1H, bd, J=15 Hz), 3.03 (2H, m), 2.85 (1H, bd, J=18 Hz). NMR (DCl, NH$_3$) m/e 535 (MH+). Anal. calcd. for C$_{29}$H$_{30}$N$_2$O$_8$.0.75 AcOH: C, 63.20, H, 5.74, N, 4.83. Found: C, 63.18, H, 5.34, N, 4.79.

EXAMPLE 17 trans,trans-2-(4-methoxyphenyl)-4-(1,3-benzodioxol-5-yl)-1-((4-bromo-2,6-diethyl) phenylaminocarbonylmethyl)-pyrrolidine-3-carboxylic acid

Example 17A

4-Bromo-2,6-diethylaniline

To a stirred solution of 2,6-diethylaniline (10.0 g, 67.0 mmol) in acetic acid (50 mL) at ambient temperature was added bromine (10.4 mL, 201 mmol). The reaction was stirred overnight at ambient temperature. The reaction mixture was diluted with diethyl ether (200 mL) and washed with 5% sodium bisulfite (4×50 mL) and brine. The organic phase was dried with sodium sulfate and the solvents were removed in vacuo. The residue was chromatographed on silica gel, eluting with 9:1 hexane-ethyl acetate to give the title compound (3.28 g, 21 % yield).

Example 17B trans,trans-2-(4-methoxyphenyl)-4-(1,3-benzodioxol-5-yl)-1-((4-bromo-2,6-diethyl) phenylaminocarbonylmethyl)-pyrrolidine-3-carboxylic acid The title compound was prepared by the procedures described in Example 1, substituting the compound of Example 17A for 2,4,6-trimethylaniline in Example 1D. $^1$H NMR (300 MHz, CDCl$_3$) δ 8.21 (1H, bs), 7.38 (2H, d, J=9 Hz), 7.23 (2H, s), 6.92 (2H, d, J=9 Hz), 6.88 (1H, d, J=2 Hz), 6.82 (1H, dd, J=8 & 2 Hz), 6.75 (1H, d, J=9 Hz), 5.93 (1H, d, J=2 Hz), 5.91 (1H, d, J=2 Hz), 3.95 (1H, d, J=9 Hz), 3.82 (3H, s), 3.72 (1H, m), 3.52 (1H, m), 3.45 (1H, d J=18 Hz), 3.14 (2H, m), 3.00 (1H, d, J=18 Hz), 2.39 (4H, q, J=9 Hz), 1.07 (6H, t, J=9 Hz). MS (DCl, NH$_3$) m/e 609 (MH+). Anal. calcd. for C$_{31}$H$_{33}$BrN$_2$O$_6$: C, 61.09, H, 5.46, N, 4.60. Found: C, 60.80, H, 5.35, N, 4.54.

EXAMPLE 18 trans,trans-2-(4-methoxyphenyl)-4-(1,3-benzodioxol-5-yl)-1-((2-ethyl-6-methyl) phenylaminocarbonylmethyl)-pyrrolidine-3-carboxylic acid The title compound was prepared by the procedures described in Example 1. $^1$H NMR (300 MHz, CDCl$_3$) δ 8.32 (1H, bs), 7.38 (2H, d, J=9 Hz), 7.20-7.10 (3H, m), 6.92 (2H, d, J=9 Hz), 6.87 (1H, d, J=2 Hz), 6.82 (1H, dd, J=8 & 2 Hz), 6.76 (1H, d, J=9 Hz), 5.94 (1H, d, J=2 Hz), 5.92 (1H, d, J=2 Hz), 3.95 (1H, d, J=9 Hz), 3.82 (3H, s), 3.73 (1H, m), 3.55 (1H, dd, J=12 & 6), 3.47 (1H, d J=18 Hz), 3.14 (2H, m), 3.02 (1H, d, J=18 Hz), 2.44 (2H, q, J=9 Hz), 2.10 (3H, s), 1.10 (3H, t, J=9 Hz). MS (DCl, NH$_3$) m/e 517 (MH+). Anal. calcd. for C$_{30}$H$_{32}$N$_2$O$_6$.0.5 H$_2$0: C, 68.56, H, 6.33, N, 5.33. Found: C, 68.58, H, 6.29, N, 5.13.

EXAMPLE 19 trans,trans-2-(4-methoxyphenyl)-4-(1,3-benzodioxol-5-yl)-1-((2,4,6-triethyl) phenylaminocarbonylmethyl)-pyrrolidine-3-carboxylic acid

Example 19A

Ethyl trans,trans-2-(4-methoxyphenyl)-4-(1,3-benzodioxol-5-yl)-1-((2,4,6-triethyl) phenylaminocarbonylmethyl)-pyrrolidine-3-carboxylate To a mixture (purged with nitrogen) of [1,1'-bis (diphenylphosphino)ferrocene] dichloropalladium (II) (1:1 complex with dichloromethane) (13 mg) and cesium carbonate (307 mg, 0.942 mmol) in anhydrous N,N-dimethylformamide (2 mL) at ambient temperature was added ethyl trans,trans-2-(4-methoxyphenyl)-4-(1,3-benzodioxol-5-yl)-1-(4-bromo-2,6-diethylphenyl) aminocarbonylmethyl)-pyrrolidine-3-carboxylate (200 mg, 0.314 mmol, prepared in Example 17) in anhydrous tetrahydrofuran (8 mL). After stirring the mixture for 10 minutes at ambient temperature, 1.0M triethylborane (0.471 mL, 0.471 mmol) in tetrahydrofuran was added. The reaction was stirred overnight at 65° C. under nitrogen. The reaction mixture was diluted with ethyl acetate (100 mL) and washed with water (2×30 mL) and brine. The organic phase dried with sodium sulfate, and the solvents were removed in vacuo . The residue was chromatographed on silica gel eluting with 3:1 hexane-ethyl acetate to give the title compound (110 mg, 60 % yield).

Example 19B trans,trans-2-(4-methoxyphenyl)-4-(1,3-benzodioxol-5-yl)-1-((2,4,6-triethyl) phenylaminocarbonylmethyl)-pyrrolidine-3-carboxylic acid The title compound was prepared by the procedures described in Example 1E. $^1$H NMR (300 MHz, CDCl$_3$) δ

8.22 (1H, bs), 7.38 (2H, d, J=9 Hz), 6.95 (2H, s), 6.91 (2H, d, J=9 Hz), 6.84 (1H, d, J=2 Hz), 6.82 (1H, dd, J=8 & 2 Hz), 6.75 (1H, d, J=9 Hz), 5.93 (1H, d, J=2 Hz), 5.91 (1H, d, J=2 Hz), 3.95 (1H, d, J=10 Hz), 3.82 (3H, s), 3.71 (1H, m), 3.52 (1H, dd, J=9 & 2 Hz), 3.46 (1H, d J=1 8 Hz), 3.13 (2H, m), 3.00 (1H, d, J=18 Hz), 2,60 (2H, q, J=9 Hz), 2.40 (4H, q, J=9 Hz), 1.22 (3H, t, J=9 Hz), 1.08 (6H, t, J=9 Hz). MS (DCl, $NH_3$) m/e 559 (MH+). Anal. calcd. for $C_{33}H_{38}N_2O_6$.0.25 $H_2O$: C, 70.38, H, 6.89, N, 4.97. Found: C, 70.18, H, 7.14, N, 4.63.

EXAMPLE 20

[2R,3R,4S]2-(4-Propoxyphenyl)-4-(1,3-benzodioxol-5-yl)-1-(N-((2,6-diethyl)phenylaminocarbonylmethyl)-pyrrolidine-3-carboxylic acid

Example 20A

[2R,3R,4S]2-(4-Propoxyphenyl)-4-(1,3-benzodioxol-5-yl)-1-tert-butoxycarbonyl-pyrrolidine-3-carboxylic acid The racemic amino ester from Example 3 (8.00 g) was combined with 4.45 g of di-tert-butyldicarbonate in 100 mL of THF; 10 mL of triethylamine was added, and the resultant solution was stirred at ambient temperature for 3 hrs. The solvents were removed in vacuo; the residue was taken up in EtOAc and washed sequentially with aqueous 1N $H_3PO_4$, bicarb, and brine. The crude product was dissolved in 30 mL of ethanol; 12 mL of 2.5N NaOH solution was added, the mixture was stirred overnight at ambient temperature, then warmed to 50° C. for 2 hrs. The solvents were removed in vacuo; the residue was partitioned between water and ether. The aqueous extract was acidified with aqueous 1N $H_3PO_4$ and extracted twice with EtOAc. The organic extracts were washed with brine and dried over $Na_2SO_4$ to give 9.2 g of trans,trans- 2-(4-propoxyphenyl)-4-(1,3-benzodioxol-5-yl)-1-tert-butoxycarbonyl-pyrrolidine-3-carboxylic acid. This material was dissolved in 30 mL of EtOAc, and 1,3 mL of (R)-(+)-α-methylbenzylamine was added. The solution was stirred for 10 min; the solvents were removed in vacuo, 50 mL of ether were added, and the resultant solution was seeded. After standing overnight, the solvents were removed in vacuo; the residue was taken up in 70 mL of ether and filtered. The solid product was recrystallized from EtOAc/ether. The crystalline material was stirred vigorously in a two-phase mixture of 1N $H_3PO_4$ and EtOAc; the organic layer was decanted, then washed with brine and dried over $Na_2SO_4$.

Example 20B

Ethyl [2R,3R,4S]2-(4-Propoxyphenyl)-4-(1,3-benzodioxol-5-yl)-pyrrolidine-3-carboxylate The compound of Example 20A was dissolved in ethanol and cooled in an ice bath. Gaseous HCl was bubbled through the solution until saturated; the resultant solution was warmed to ambient temperature and allowed to stir overnight under a blanket of nitrogen. The solvents were removed in vacuo; the residue was taken up in bicarb and extracted with EtOAc. The organic layer was decanted, then washed with brine and dried over $Na_2SO_4$.

Example 20C

[2R,3R,4S]2-(4-Propoxyphenyl)-4-(1,3-benzodioxol-5-yl)-1-(N-(2,6-diethylphenyl) aminocarbonylmethyl)-pyrrolidine-3-carboxylic acid The title compound was prepared from the compound of Example 20B according to the procedures of Example 1E.

MS (DCl/$NH_3$) m/e 559 (M+H)+. Anal calcd for $C_{33}H_{38}N_2O_6$.0.2 $H_2O$: C, 70.49; H, 6.88; N, 4.98. Found: C, 70.52; H, 6.78; N, 4.85.

EXAMPLE 21 trans,trans-2-(4-methoxyphenyl)-4-(1,3-benzodioxol-5-yl)-1-((2,6-diisopropyl) phenylaminocarbonylmethyl)-pyrrolidine-3-carboxylic acid The title compound was prepared by the procedures described in Example 1. $^1$H NMR (300 MHz, $CDCl_3$, δ) 8.29 (1H, bs), 7.39 (2H, d, J=9 Hz), 7.29 (1H, m), 7.15 (2H, d, J=9 Hz), 6.93 (2H, d, J=9 Hz), 6.85 (1H, d, J=2 Hz), 6.83 (1H, dd, J=8 & 2 Hz), 6.74 (1H, d, J=9 Hz), 5.93 (1H, d, J=2 Hz), 5.91 (1H, d, J=2 Hz), 3.96 (1H, d, J=10 GHz), 3.83 (3H, s), 3.73 (1H, m), 3.55 (1H, dd, J=12 & 6), 3.50 (1H, d J=18 Hz), 3.14 (2H, m), 3.01 (1H, d, J=18 Hz), 2.84 (2H, m), 1.16 (6H, d, J=8 Hz), 1.05 (6H, d J=8 Hz). MS (DCl, $NH_3$) m/e 559 (MH+). Anal. calcd. for $C33H_{38}N206$ 0.5 $H_2O$: C, 69.82, H, 6.92, N, 4.93. Found: C, 69.69, H, 6.63, N, 4.89.

EXAMPLE 22 trans,trans-2-(4-methoxyphenyl)-4-(1,3-benzodioxol-5-yl)-1-((2,6-diethyl-4-methyl) phenylaminocarbonylmethyl)-pyrrolidine-3-carboxylic acid The title compound was prepared by the procedures described in Example 19. $^1$H NMR (300 MHz, $CDCl_3$) δ 8.20 (1H, bs), 7.38 (2H, d, J=9 Hz), 6.92 (4H, m), 6.86 (1H, d, J=2 Hz), 6.82 (1H, dd, J=8 & 2 Hz), 6.75 (1H, d, J=9 Hz), 5.93 (1H, d, J=2 Hz), 5.91 (I H, d, J=2 Hz), 3.95 (1H, d, J=10 Hz), 3.81 (3H, s), 3.72 (1H, m), 3.55 (1H, dd, J=9 & 2 Hz), 3.45 (1H, d J=18 Hz), 3.13 (2H, m), 3.00 (1H, d, J=18 Hz), 2.39 (4H, q, J=9 Hz), 2.28 (3H, s), 1.07 (6H, t, J=9 Hz). NMR (DCl, $NH_3$) 545 mle (MH+). Anal. calcd. for $C_{32}H_{36}N_2O_6$.0.5 $H_2O$: C, 69.42, H, 6.74, N, 5.06. Found: C, 69.43, H, 6.57, N,4.94.

EXAMPLE 23

(2R,3R,4S)-2-(4-ethoxyphenyl)-4-(1,3-benzodioxol-5-yl)-1-((2,6-diethyl)phenylaminocarbonylmethyl)-pyrrolidine-3-carboxylic acid The title compound was prepared from the racemic amino ester of Example 10 according to the procedures of Example 20. $^1$H NMR (300 MHz, $CDCl_3$) δ 8.32 (1H, bs), 7.38 (2H, d, J=9 Hz), 7.21 (1H, m), 7.12 (2H, d, J=10 Hz), 6.90 (3H, m), 6.83 (1H, dd, J=8 & 2 Hz), 6.74 (1H, d, J=9 Hz), 5.94 (1H, d, J=2 Hz), 5.92 (1H, d, J=2 Hz), 4.05 (2H, m), 3.96 (1H, d, J=10 Hz), 3.72 (1H, m), 3.53 (1H, dd, J=10 & 3 Hz), 3.47 (1H, d, J=18 Hz), 3.13 (2H, m), 3.02 (1H, d J=18 Hz), 2.44 (4H, q, J=9 Hz), 1.42 (3H, t, J=9 Hz), 1.08 (6H, t, J=9 Hz). MS (DCl, $NH_3$) m/e 545 (MH+). Anal. calcd. for $C_{32}H_{36}N_2O_6$.0.5 $H_2O$: C, 69.42, H, 6.74, N, 5.06. Found: C, 69.67, H, 6.73, N, 4.98.

EXAMPLE 24 trans,trans-2-(4-methoxyphenyl-1-4-(1,3-benzodioxol-5-yl)-1-((4-carboxy-2,6-diethyl) phenylaminocarbonylmethyl)-pyrrolidine-3-carboxylic acid The title compound was prepared by the procedures described in Example 19. $^1$H NMR (300 MHz, DMSO) δ

7.68 (2H, bs), 7.54 (2H, d, J=9 Hz), 7.27 (2H, m), 6.93 (2H, d, J=9 Hz), 6.83 (2H, m), 5.98 (2H, s), 3.92 (1H, d, J=9 Hz), 3.76 (3H, s), 3.62 (1H, m), 3.45-3.00 (2H, m), 3.00-2.80 (3H, m), 2.44 (4H, q, J=9 Hz), 1.04 (6H, t, J=9 Hz). NMR (DCl, NH$_3$) m/e 575 (MH+). Anal. calcd. for C$_{32}$H$_{34}$N$_2$O$_8$.0.5 H$_2$O: C, 65.85, H, 6.04, N, 4.80. Found: C, 66.03, H, 5.84, N, 4.67.

EXAMPLE 25 trans,trans-2-(4-methoxyphenyl)-4-(1,3-benzodioxol-5-yl)-1-((4-nitro-2,6-diethyl)phenylaminocarbonylmethyl)-pyrrolidine-3-carboxylic acid Example 25A 2,6-Diethyl-4-nitroaniline To a stirred solution of 2,6-diethylaniline (5.0 g, 34 mmol) in concentrated sulfuric acid (30 mL) at 0° C. was added dropwise concentrated nitric acid (15.9M, 2.10 mL, 34 mmol). The cooling bath was removed, and the reaction was stirred for 3 hours at ambient temperature. After pouring the reaction mixture into ice, the solution was neutralized using 4N sodium hydroxide and extracted with methylene chloride (3×50 mL). The extracts were dried with sodium sulfate, and solvents were removed in vacuo to give the title compound.

Example 25B trans,trans-2-(4-methoxyphenyl)-4-(1,3-benzodioxol-5-yl)-1-((4-nitro-2,6-diethyl)phenylaminocarbonylmethyl)-pyrrolidine-3-carboxylic acid The title compound was prepared by the procedures described in Example 1, substituting the compound of Example 25A for 2,4,6-trimethylani line in Example 1D. $^1$H NMR (300 MHz, CDCl$_3$) δ 8.38 (1H, bs), 7.77 (1H, d, J=9 Hz), 7.38 (2H, d, J=9 Hz), 7.24 (1H, d, J=9 Hz), 6.92 (2H, d, J=9 Hz), 6.88 (1H, d, J=2 Hz), 6.82 (1H, dd, J=8 & 2 Hz), 6.75 (1H, d, J=9 Hz), 5.93 (1H, d, J=2 Hz), 5.91 (1H, d, J=2 Hz), 3.97 (1H, d, J=9 Hz), 3.83 (3H, s), 3.74 (1H, m), 3.48 (2H, m), 3.18 (2H, m), 3.04 (1H, d, J=18 Hz), 2,63 (2H, m), 2.44 (2H, q, J=9 Hz), 1.10 (3H, t, J=9 Hz), 1.08 (3H, t, J=9 Hz). MS (DCl, NH$_3$) m/e 576 (MH+). Anal. calcd. for C$_{31}$H$_{33}$N$_3$O$_8$.0.75 H$_2$O: C, 63.20, H, 5.90, N, 7.13. Found: C, 63.30, H, 5.81, N, 7.14.

EXAMPLE 26 trans,trans-2-(4-methoxyphenyl)-4-(1,3-benzodioxol-5-yl)-1-((2-isopropyl-6-methyl)phenylaminocarbonylmethyl)-pyrrolidine-3-carboxylic acid The title compound was prepared by the procedures described in Example 1. $^1$H NMR (300 MHz, CDCl$_3$) δ 8.35 (1H, bs), 7.39 (2H, d, J=9 Hz), 7.18 (2H, m), 7.07 (1H, dd, J=9 & 2 Hz), 6.92 (2H, d, J=9 Hz), 6.86 (1H, d, J=2 Hz), 6.82 (1H, dd, J=8 & 2 Hz), 6.75 (1H, d, J=9 Hz), 5.94 (1H, d, J=2 Hz), 5.92 (1H, d, J=2 Hz), 3.96 (1H, d, J=10 Hz), 3.83 (3H, s), 3.72 (1H, m), 3.50 (2H, m), 3.15 (2H, m), 3.02 (1H, d, J=18 Hz), 2.86 (1H, m), 2.09 (3H, s), 1.16 (3H, d, J=8 Hz), 1.07 (3H, d J=8 Hz). MS (DCl, NH$_3$) m/e 531 (MH+). Anal. calcd. for C$_{31}$H$_{34}$N$_2$O$_6$.0.5 H$_2$O: C, 69.00, H, 6.54, N, 5.19. Found: C, 69.27, H, 6.67, N, 5.21.

EXAMPLE 27 trans,trans-2-(4-Methoxyphenyl)-4-(1,3-benzodioxol-5-yl)-1-(N-(2-ethyl-6-methoxy)phenylaminocarbonylmethyl)-pyrrolidine-3-carboxylic acid Example 27A Ethyl 3-oxo-4-(3-methoxy-2-nitrophenyl)propionate Potassium ethylmalonate (3.68 g) was combined with 2.29 g of magnesium chloride in 12 mL of DMF; the reaction mixture was heated at 60° C. for 4 hrs. The resultant mixture was cooled to ambient temperature. Simultaneously, 3-methoxy-2-nitrobenzoic acid (3.4 g) was dissolved in 12 mL of DMF; 3.06 g of 1,1-carbonyldiimidazole was added (gas evolves), and the resultant solution (after stirring at ambient temperature for 4 hrs) was added to the malonate mixture. The resultant slurry was stirred at ambient temperature for 14 hrs. Solvents were removed in vacuo; the residue was taken up in EtOAc and washed sequentially with 1N H$_3$PO$_4$, bicarb, and brine, and was concentrated in vacuo..

Example 27B

2-Nitro-3-(1-hydroxyethyl)anisole

The compound of Example 27A (3.2 g) was dissolved in 50 mL of concentrated sulfuric acid and stirred at ambient temperature for 48 hrs. The reaction mixture was poured onto 300 mL of ice and extracted twice with EtOAc. The organic extracts were washed sequentially with water, bicarb, and brine, and were concentrated in vacuo. The crude product was heated neat at 160° C. for 3 hrs. The resultant dark brown residue was extracted with EtOAc. The organic extracts were concentrated. The crude product was dissolved in 15 mL of ethanol; sodium borohydride (450 mg) was added, and the resultant solution was stirred at ambient temperature for for 2 hrs. The solvents were removed in vacuo; the residue was taken up in 10% aqueous HCl and stirred for 15 min. The mixture was extracted with EtOAc; the organic extracts were washed sequentially with bicarb and brine, and were concentrated in vacuo. The crude product was purified by flash chromatography on silica gel, eluting with 1:1 EtOAc/hexanes, to give 1.08 g (32% overall) of the title compound as a colorless oil.

Example 27C

2-Ethyl-6-methoxyaniline

The compound of Example 27B (310 mg) was dissolved in 10 mL of THF; 1.5 mL of H3PO4 was added, followed by 50 mg of 10% palladium-on-charcoal. The resultant mixture was purged with nitrogen, then placed under a balloon of hydrogen, and stirred overnight. Bicarb was added carefully, and the mixture was filtered through a pad of Celite. The filtrate was extracted with EtOAc; the organic extracts were washed with bicarb and brine, and were concentrated in vacuo. The crude product was purified by flash chromatography on silica gel, eluting with 1:1 ether/hexanes, to give 102 mg (43% yield) of the title compound as a colorless oil.

Example 27D trans,trans-2-(4-Methoxyphenyl)-4-(1,3-benzodioxol-5-yl)-1-(N-(2-ethyl-6-methoxy)phenylaminocarbonylmethyl)-pyrrolidine-3-carboxylic acid The title compound was prepared according to the procedures of Example, substituting the compound of Example 27C for 2,4,6-trimethylaniline. $^1$H NMR (300 MHz, CD$_3$OD) δ 1.10 (t, J=8 Hz, 3H), 2.48 (d, J=8 Hz, 2H), 3.4-3.9 (m, 7H), 3.73 (s, 3H), 3.84 (s, 3H), 5.93 (s, 2H), 6.80 (d, J=8 Hz, 1H), 6.86 (d, J=8 Hz, 2H), 6.93 (dd, J=2,8 Hz, 1H), 7.03 (bd d, J=9 Hz, 2H), 7.07 (d, J=2 Hz, 1H), 7.23 (t, J=8 Hz, 1H), 7.53 (bd d, J=9 Hz, 2H). MS (APCI) m/e 533 (M+H)$^+$. Anal calcd for C$_{30}$H$_{32}$N$_2$O$_7$. 0.7 TFA: C, 61.59 H, 5.38; N, 4.57. Found: C, 61.27; H, 5.44; N, 4.61.

EXAMPLE 28 trans,trans-2-(4-iso-Propoxyphenyl)-4-(1,3-benzodioxol-5-yl)-1-(2,6-diethylphenylaminocarbonylmethyl)-pyrrolidine-3-carboxylic acid The title compound was prepared by the procedures described in Example 1. $^1$H NMR (300 MHz, CDCl$_3$) δ 7.51 (2H, bd d, J=9 Hz), 7.22 (1H, dd, J=8,9 Hz), 7.13 (1H, s), 7.11 (1H, dd, J=1,8 Hz), 7.05 (1H, d, J=2 Hz), 6.99 (2H, bd d, J=9 Hz), 6.91 (1H, dd, J=2,8 Hz), 6.78 (1H, d, J=8 Hz), 5.93 (1H, d, J=3 Hz), 5.92 (1H, d, J=3 Hz), 4.64 (1H, septet, J=7 Hz), 3.80 (3H, m), 3.55 (2H, m), 2.47 (4H, q, J=7 Hz), 1,33 (6H, dd, J=2,7 Hz), 1.09 (6H, t, J=7 Hz). MS (ESI+) m/e 559 (M+H$^+$). Anal. Calc for C$_{33}$H$_{38}$N$_2$O$_6$.0.7 TFA: C, 64.71, H, 6.11, N 4.39. Found: C, 64.54, H, 5.78, N, 4.21.

EXAMPLE 29 trans,trans-2-(2-Fluoro-4-Propoxyphenyl)-4-(1,3-benzodioxol-5-yl)-1-(2,6-diethylphenylaminocarbonylmethyl)-pyrrolidine-3-carboxylic acid The title compound was prepared by the procedures described in Example 1. $^1$H NMR (300 MHz, CDCl$_3$) δ 1.06 (t, 3H, J=7 Hz), 1.09 (t, 6H, J=7 Hz), 1.83 (m, 2H), 2.44 (q, 4H, J=7 Hz), 3.4-3.9 (m, 5H), 3.99 (t, 2H, J=6 Hz), 5.95 (dd, 2H, J=1,2 Hz), 6.8-6.9 (m, 4H), 7.03 (d, 1H, J=2 Hz), 7.11 (d, 1H, J=8 Hz), 7.13 (s, 1H), 7.22 (dd, 1H, J=7,9 Hz), 7.63 (t, 1H, J=9 Hz). MS (ESI+) m/e 577 (M+H$^+$). Anal. Calc for C$_{33}$H$_{37}$N$_2$O$_6$F. 1.OTFA: C, 60.87, H, 5.55, N 4.06. Found: C, 60.74, H, 5.61, N, 3.97.

EXAMPLE 30 trans,trans-2-(4-(2-Methoxyethoxy)phenyl)-4-(1,3-benzodioxol-5-yl)-1-(2,6-diethylphenylaminocarbonylmethyl)-pyrrolidine-3-carboxylic acid The title compound was prepared by the procedures described in Example 1. $^1$H NMR (300 MHz, CDCl$_3$) δ 1.08 (t, J=7 Hz, 6H), 2.43 (q, J=7 Hz, 4H), 3.00 (d, J=11 Hz, 1H), 3.05-3.15 (m, 2H), 3.44 (s, 3H), 3.46 (d, J=11 Hz, 1H), 3.45-3.55 (m, 1H), 3.65-3.75 (m, 1H), 3.75-3.80 (m, 2H), 3.93 (d, J=7 Hz, 1H), 4.12-4.17 (m, 2H), 5.94 (dd, J=2 Hz, 4 Hz, 2H), 6.75 (d, J=8 Hz, 1H), 6.82 (dd, J=2 Hz, 9 Hz, 1H), 6.87 (d, J=2 Hz,1H), 6.95 (d, J=8 Hz,1H), 7.10 (d, J=6 Hz, 2H), 7.19-7.24 (m,1H), 7.37 (d, d=8 Hz, 2H), 8.29 (s, 1H). MS (APCl+) m/e 575 (M+H$^+$). Anal. Calc for C$_{33}$H$_{38}$N$_2$O$_7$: C, 68.97 H, 6.67, N 4.87. Found: C, 68.92, H, 6.83, N, 4.77.

Example 30A

Ethyl [4-(2-methoxyethoxy)benzoyl]-acetate

Methyl 4-hydroxybenzoate was reacted with 1-bromo-2-methoxyethane, and potassium carbonate in dimethylformamide. The resultant ester was hydrolyzed to the acid with NaOH in alcohol. This acid was reacted with carbonyl diimidazole in THF; the resulting imidazolide was reacted with the potassium salt of the mono ethyl ester of malonic acid, and magnesium chloride, to give the title compound as a colorless oil.

Example 30B trans,trans-2-(4-(2-Methoxyethoxy)phenyl)-4-(1,3-benzodioxol-5-yl)-1-(2,6-diethylphenylaminocarbonylmethyl)-pyrrolidine-3-carboxylic acid The title compound was prepared by the procedures described in Example 1, employing the b-ketoester described above as starting material. 1H NMR (300 MHz, CDCl3) d 1.08 (t, J=7 Hz, 6H), 2.43 (q, J=7 Hz, 4H), 3.00 (d, J=11 Hz, 1H), 3.05-3.15 (m, 2H), 3.44 (s, 3H), 3.46 (d, J=11 Hz, 1H), 3.45-3.55 (m, 1H), 3.65-3.75 (m, 1H), 3.75-3.80 (m, 2H), 3.93 (d, J=7 Hz, 1H), 4.12-4.17 (m, 2H), 5.94 (dd, J=2 Hz, 4 Hz, 2H), 6.75 (d, J=8 Hz, 1H), 6.82 (dd, J=2 Hz, 9 Hz, 1H), 6.87 (d, J=2 Hz, 1H), 6.95 (d, J=8 Hz, 1H), 7.10 (d, J=6 Hz, 2H), 7.19-7.24 (m, 1H), 7.37 (d, d=8 Hz, 2H), 8.29 (s, 1H). MS (APCl+) m/e 575 (M+H+). Anal. Calc for C33H38N2O7: C, 68.97 H, 6.67, N 4.87. Found: C, 68.92, H, 6.83, N, 4.77.

The following compounds of Examples 31–857 can be prepared using the methods described in the above examples.

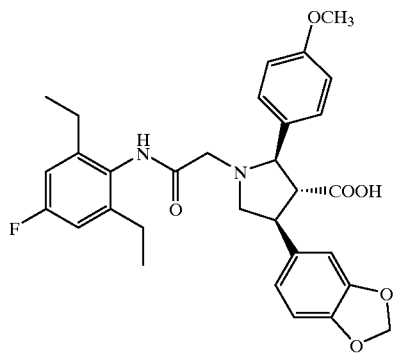

31

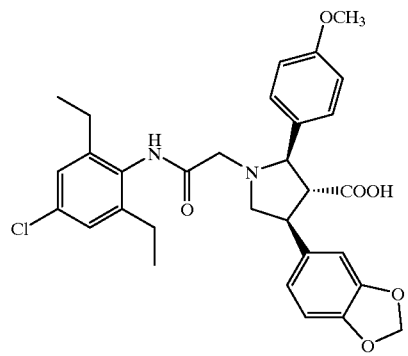

32

-continued
33
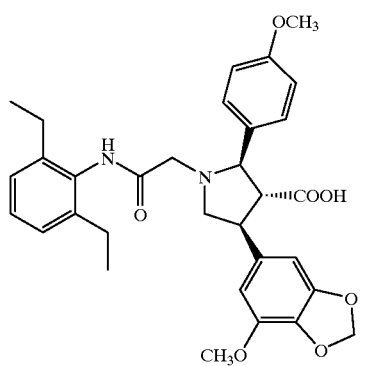
34
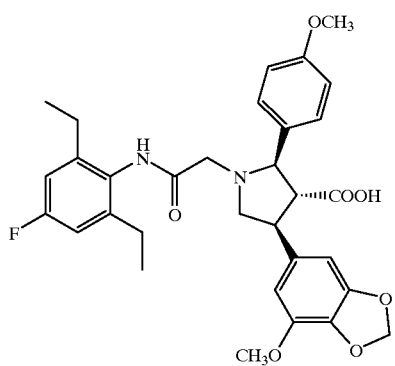
35
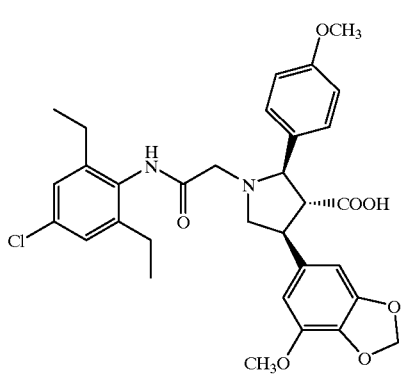
36
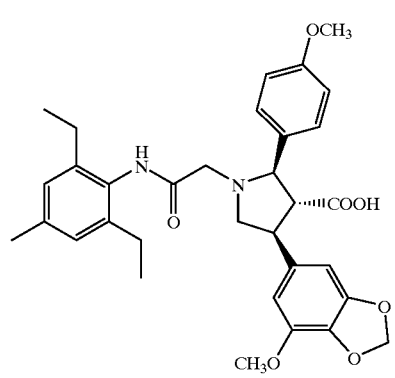
37
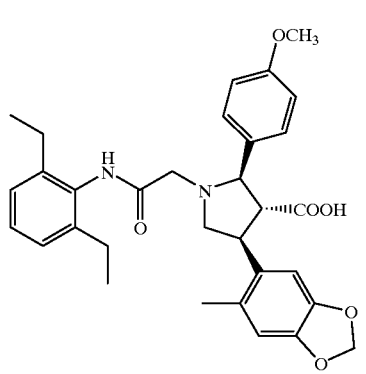
38
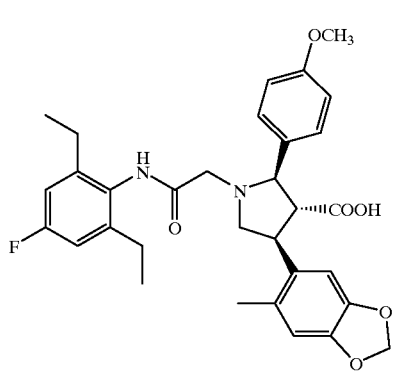
39
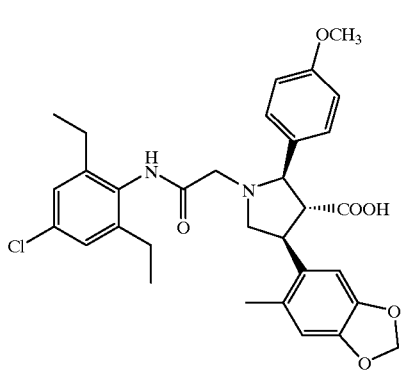
40
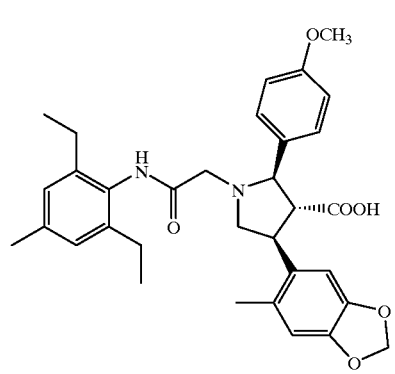

-continued
41
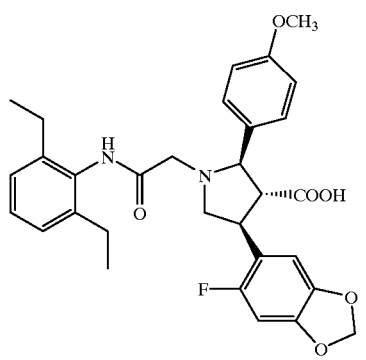
42
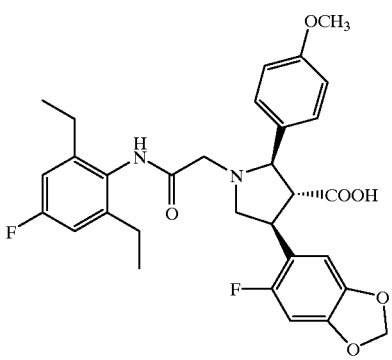
43
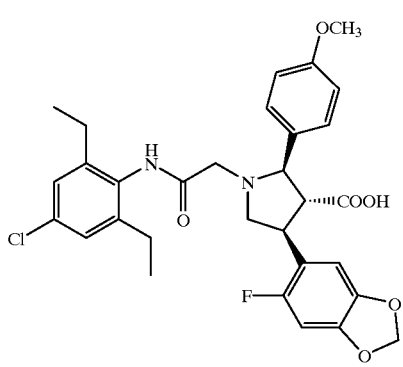
44
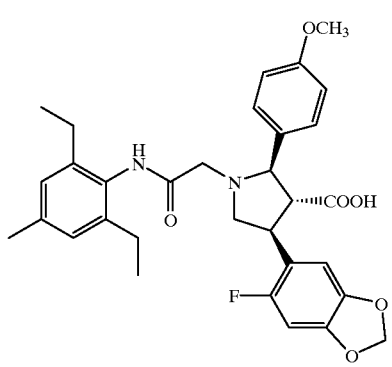
45
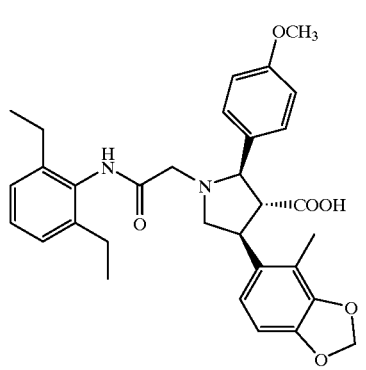
46
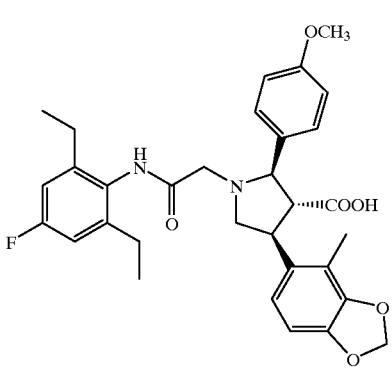
47
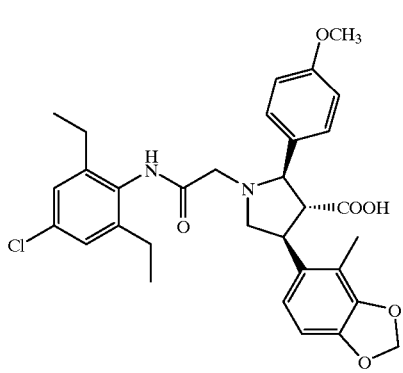
48
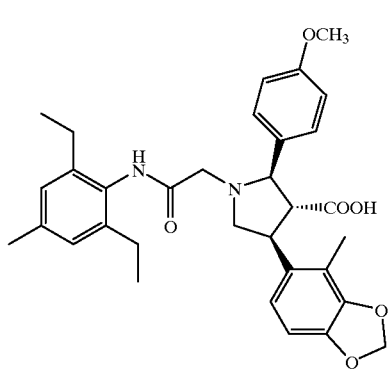

-continued
49
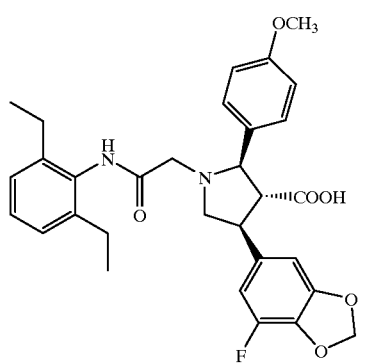
50
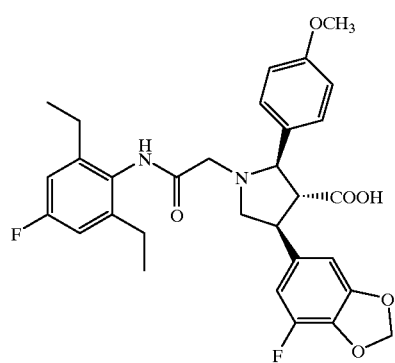
51
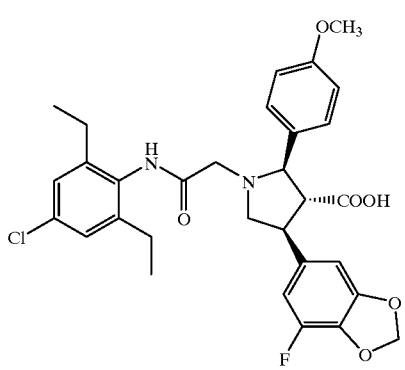
52
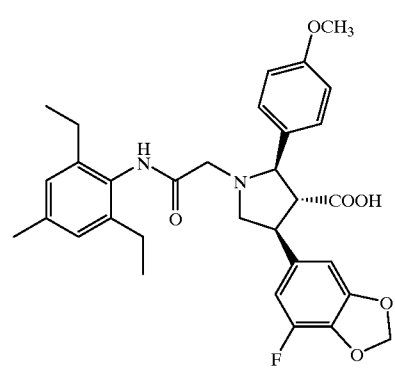
53
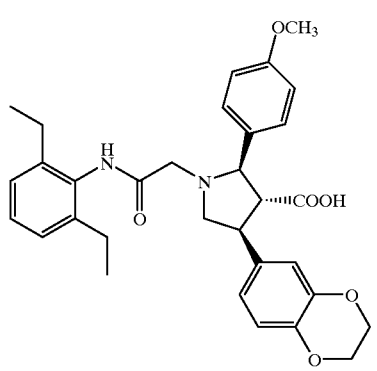
54
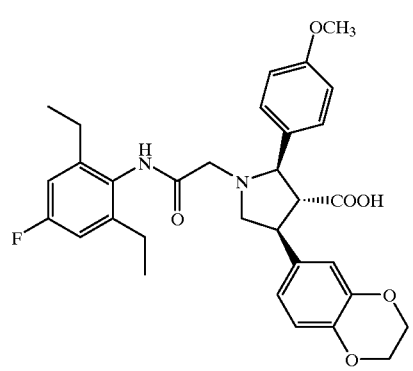
55
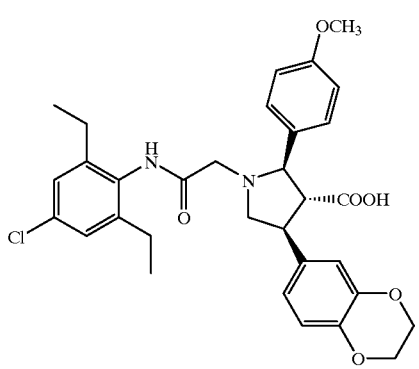
56
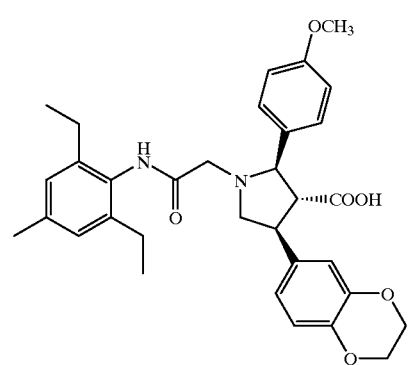

-continued
57
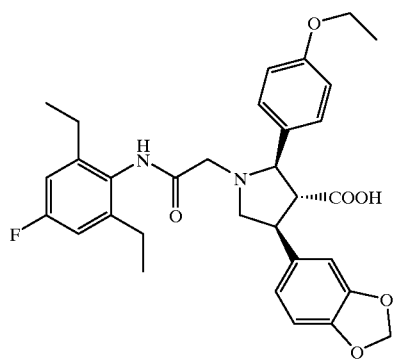
58
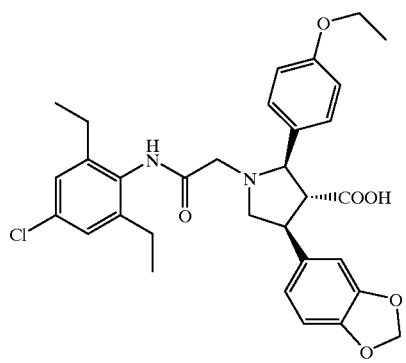
59
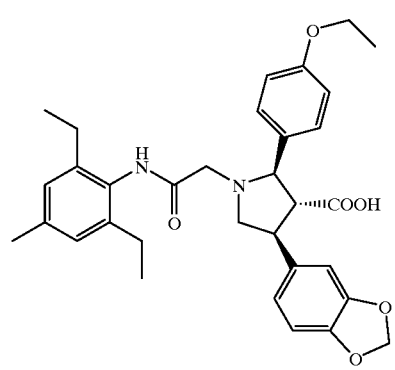
60
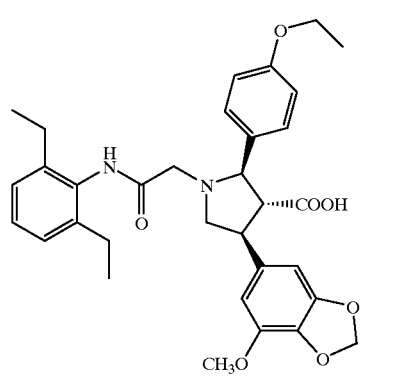
61
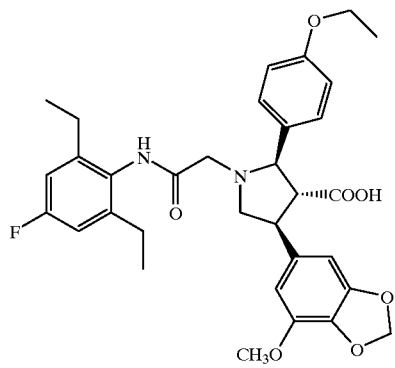
62
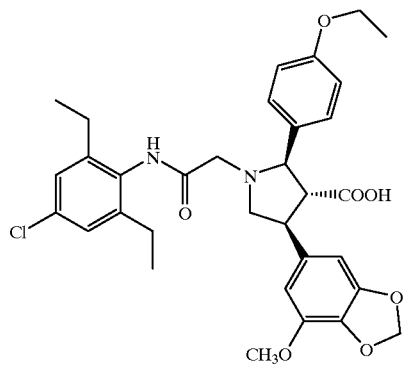
63
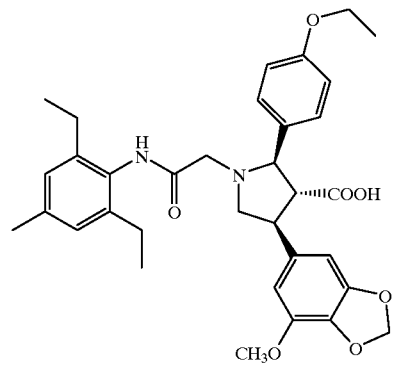
64
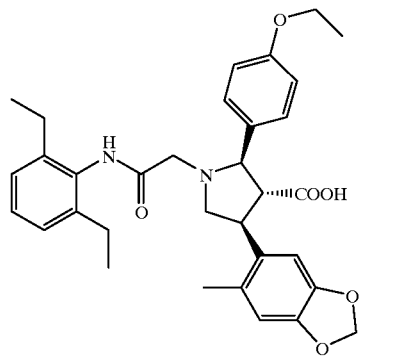

-continued
| 65 | 66 |
|---|---|
| 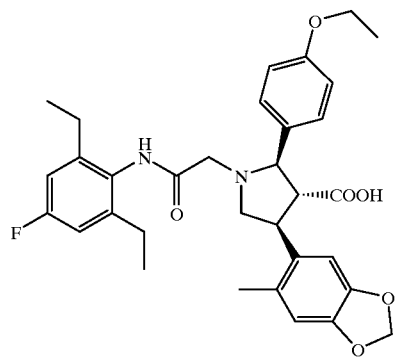 | 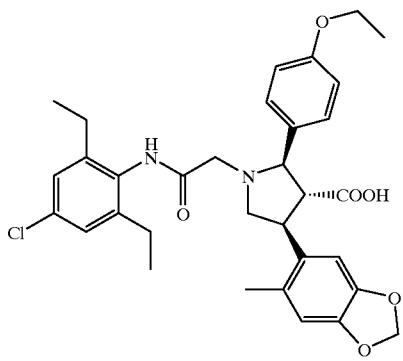 |
| 67 | 68 |
|---|---|
| 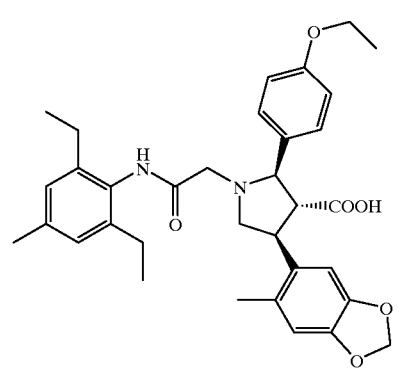 | 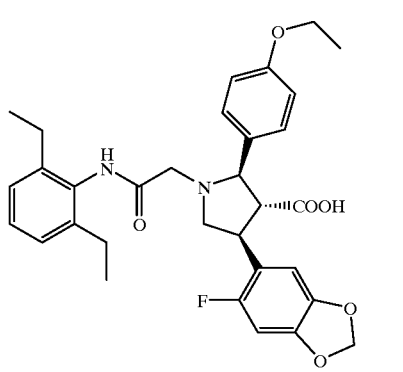 |
| 69 | 70 |
|---|---|
| 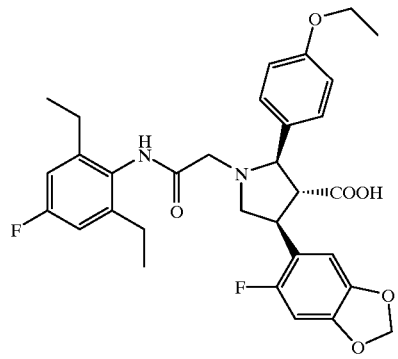 | 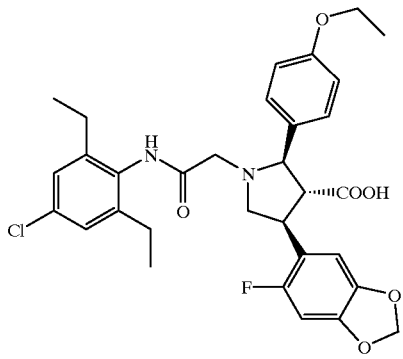 |
| 71 | 72 |
|---|---|
| 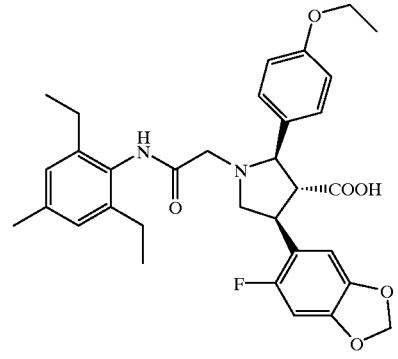 | 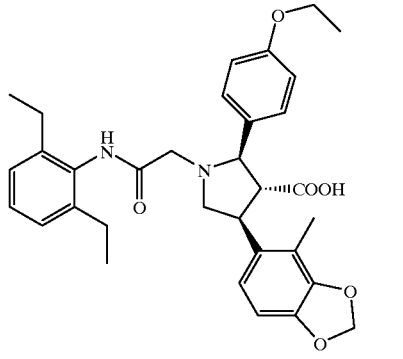 |

-continued
73
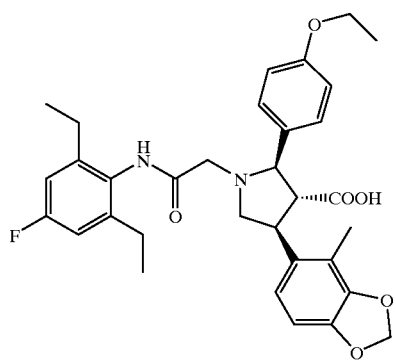
74
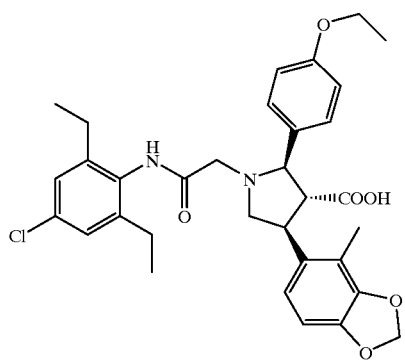
75
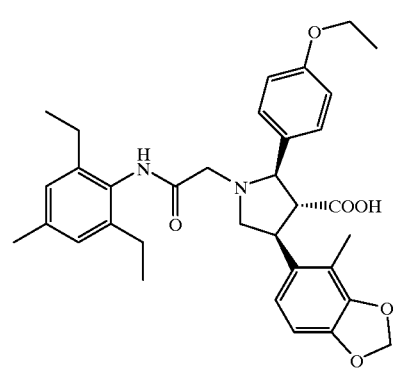
76
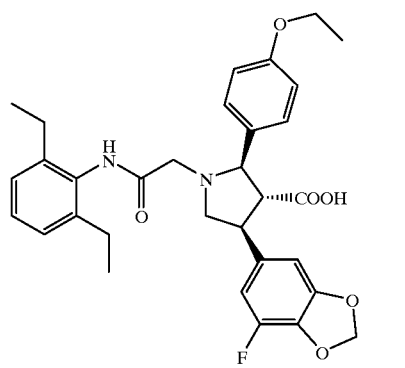
77
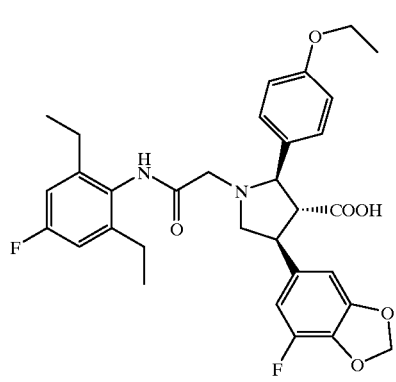
78
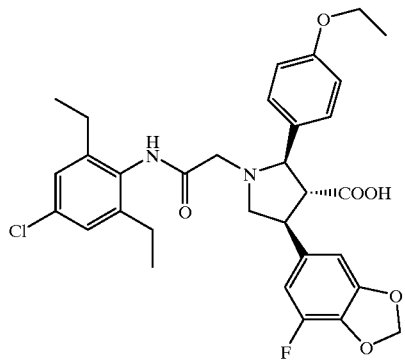
79
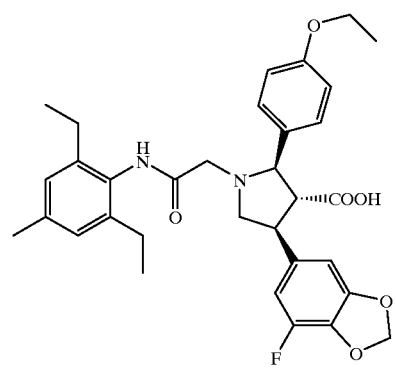
80
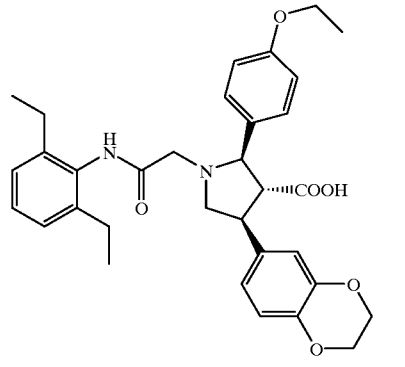

-continued
| 81 | 82 |
|---|---|
| 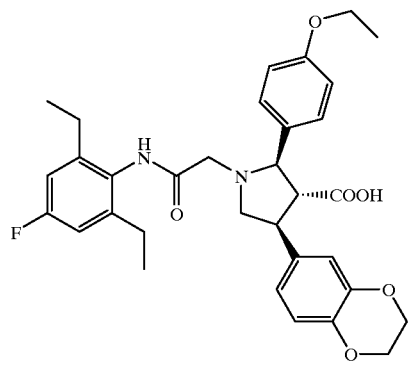 | 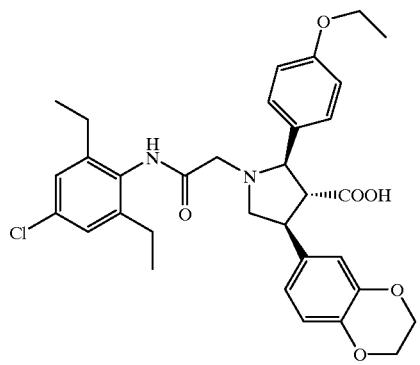 |
| 83 | 84 |
|---|---|
| 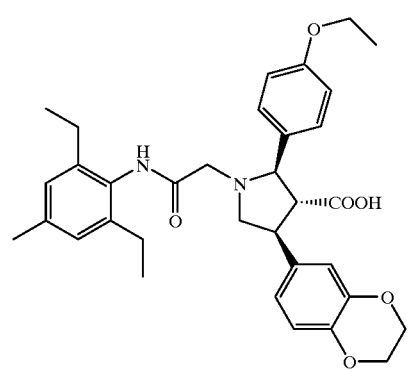 | 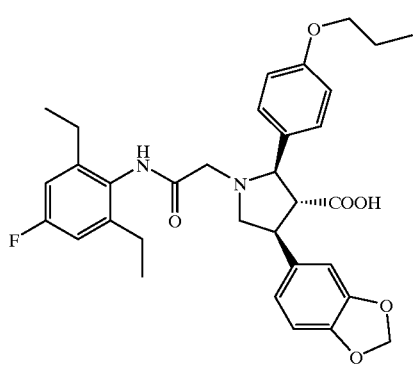 |
| 85 | 86 |
|---|---|
| 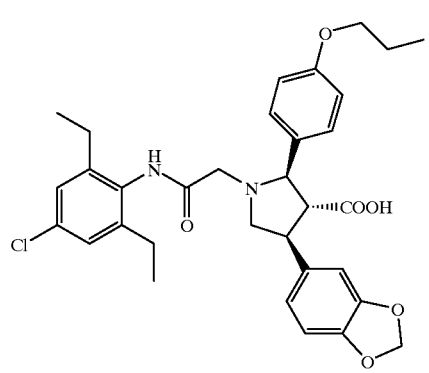 | 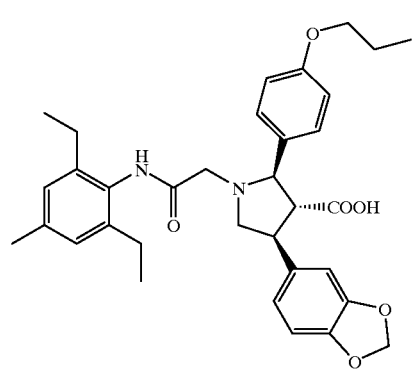 |
| 87 | 88 |
|---|---|
| 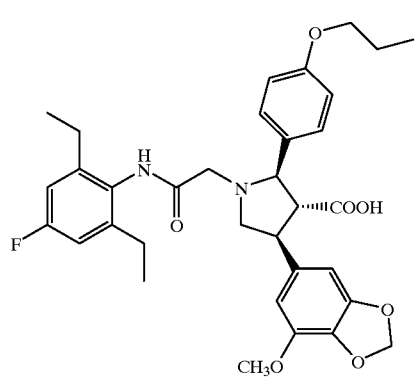 | 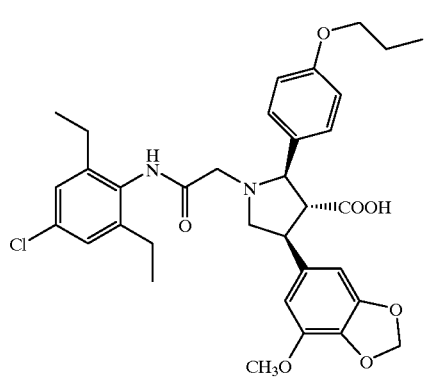 |

-continued
89
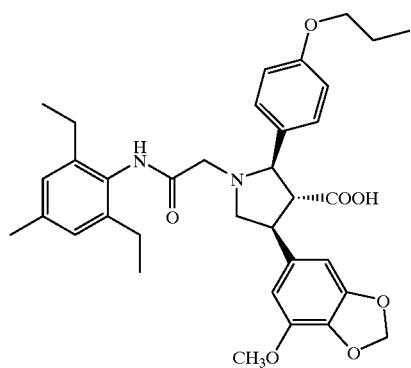
90
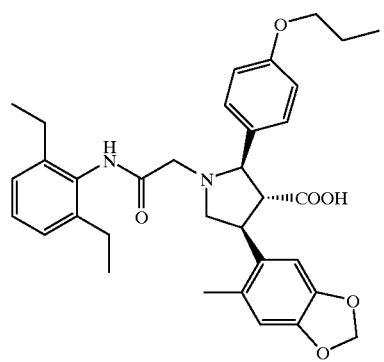
91
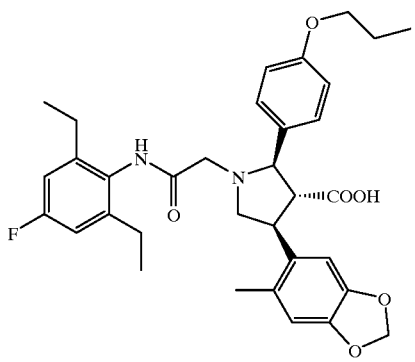
92
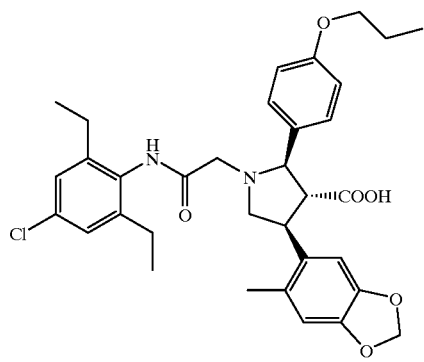
93
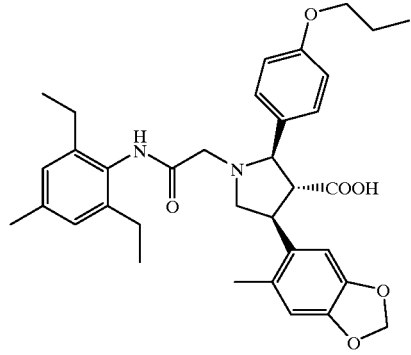
94
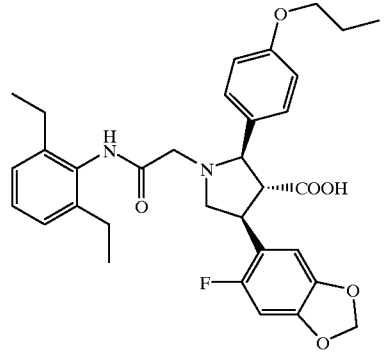
95
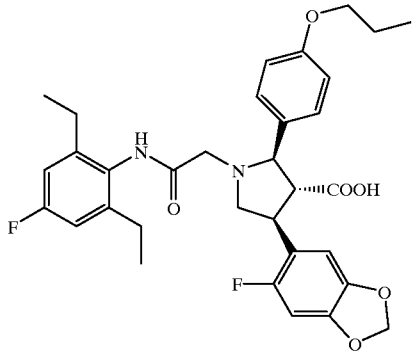
96
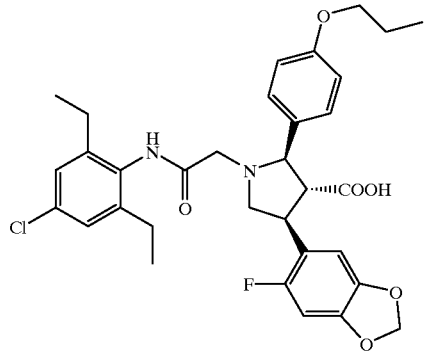

-continued
97
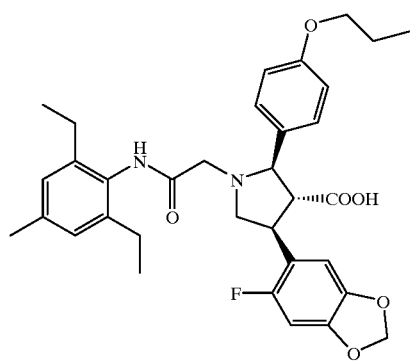
98
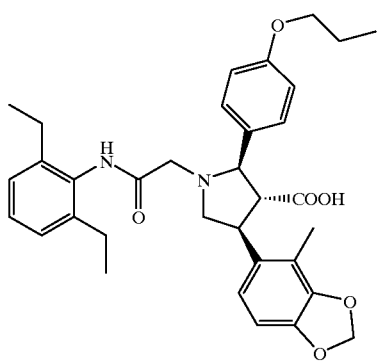
99
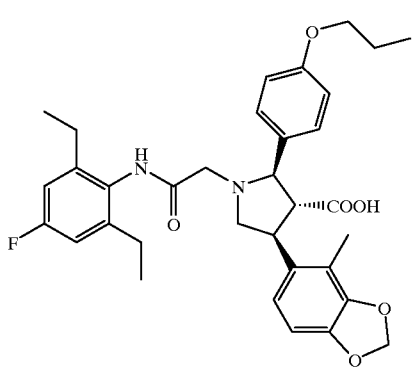
100
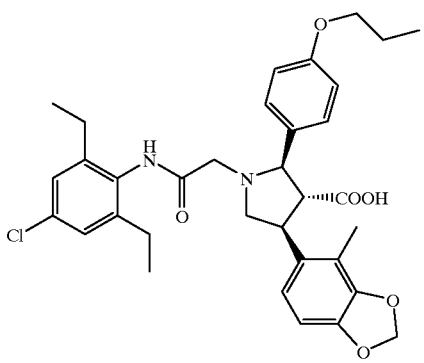
101
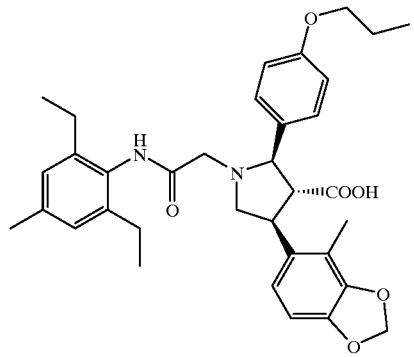
102
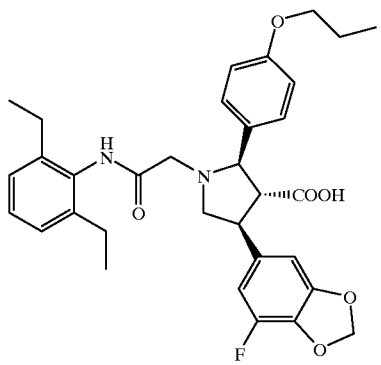
103
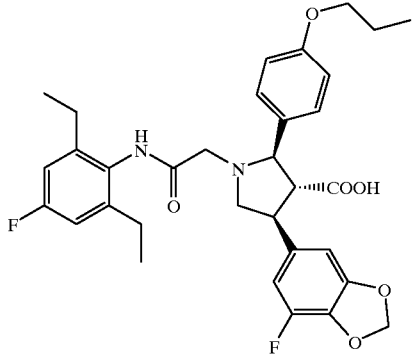
104
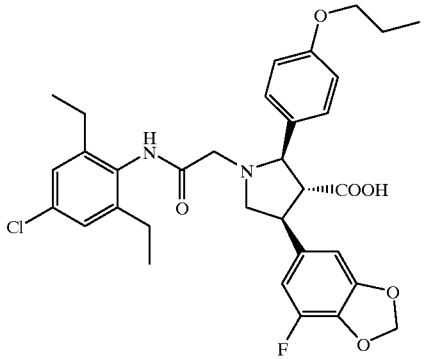

-continued
| 105 | 106 |
|---|---|
| 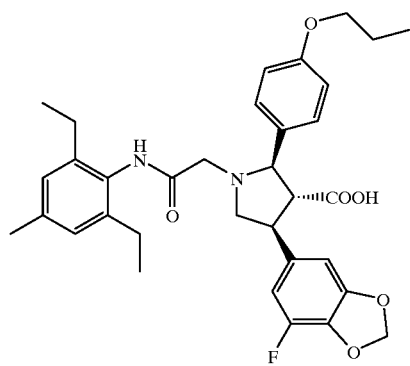 | 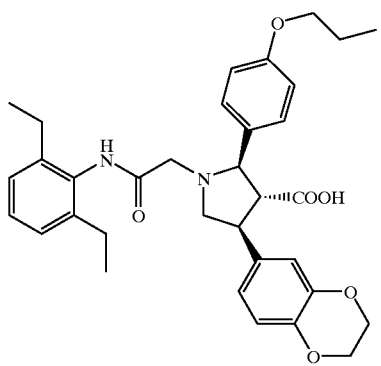 |
| 107 | 108 |
| 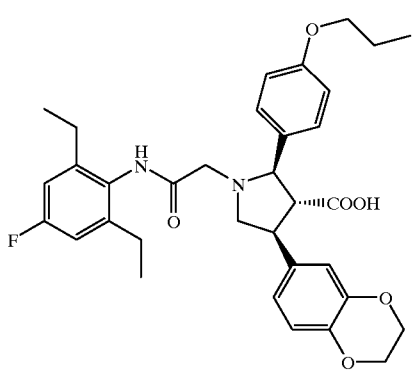 | 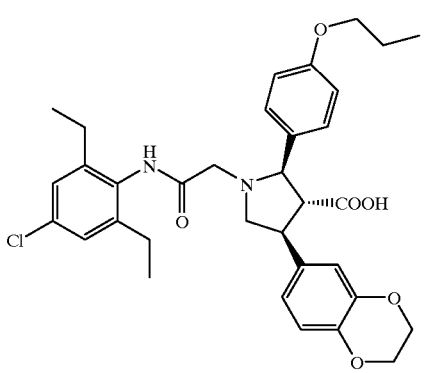 |
| 109 | 110 |
| 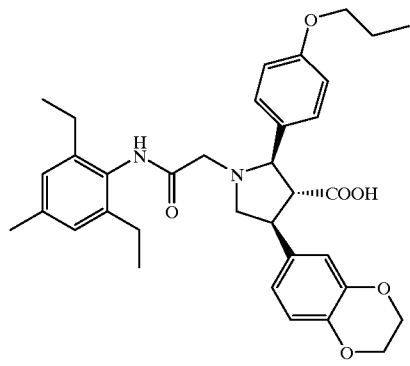 | 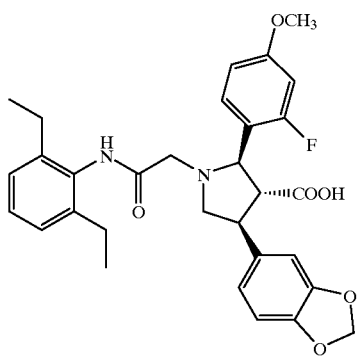 |
| 111 | 112 |
| 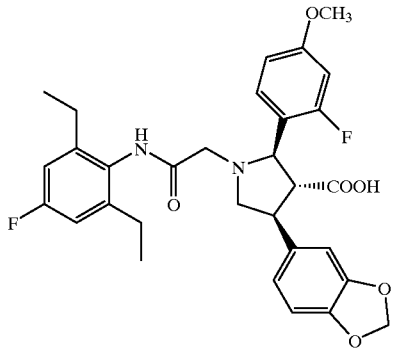 | 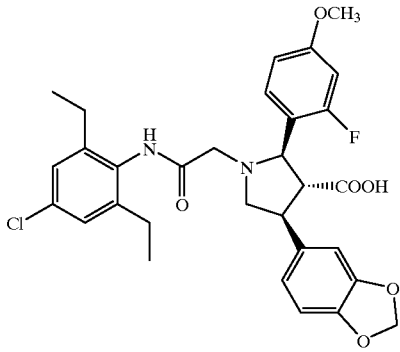 |

-continued
113
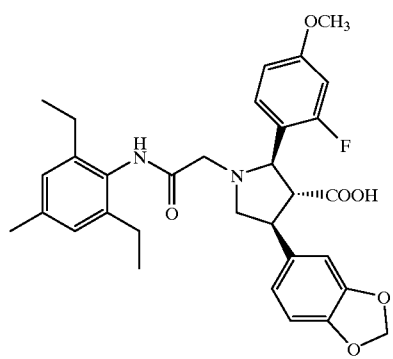
114
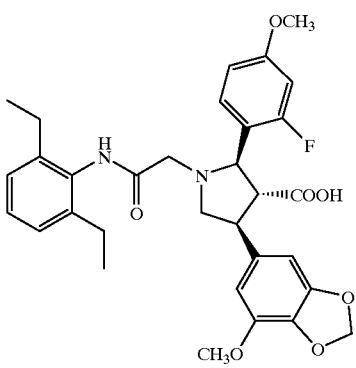
115
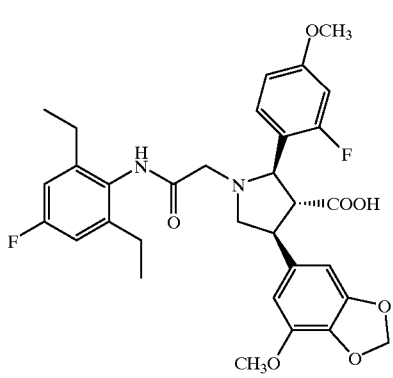
116
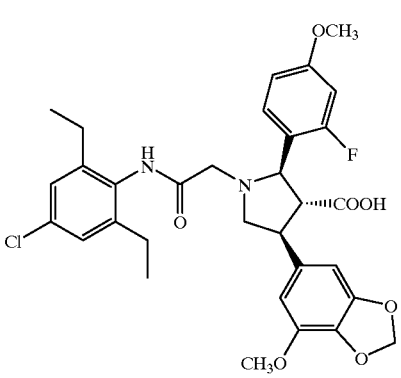
117
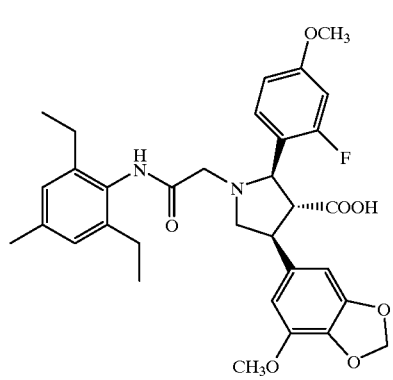
118
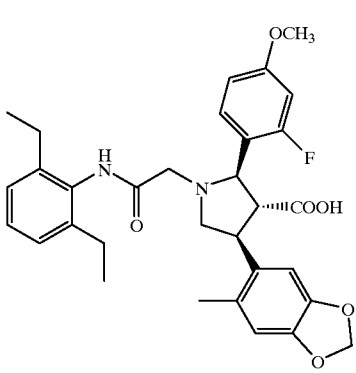
119
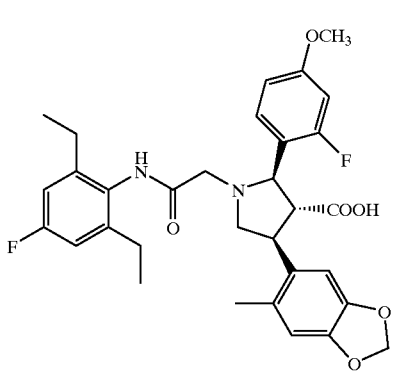
120
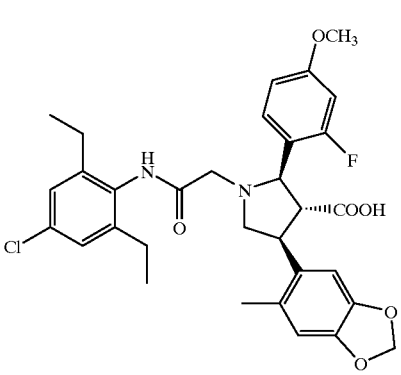

-continued
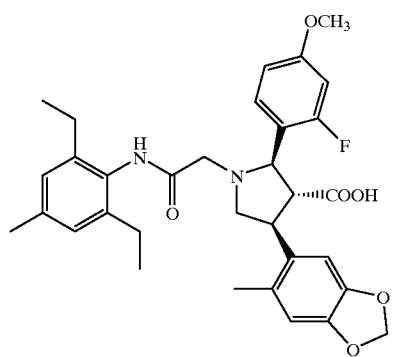
121
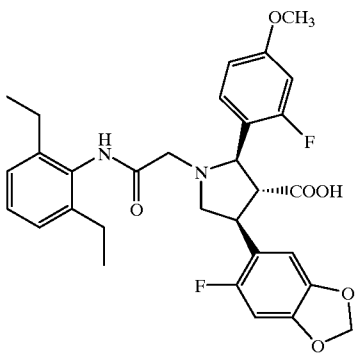
122
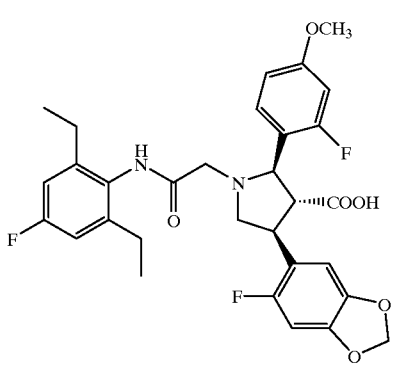
123
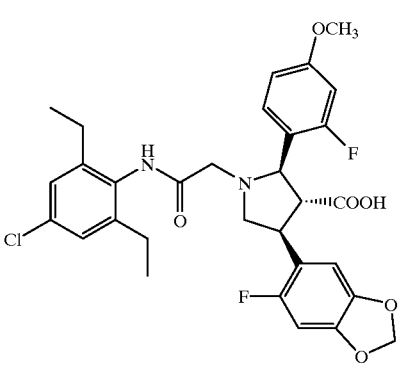
124
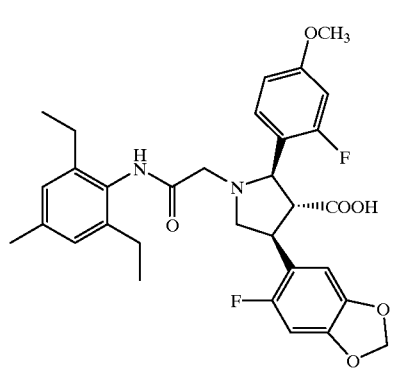
125
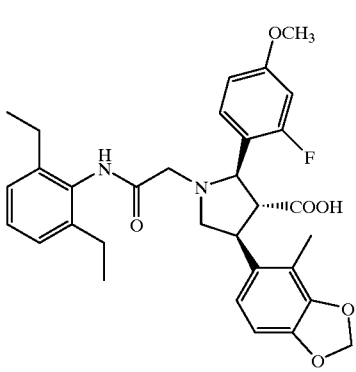
126
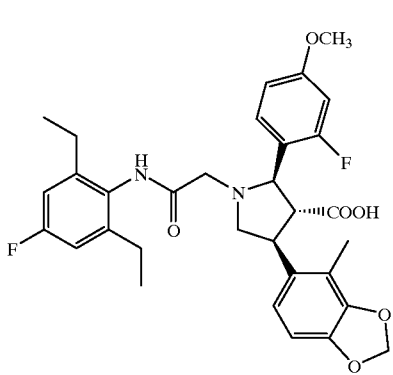
127
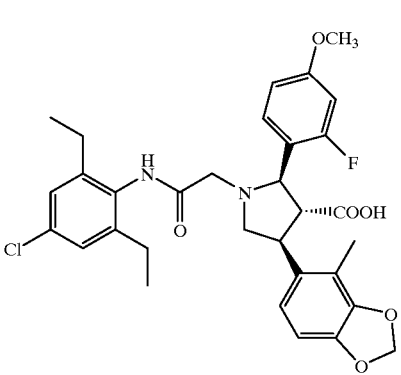
128

-continued
129
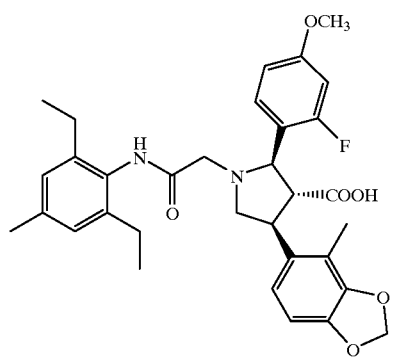
130
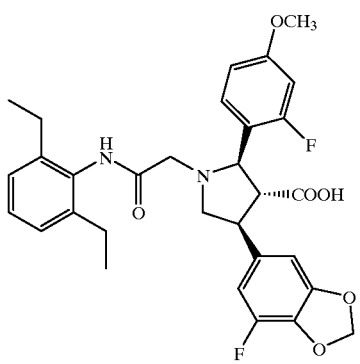
131
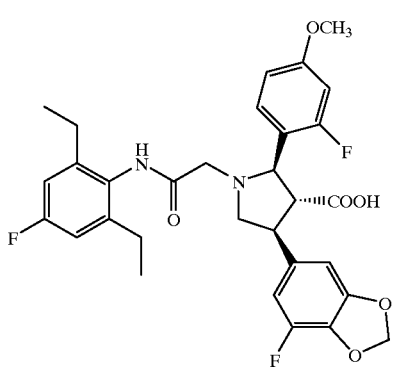
132
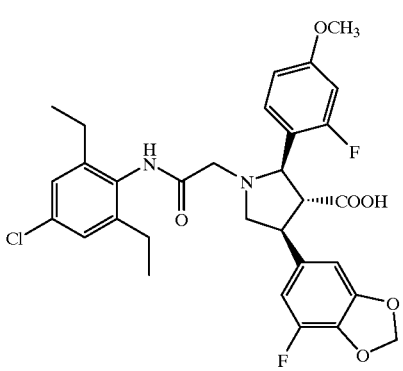
133
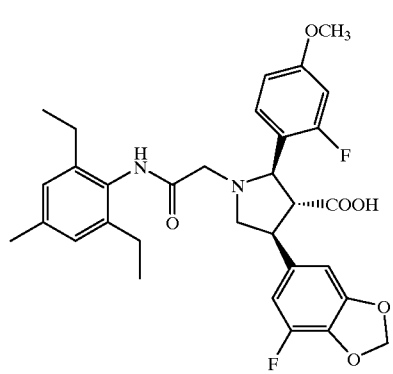
134
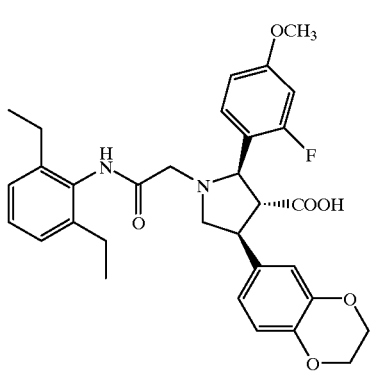
135
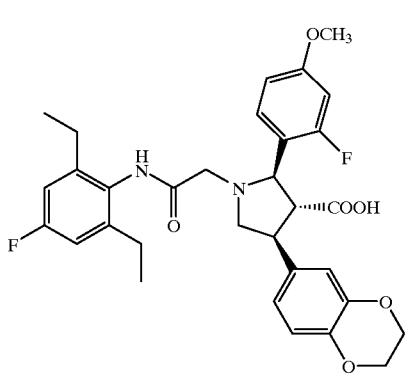
136
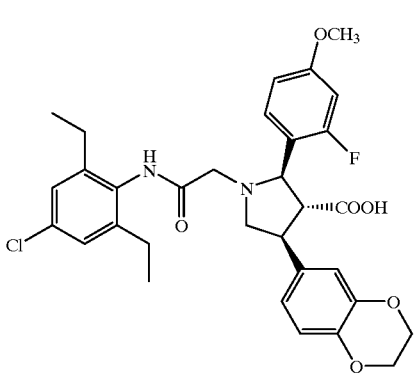

-continued
137
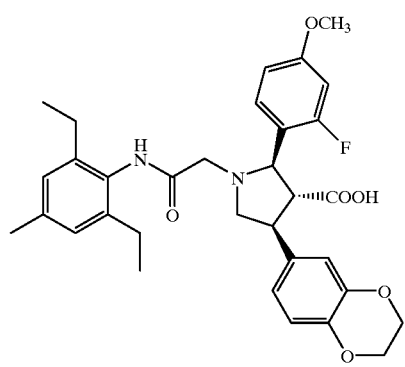
138
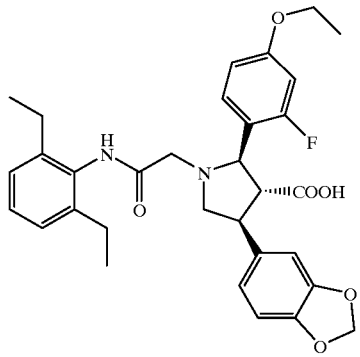
139
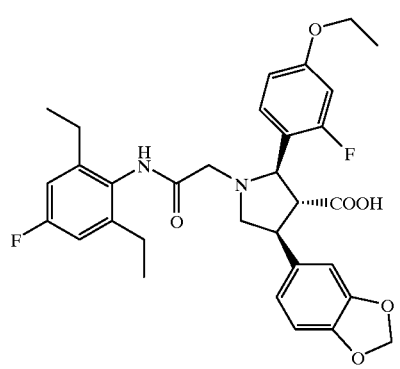
140
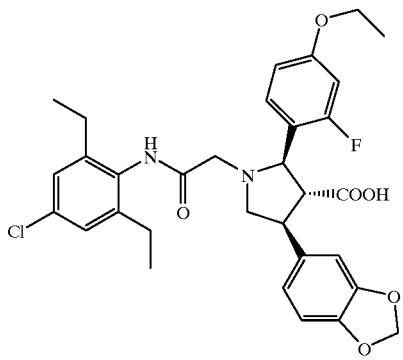
141
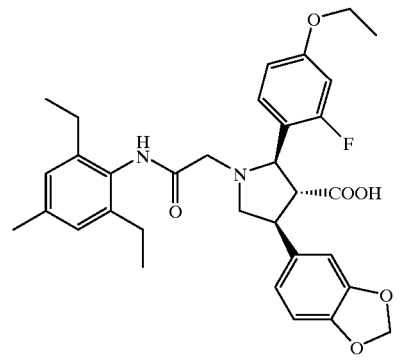
142
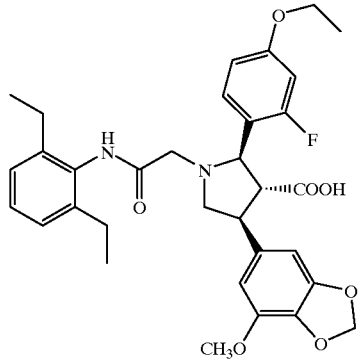
143
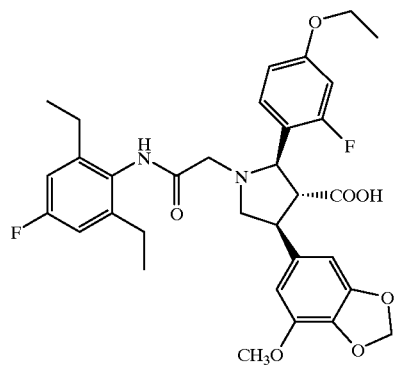
144
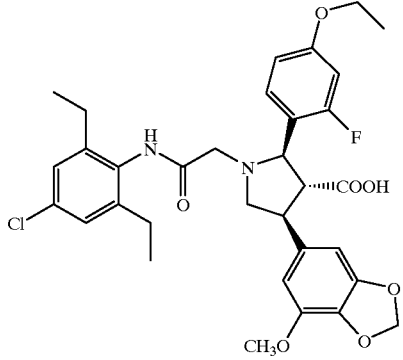

145
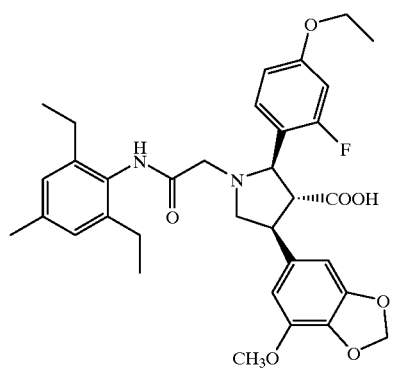
146
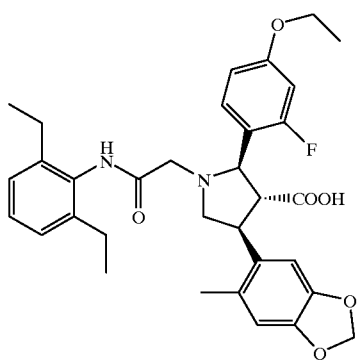
147
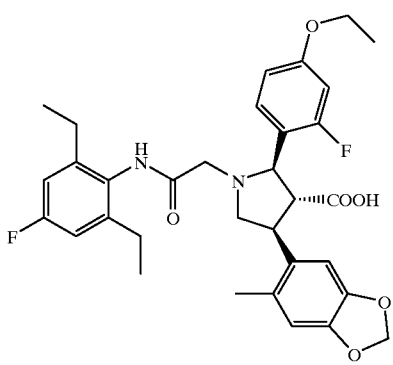
148
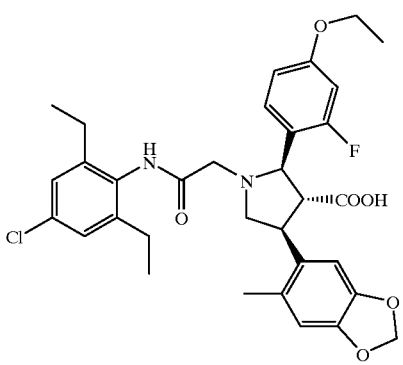
149
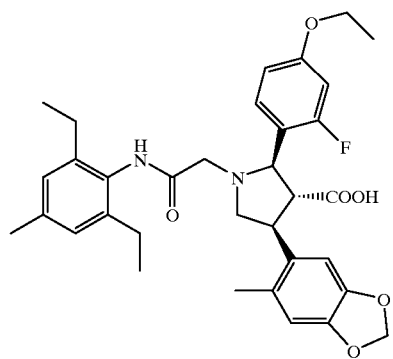
150
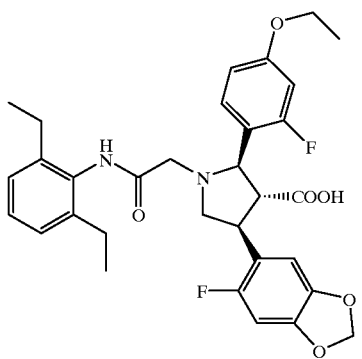
151
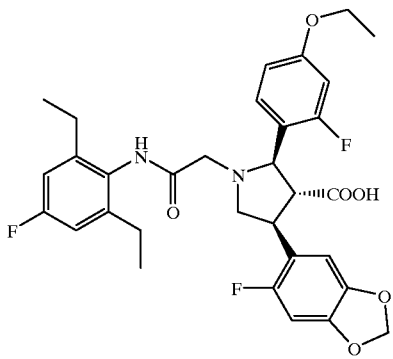
152
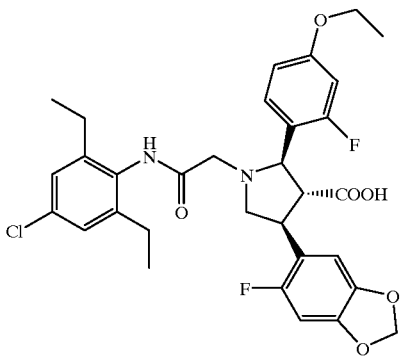

-continued
153
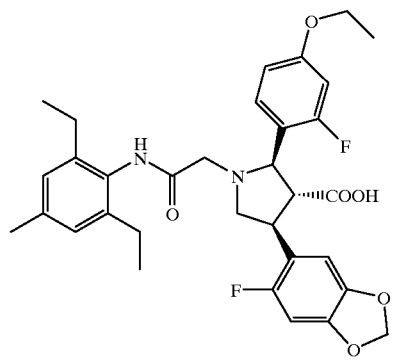
154
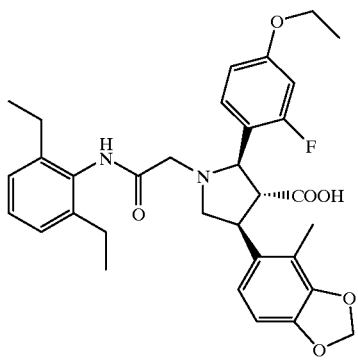
155
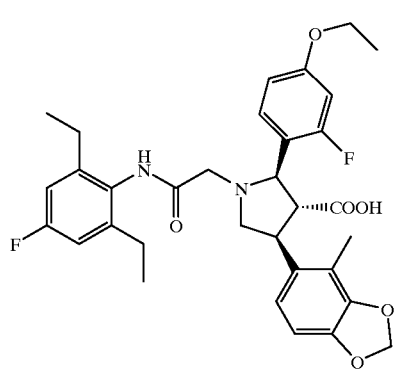
156
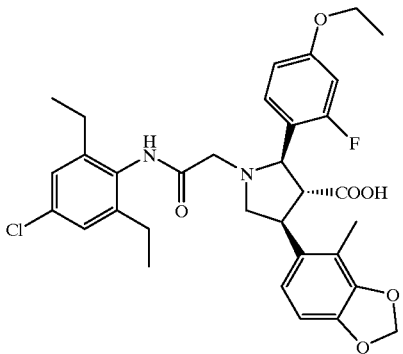
157
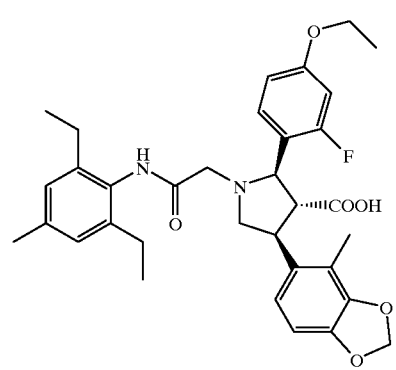
158
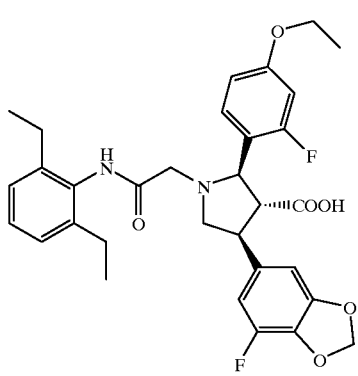
159
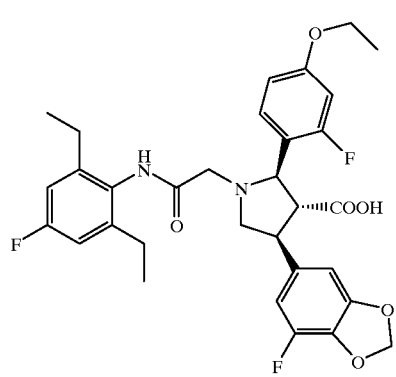
160
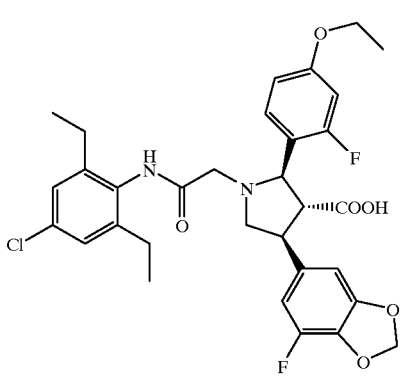

-continued
| 161 | 162 |
|---|---|
| 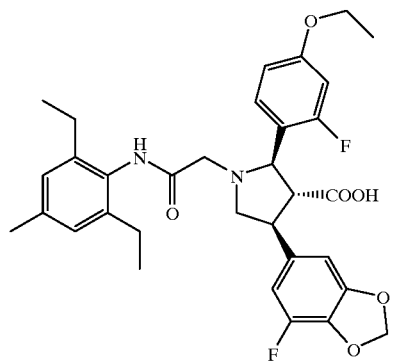 | 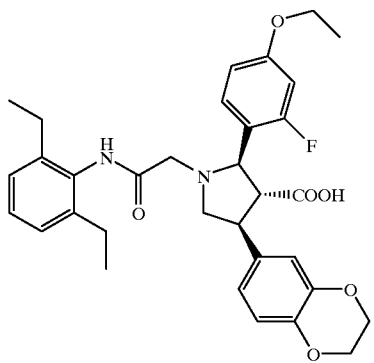 |
| 163 | 164 |
| 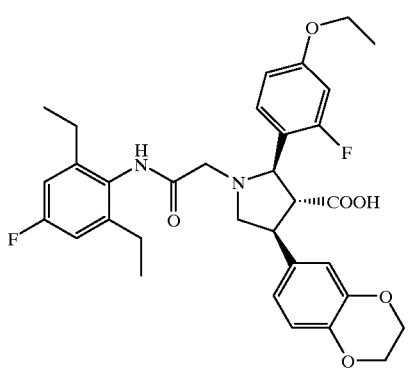 | 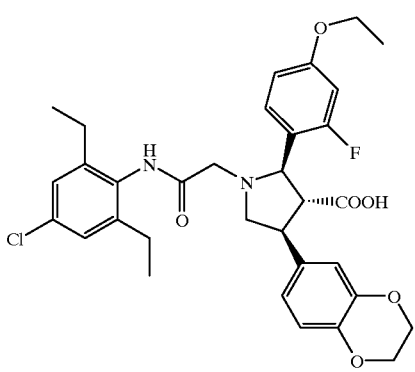 |
| 165 | 166 |
| 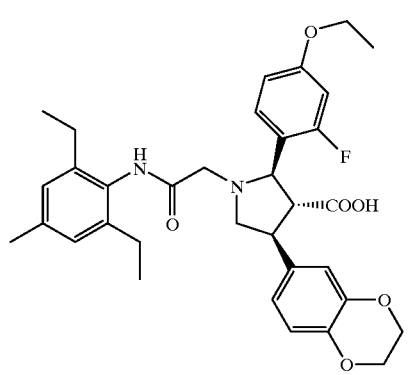 | 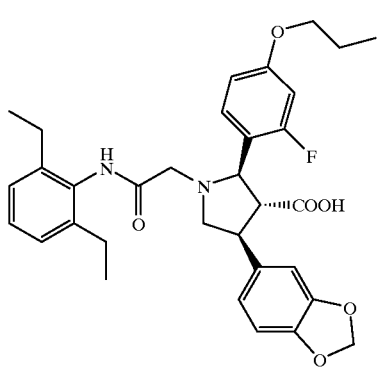 |
| 167 | 168 |
| 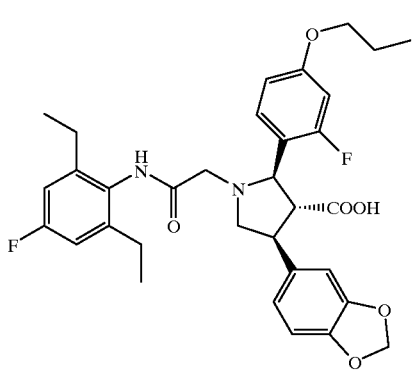 | 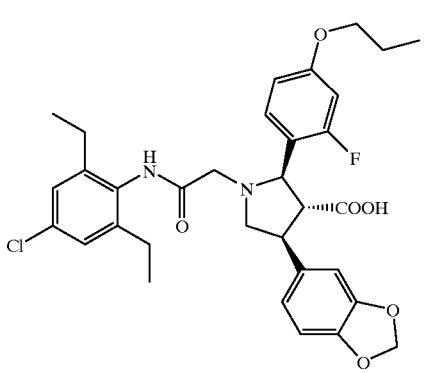 |

169
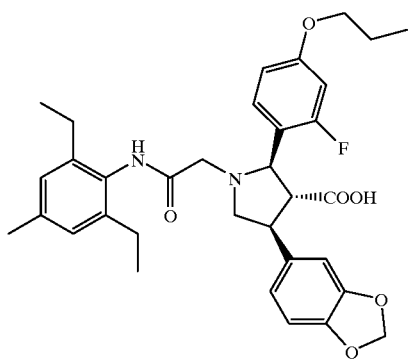
170
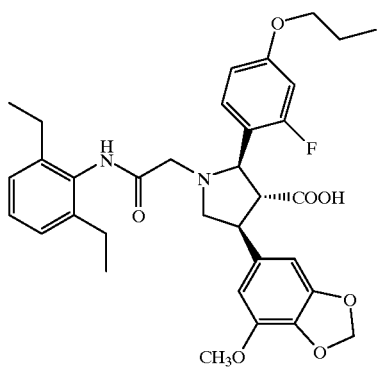
171
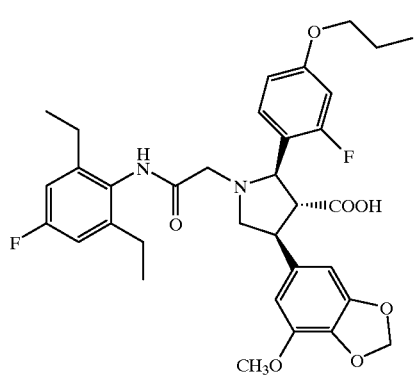
172
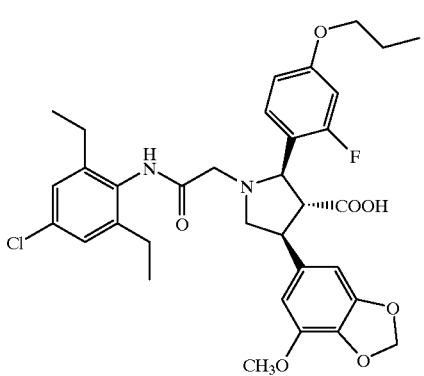
173
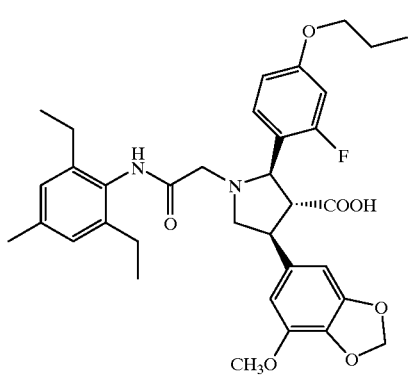
174
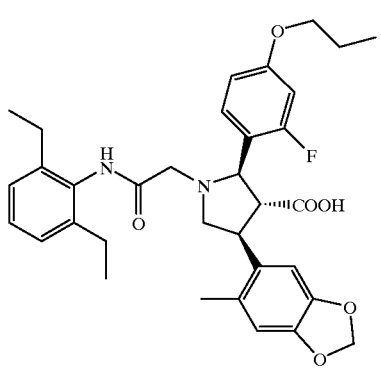
175
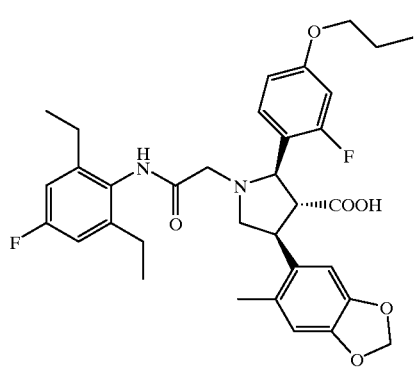
176
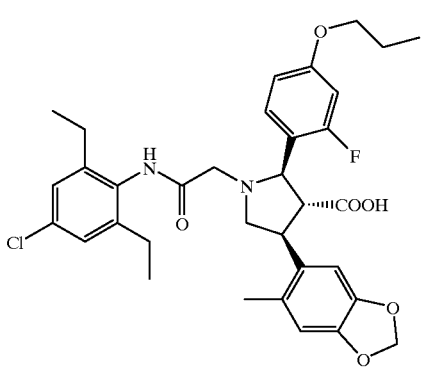

-continued
| 177 | 178 |
|---|---|
| 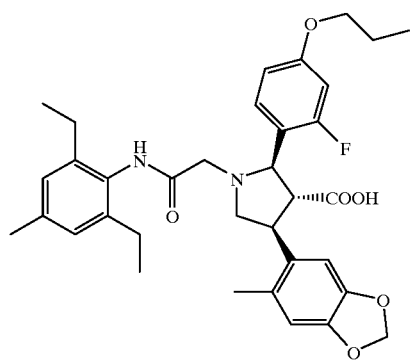 | 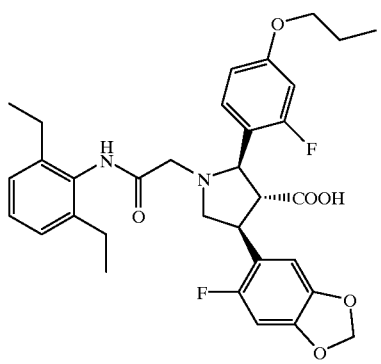 |
| 179 | 180 |
| 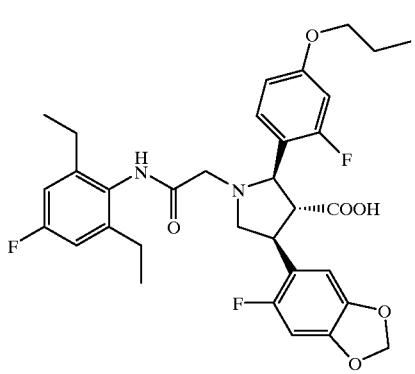 | 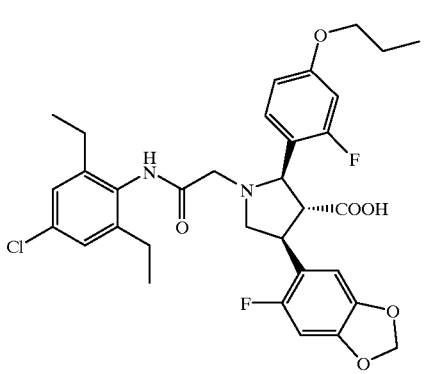 |
| 181 | 182 |
| 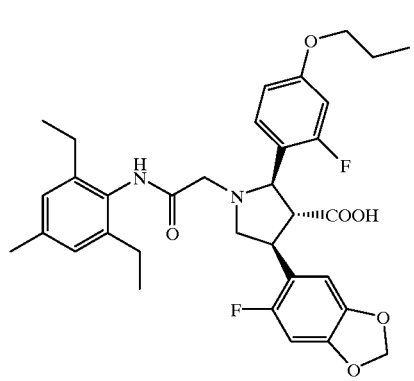 | 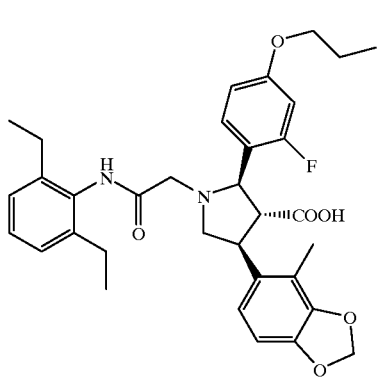 |
| 183 | 184 |
| 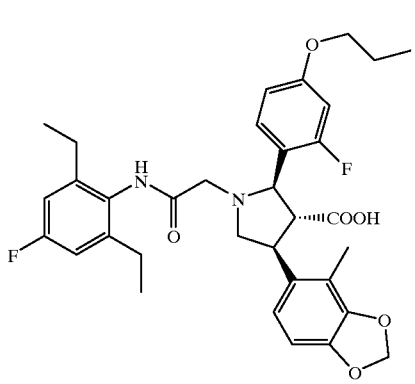 | 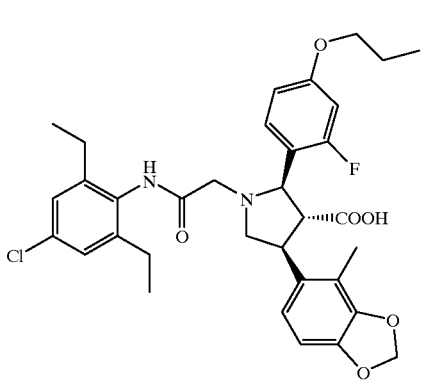 |

185 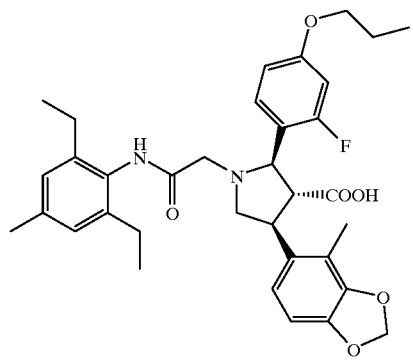 186 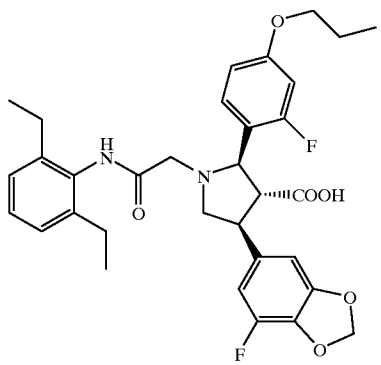
187 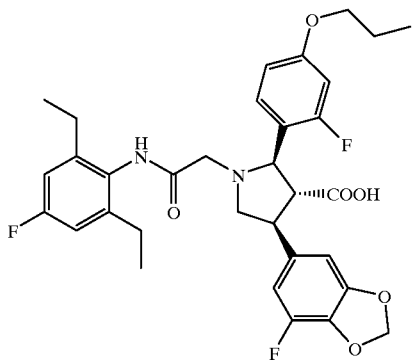 188 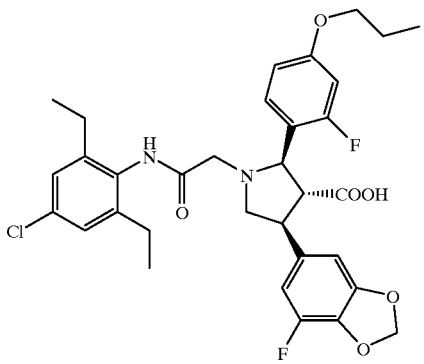
189 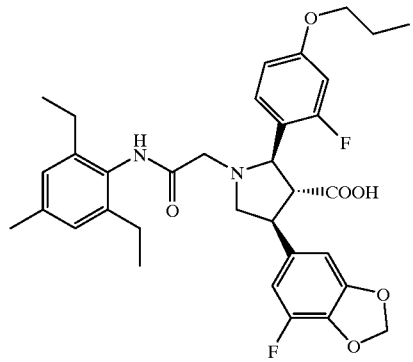 190 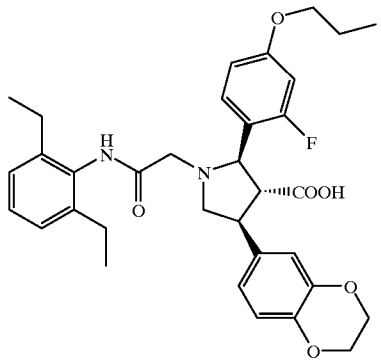
191 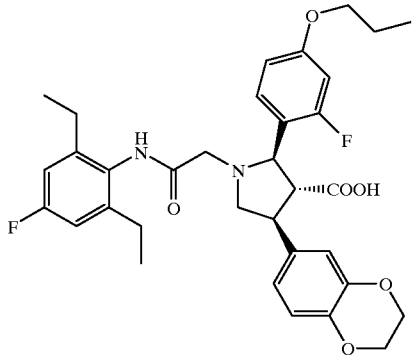 192 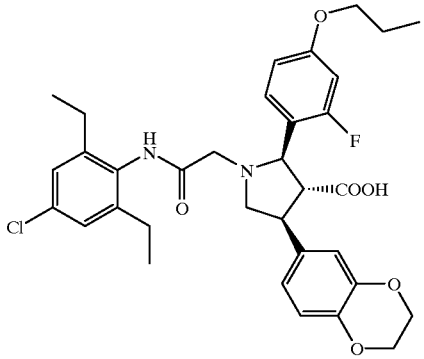

-continued
193 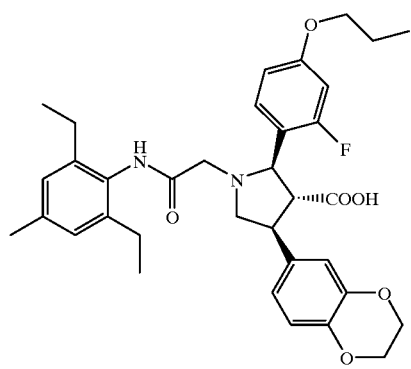 194 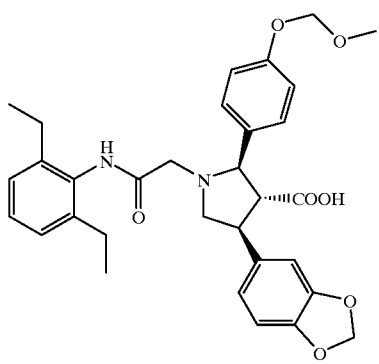
195 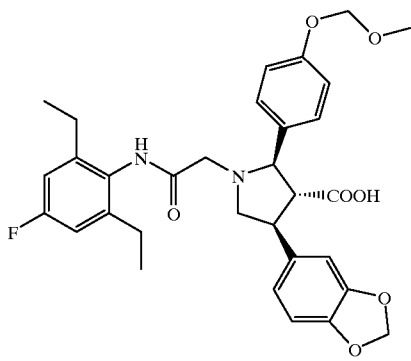 196 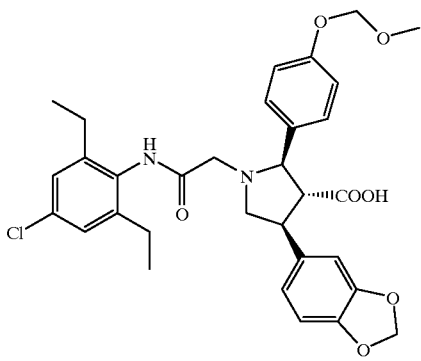
197 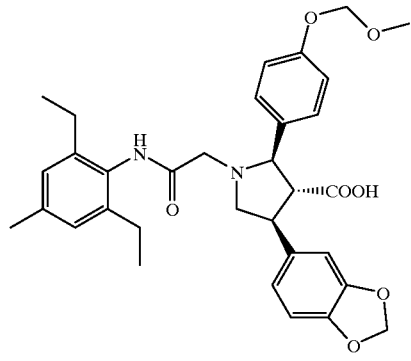 198 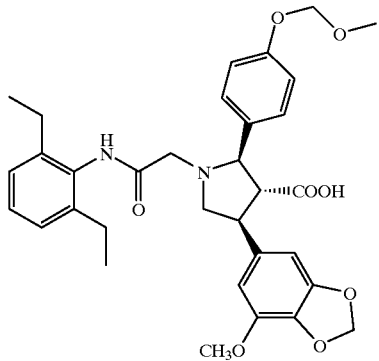
199 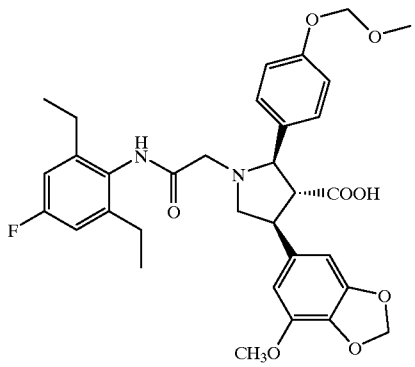 200 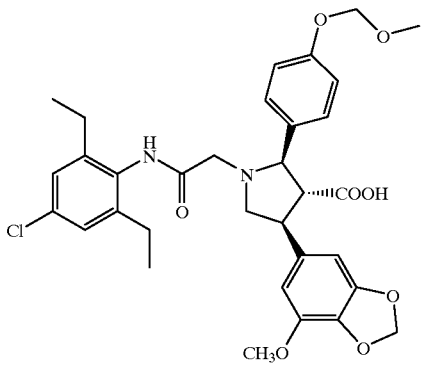

-continued
| 201 | 202 |
|---|---|
| 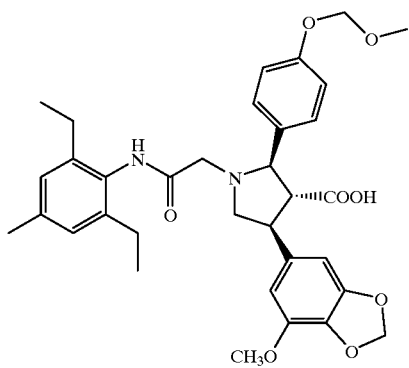 | 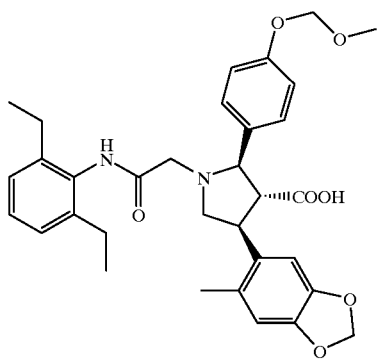 |
| 203 | 204 |
| 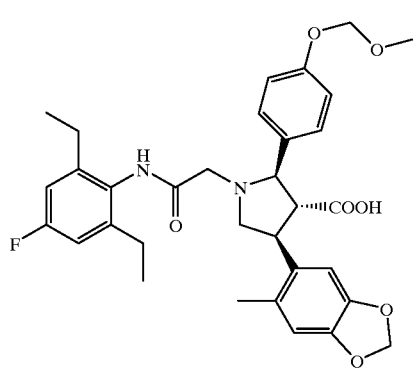 | 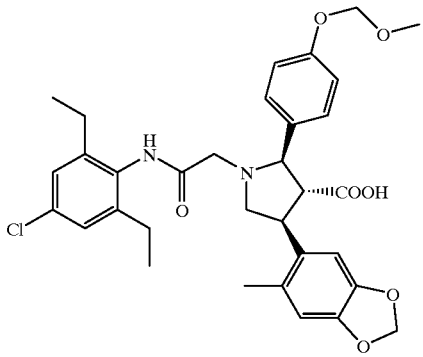 |
| 205 | 206 |
| 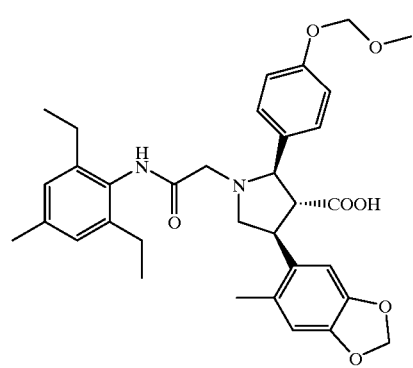 | 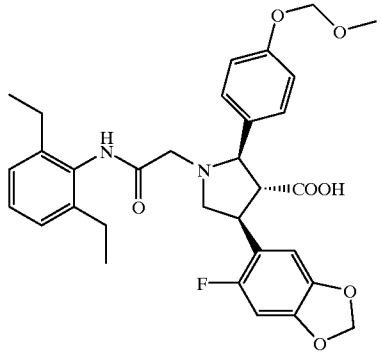 |
| 207 | 208 |
| 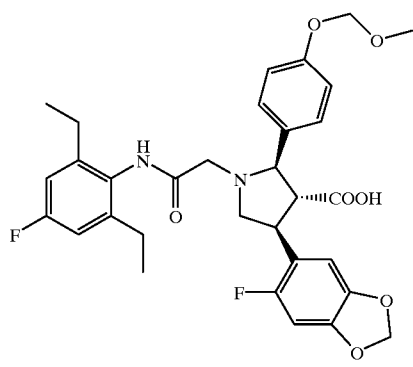 | 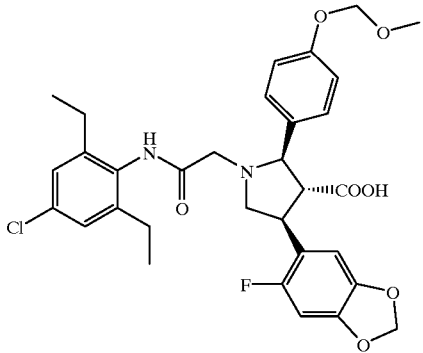 |

-continued
209
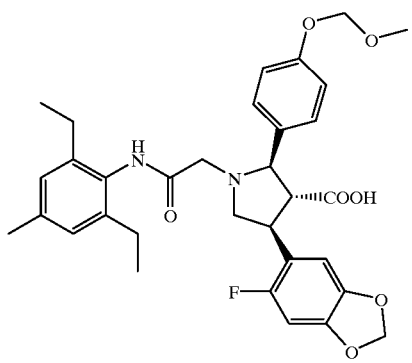
210
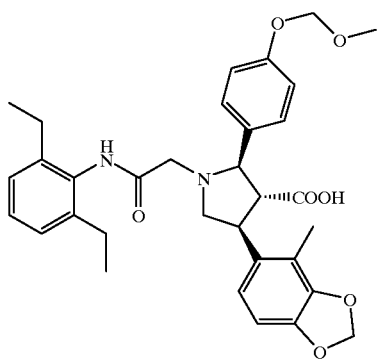
211
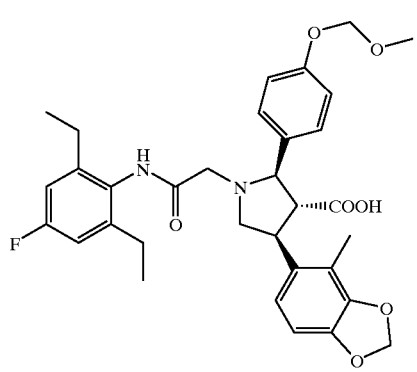
212
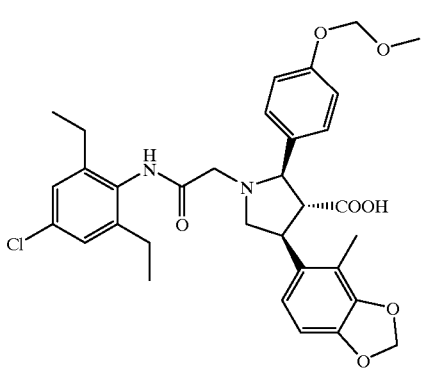
213
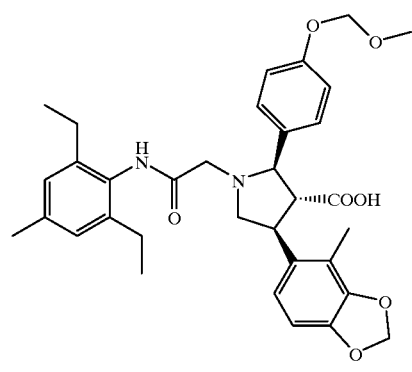
214
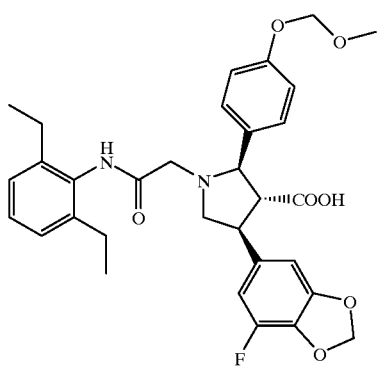
215
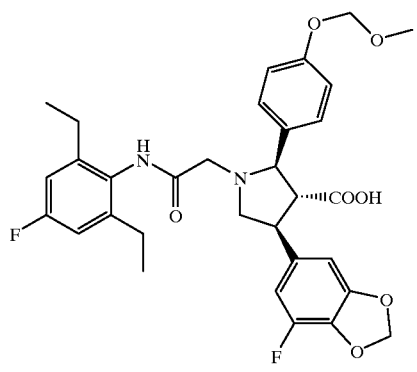
216
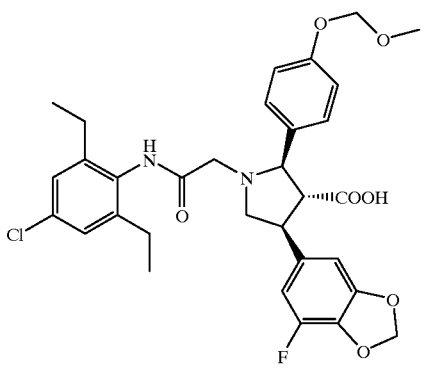

-continued
217
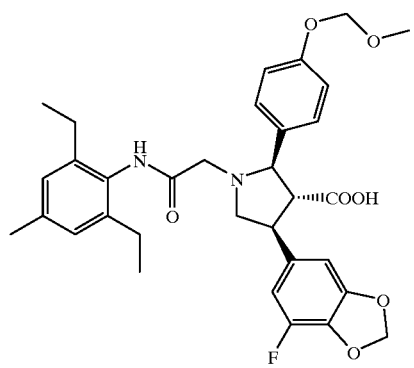
218
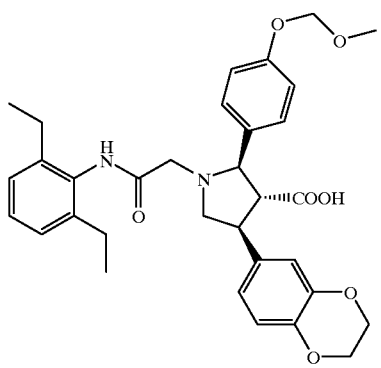
219
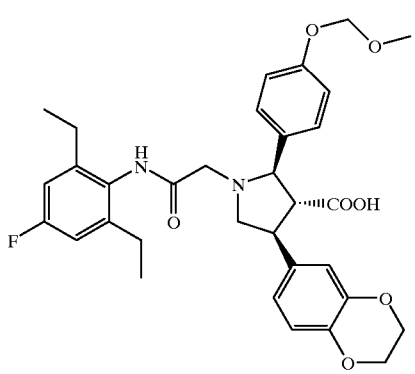
220
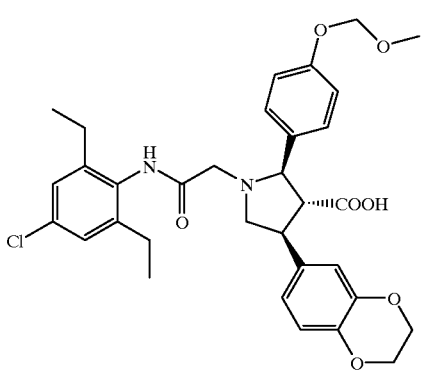
221
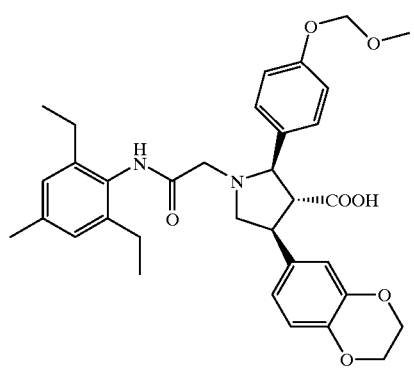
222
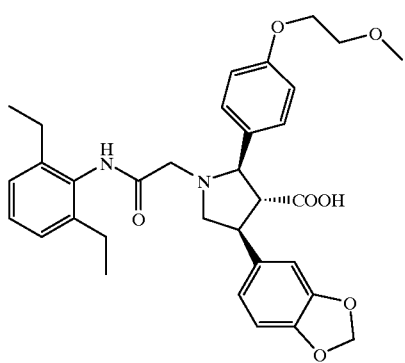
223
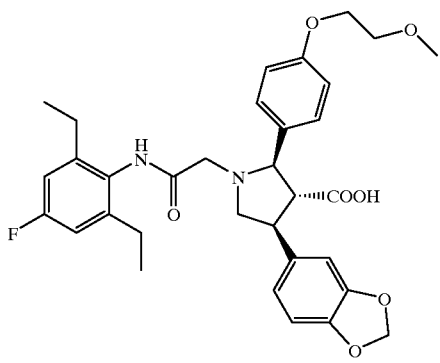
224
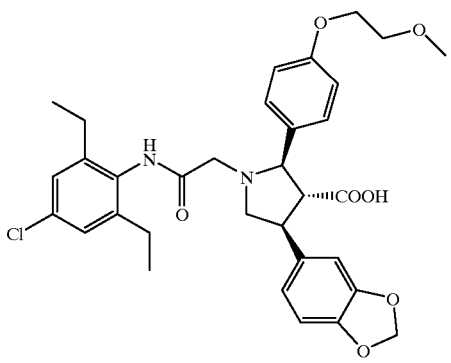

101 102
-continued
225 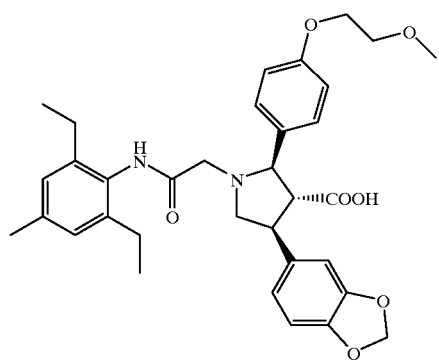 226 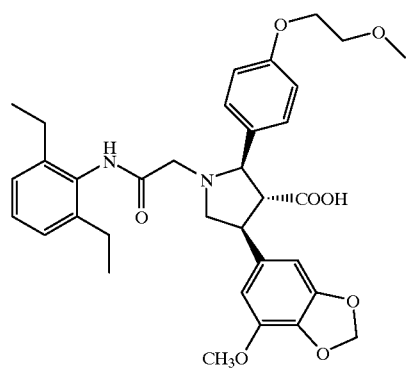
227 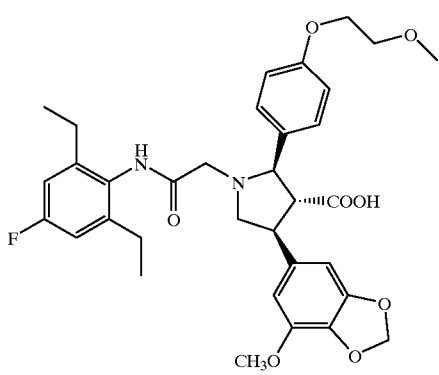 228 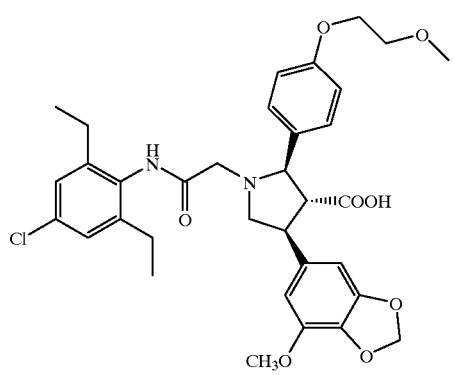
229 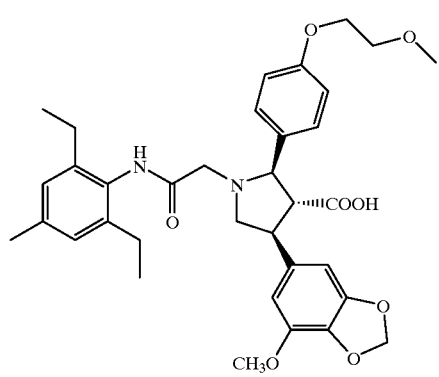 230 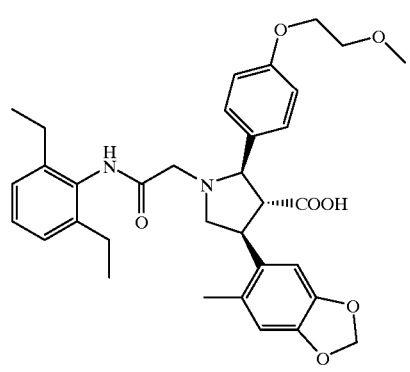
231 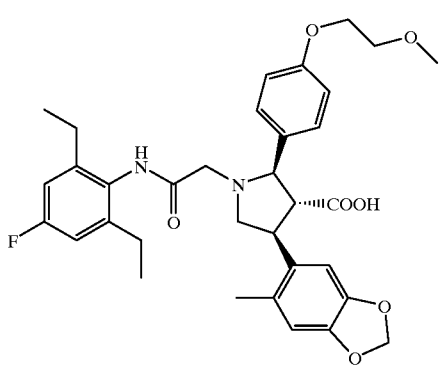 232 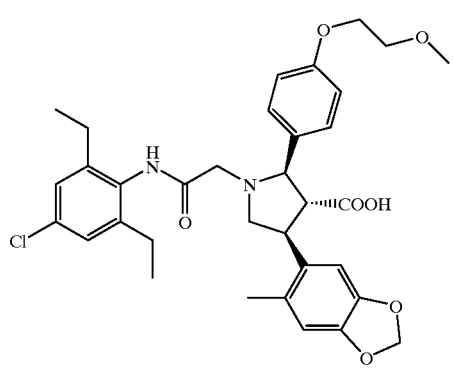

233 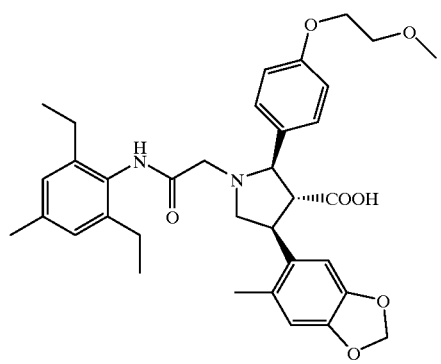
234 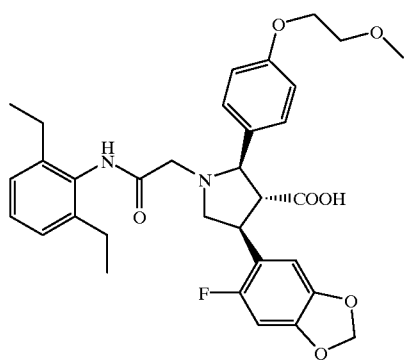
235 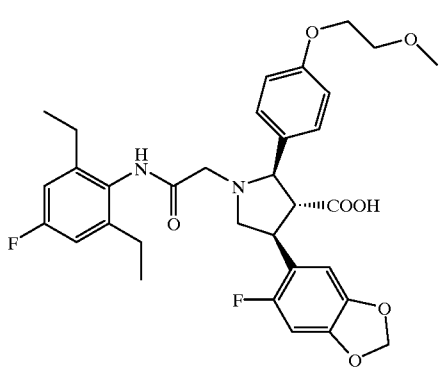
236 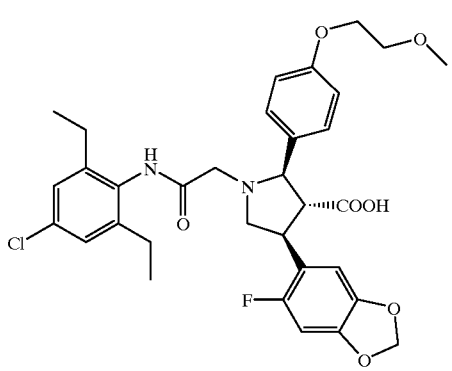
237 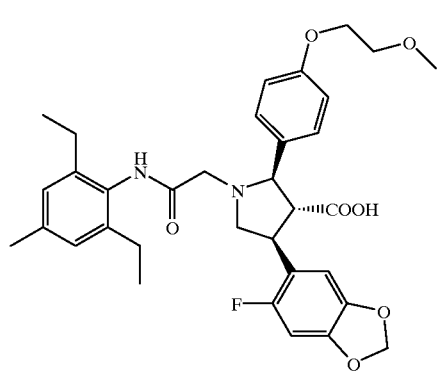
238 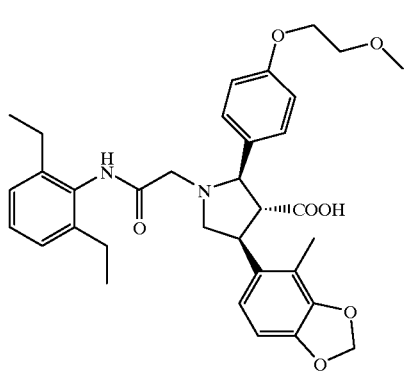
239 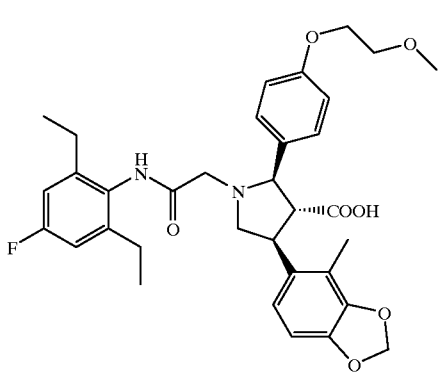
240 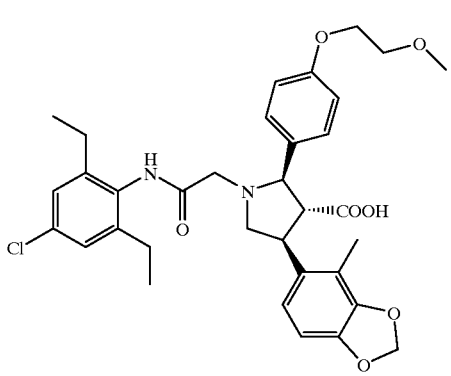

241
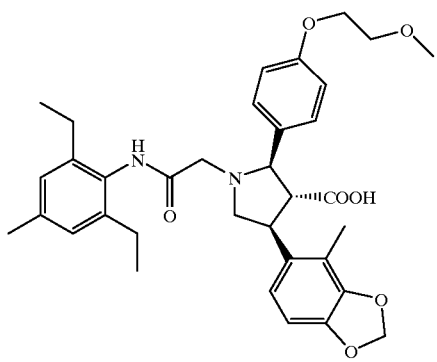
242
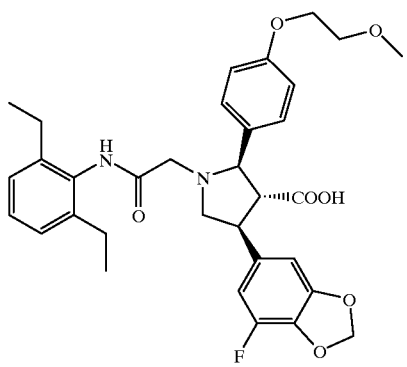
243
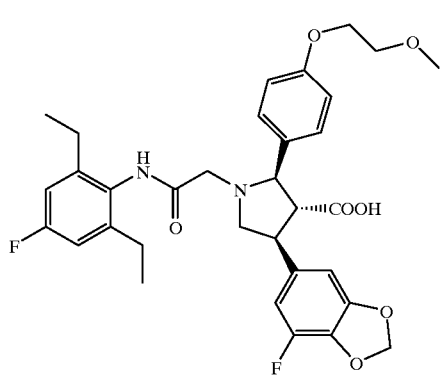
244
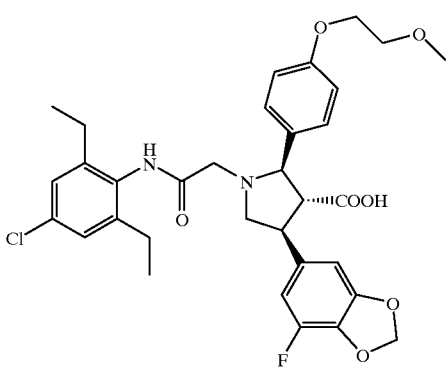
245
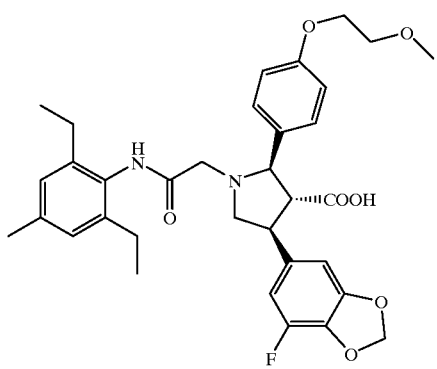
246
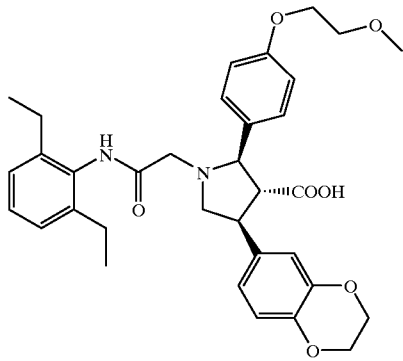
247
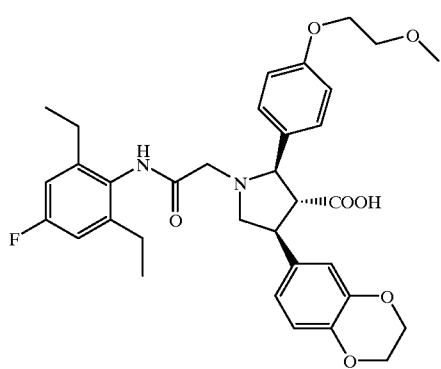
248
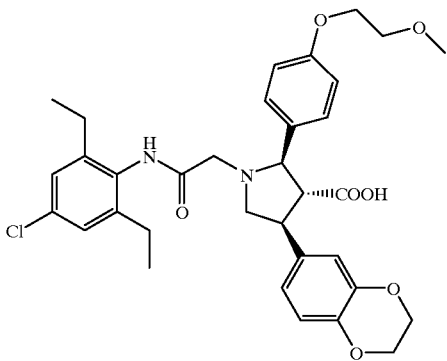

-continued
249 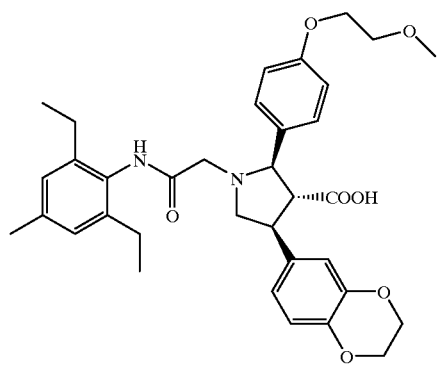
250 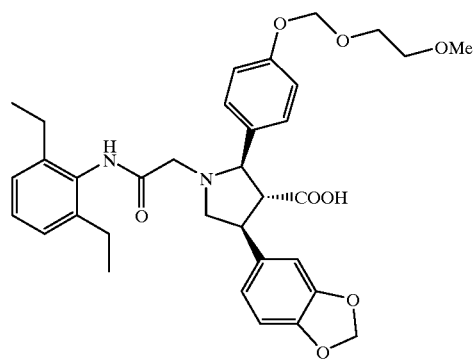
251 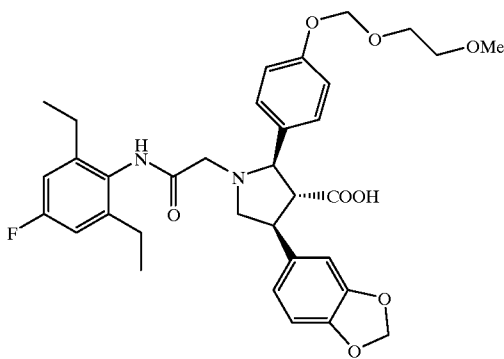
252 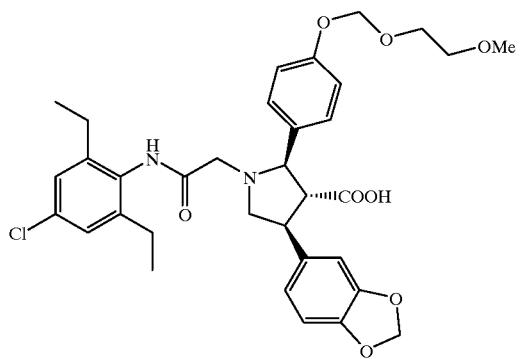
253 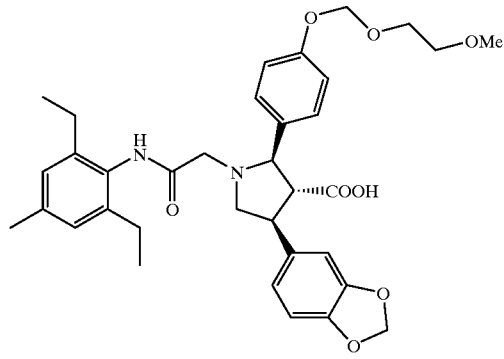
254 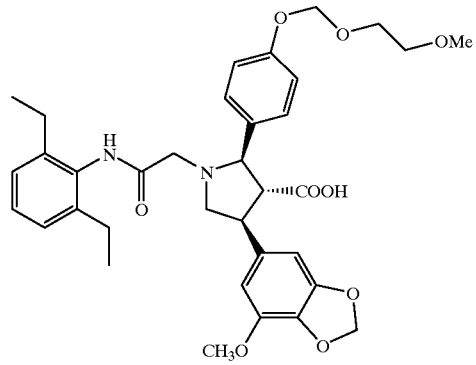
255 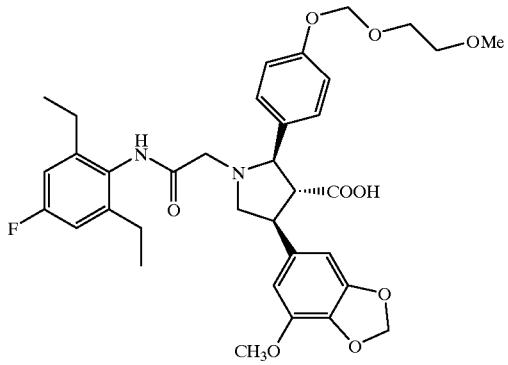
256 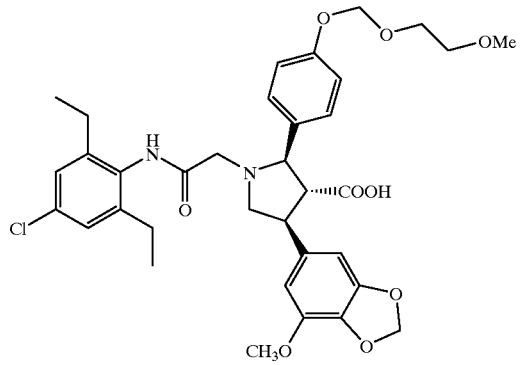

-continued
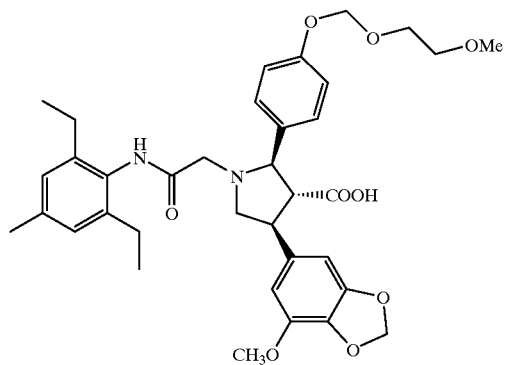
257
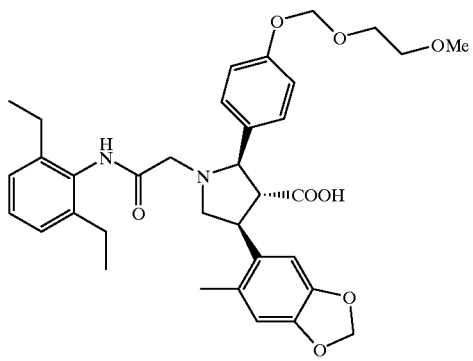
258
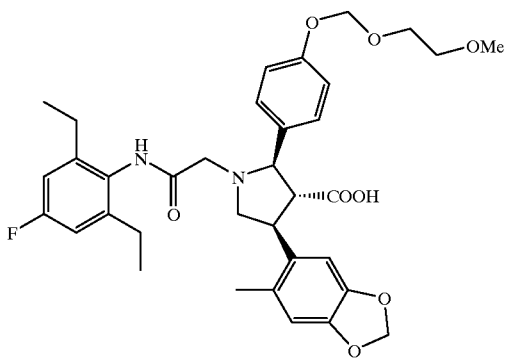
259
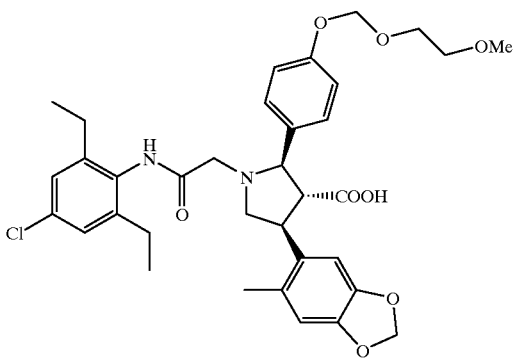
260
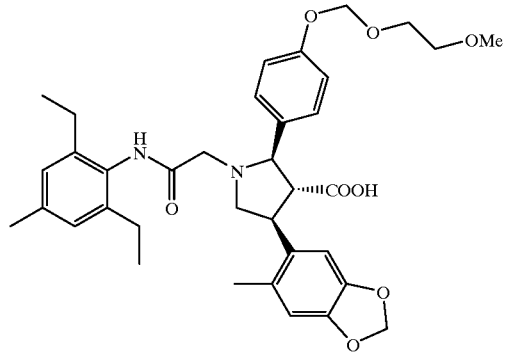
261
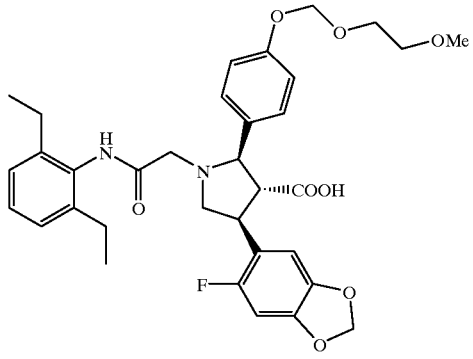
262
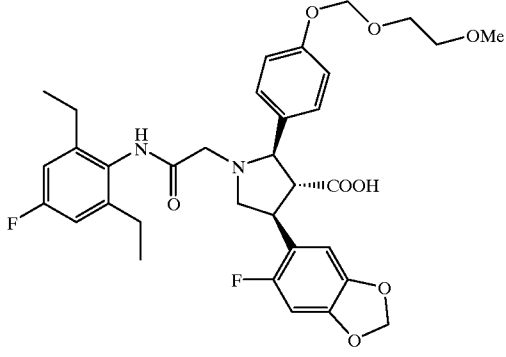
263
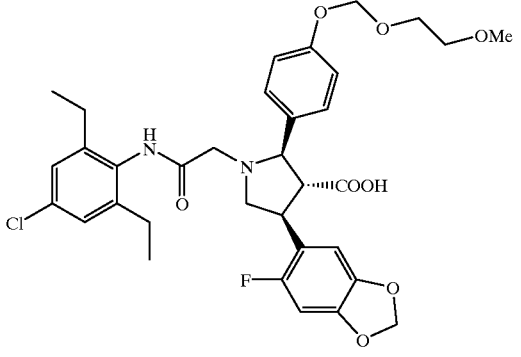
264

265 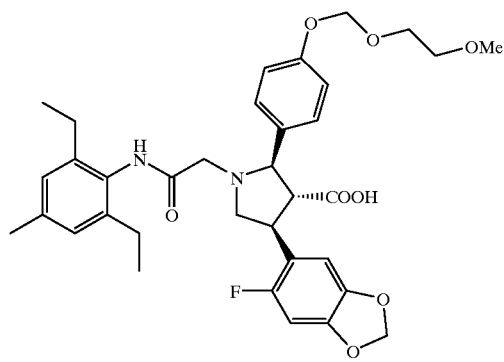
266 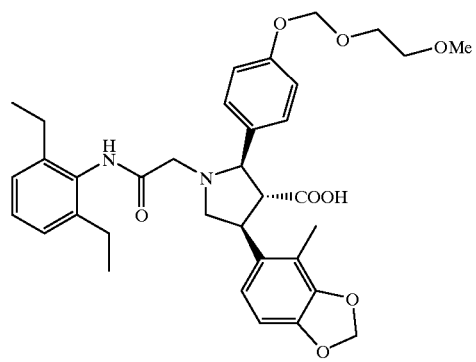
267 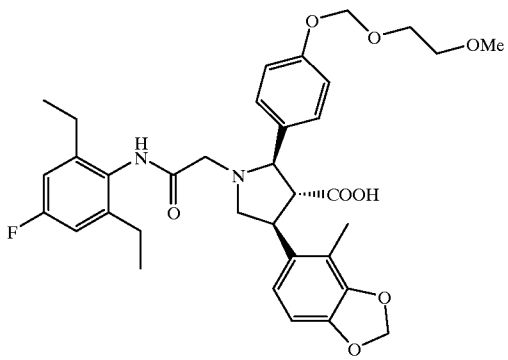
268 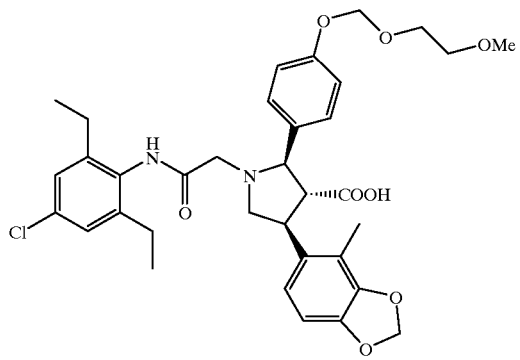
269 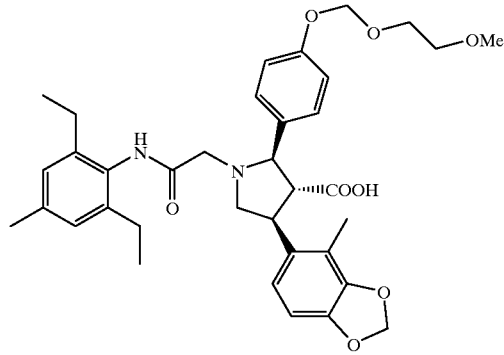
270 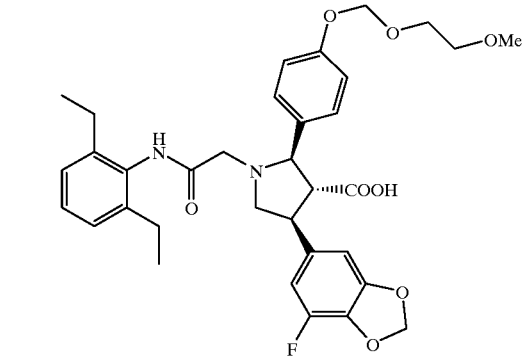
271 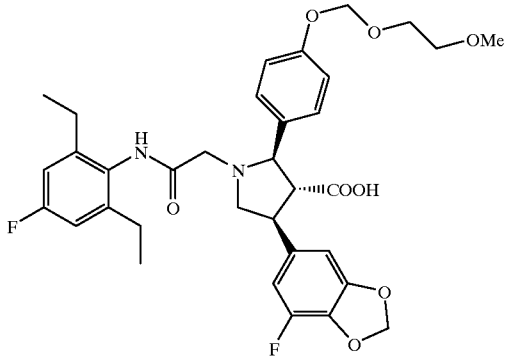
272 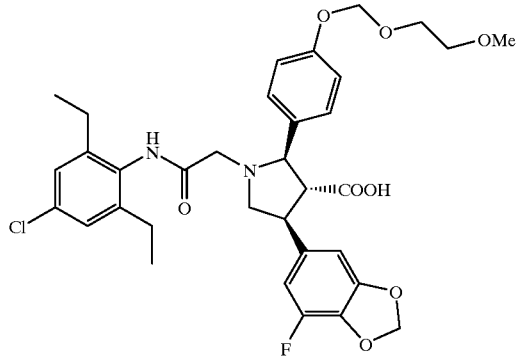

-continued
273
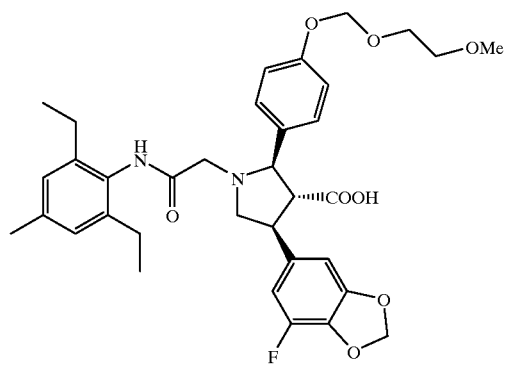
274
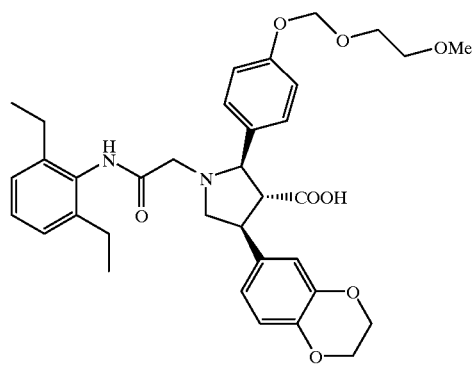
275
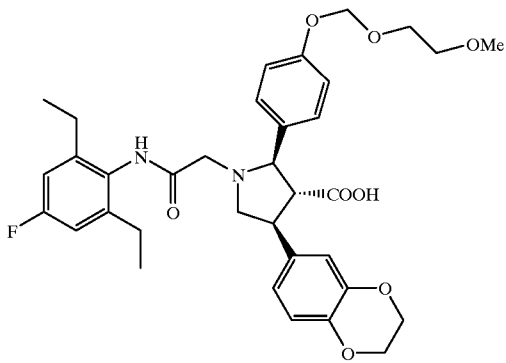
276
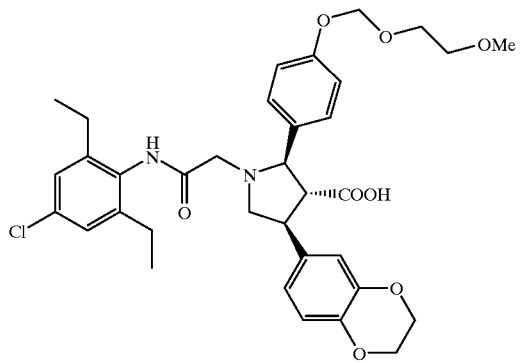
277
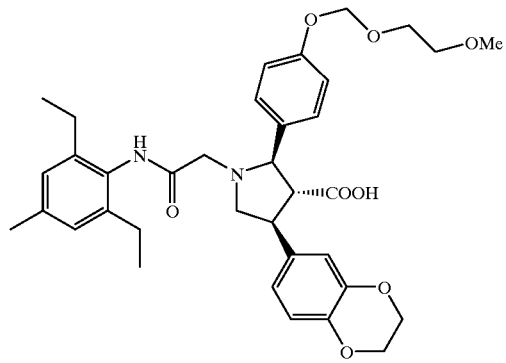
278
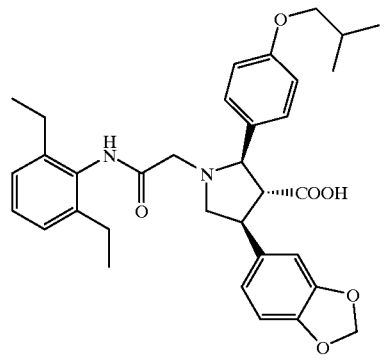
279
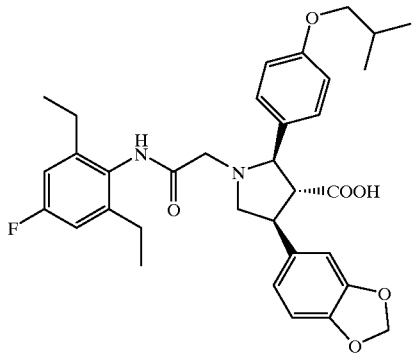
280
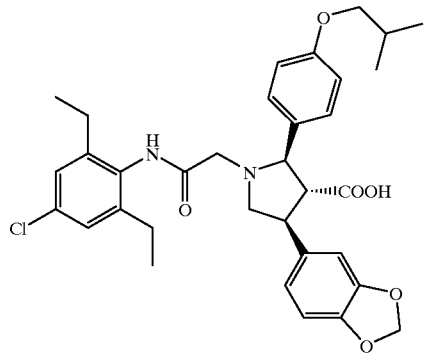

-continued
281
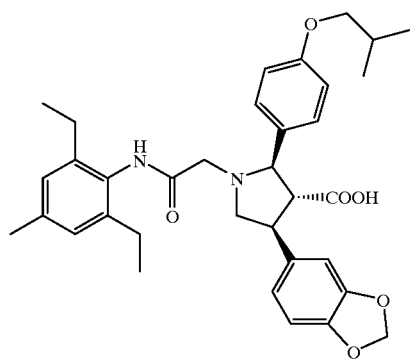
282
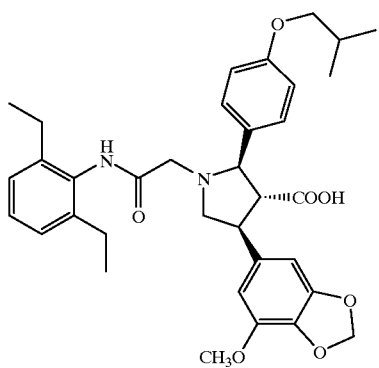
283
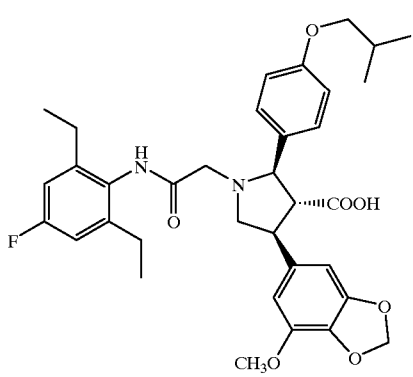
284
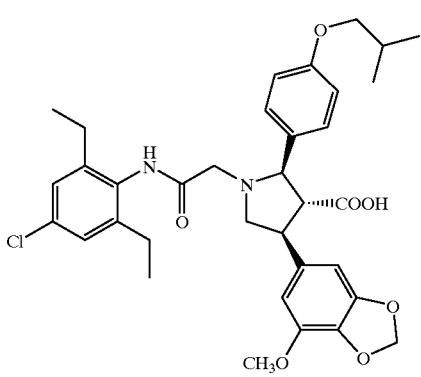
285
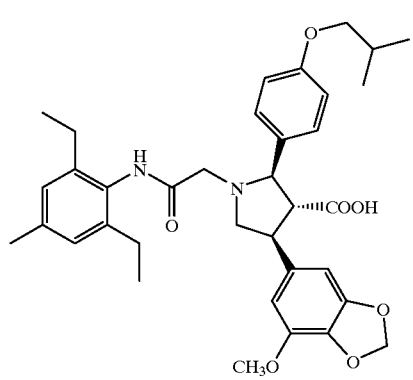
286
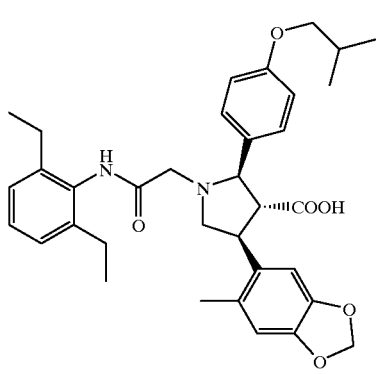
287
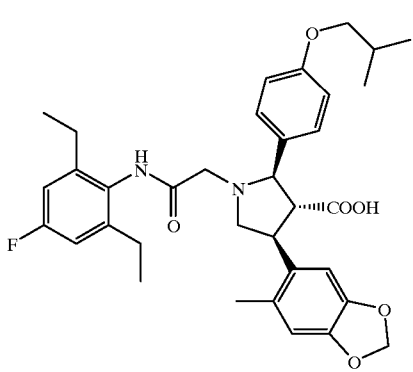
288
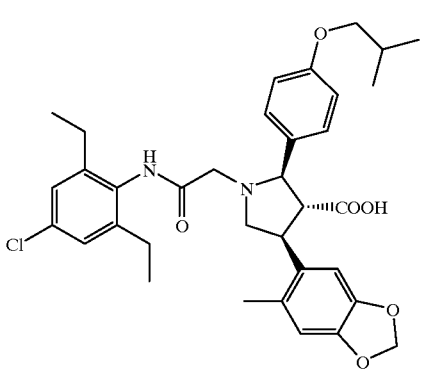

-continued
289
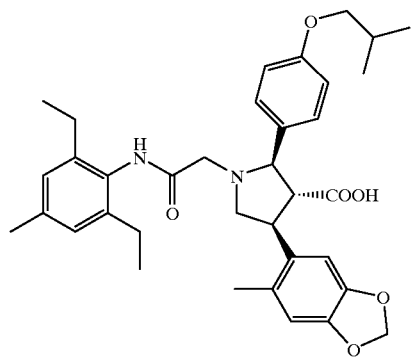
290
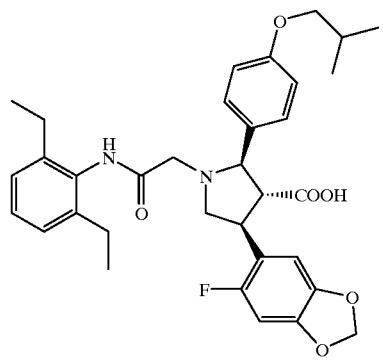
291
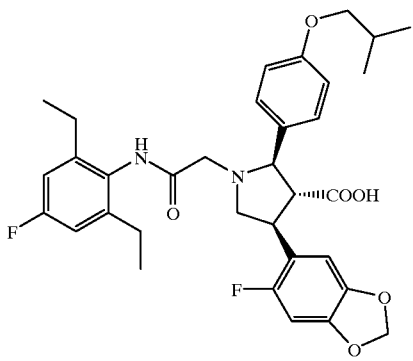
292
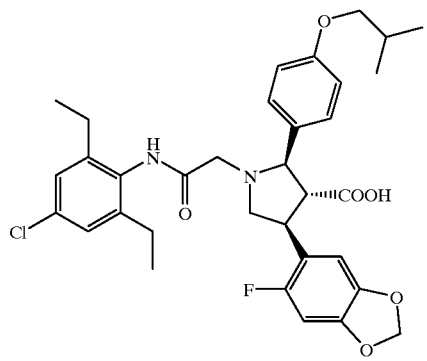
293
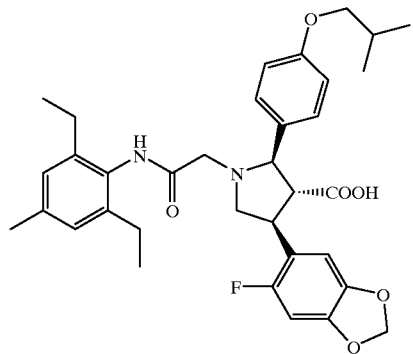
294
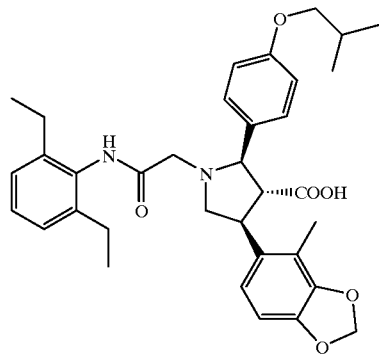
295
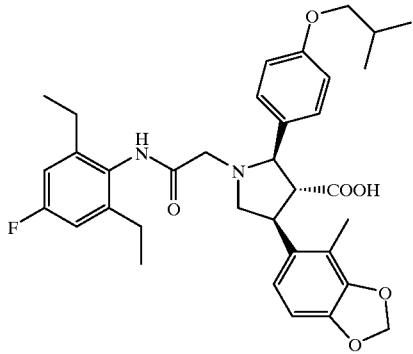
296
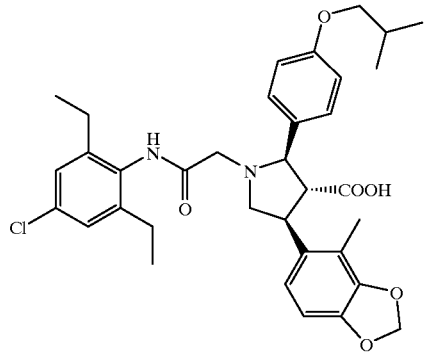

-continued
| 297 | 298 |
|---|---|
| 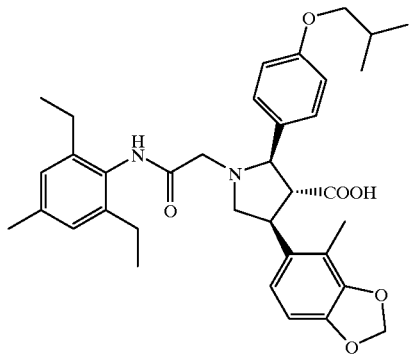 | 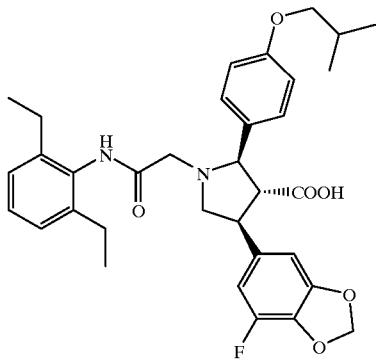 |
| 299 | 300 |
| 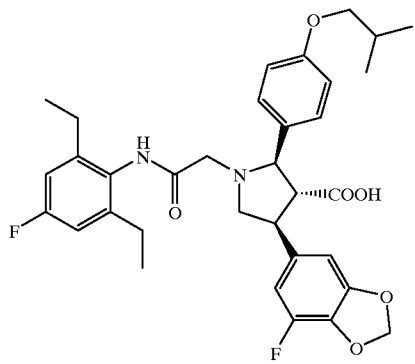 | 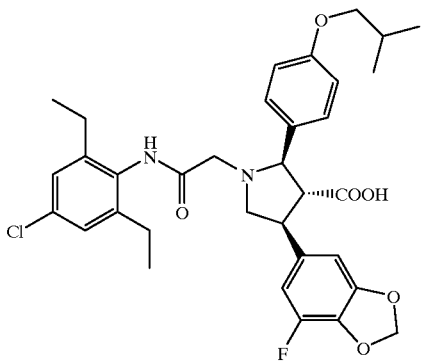 |
| 301 | 302 |
| 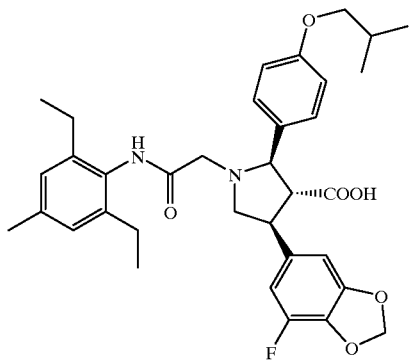 | 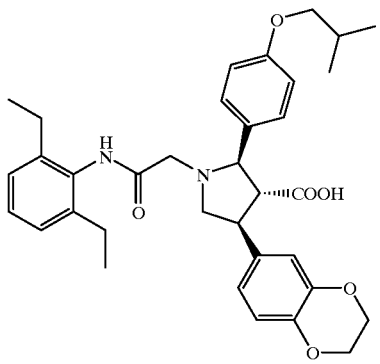 |
| 303 | 304 |
| 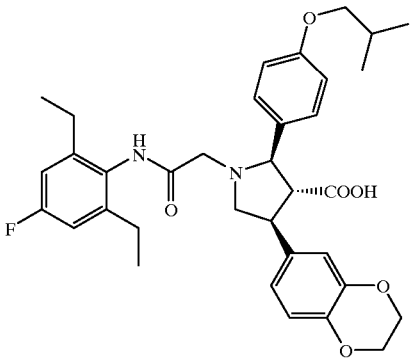 | 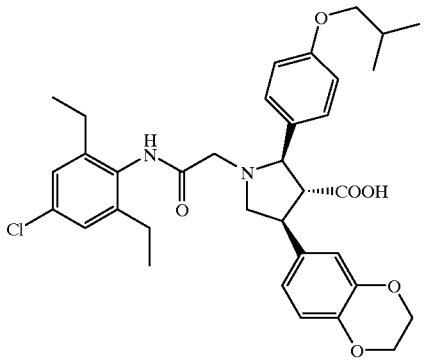 |

-continued
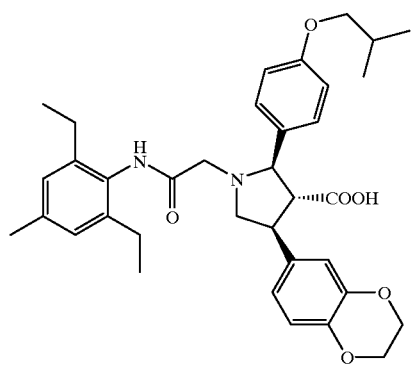
305
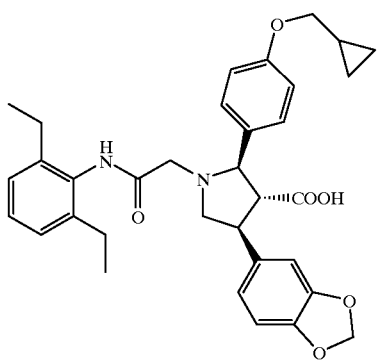
306
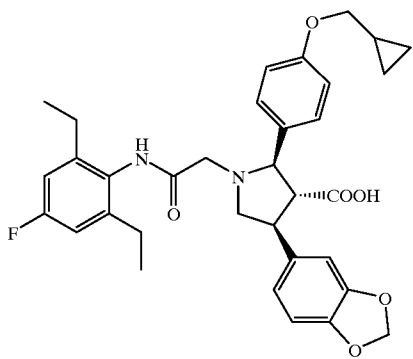
307
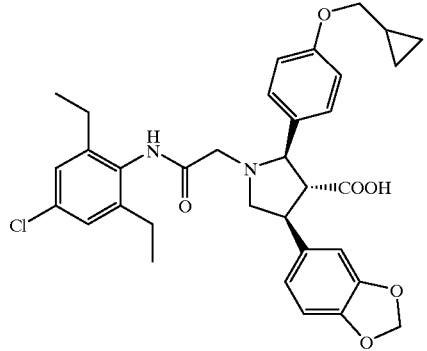
308
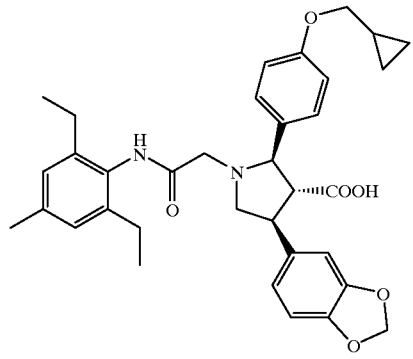
309
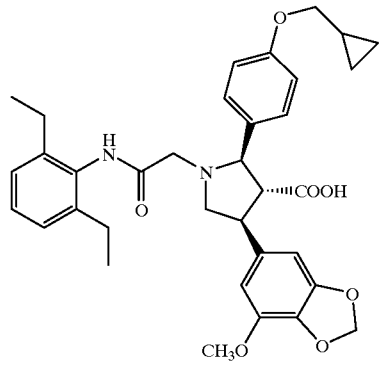
310
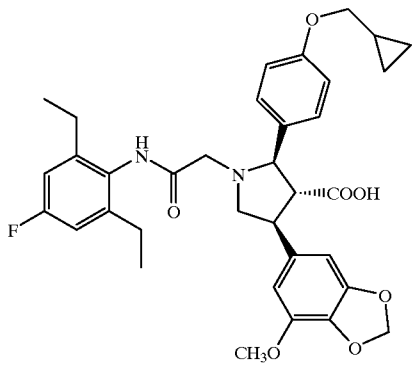
311
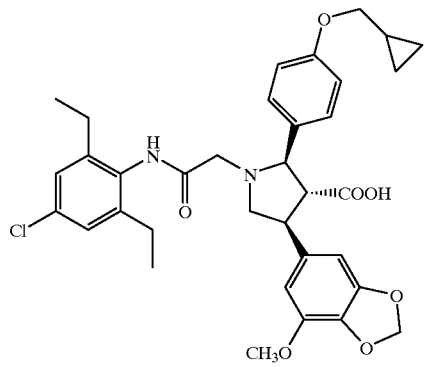
312

-continued
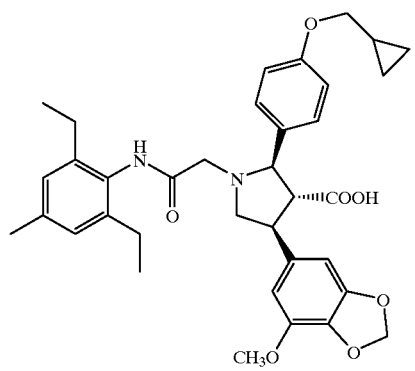
313
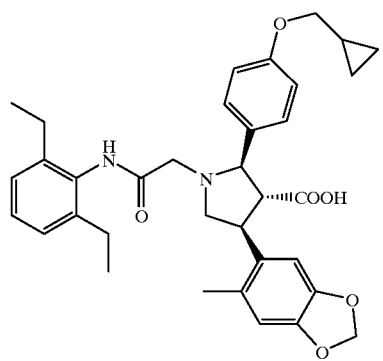
314
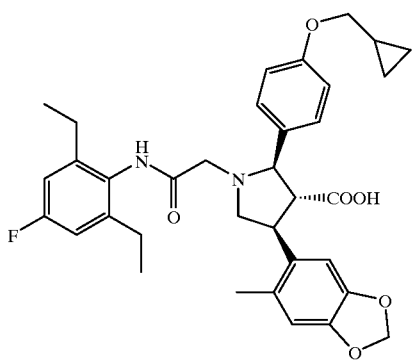
315
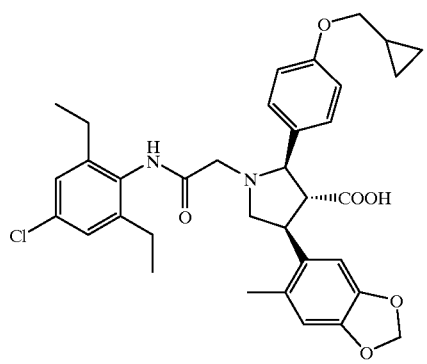
316
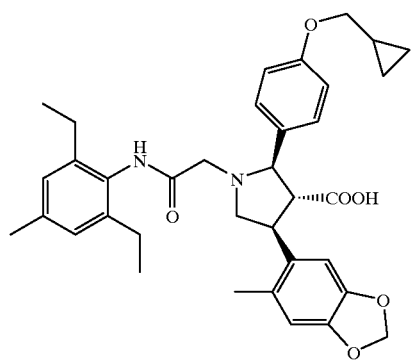
317
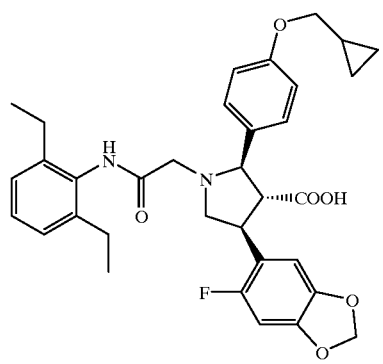
318
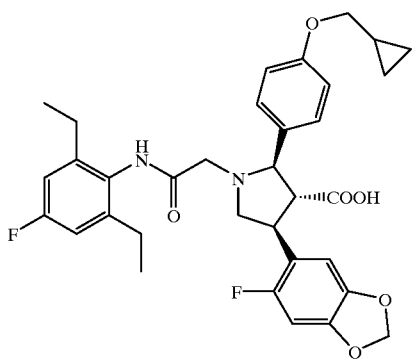
319
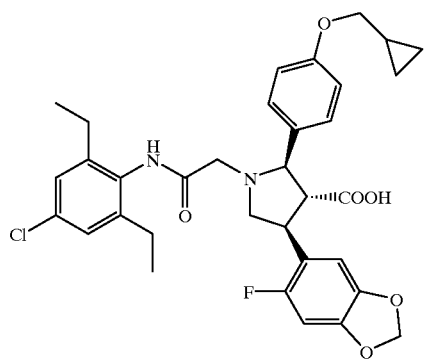
320

-continued
| 321 | 322 |
|---|---|
| 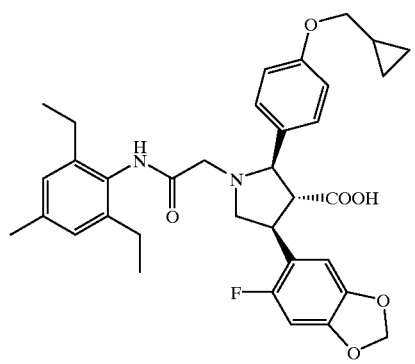 | 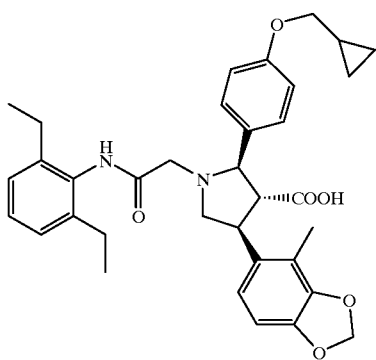 |
| 323 | 324 |
| 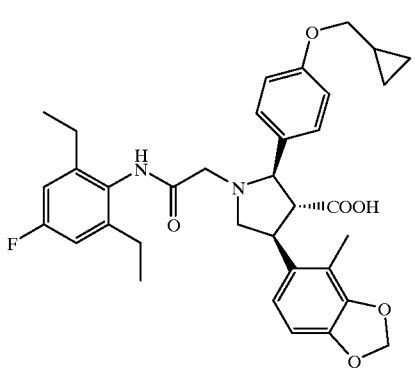 | 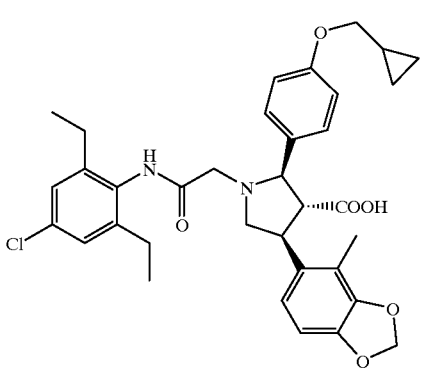 |
| 325 | 326 |
| 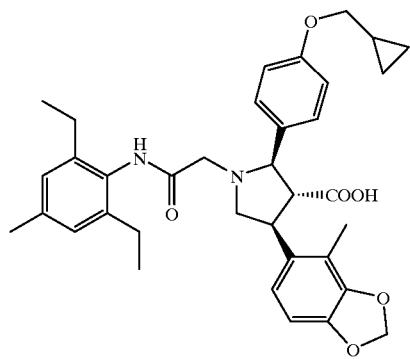 | 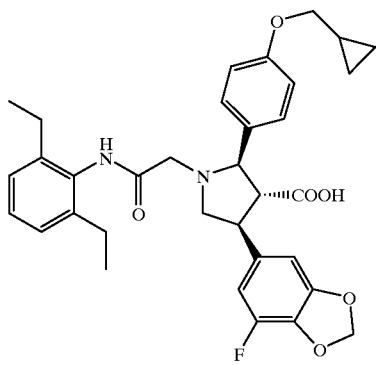 |
| 327 | 328 |
| 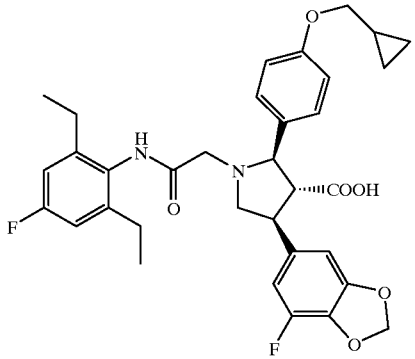 | 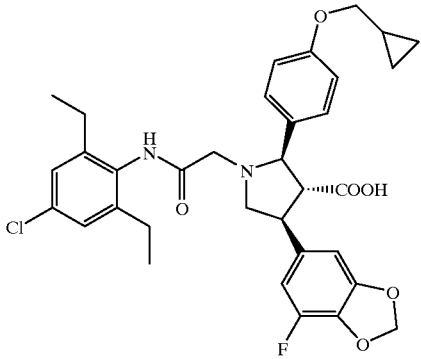 |

127 128
-continued
| 329 | 330 |
|---|---|
| 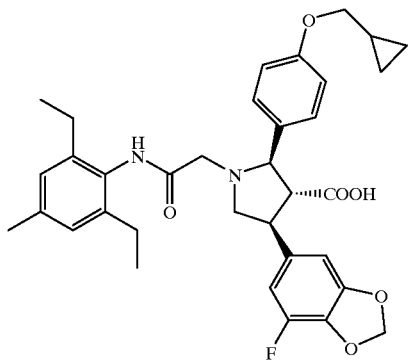 | 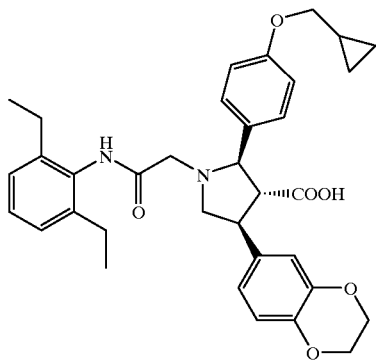 |
| 331 | 332 |
| 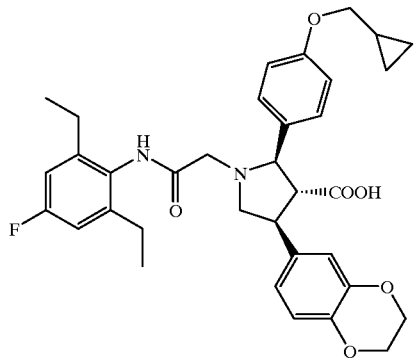 | 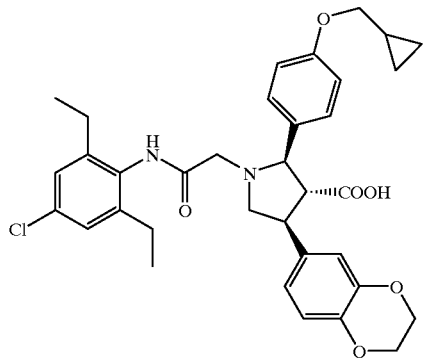 |
| 333 | 334 |
| 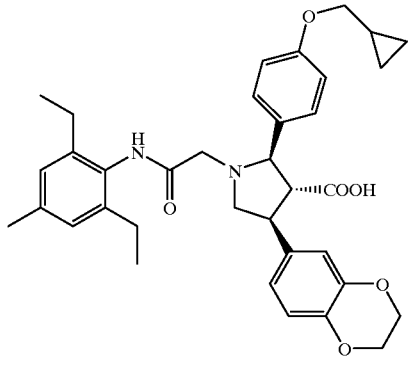 | 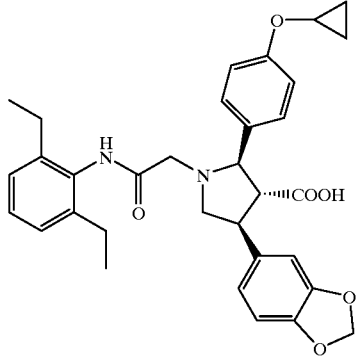 |
| 335 | 336 |
| 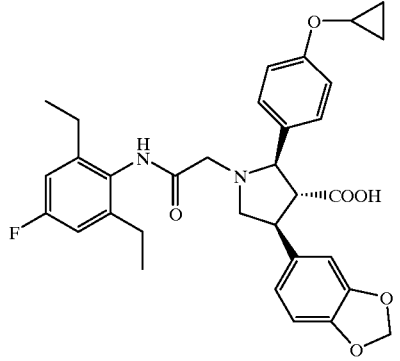 | 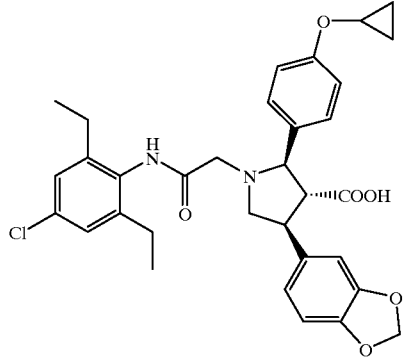 |

129 130
-continued
337 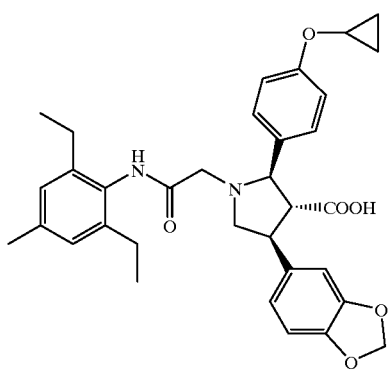 338 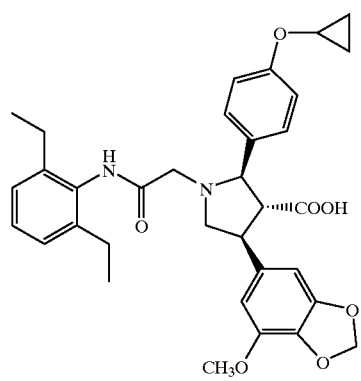
339 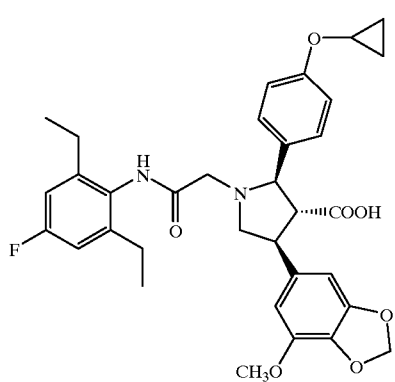 340 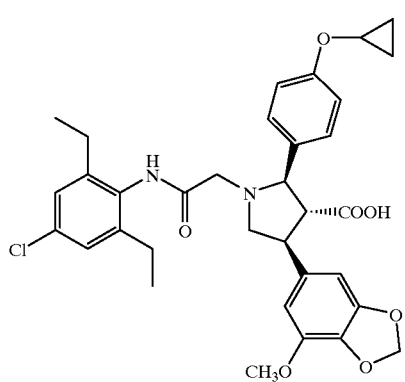
341 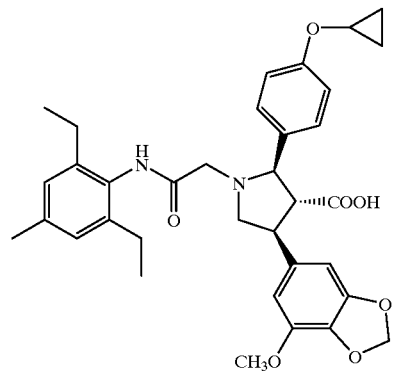 342 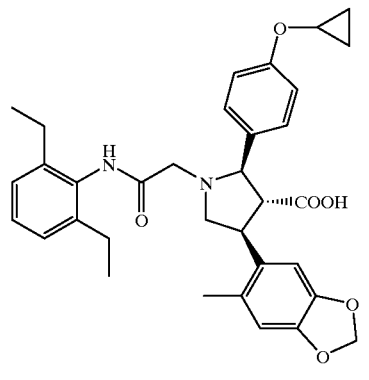
343 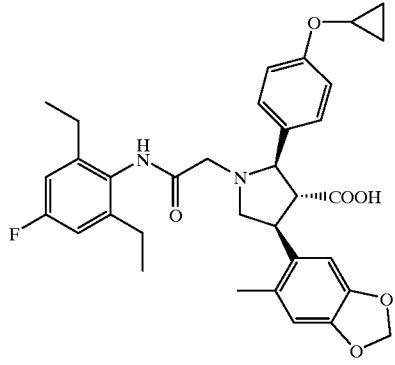 344 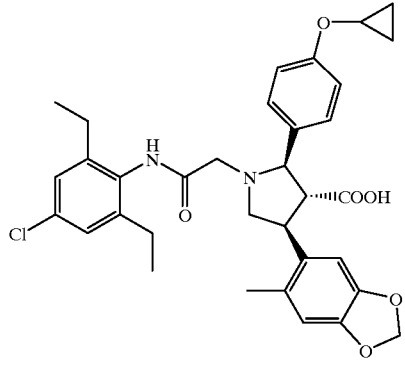

-continued
345
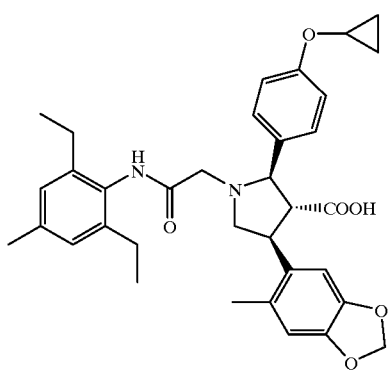
346
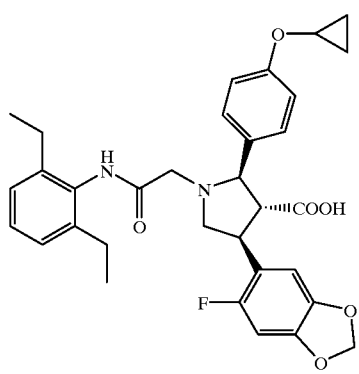
347
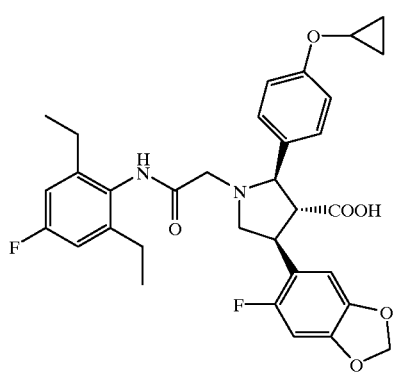
348
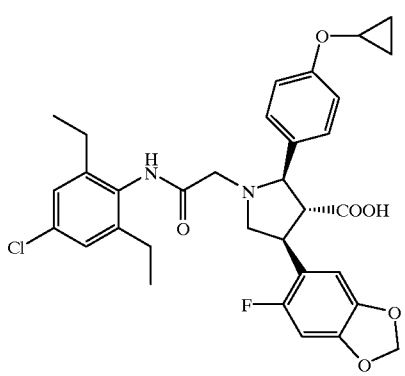
349
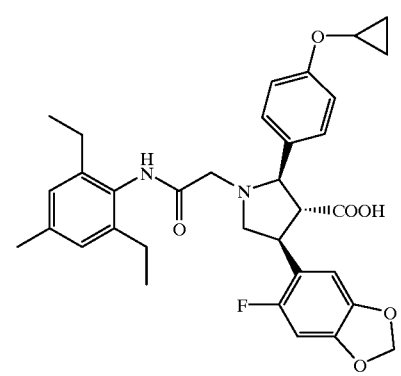
350
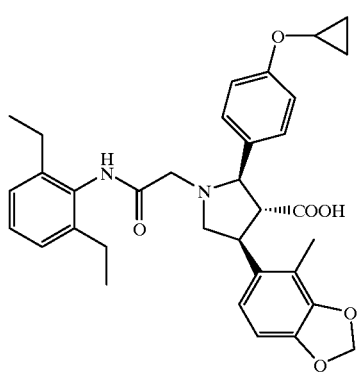
351
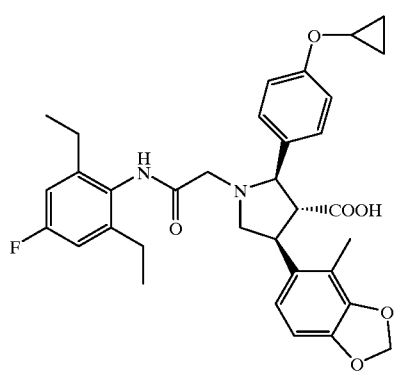
352
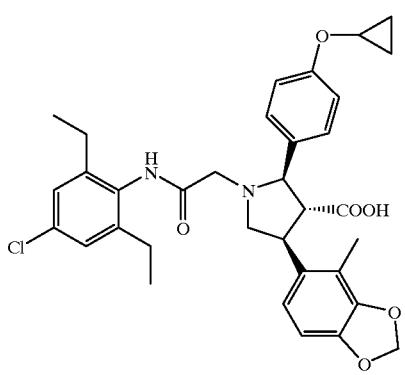

-continued
353
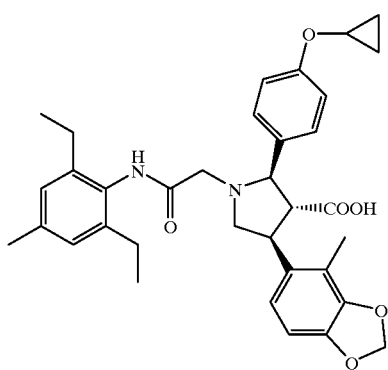
354
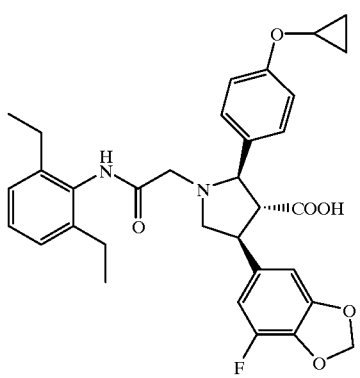
355
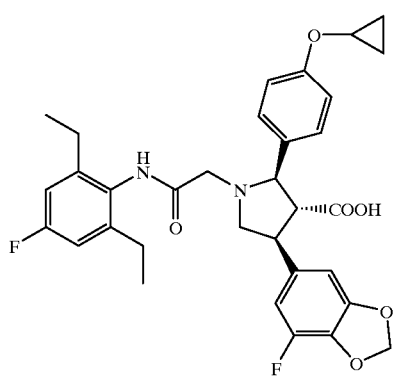
356
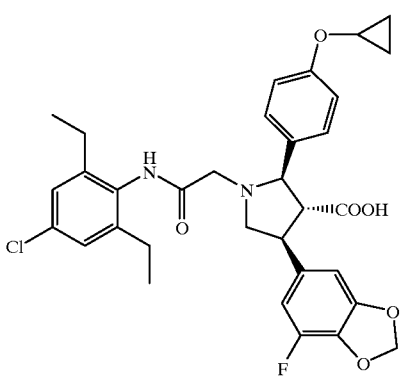
357
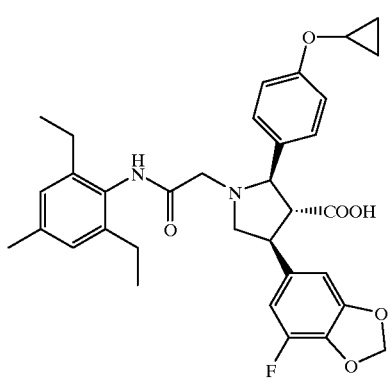
358
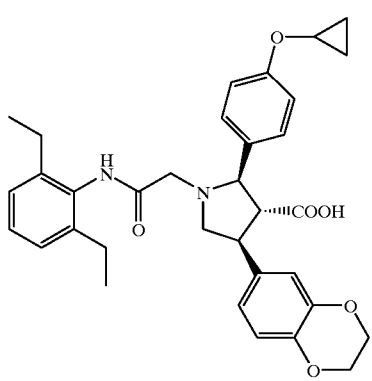
359
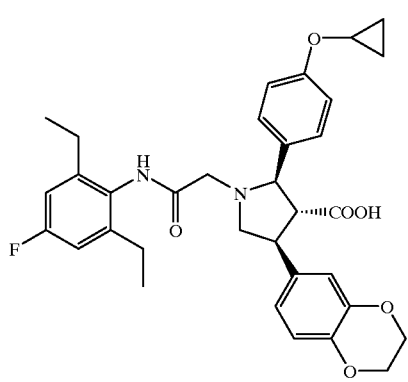
360
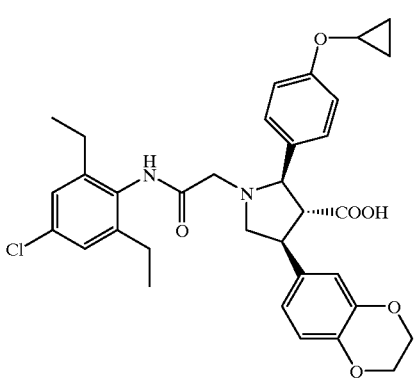

135 136
-continued
361 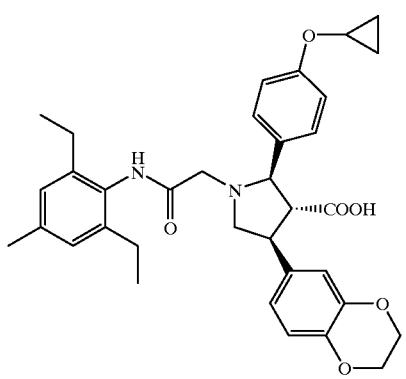 362 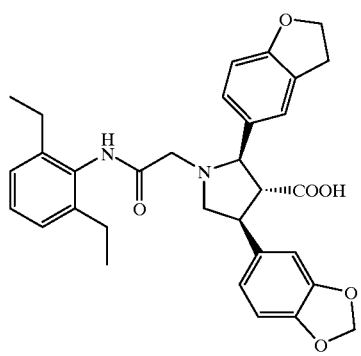
363 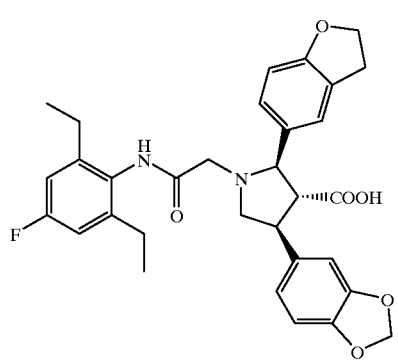 364 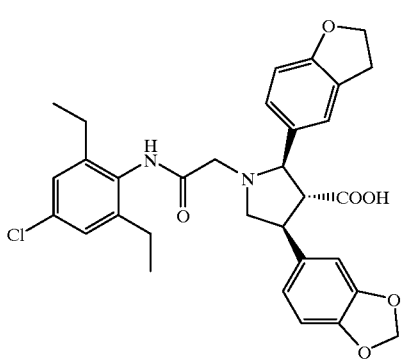
365 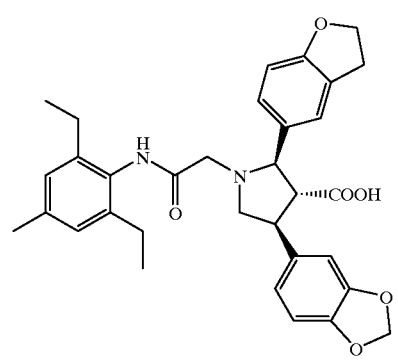 366 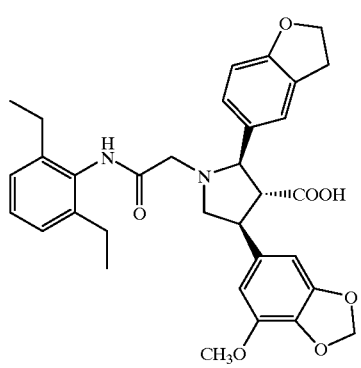
367 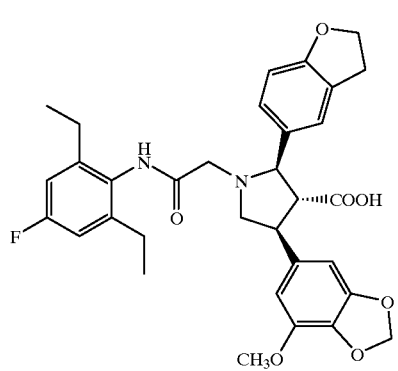 368 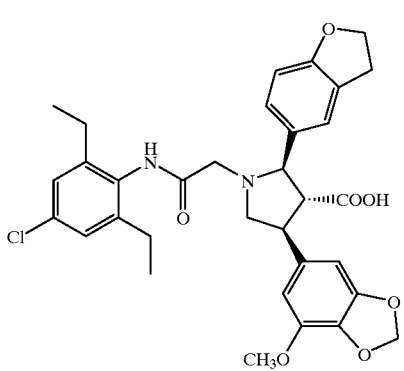

369 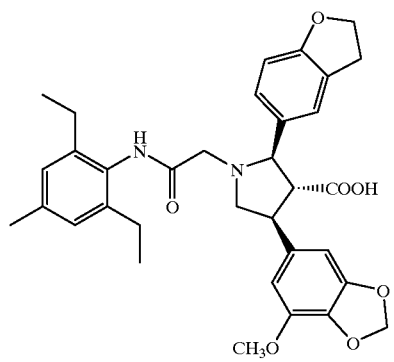
370 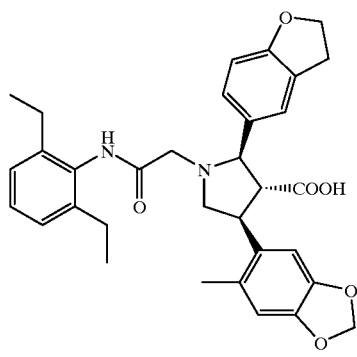
371 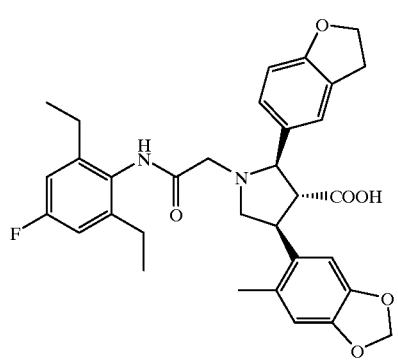
372 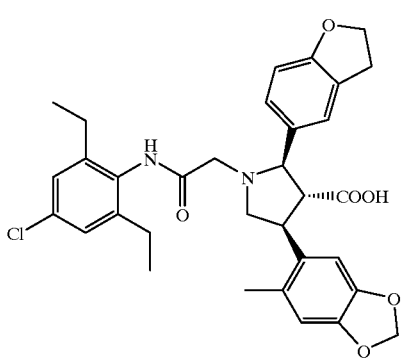
373 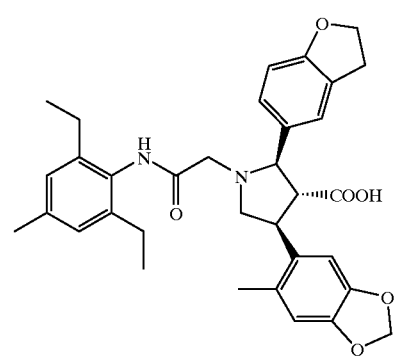
374 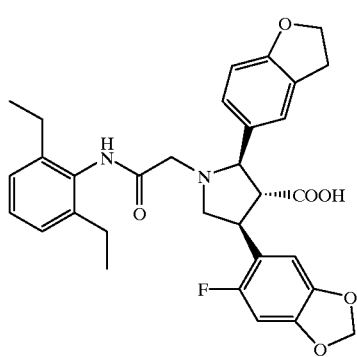
375 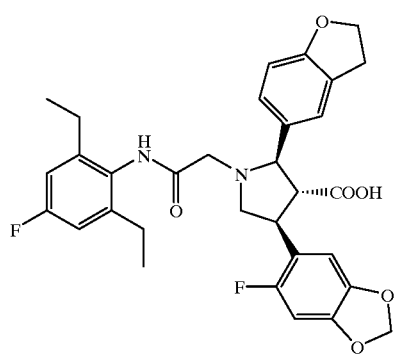
376 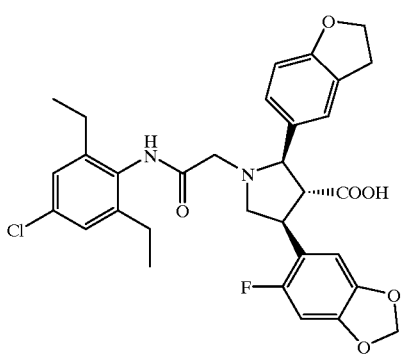

-continued
377
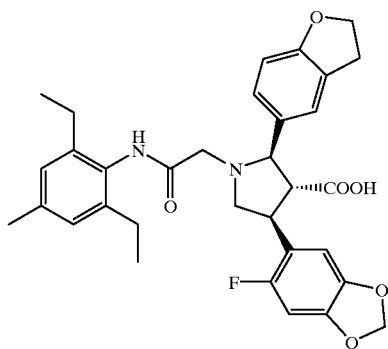
378
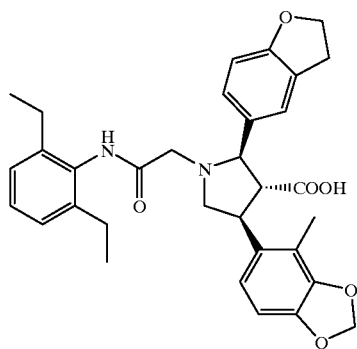
379
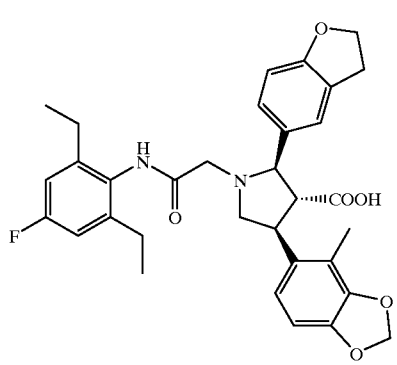
380
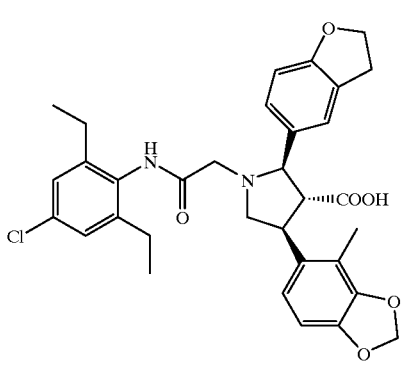
381
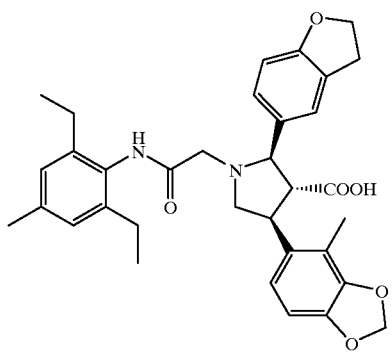
382
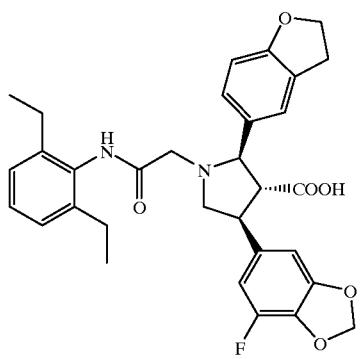
383
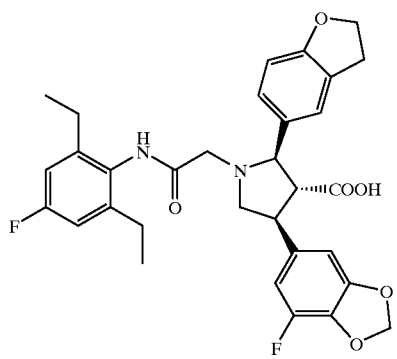
384
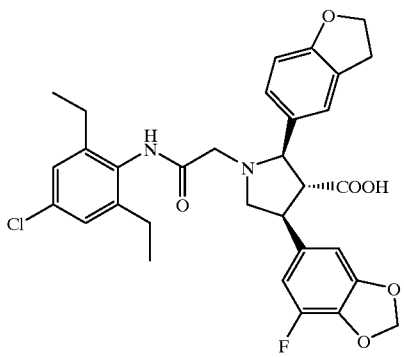

-continued
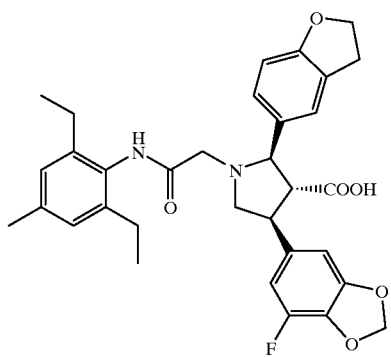
385
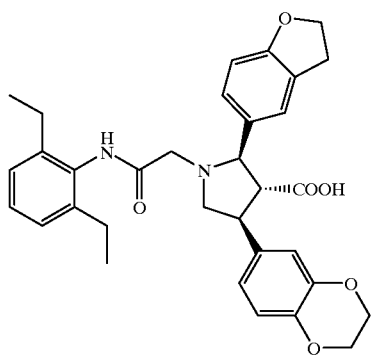
386
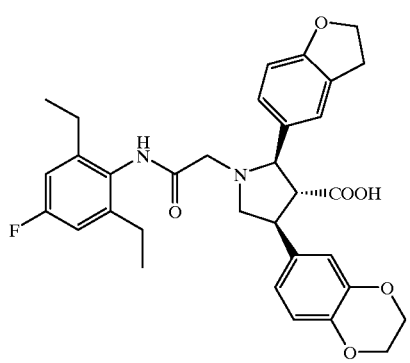
387
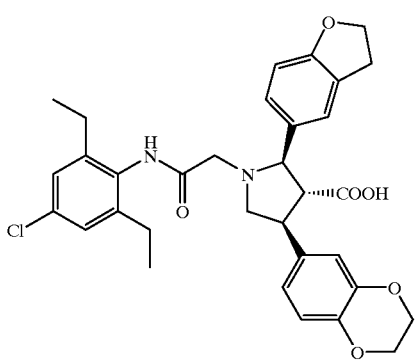
388
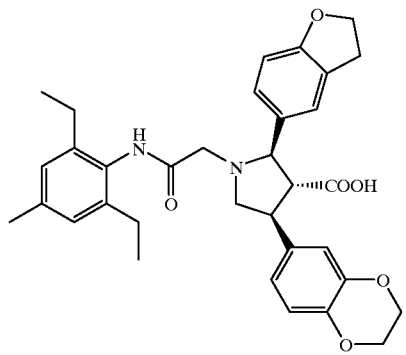
389
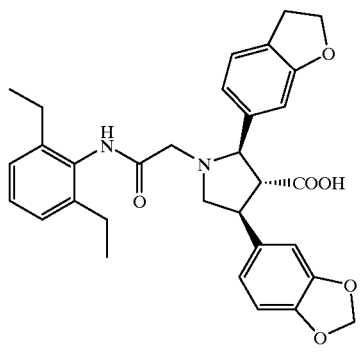
390
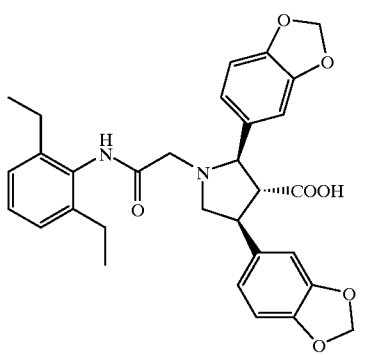
391
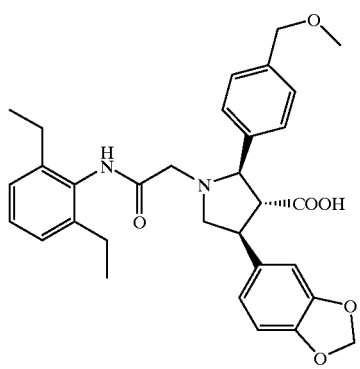
392

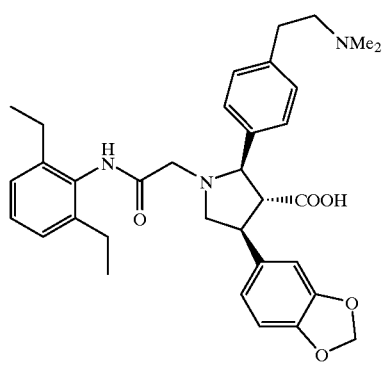
393
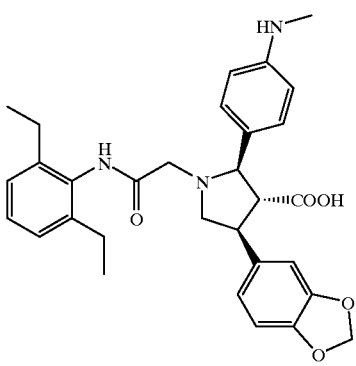
394
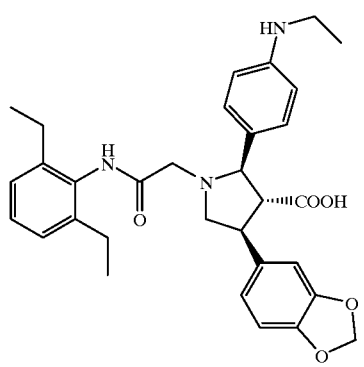
395
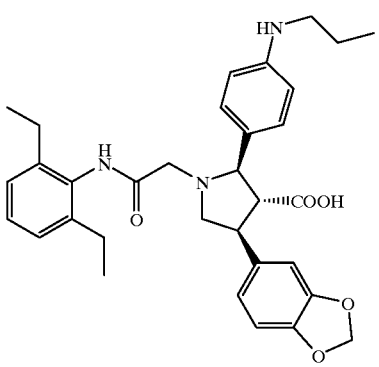
396
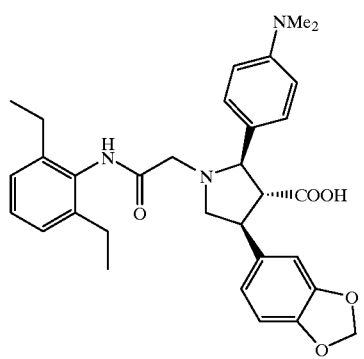
397
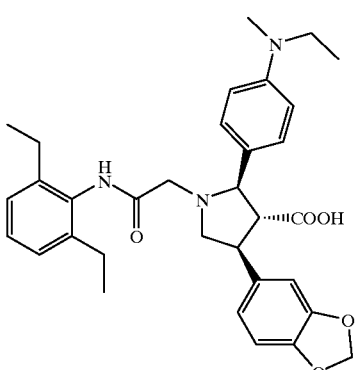
398
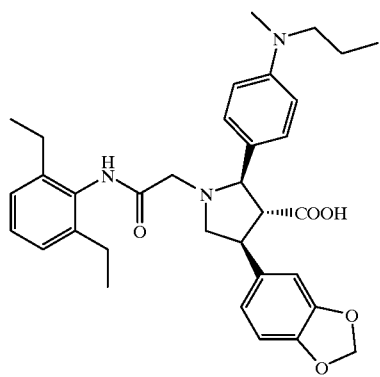
399
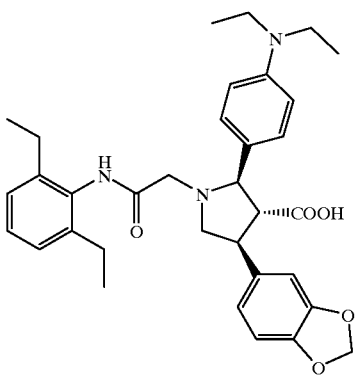
400

-continued
401
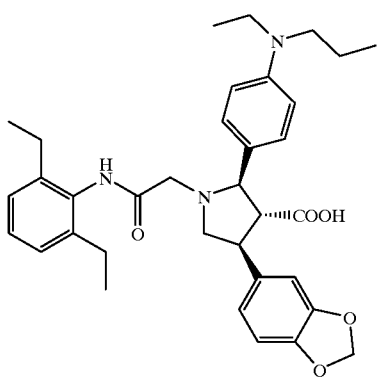
402
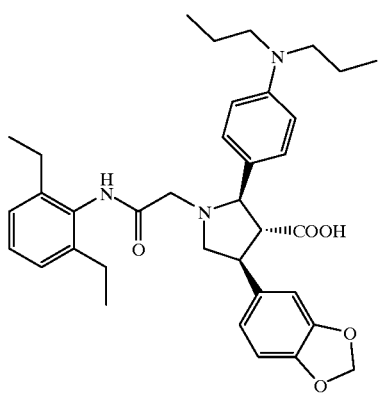
403
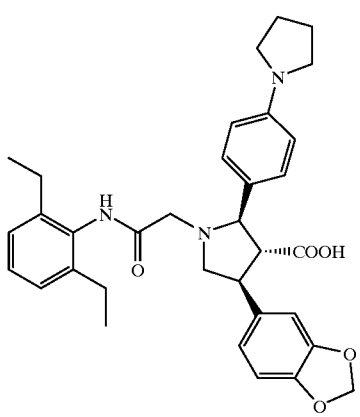
404
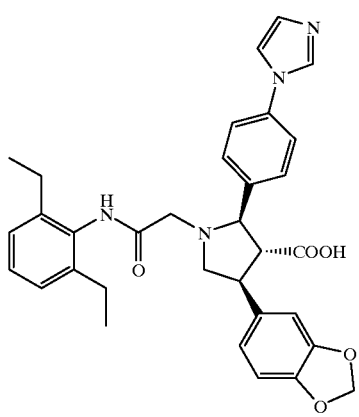
405
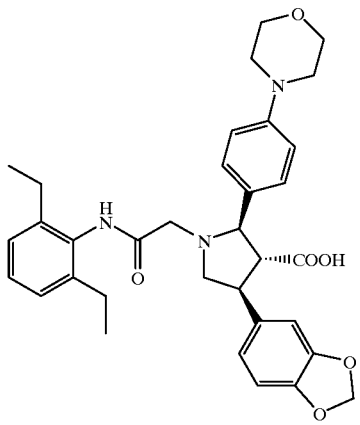
406
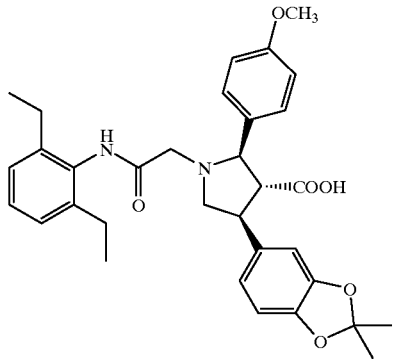
407
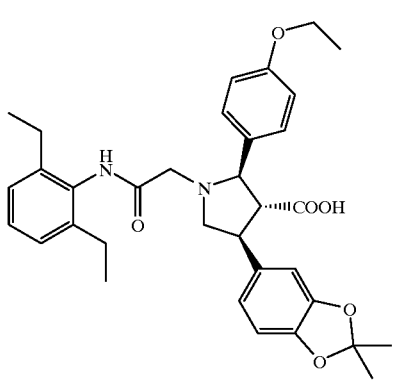
408
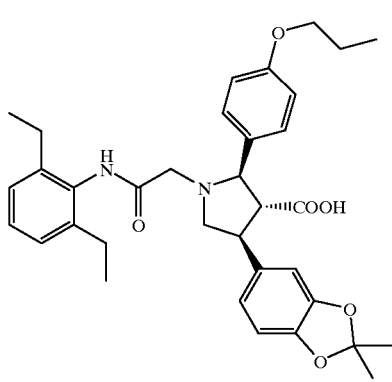

-continued
| 409 | 410 |
|---|---|
| 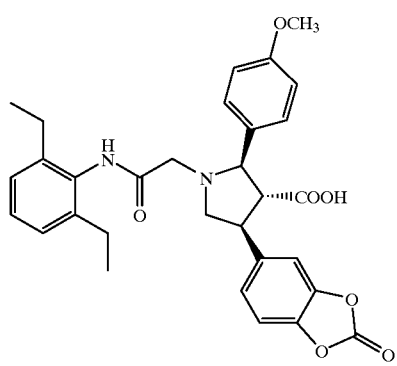 | 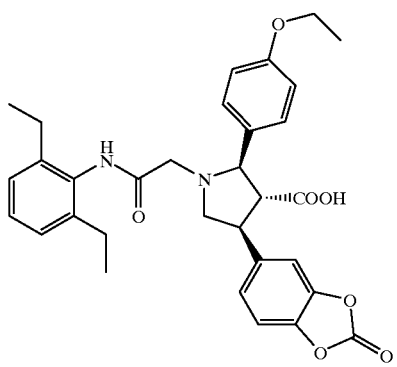 |
| 411 | 412 |
| 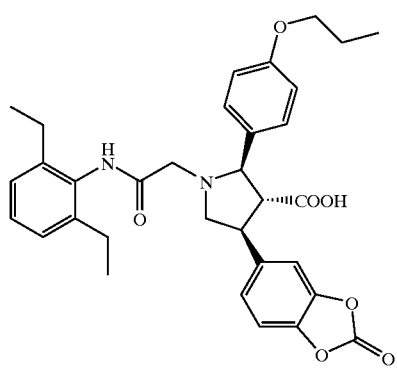 | 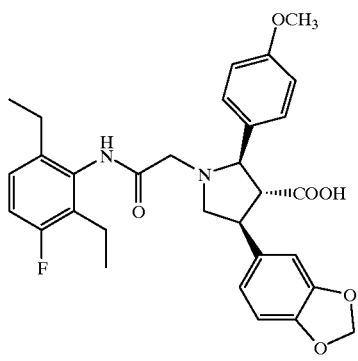 |
| 413 | 414 |
| 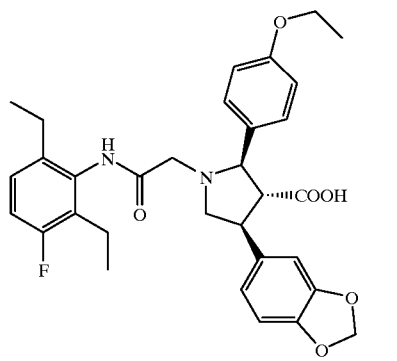 | 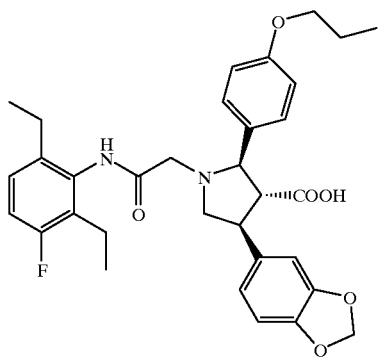 |
| 415 | 416 |
| 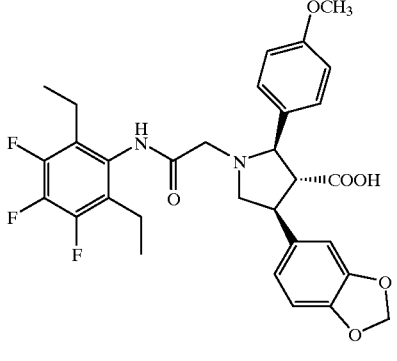 | 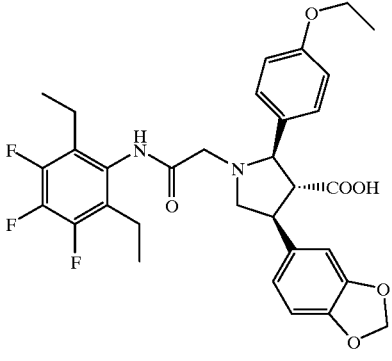 |

-continued
| 417 | 418 |
|---|---|
| 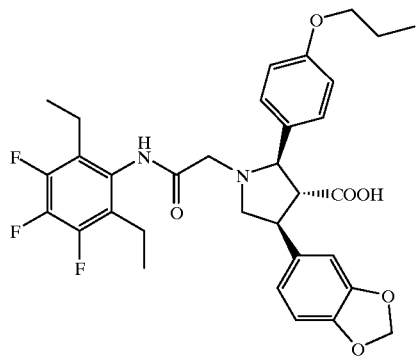 | 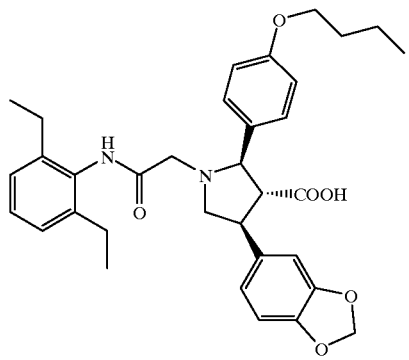 |
| 419 | 420 |
| 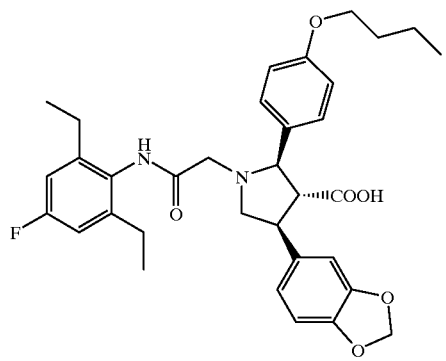 | 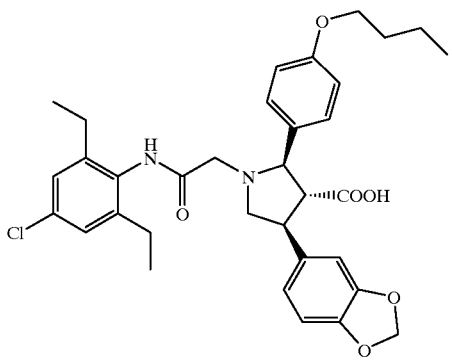 |
| 421 | 422 |
| 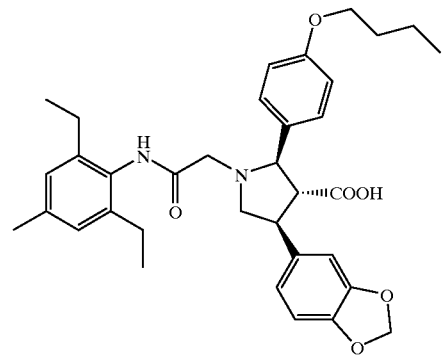 | 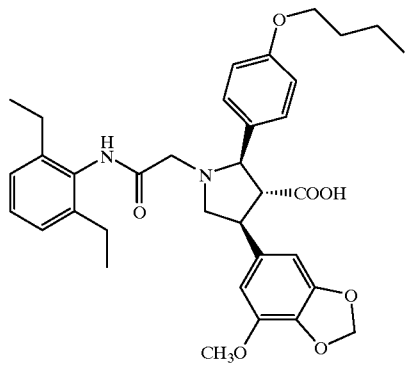 |
| 423 | 424 |
| 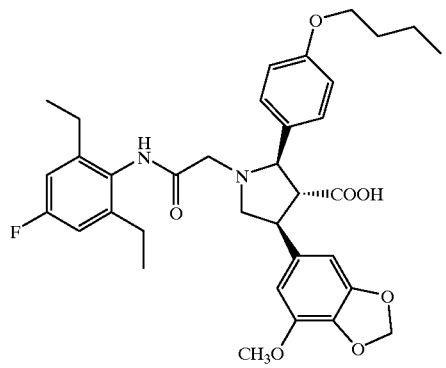 | 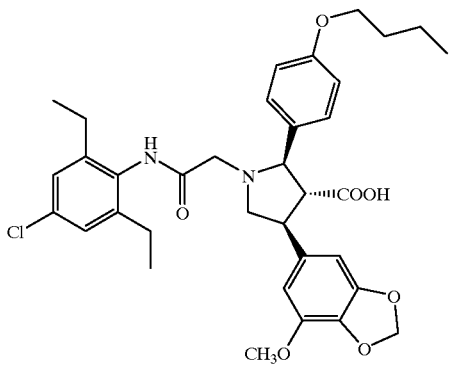 |

151	152
-continued
425 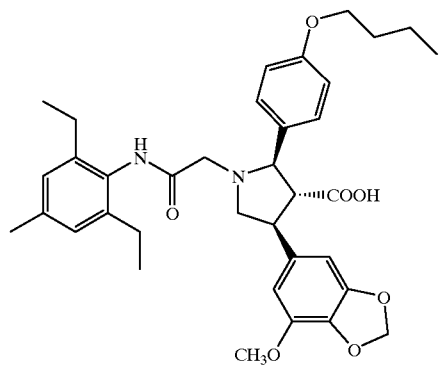 426 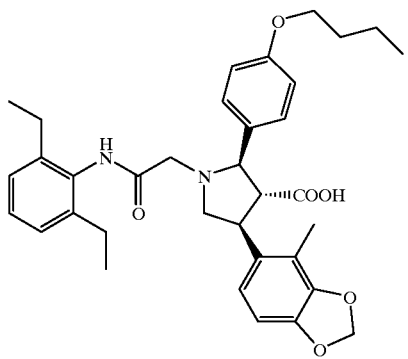
427 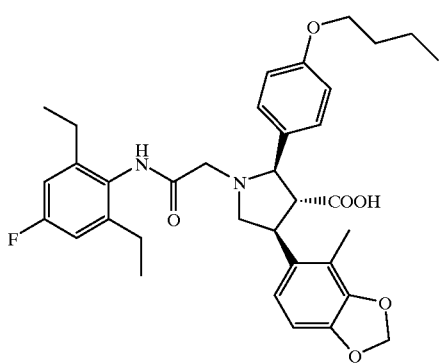 428 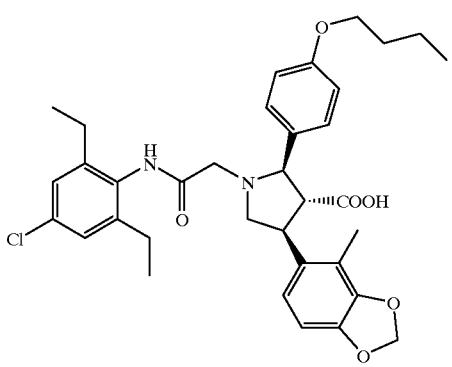
429 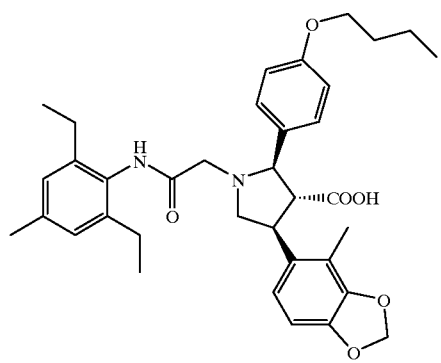 430 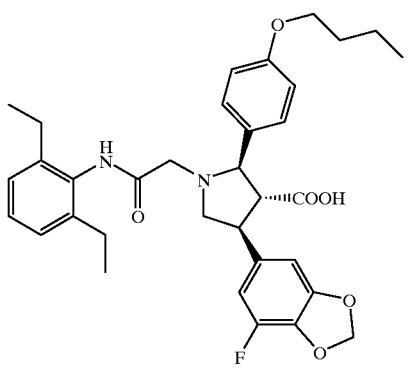
431 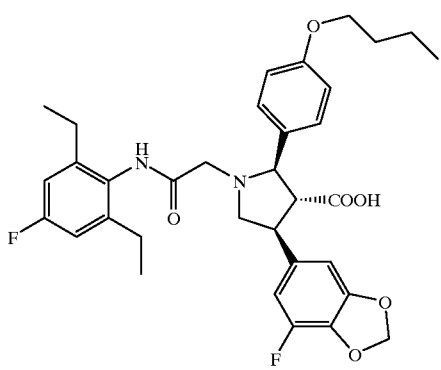 432 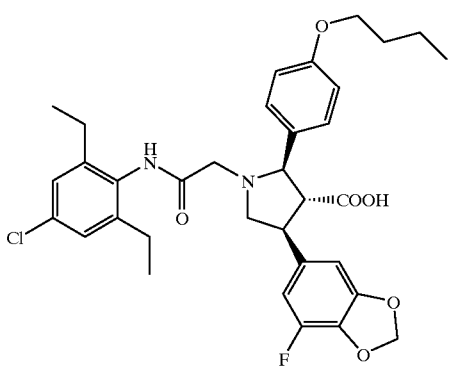

153               154
                -continued
        433                        434
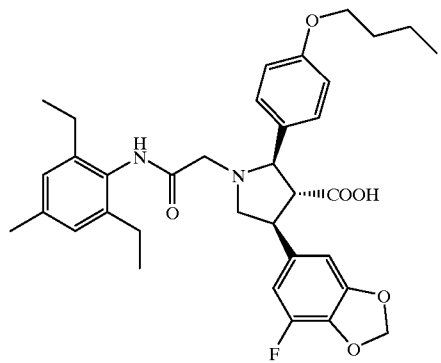              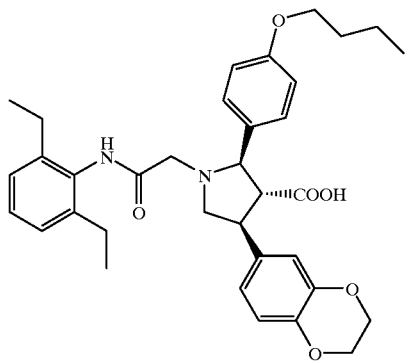
        435                        436
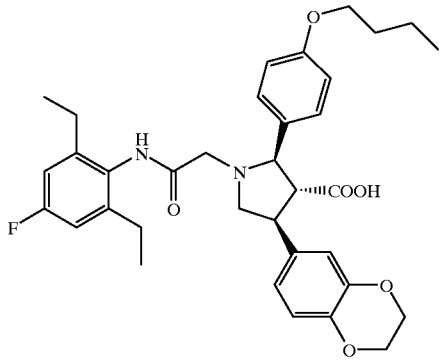              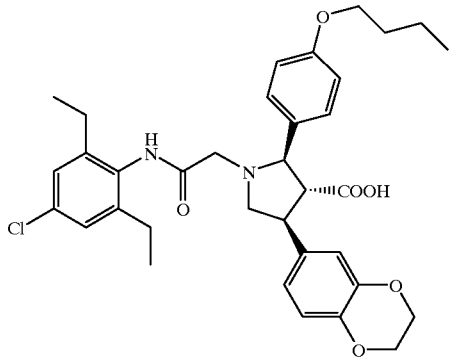
        437                        438
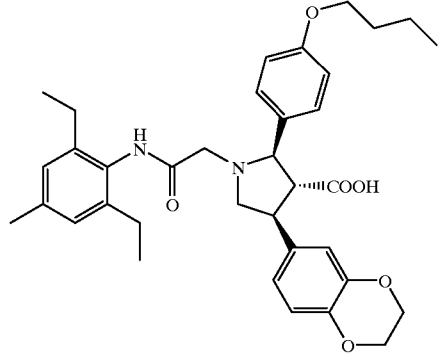              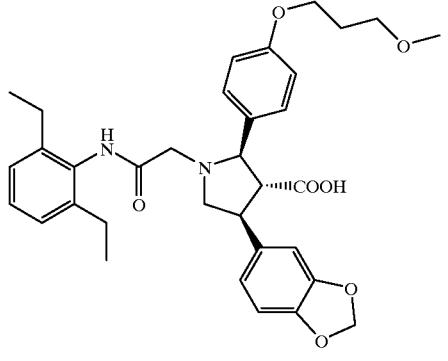
        439                        440
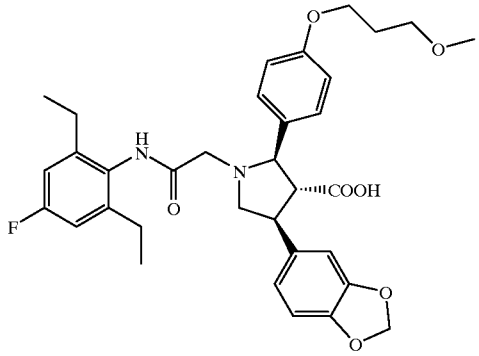              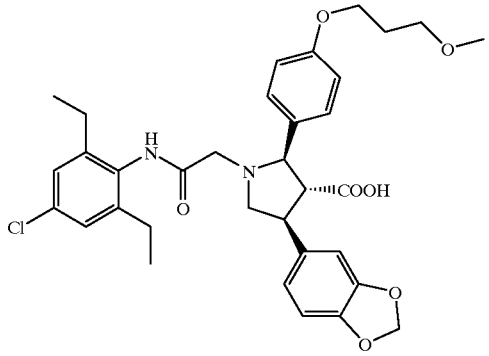

155
-continued
156
441
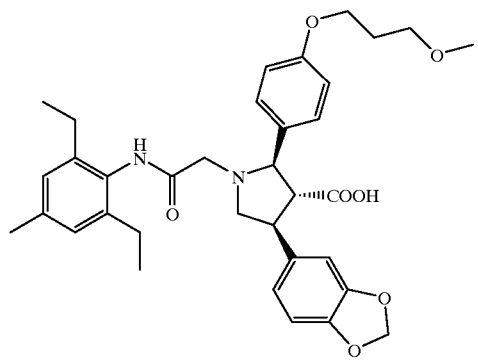
442
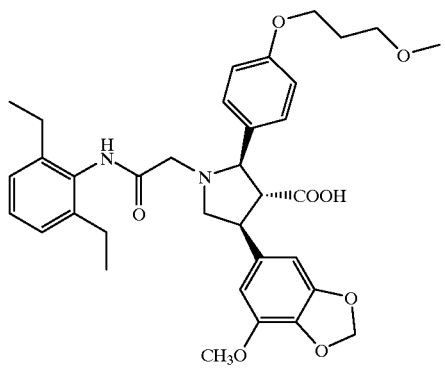
443
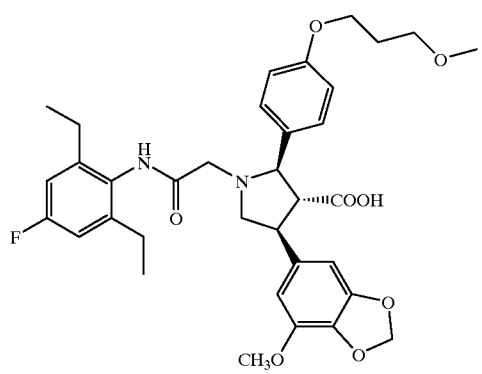
444
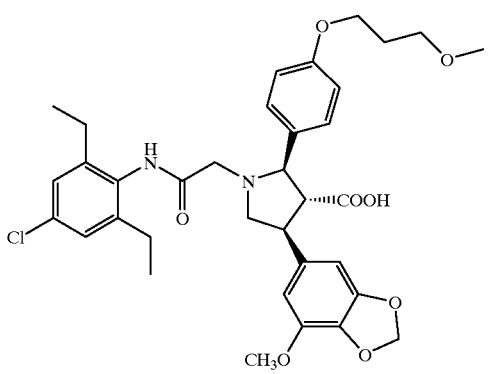
445
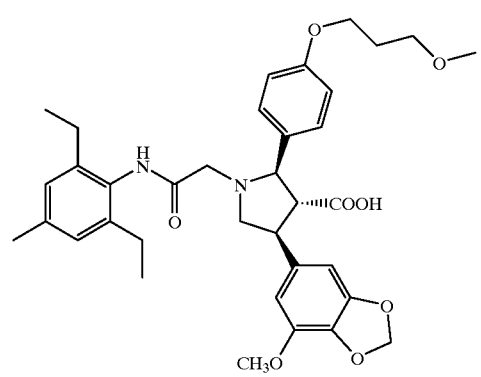
446
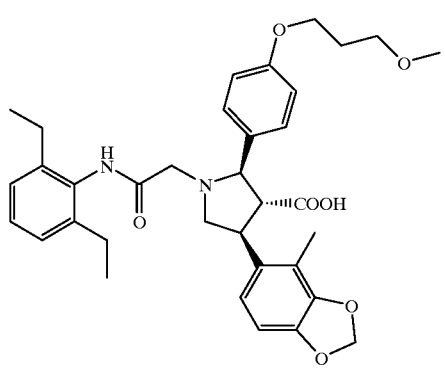
447
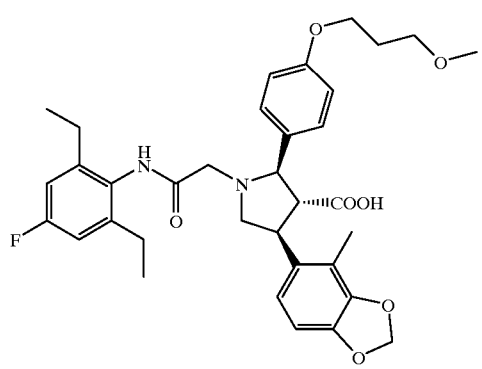
448
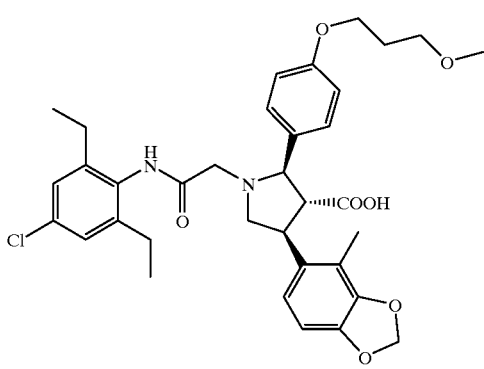

| 449 | 450 |
|---|---|
| 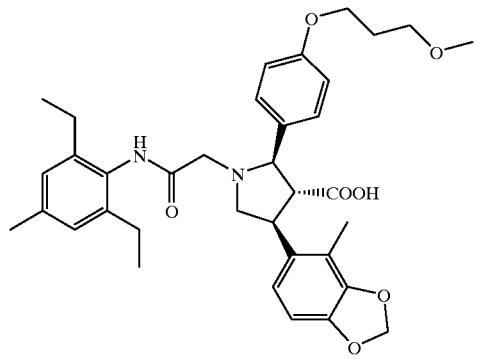 | 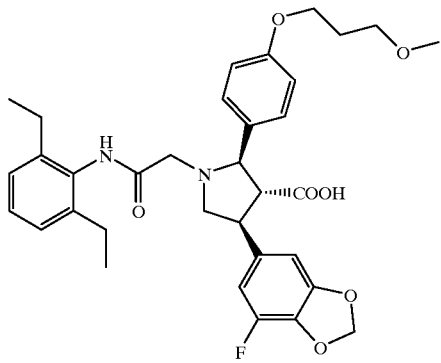 |
| 451 | 452 |
| 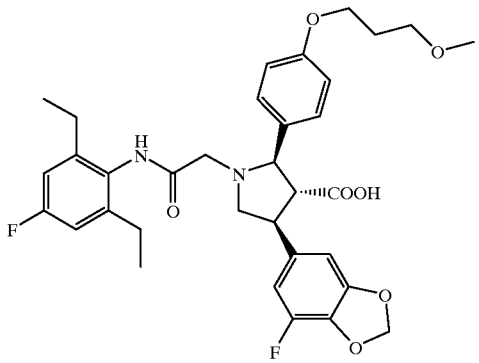 | 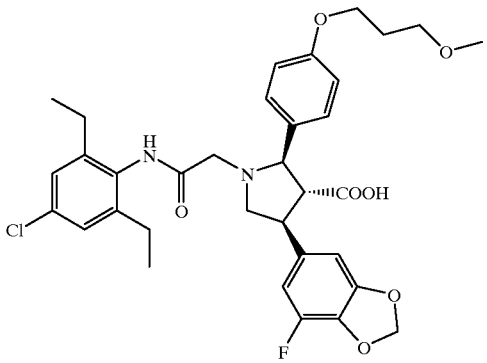 |
| 453 | 454 |
| 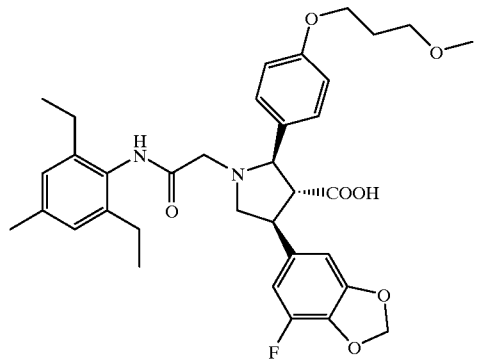 | 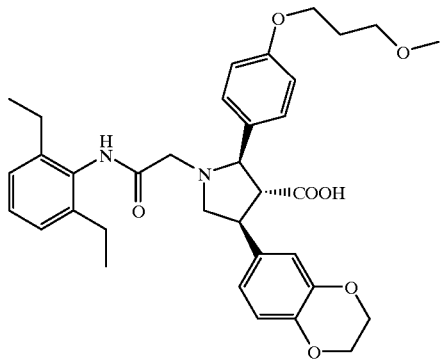 |
| 455 | 456 |
| 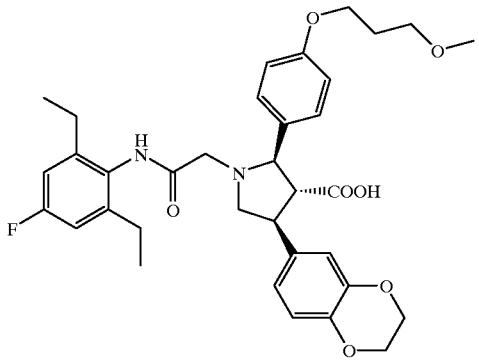 | 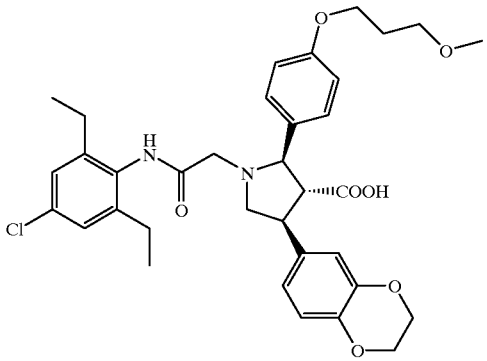 |

-continued
| 159 | 160 |
|---|---|
| 457 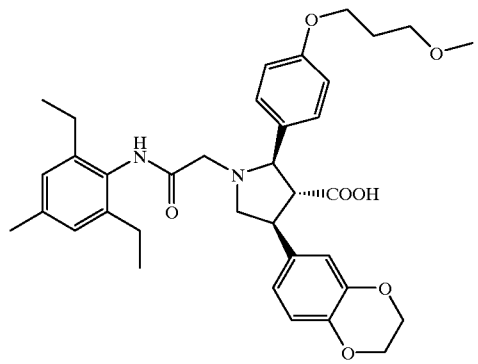 | 458 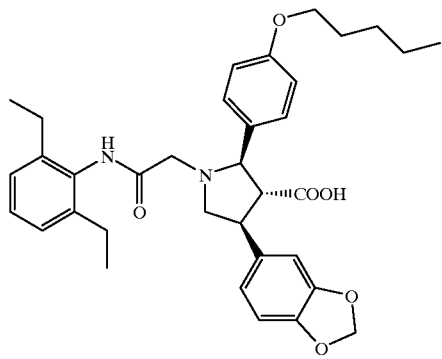 |
| 459 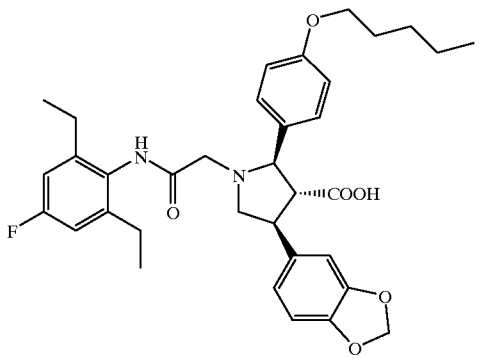 | 460 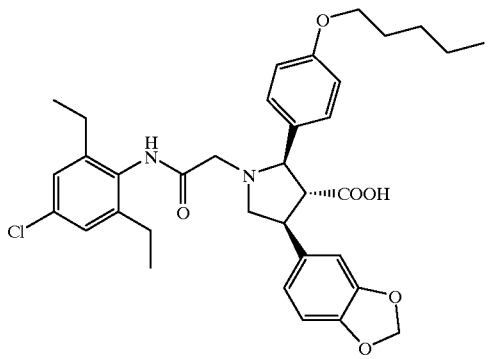 |
| 461 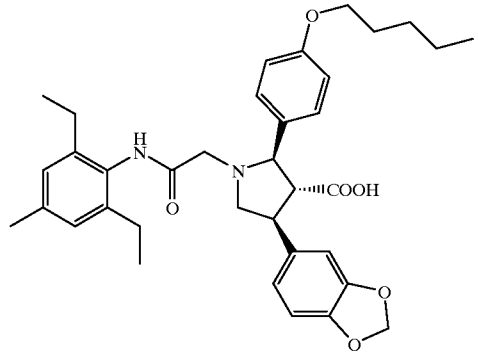 | 462 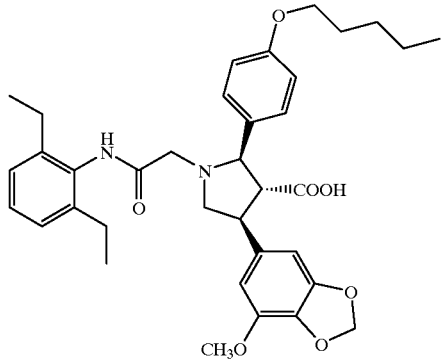 |
| 463 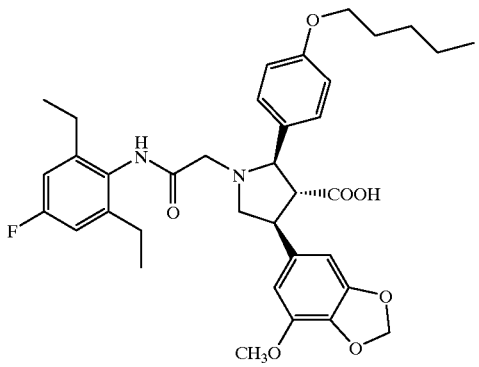 | 464 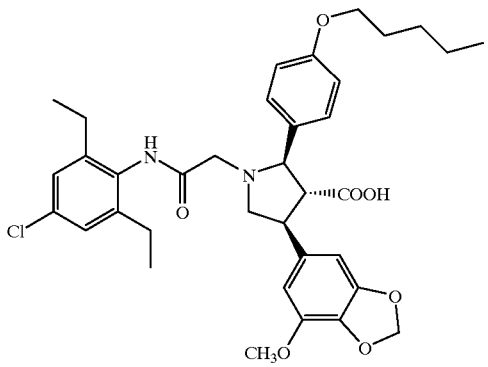 |

6,124,341
-continued
| 161 | 162 |
|---|---|
| 465 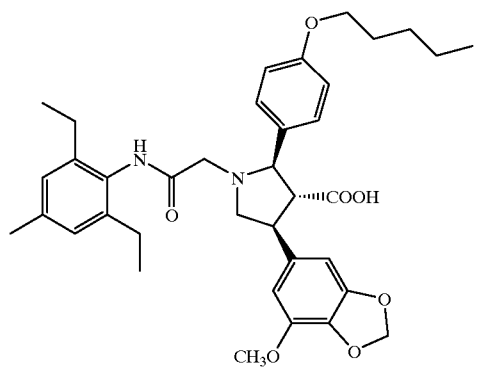 | 466 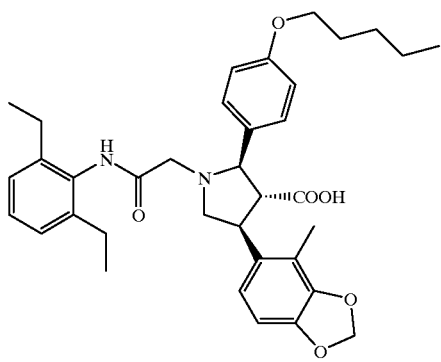 |
| 467 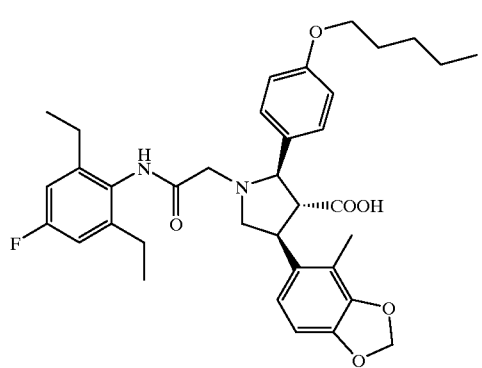 | 468 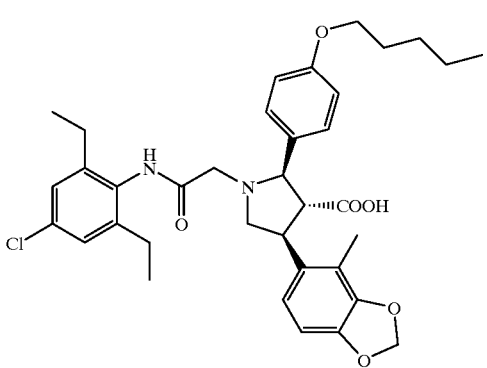 |
| 469 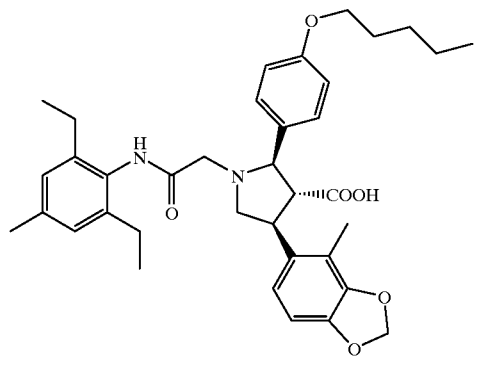 | 470 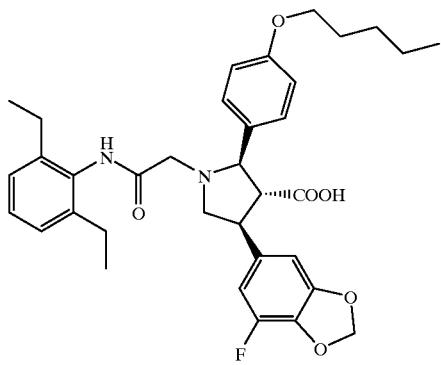 |
| 471 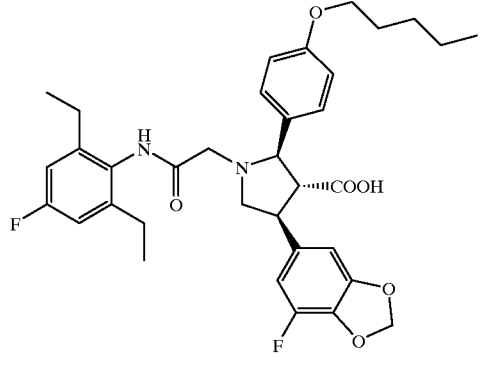 | 472 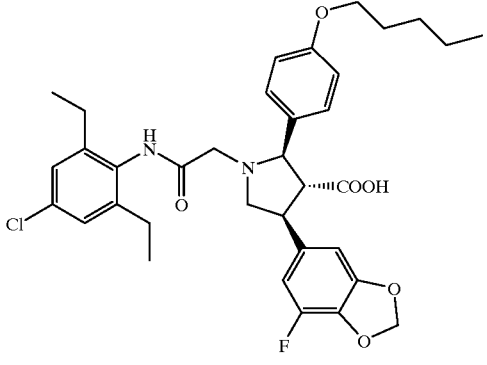 |

-continued
| 163 | 164 |
|---|---|
| 473 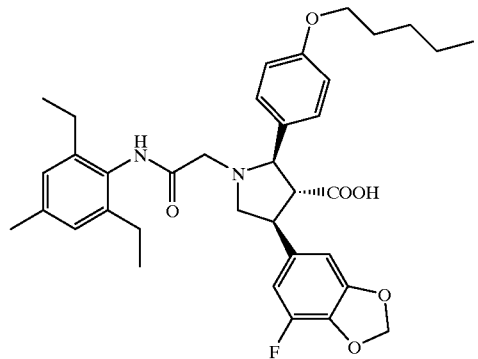 | 474 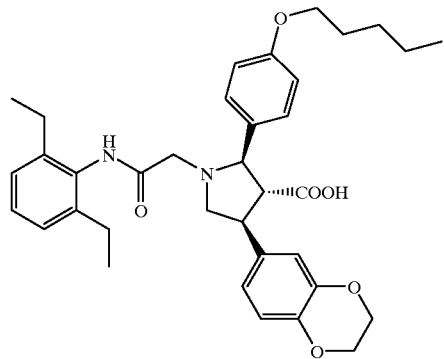 |
| 475 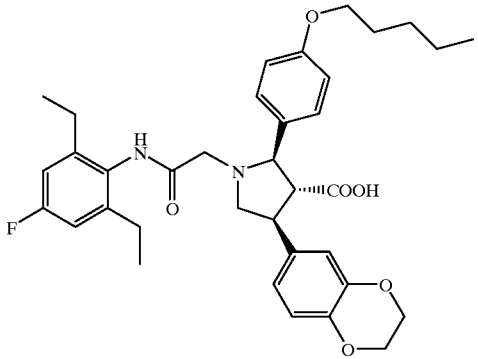 | 476 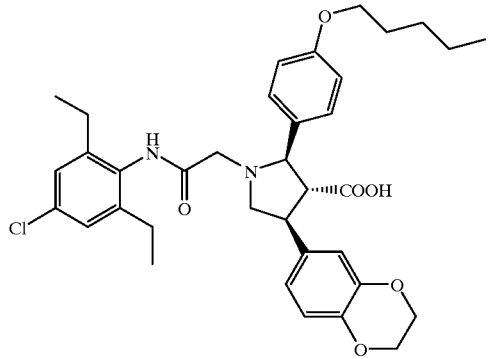 |
| 477 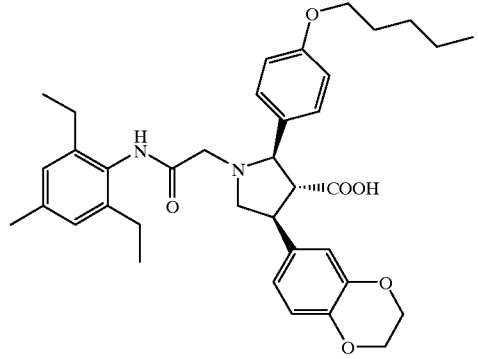 | 478 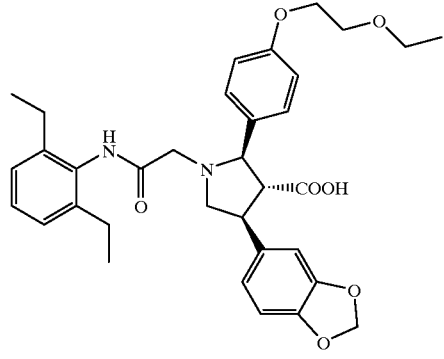 |
| 479 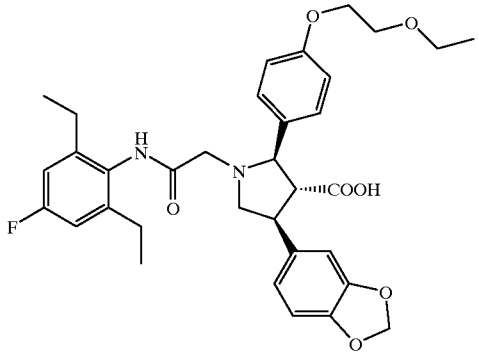 | 480 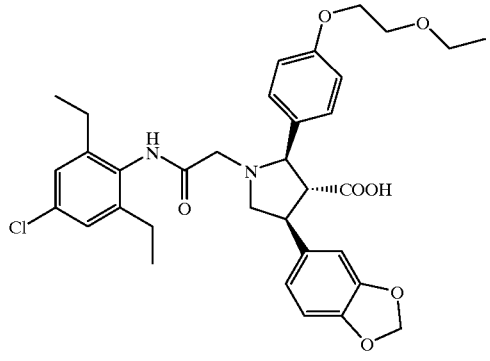 |

-continued
| 481 | 482 |
|---|---|
| 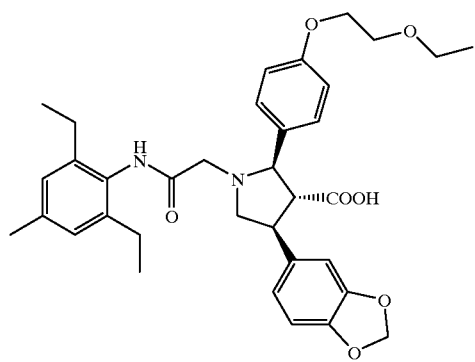 | 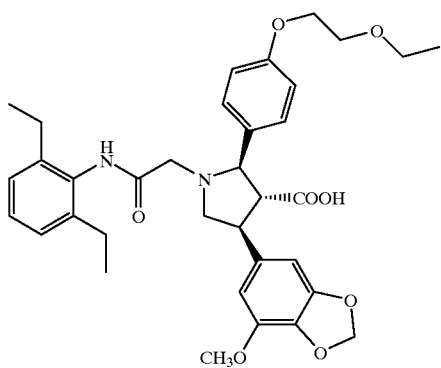 |
| 483 | 484 |
| 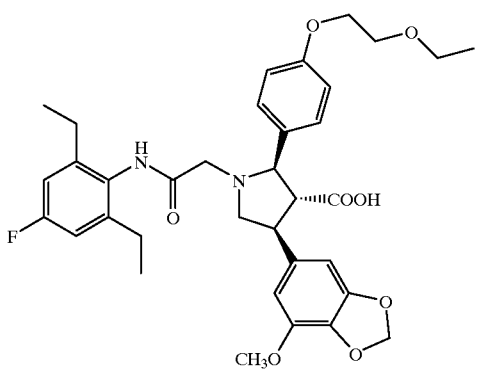 | 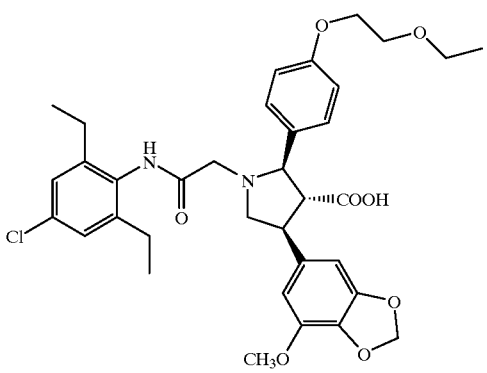 |
| 485 | 486 |
| 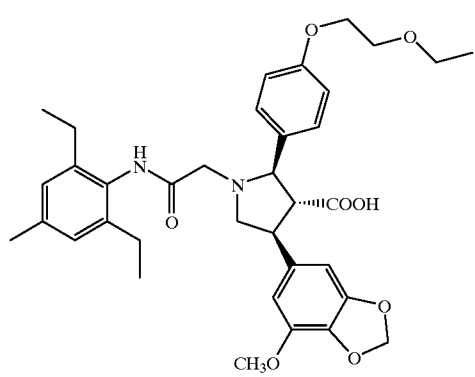 | 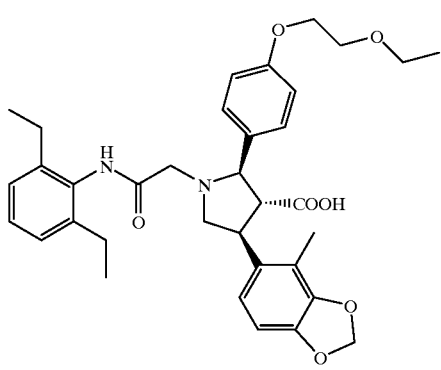 |
| 487 | 488 |
| 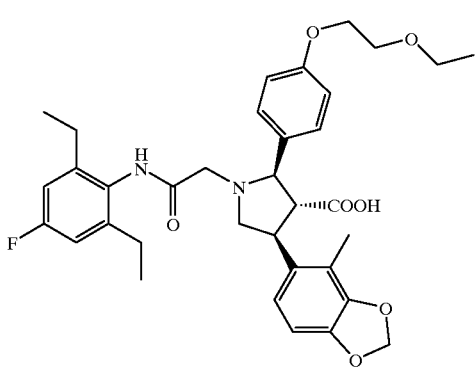 | 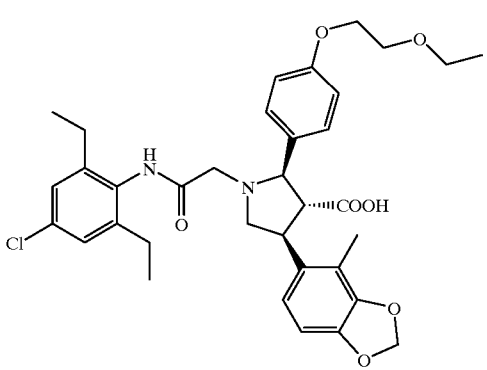 |

6,124,341
167                                                                 168
-continued
| 489 | 490 |
|---|---|
| 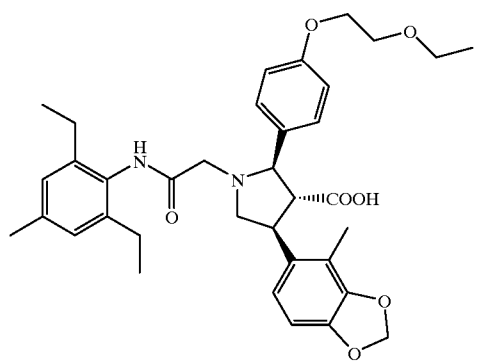 | 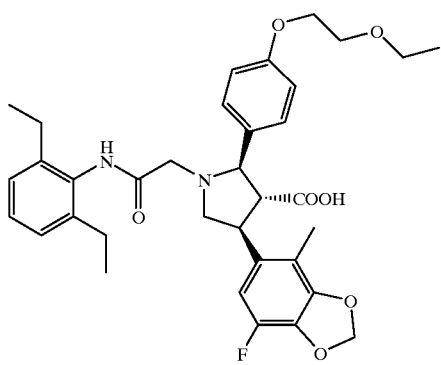 |
| 491 | 492 |
| 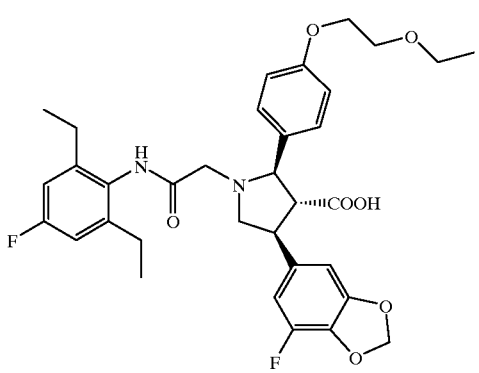 | 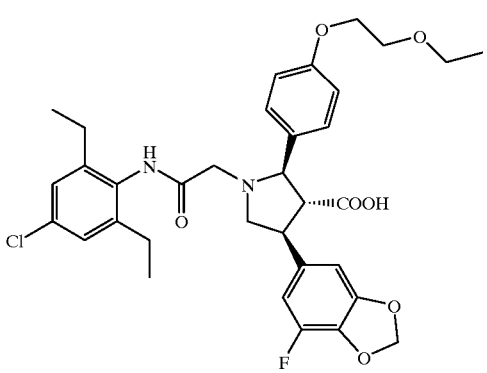 |
| 493 | 494 |
| 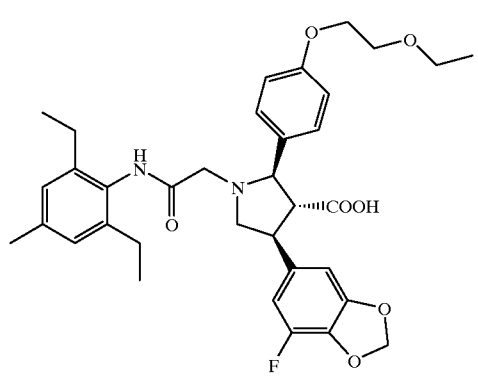 | 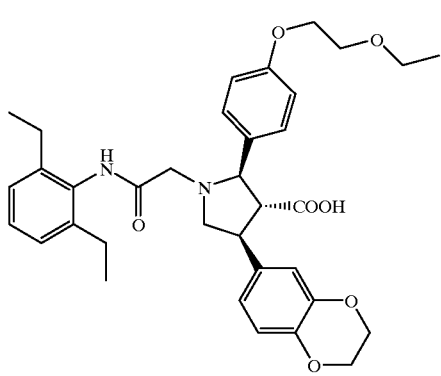 |
| 495 | 496 |
| 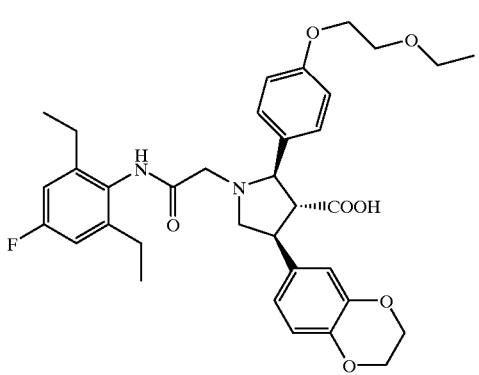 | 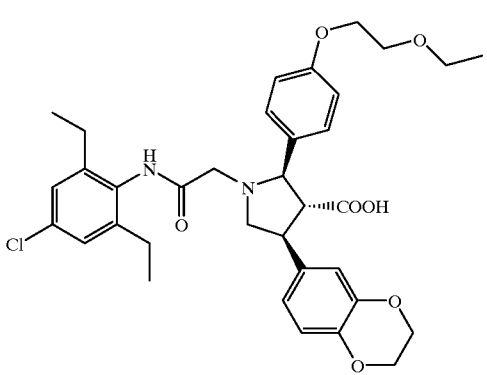 |

-continued
497 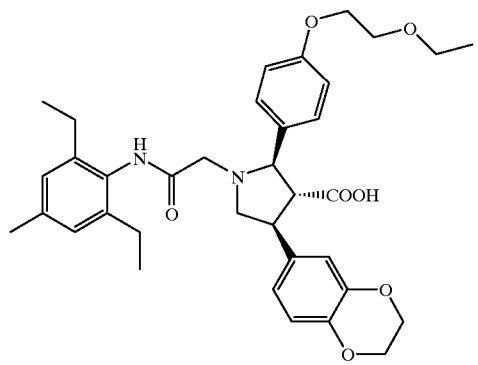
498 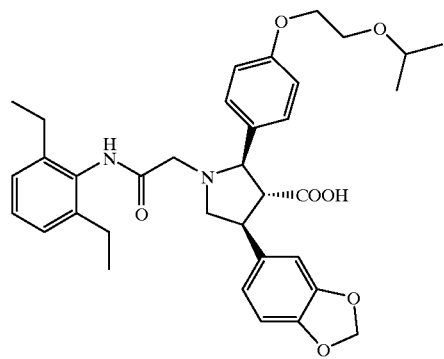
499 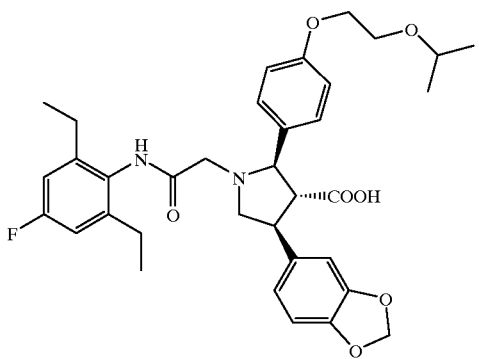
500 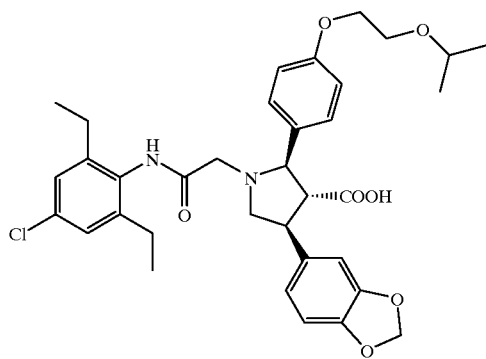
501 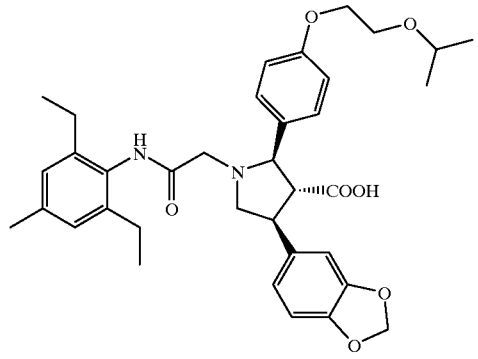
502 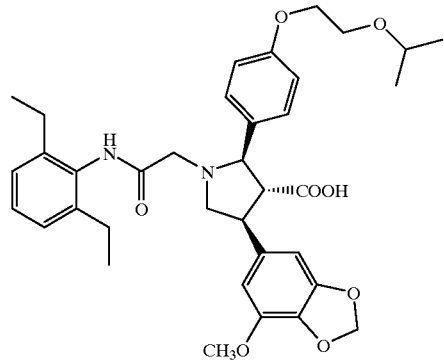
503 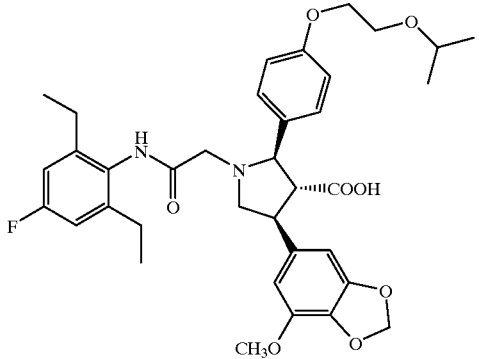
504 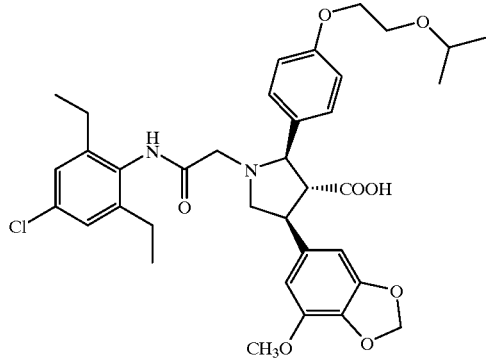

-continued
505
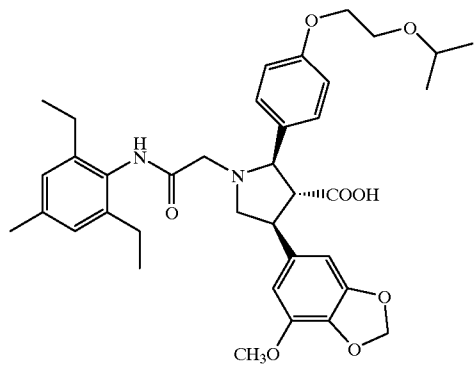
506
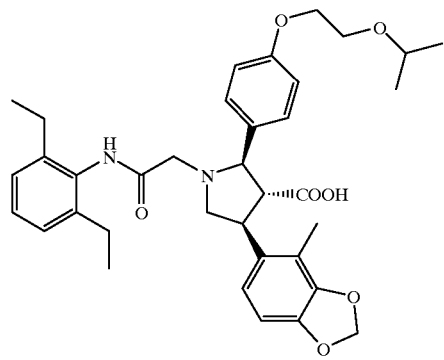
507
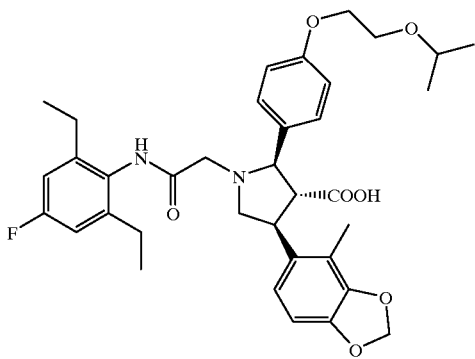
508
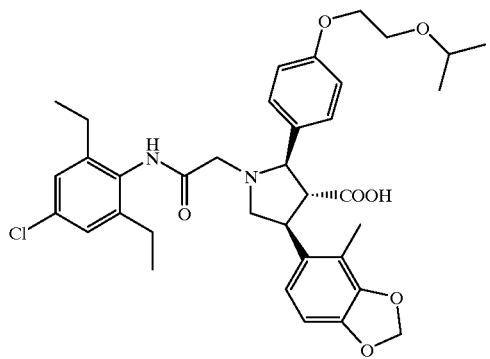
509
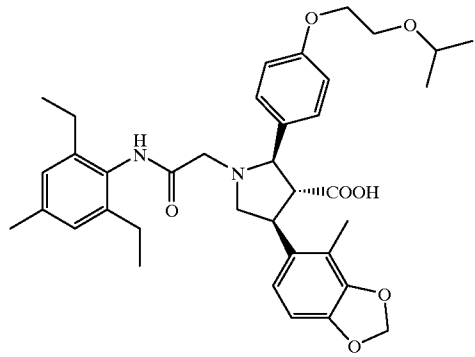
510
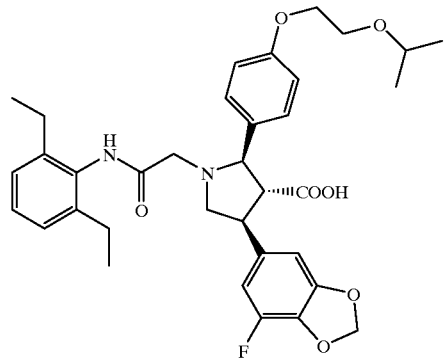
511
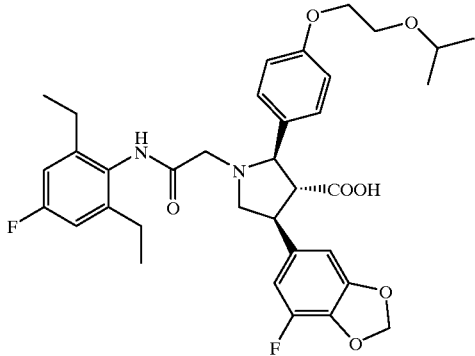
512
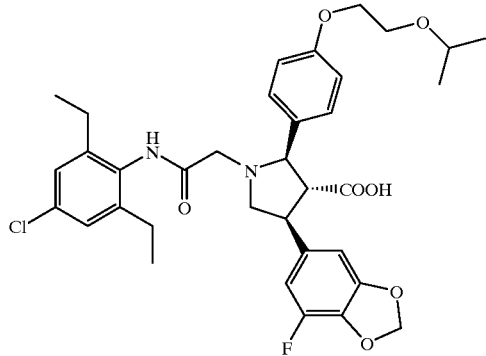

| 173 | 174 |
|---|---|
| 513 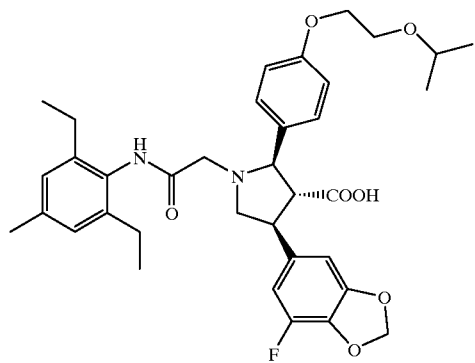 | 514 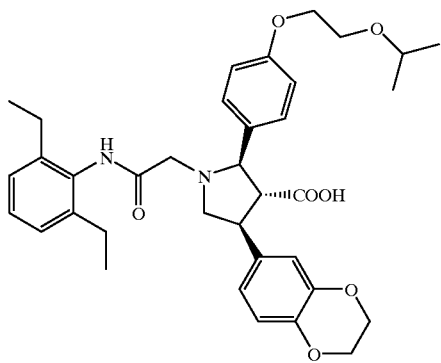 |
| 515 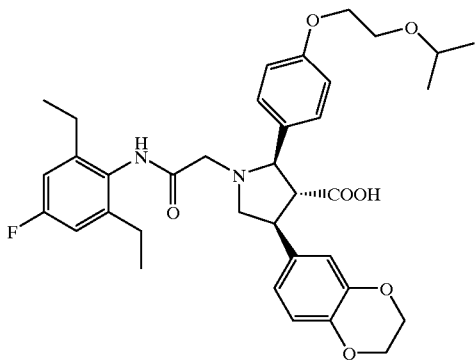 | 516 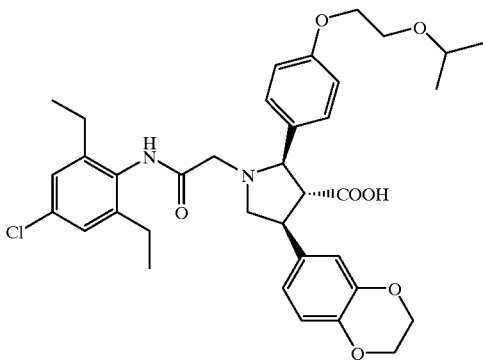 |
| 517 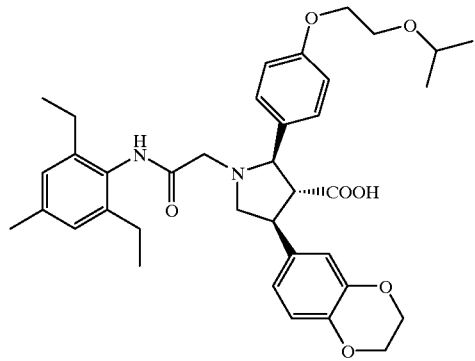 | 518 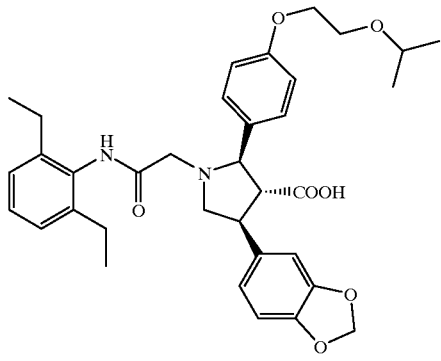 |
| 519 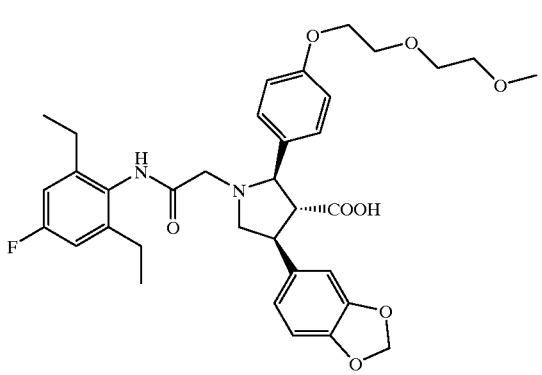 | 520 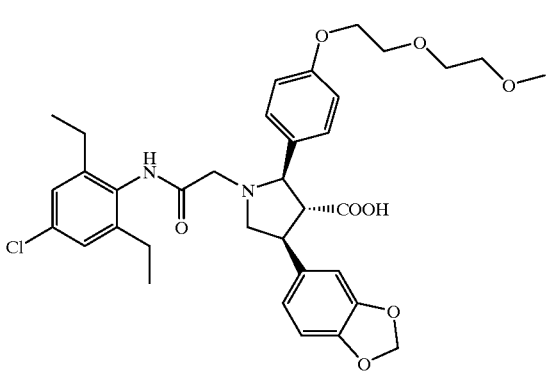 |

521
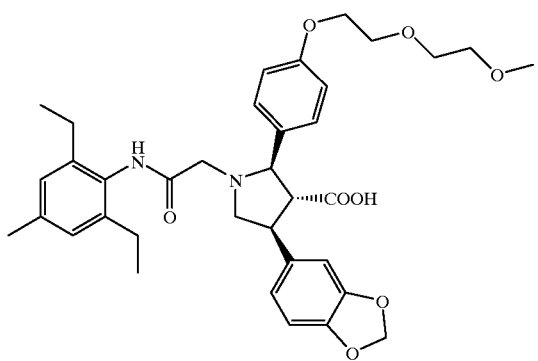
523
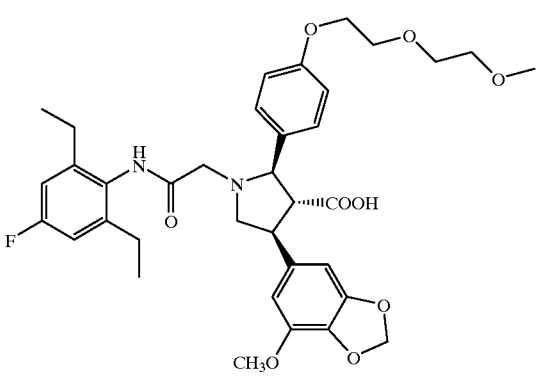
525
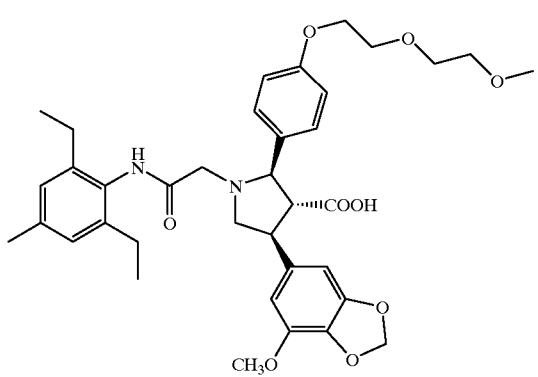
527
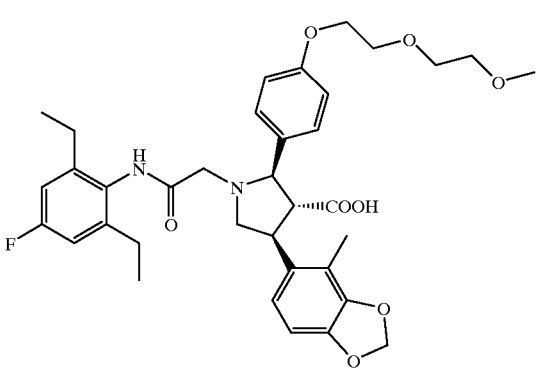
522
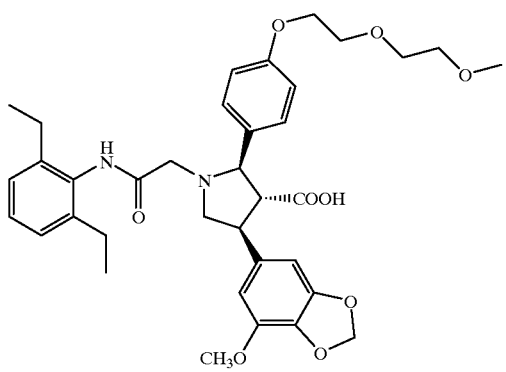
524
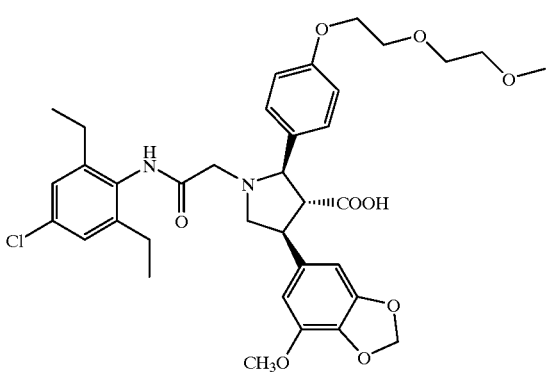
526
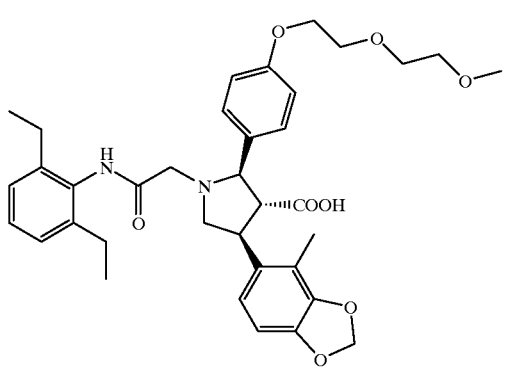
528
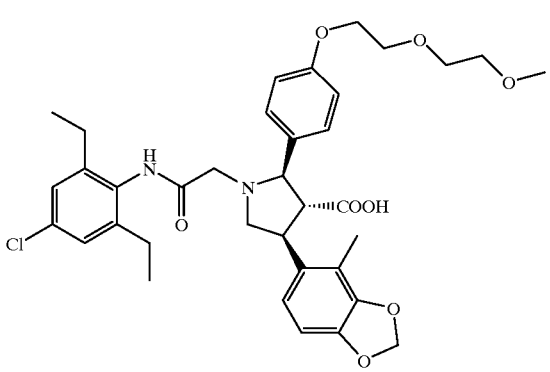

529
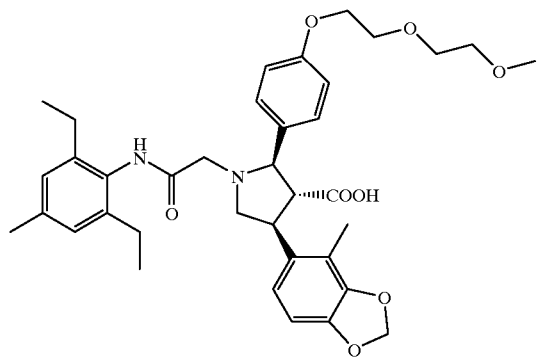
530
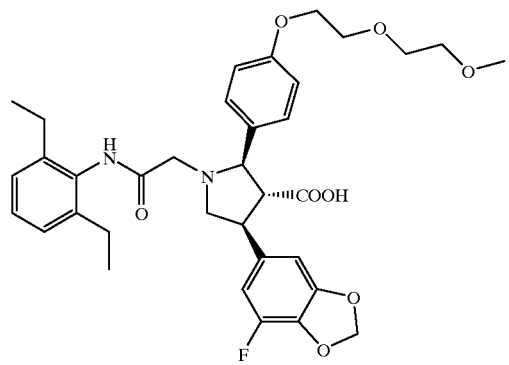
531
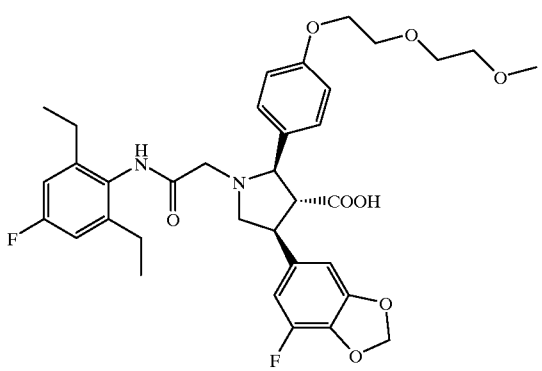
532
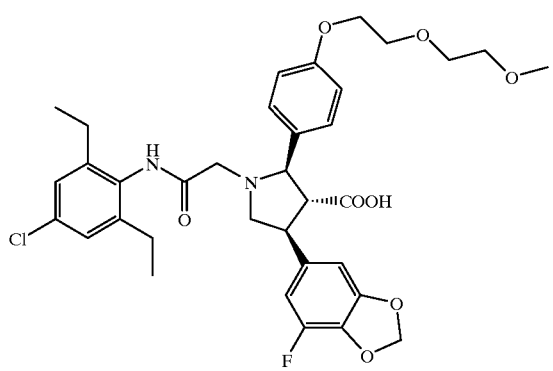
533
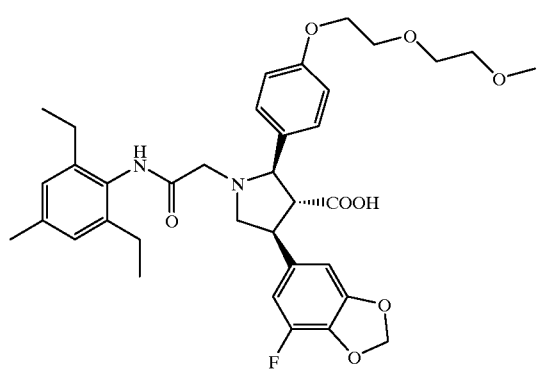
534
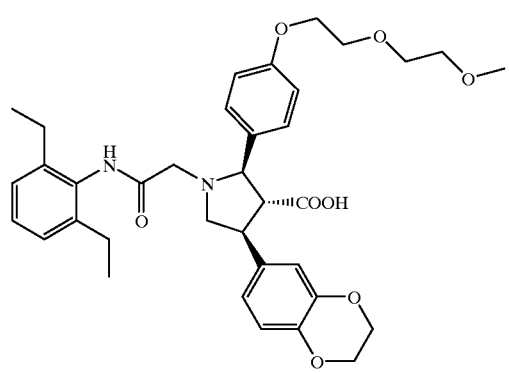
535
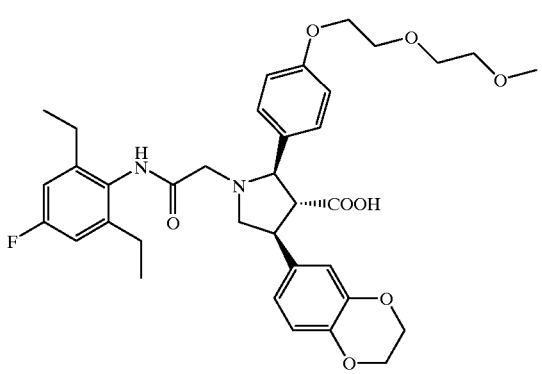
536
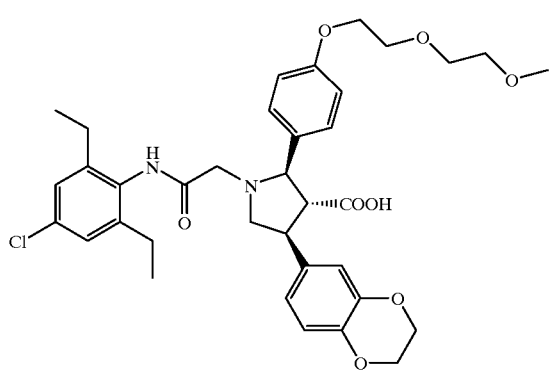

537
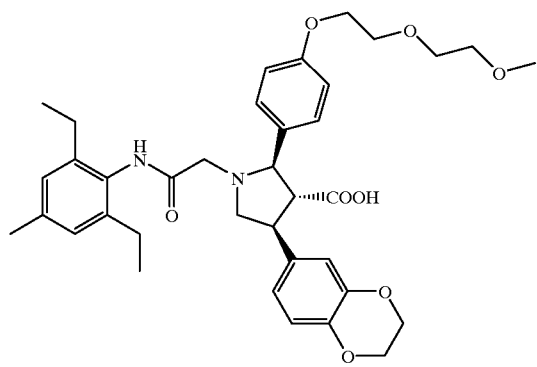
538
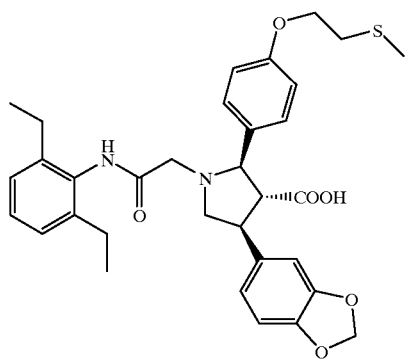
539
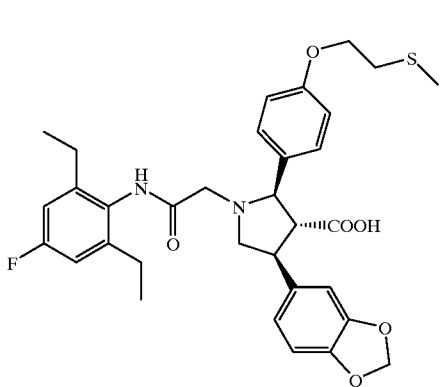
540
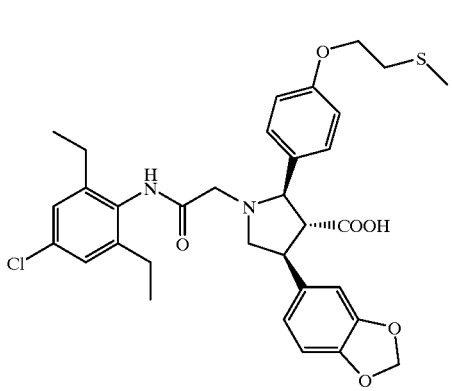
541
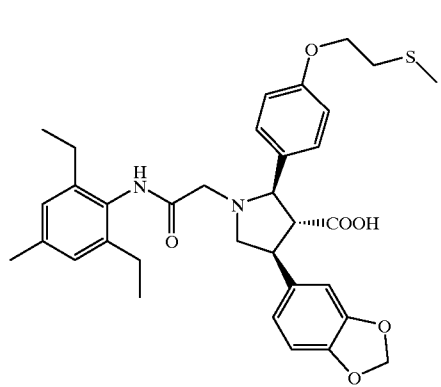
542
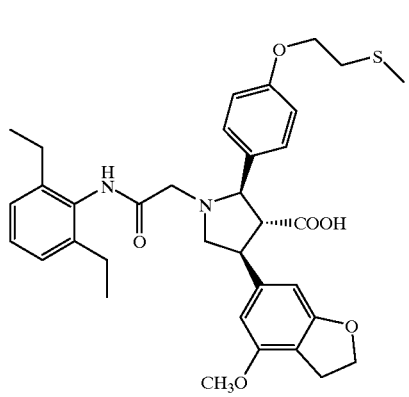
543
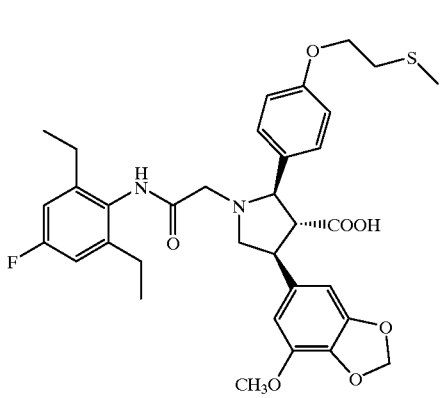
544
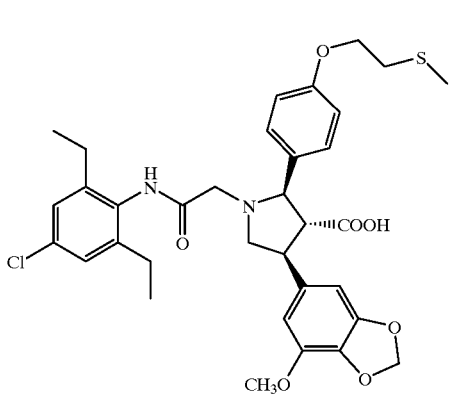

-continued
545
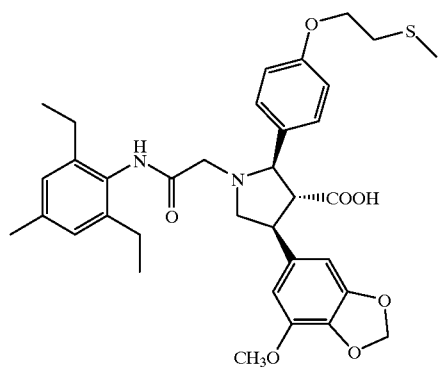
546
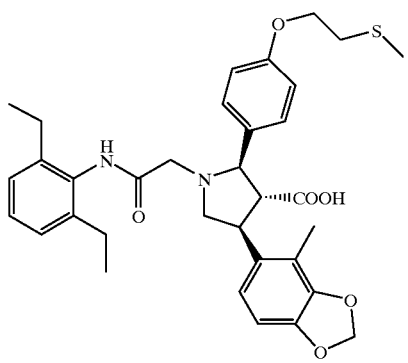
547
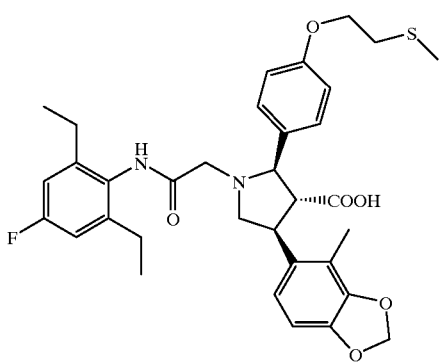
548
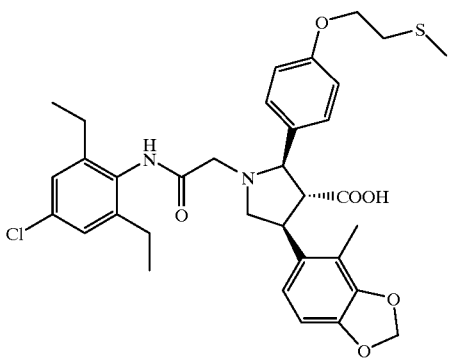
549
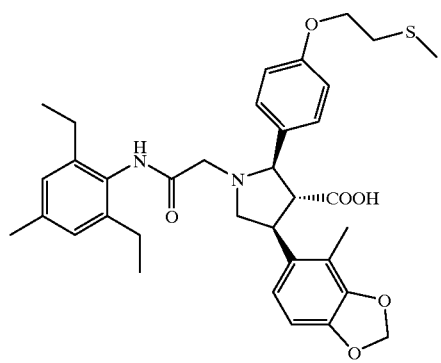
550
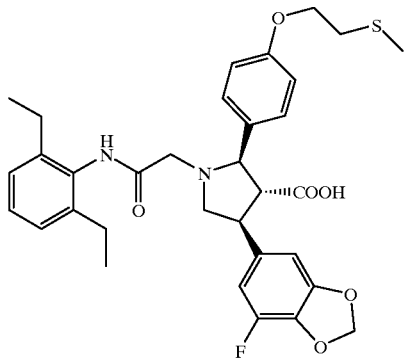
551
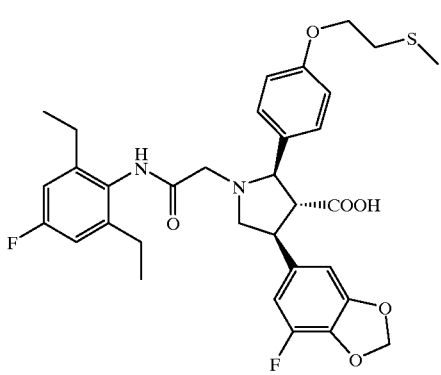
552
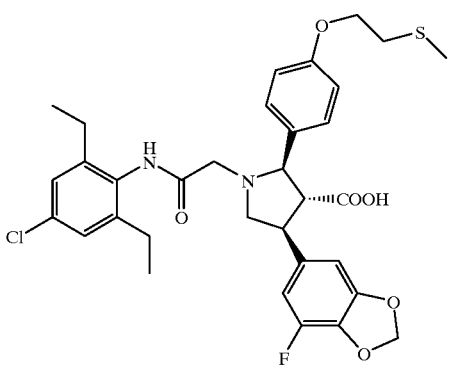

-continued
553 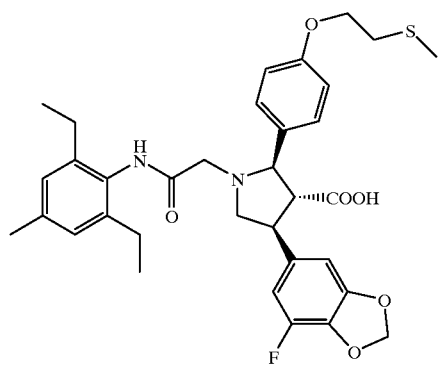
554 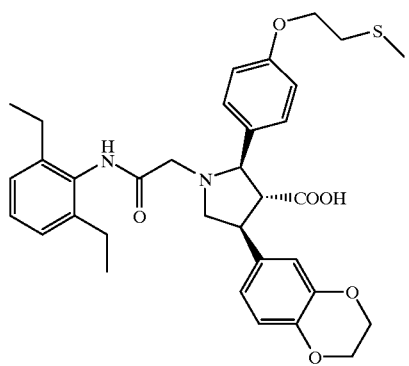
555 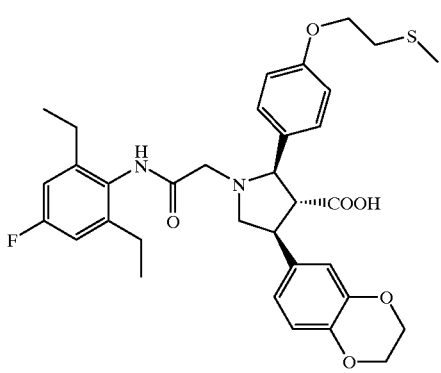
556 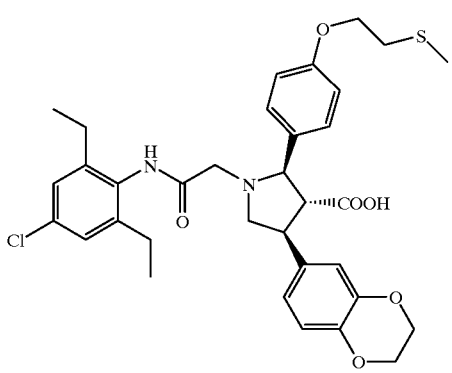
557 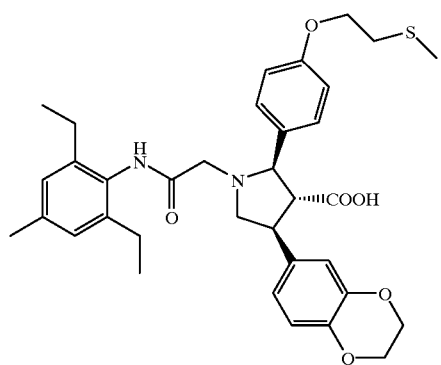
558 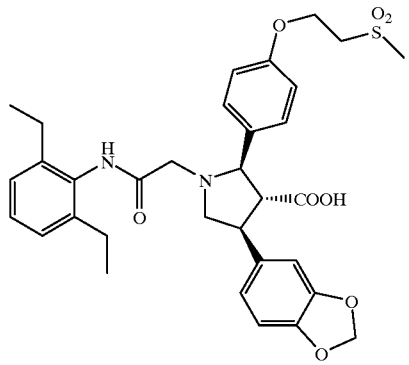
559 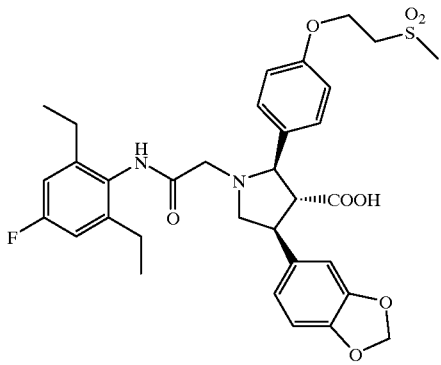
560 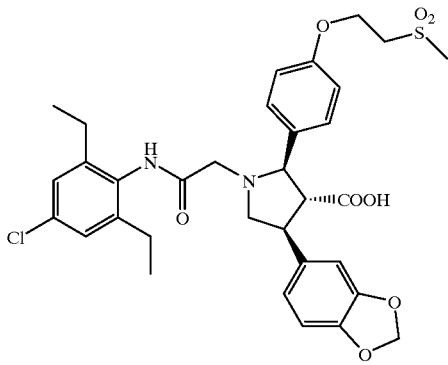

-continued
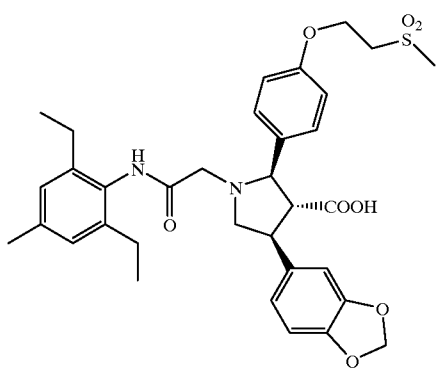
561
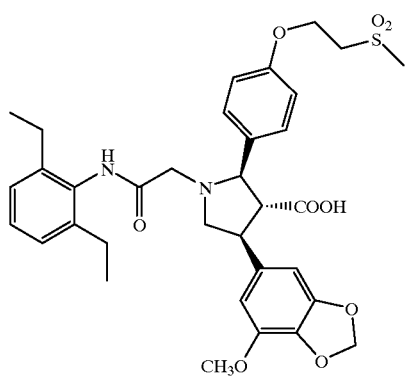
562
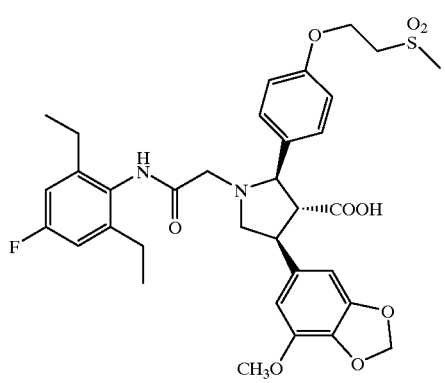
563
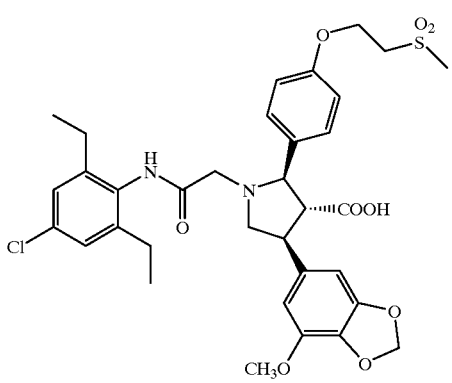
564
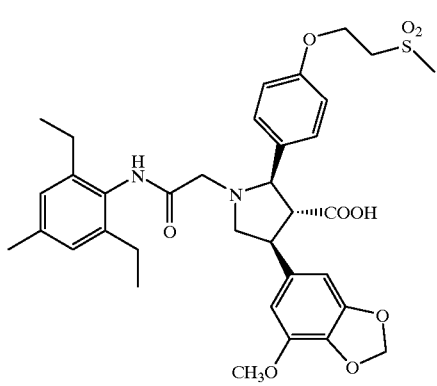
565
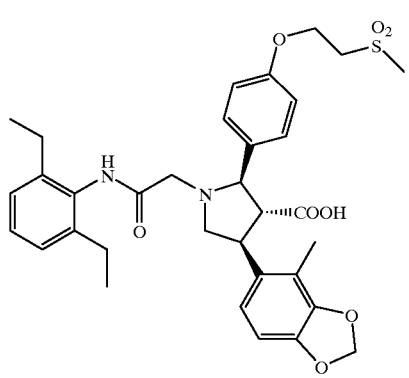
566
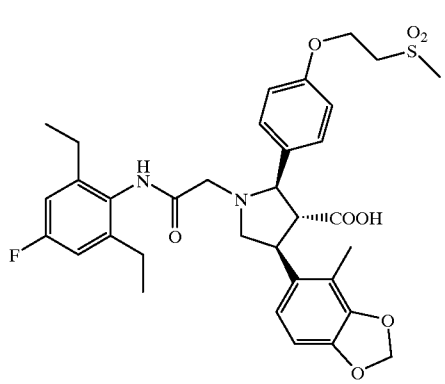
567
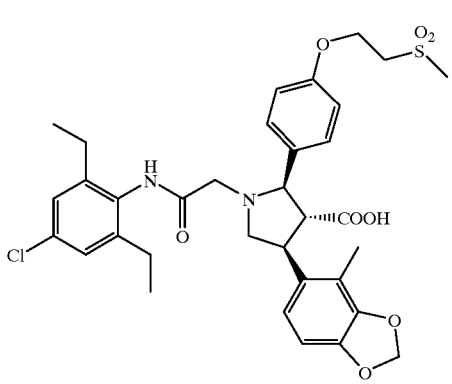
568

187 188
-continued
| 569 | 570 |
|---|---|
| 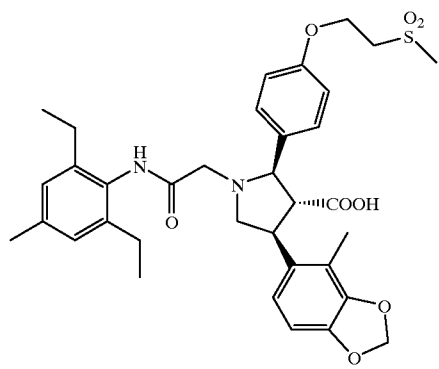 | 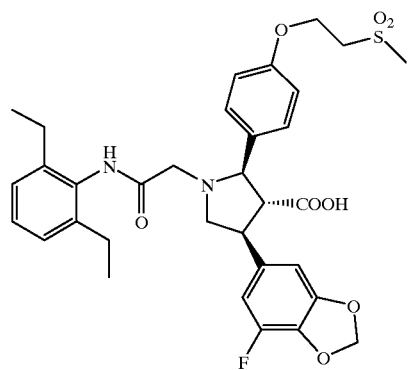 |
| 571 | 572 |
| 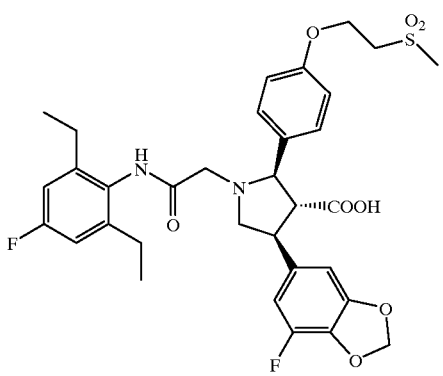 | 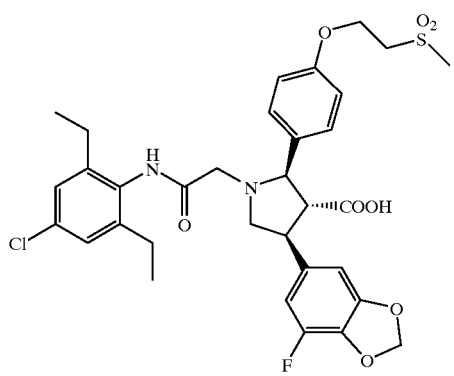 |
| 573 | 574 |
| 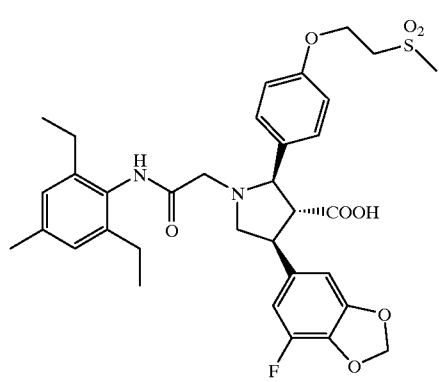 | 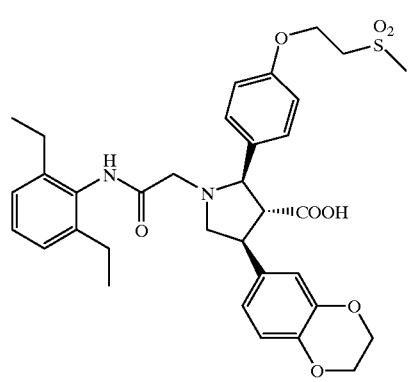 |
| 575 | 576 |
| 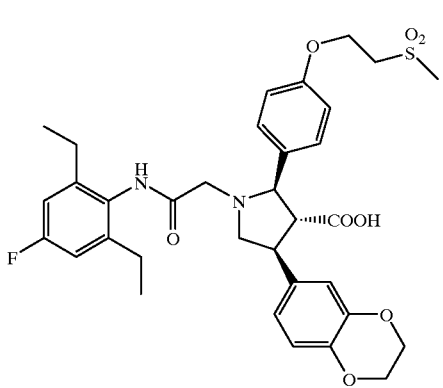 | 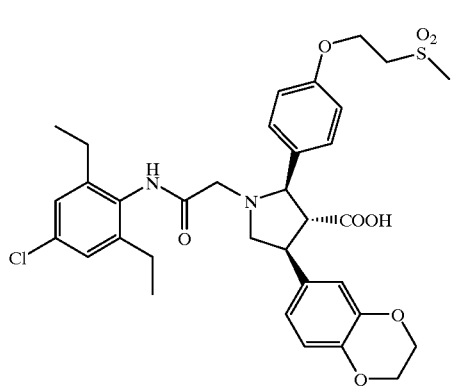 |

577
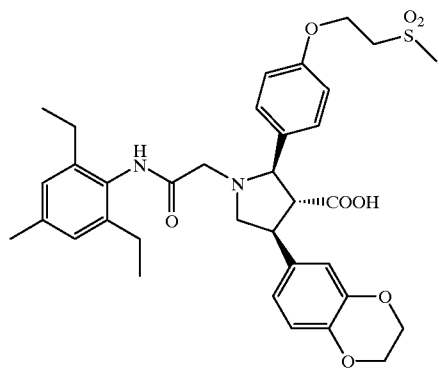
578
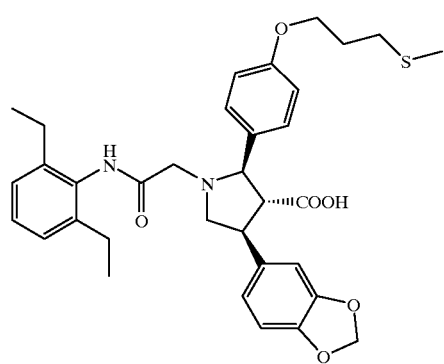
579
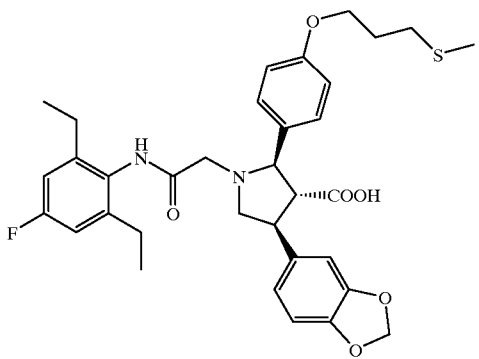
580
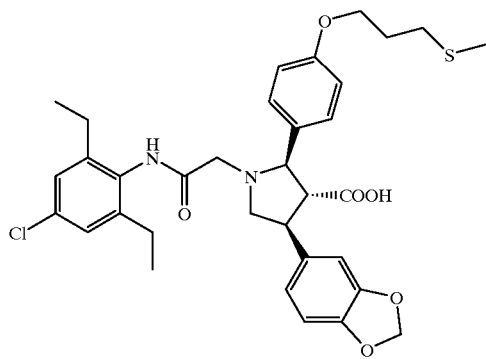
581
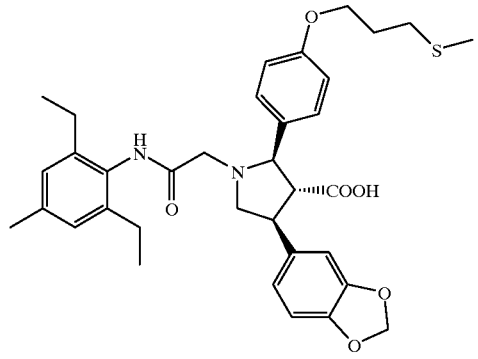
582
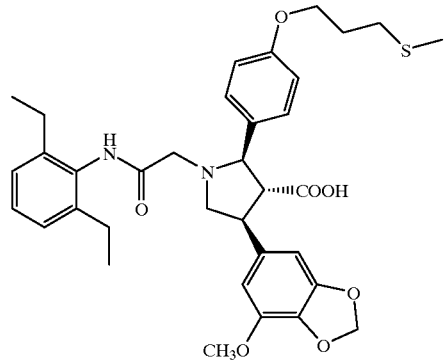
583
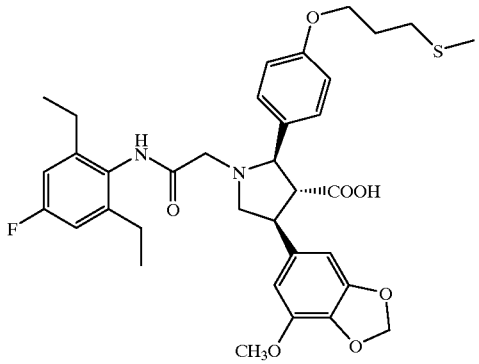
584
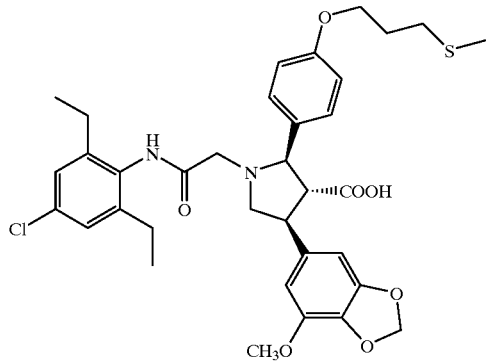

-continued
585
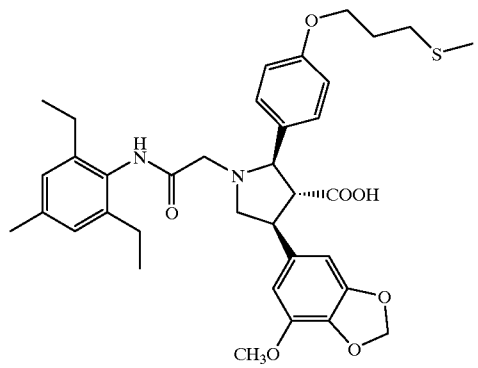
586
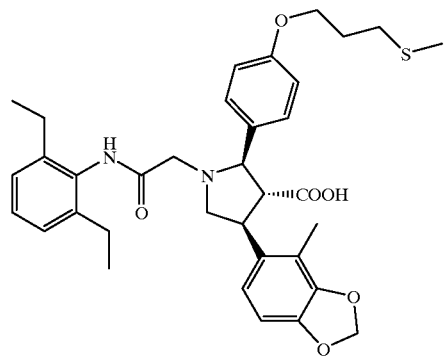
587
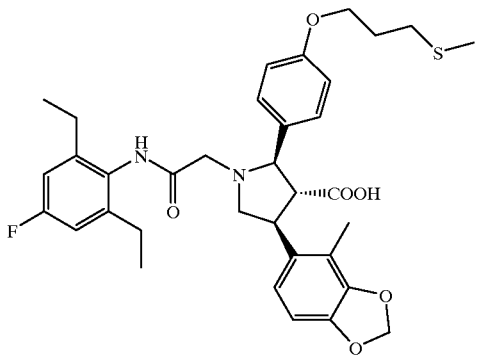
588
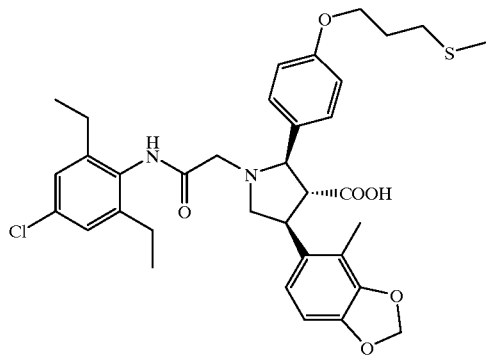
589
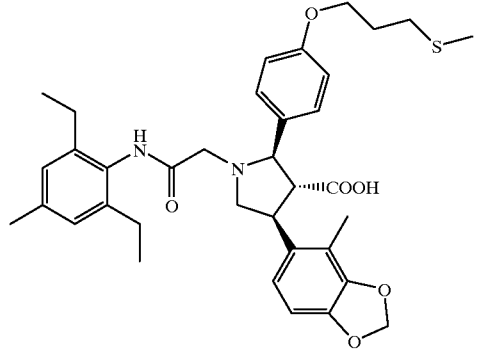
590
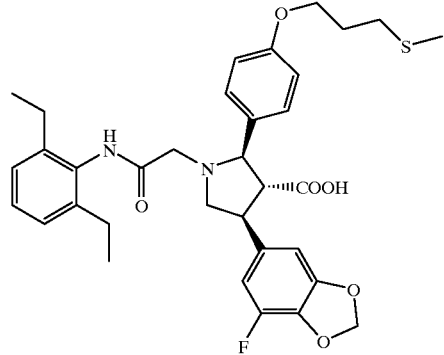
591
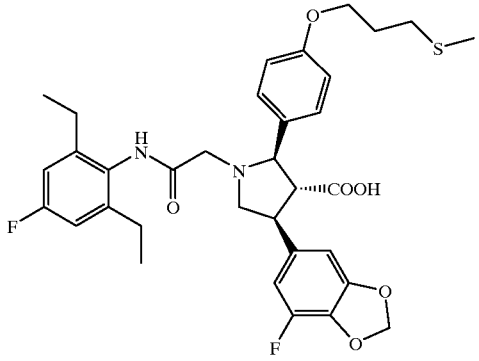
592
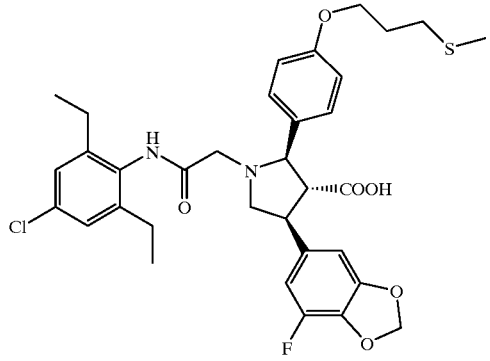

193                                                                 194
-continued
593 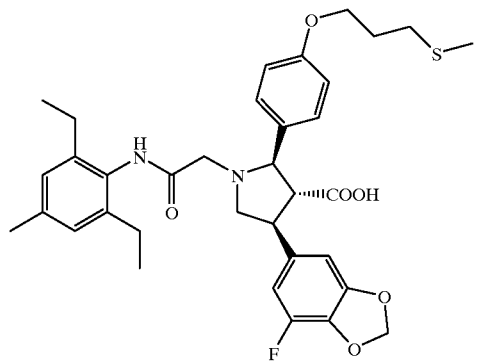
594 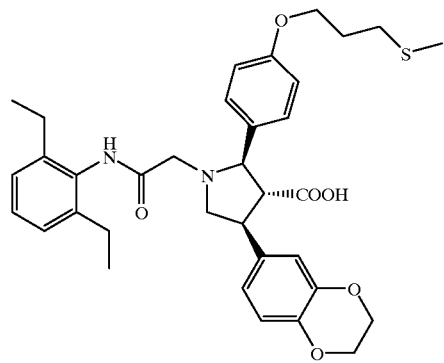
595 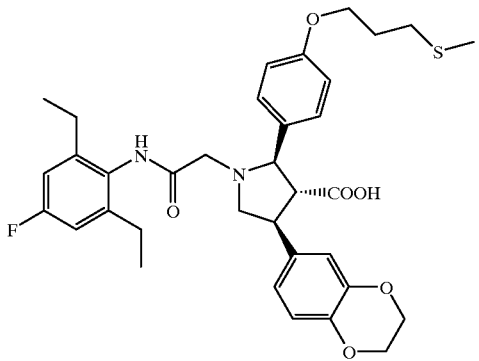
596 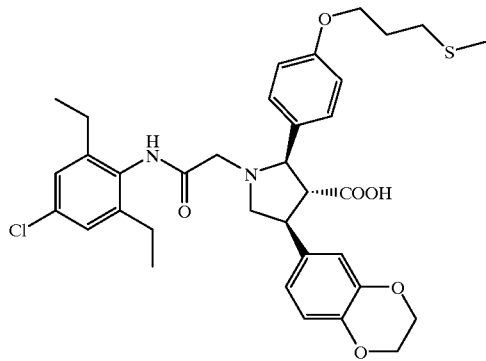
597 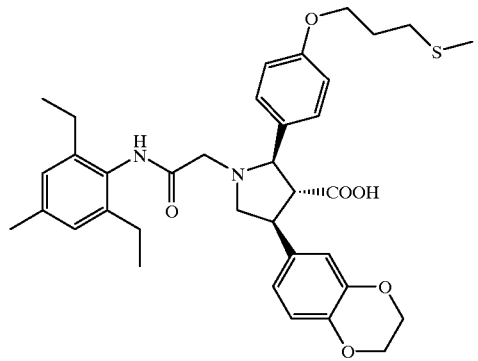
598 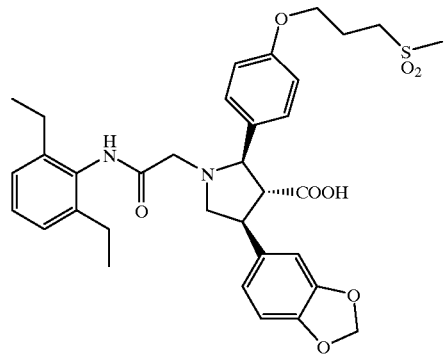
599 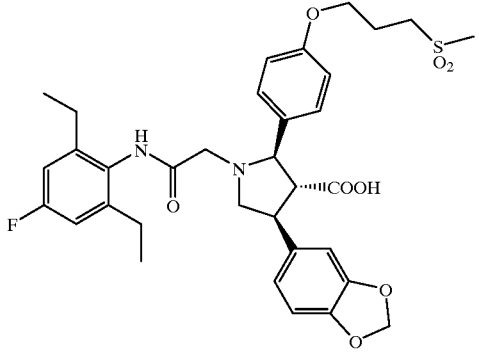
600 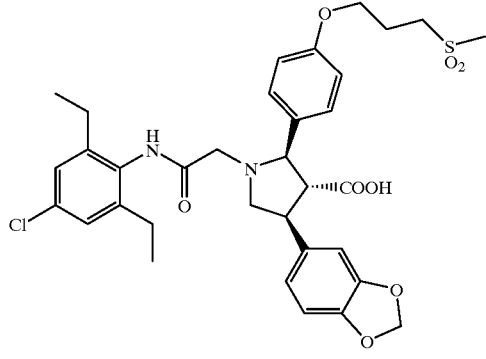

-continued
| 195 | 196 |
|---|---|
| 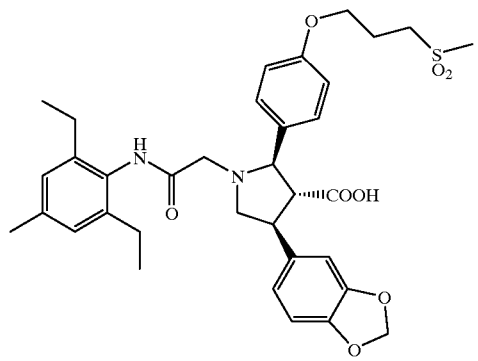 601 | 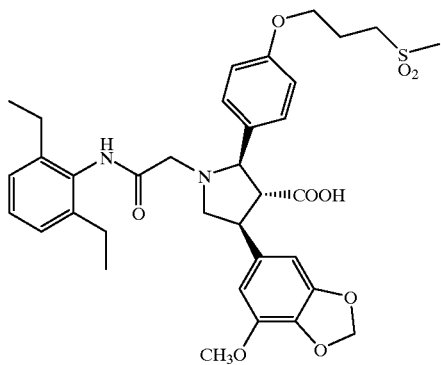 602 |
| 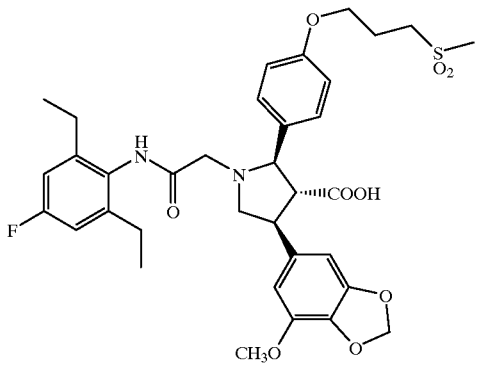 603 | 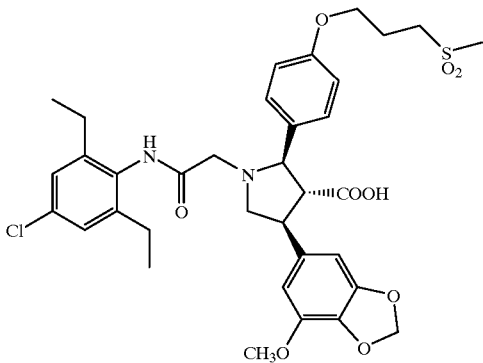 604 |
| 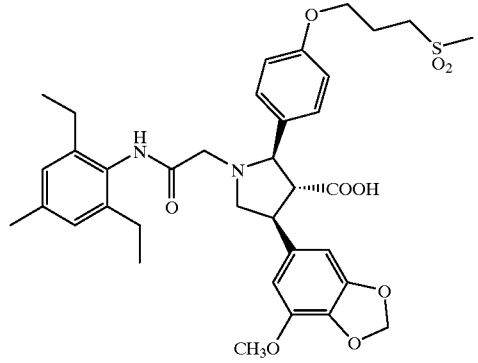 605 | 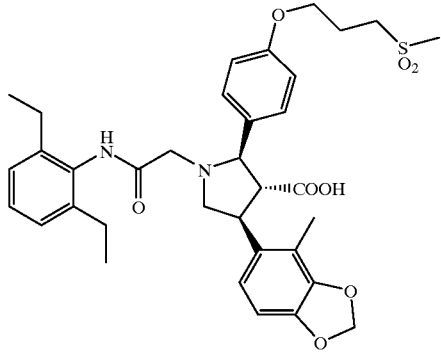 606 |
| 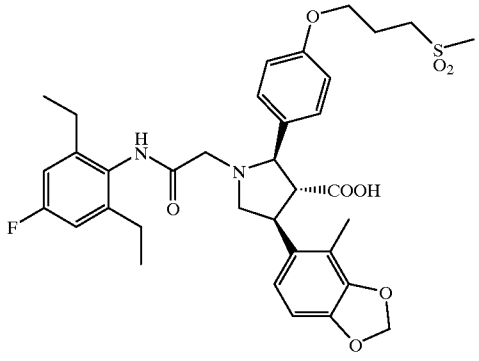 607 | 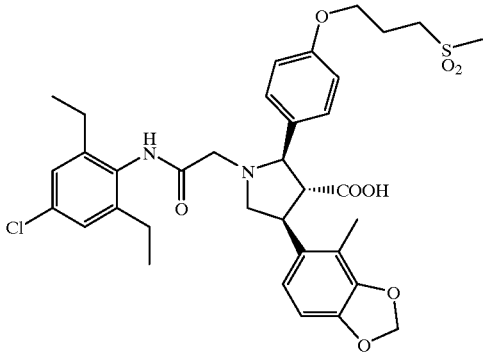 608 |

-continued
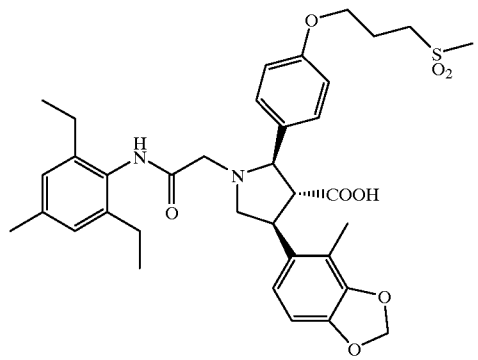
609
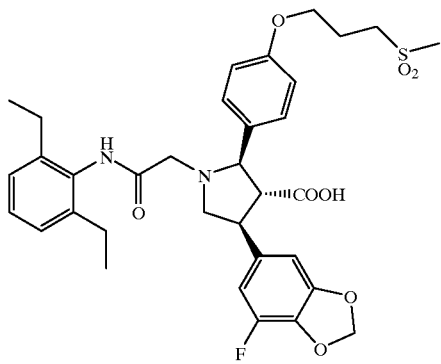
610
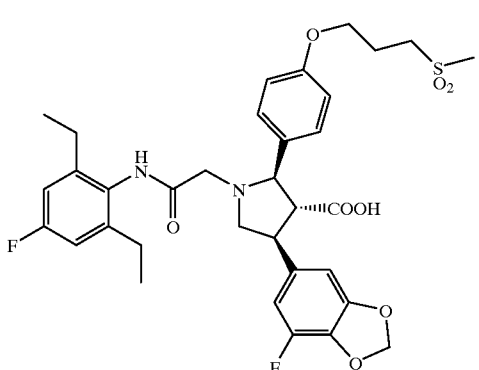
611
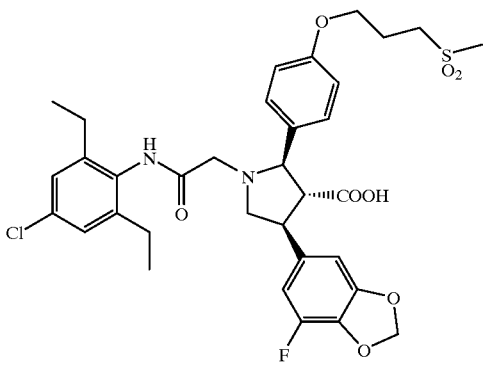
612
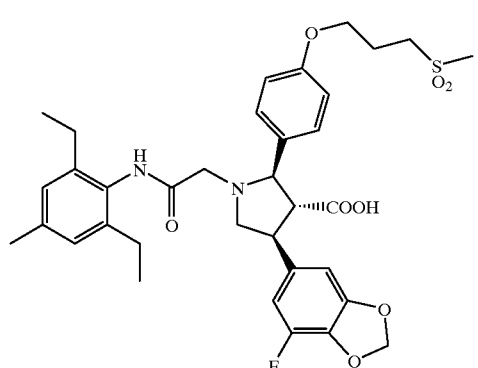
613
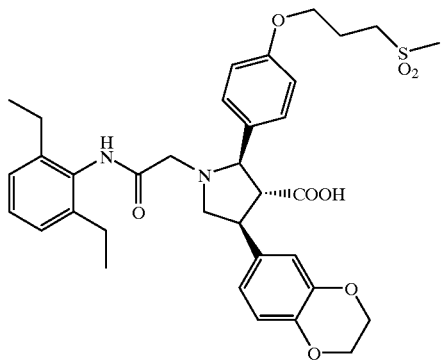
614
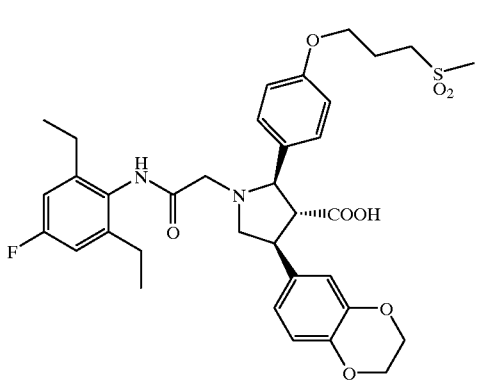
615
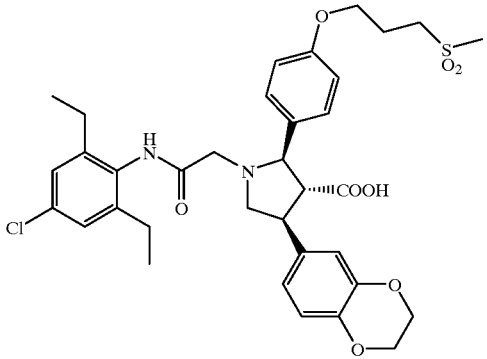
616

199
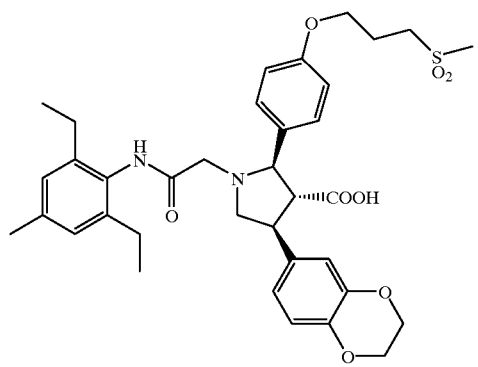
617
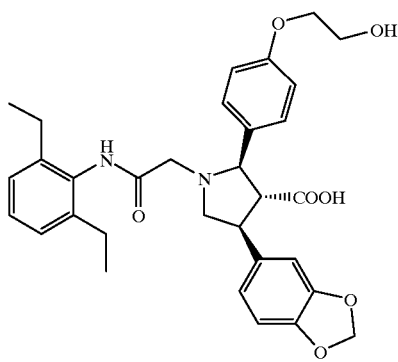
618
-continued
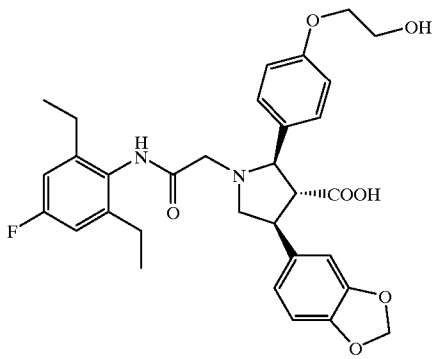
619
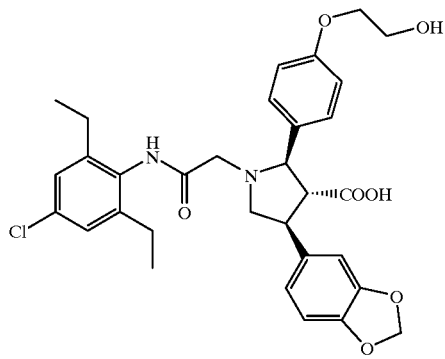
620
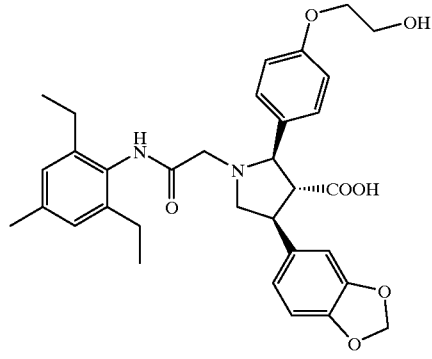
621
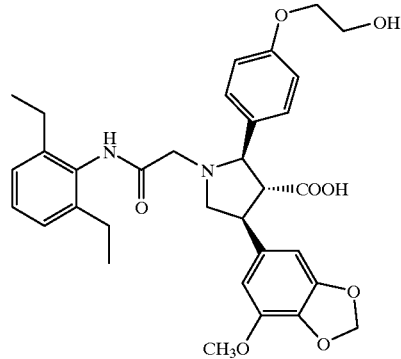
622
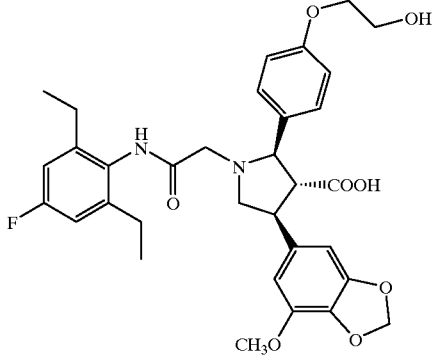
623
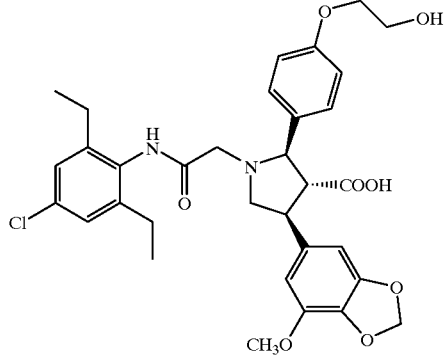
624
200

-continued
| 625 | 626 |
|---|---|
| 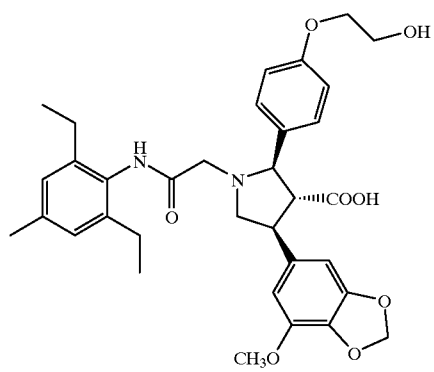 | 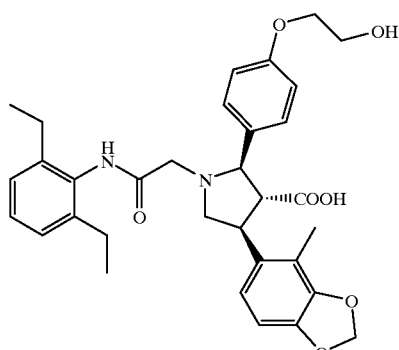 |
| 627 | 628 |
| 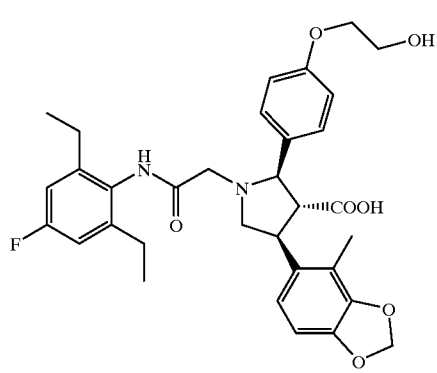 | 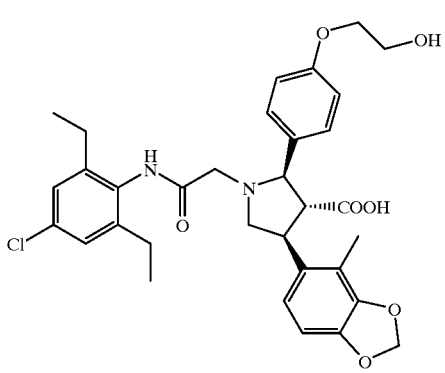 |
| 629 | 630 |
| 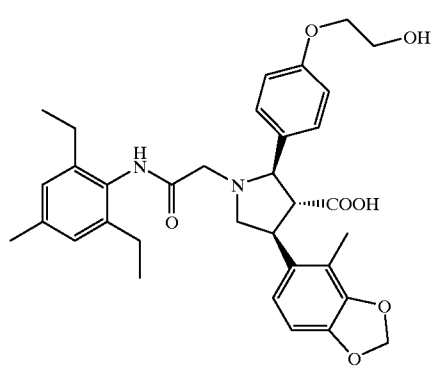 | 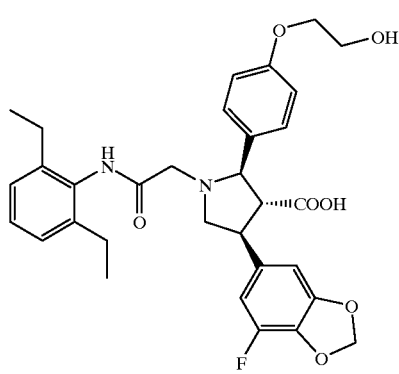 |
| 631 | 632 |
| 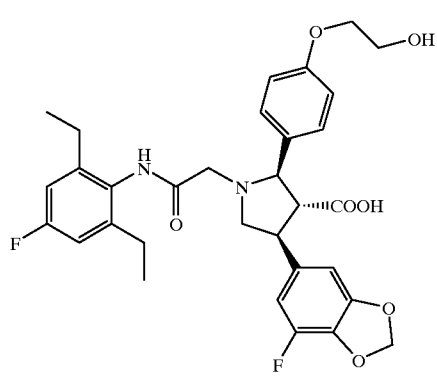 | 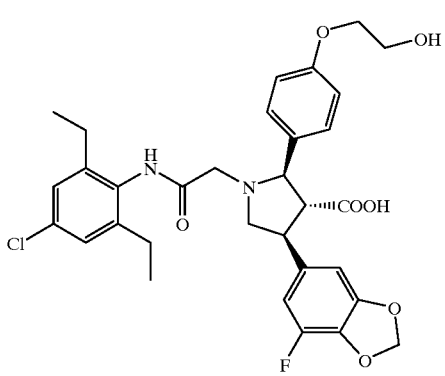 |

203 204
-continued
633 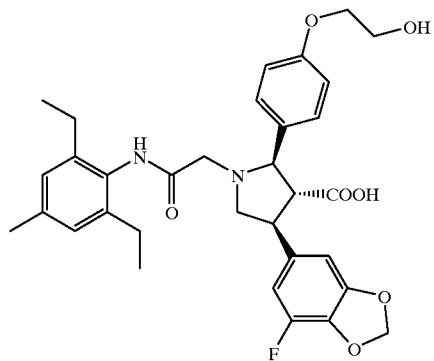 634 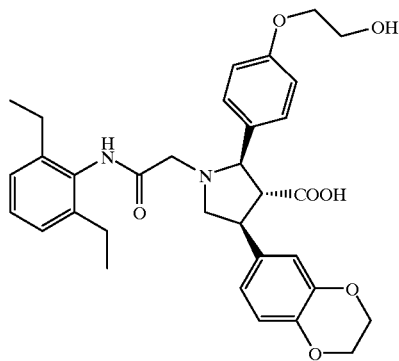
635 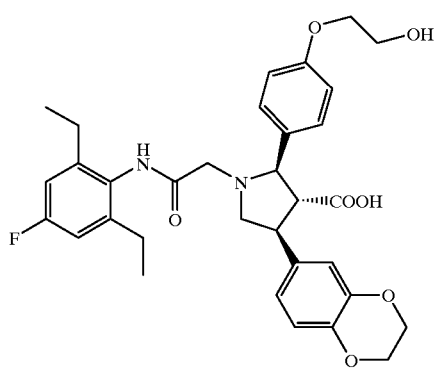 636 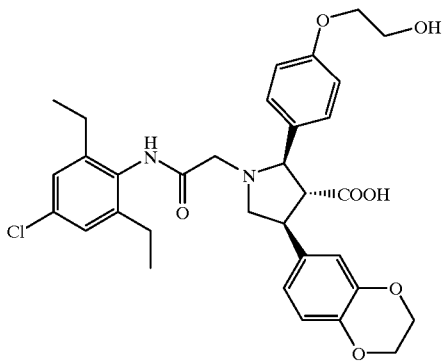
637 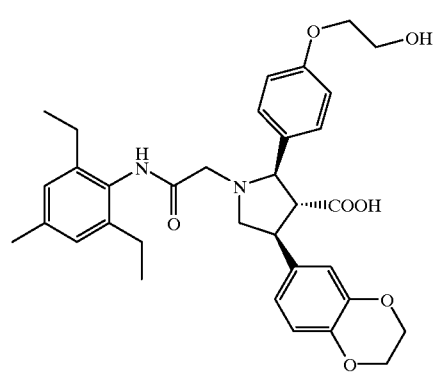 638 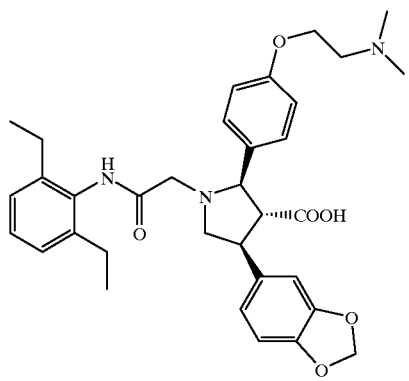
639 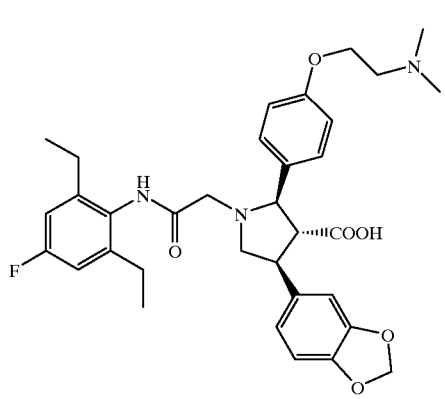 640 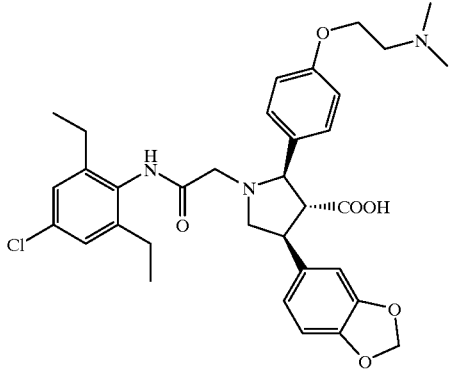

205 206
-continued
641 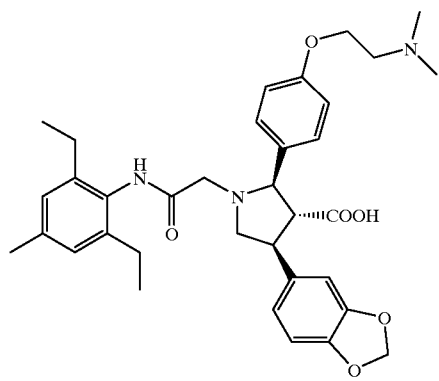 642 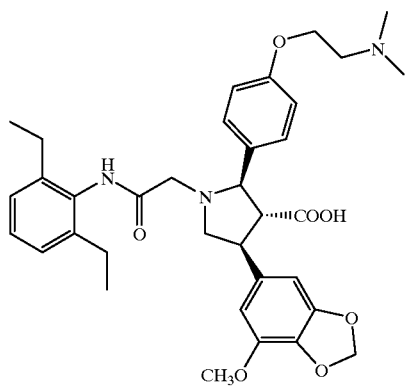
643 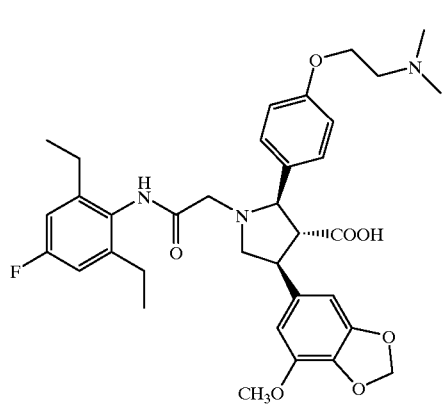 644 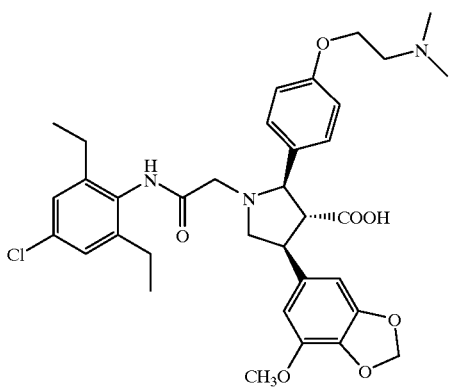
645 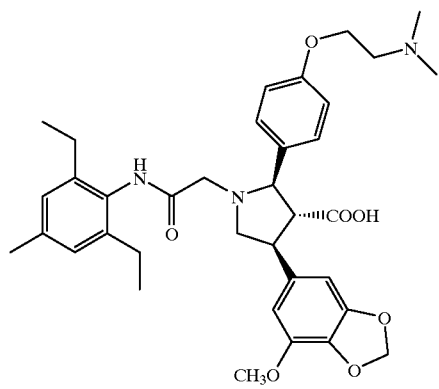 646 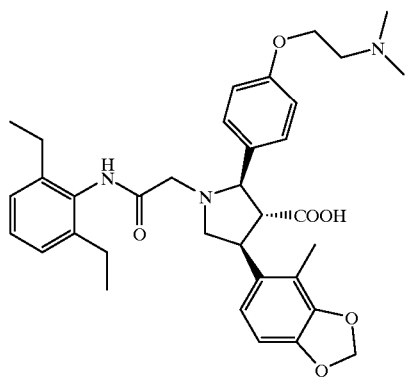
647 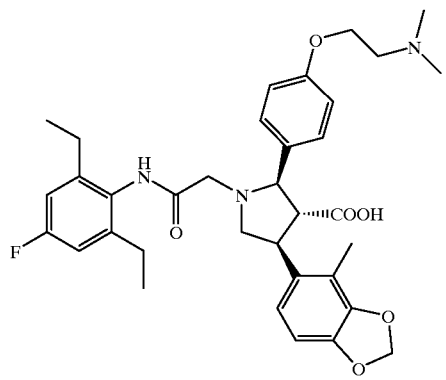 648 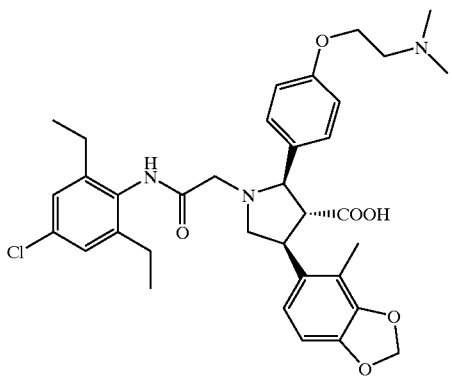

-continued
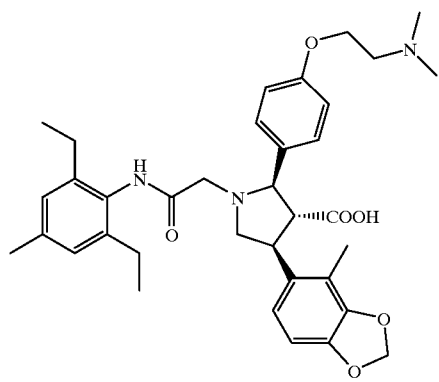
649
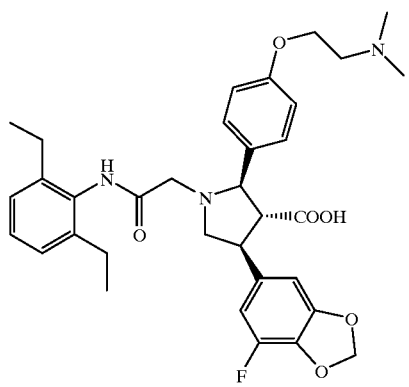
650
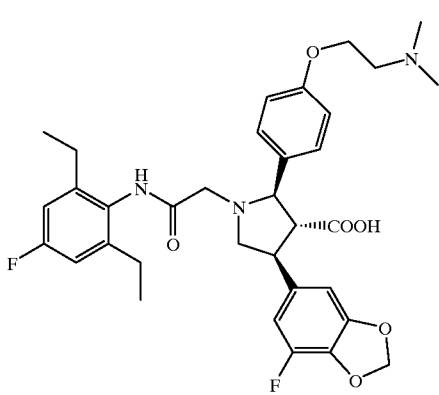
651
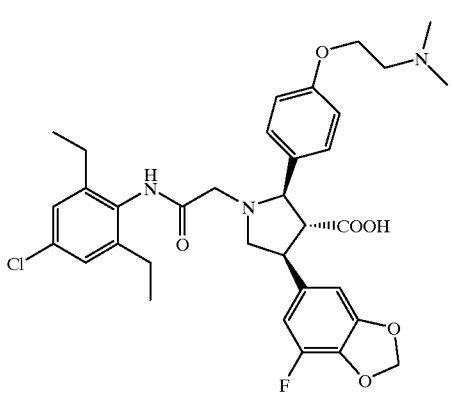
652
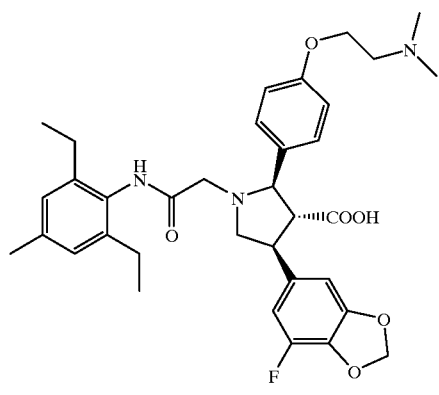
653
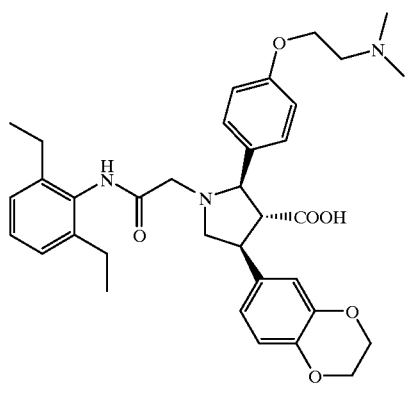
654
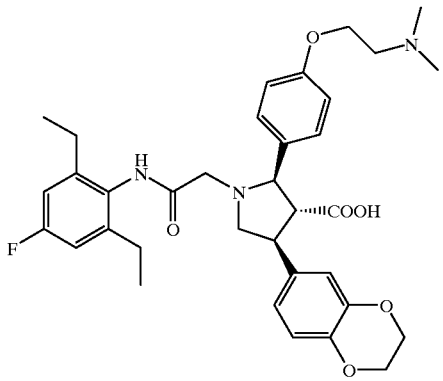
655
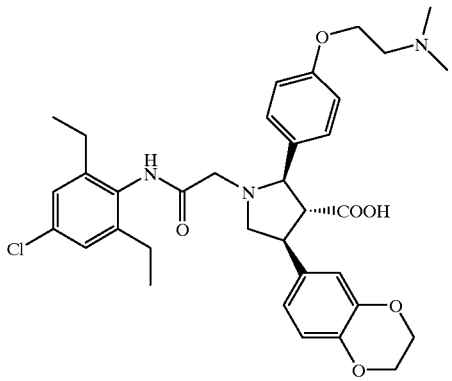
656

-continued
| 657 | 658 |
|---|---|
| 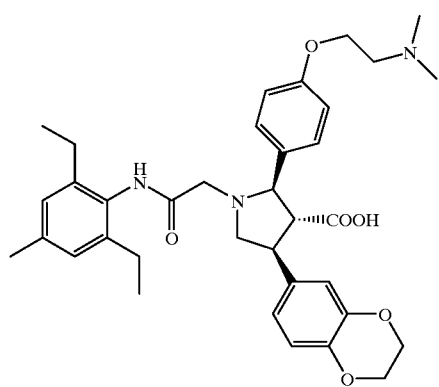 | 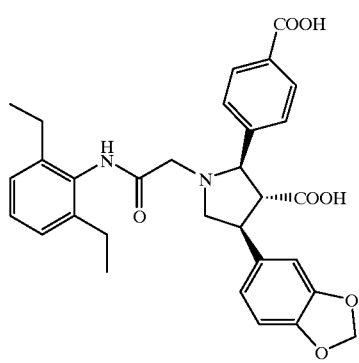 |
| 659 | 660 |
| 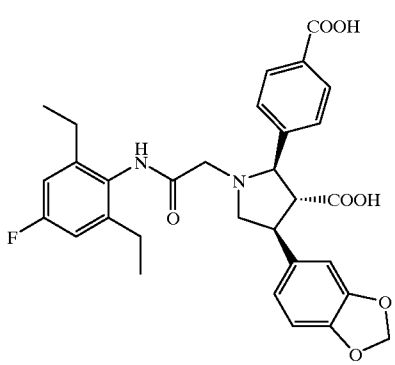 | 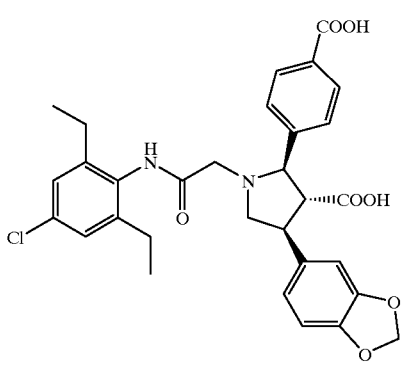 |
| 661 | 662 |
| 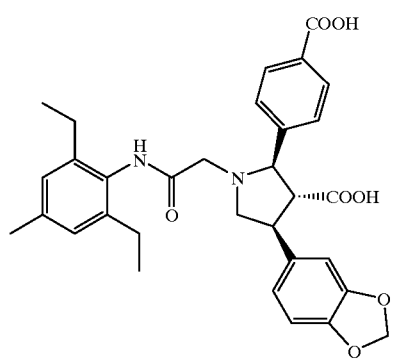 | 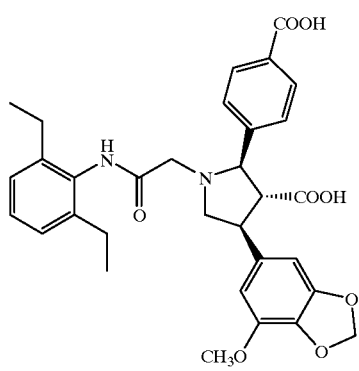 |
| 663 | 664 |
| 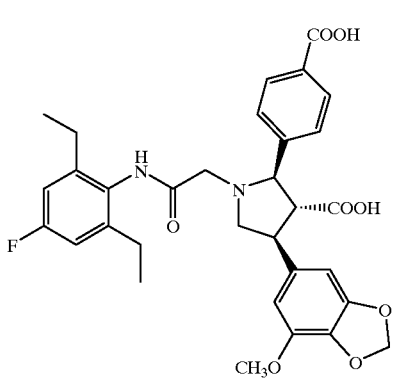 | 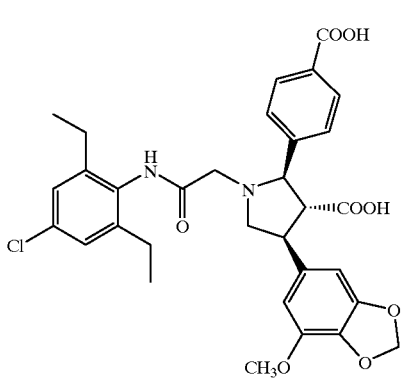 |

665
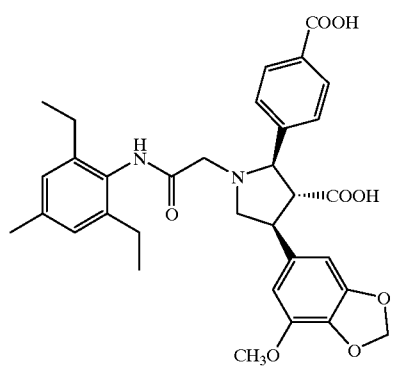
666
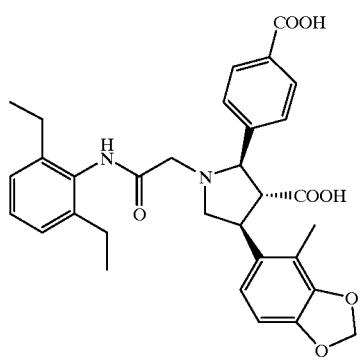
667
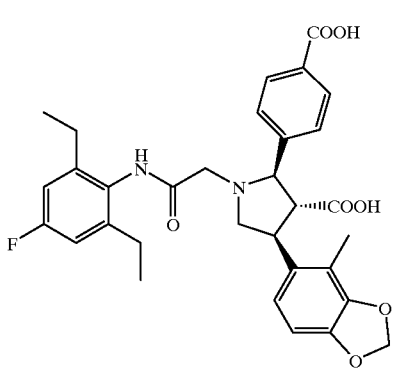
668
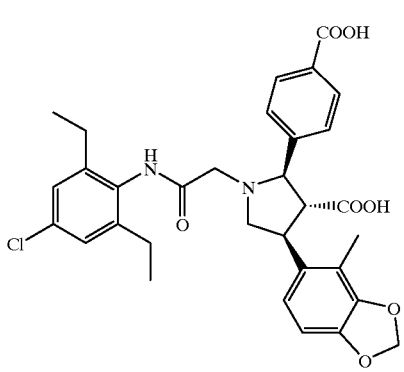
669
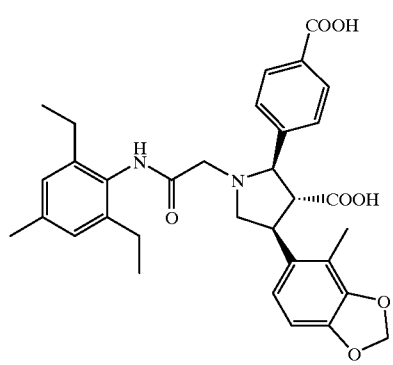
670
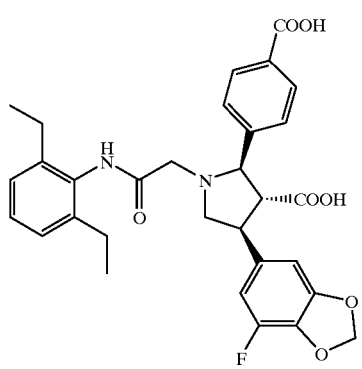
671
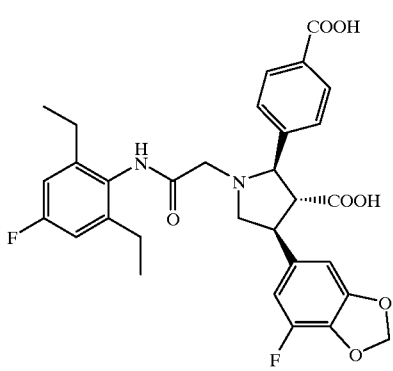
672
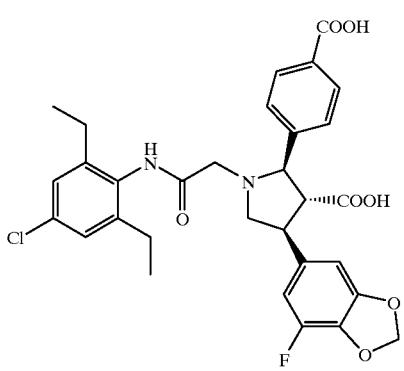

673
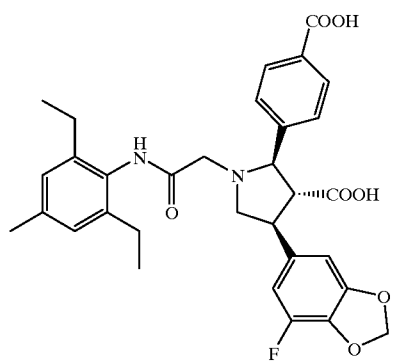
674
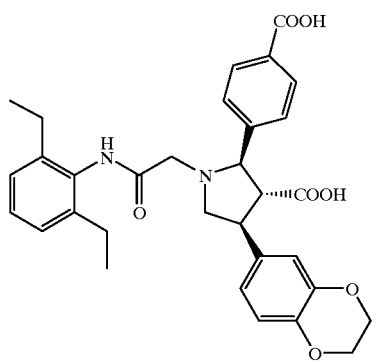
675
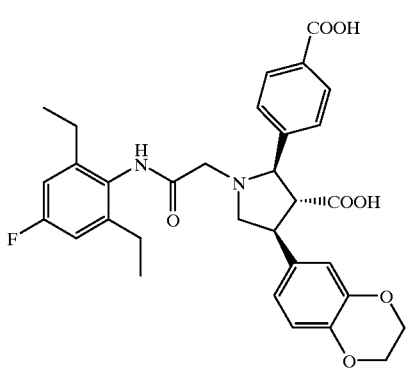
676
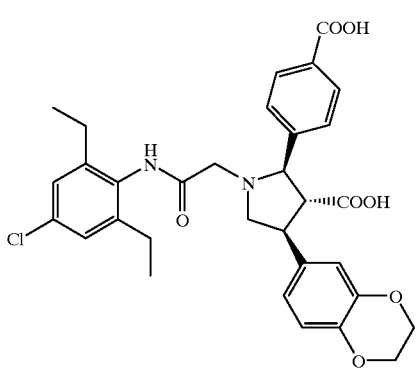
677
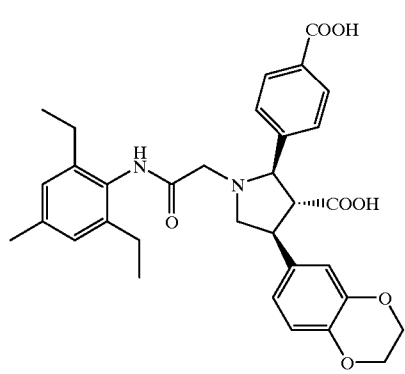
678
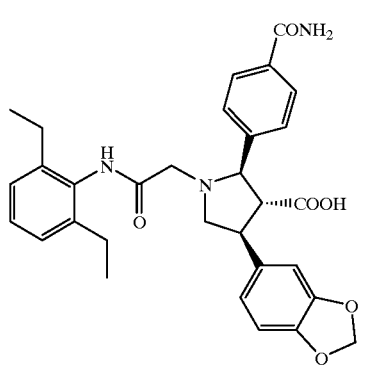
679
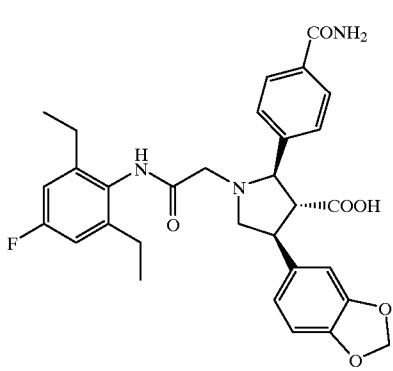
680
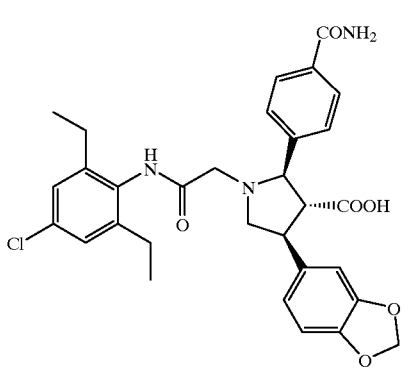

215
681
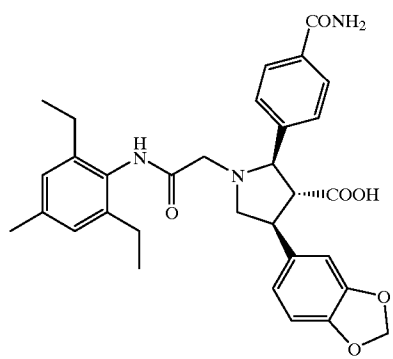
683
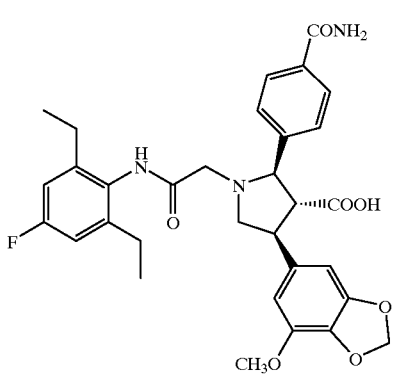
685
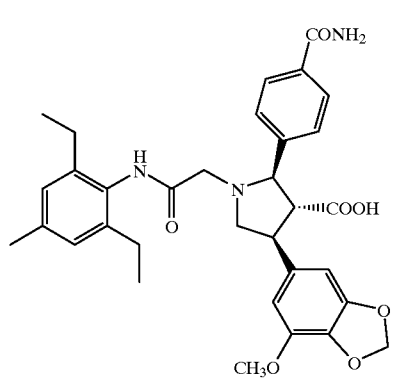
687
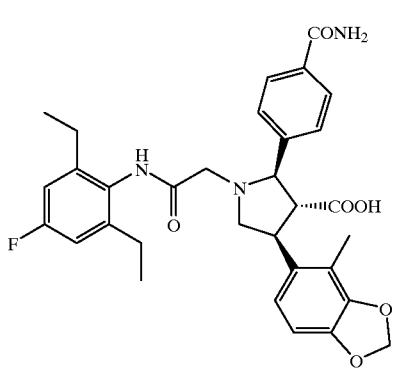
216
-continued
682
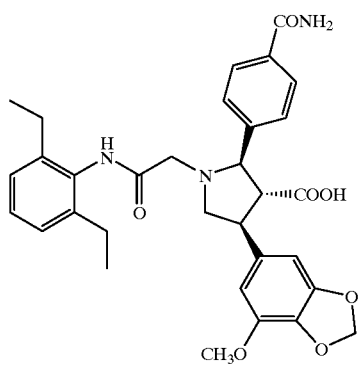
684
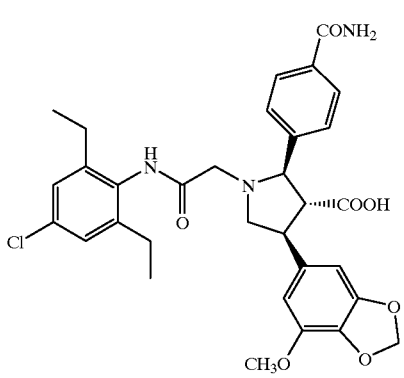
686
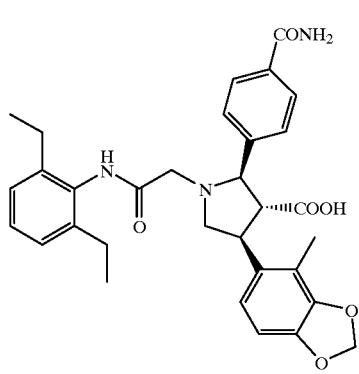
688
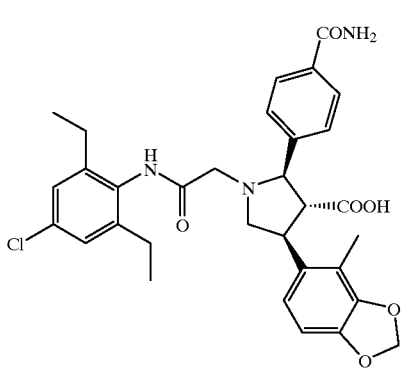

-continued
| 689 | 690 |
|---|---|
| 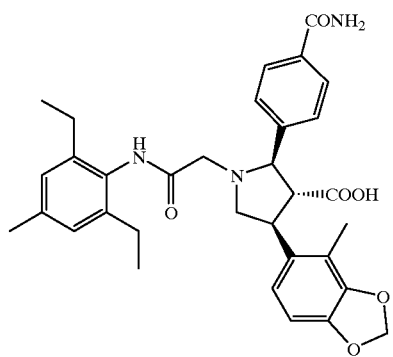 | 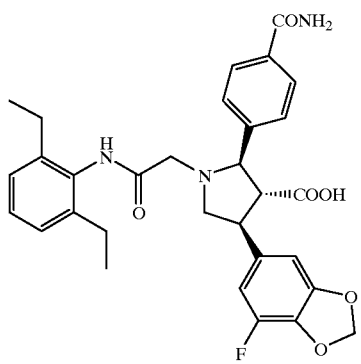 |
| 691 | 692 |
| 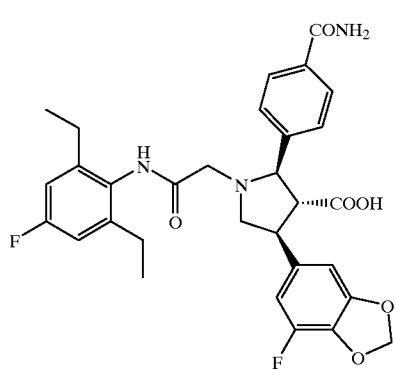 | 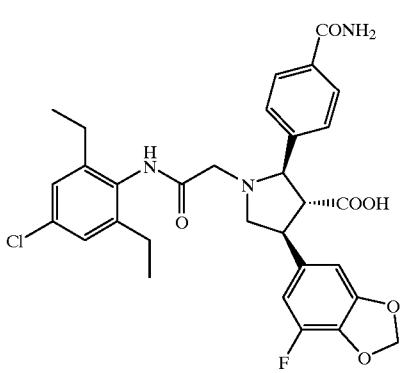 |
| 693 | 694 |
| 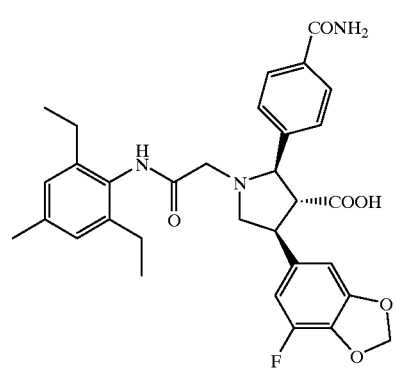 | 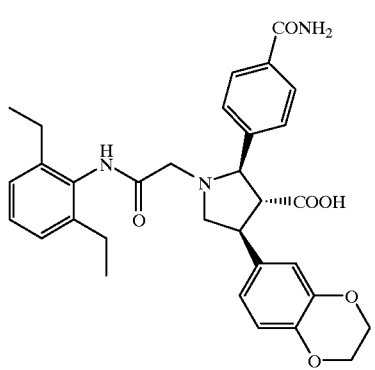 |
| 695 | 696 |
| 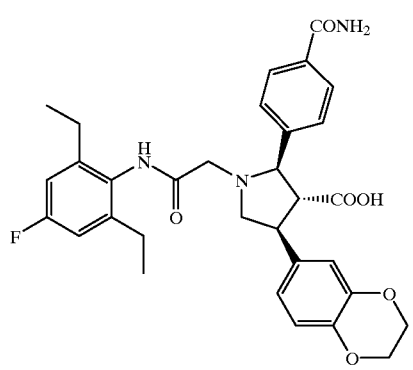 | 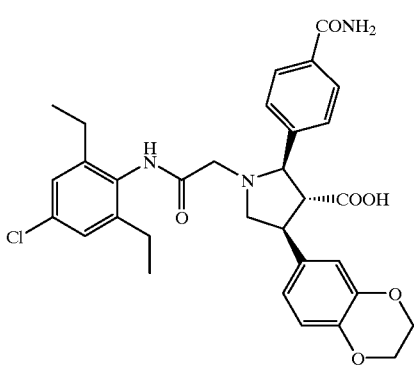 |

697
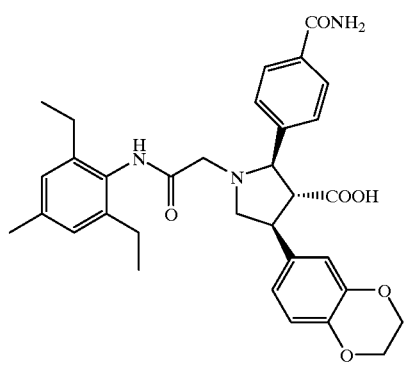
698
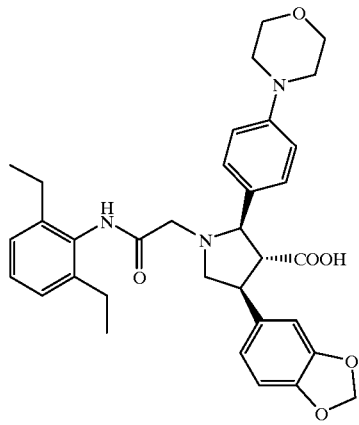
699
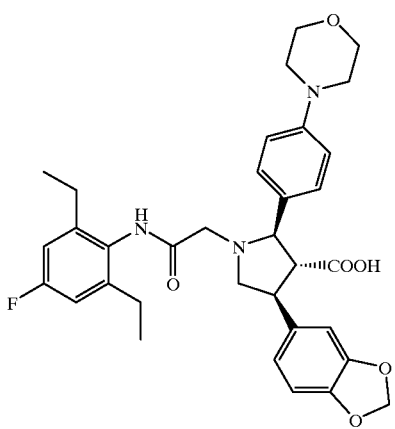
700
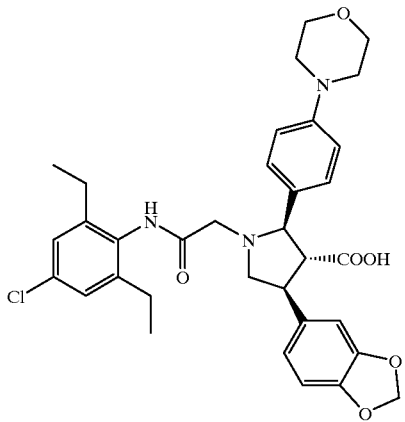
701
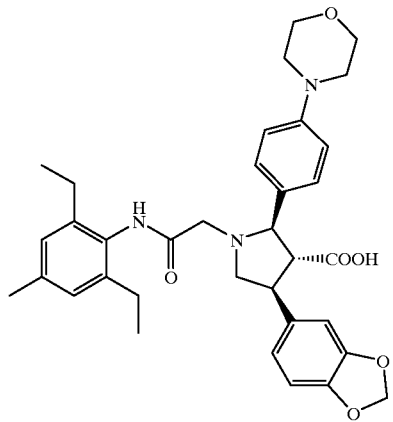

-continued
702
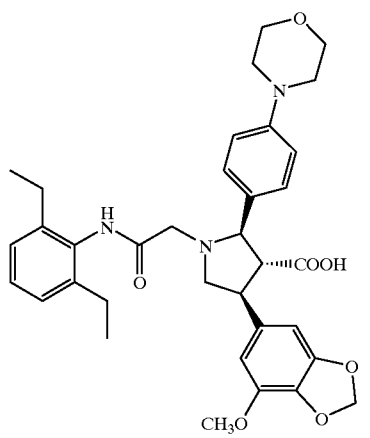
703
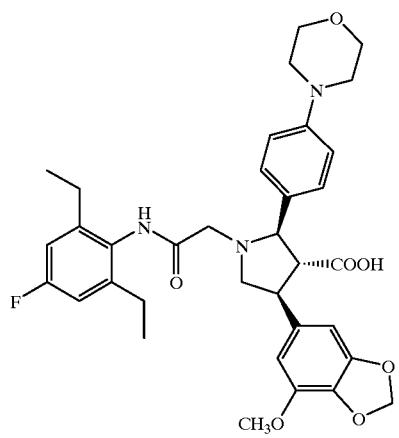
704
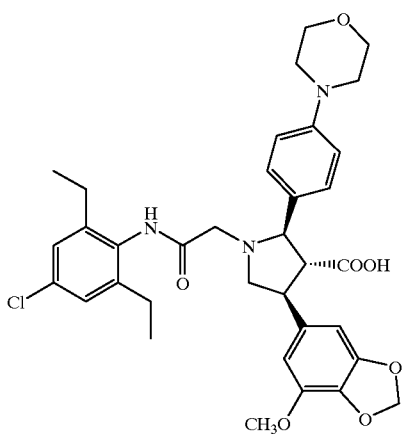
705
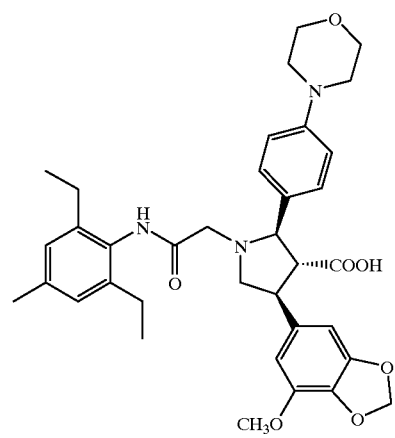
706
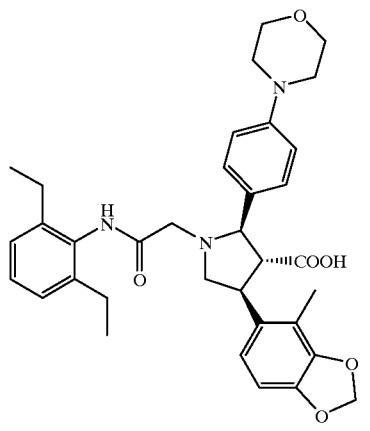
707
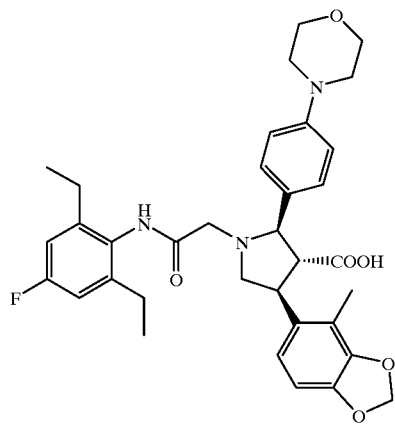

-continued
708
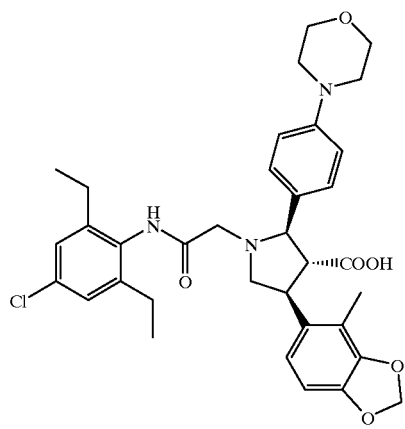
709
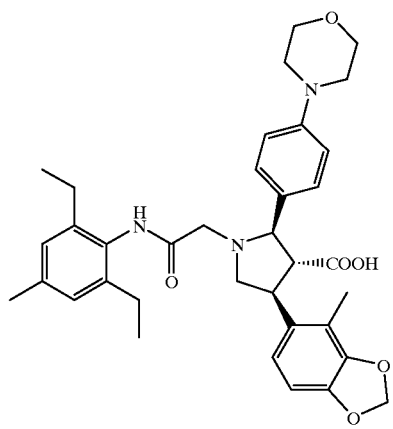
710
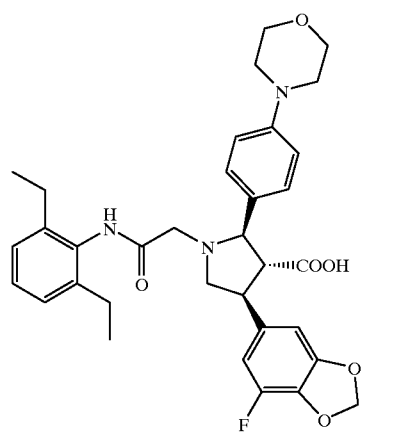
711
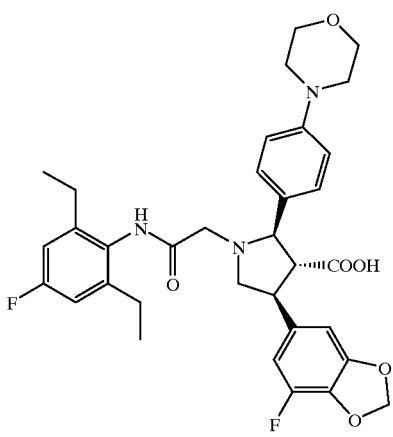
712
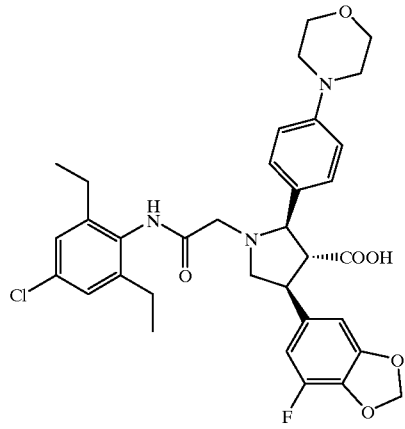
713
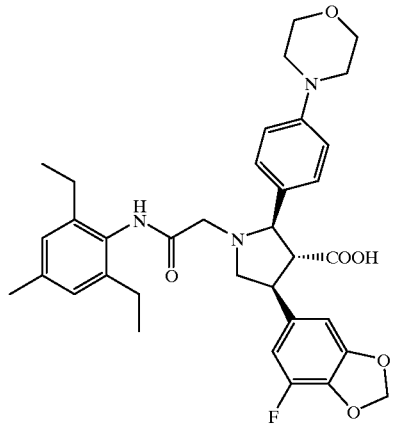

-continued
| | |
|---|---|
| 714 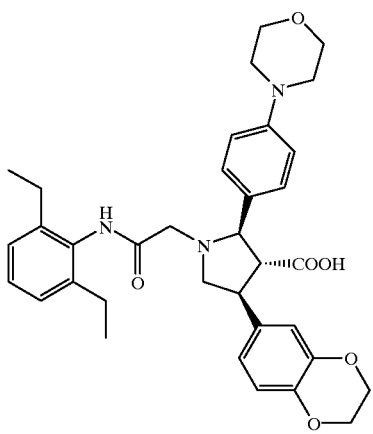 | 715 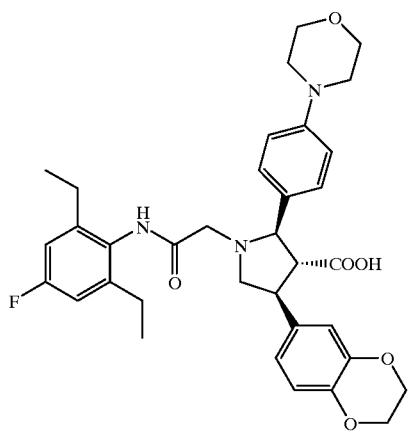 |
| 716 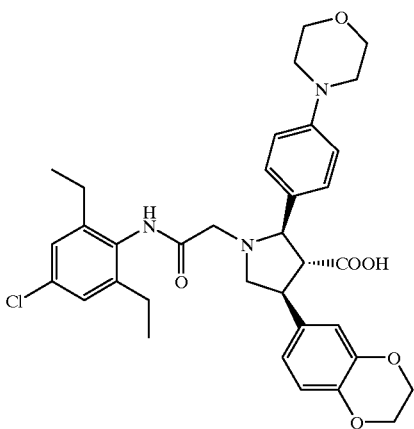 | 717 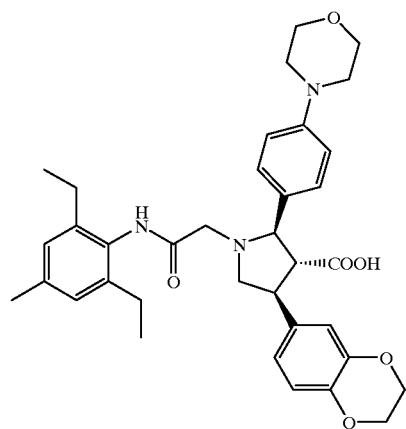 |
| 718 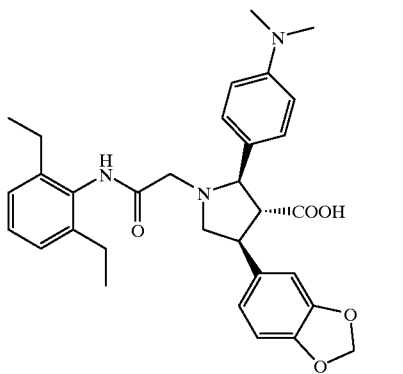 | 719 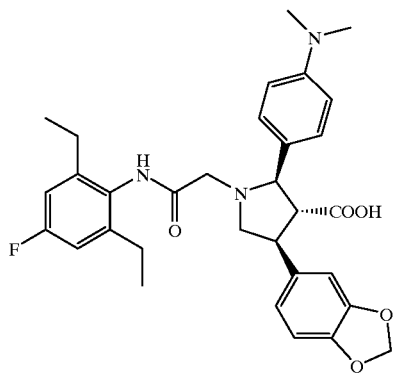 |
| 720 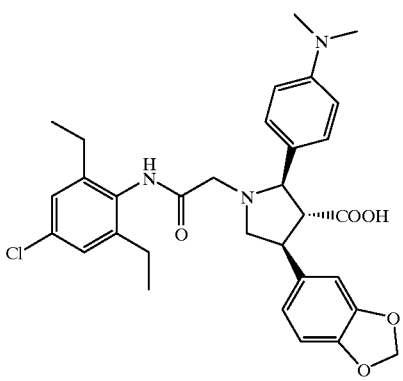 | 721 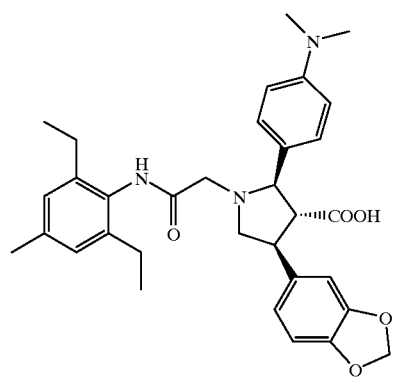 |

-continued
| 722 | 723 |
|---|---|
| 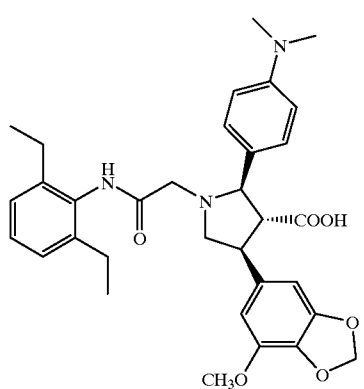 | 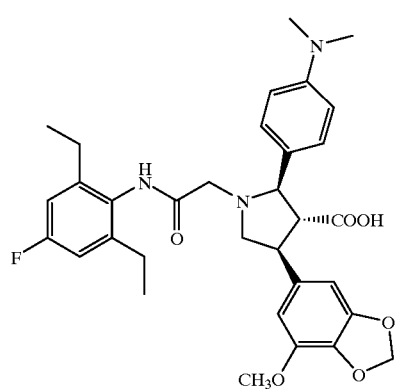 |
| 724 | 725 |
| 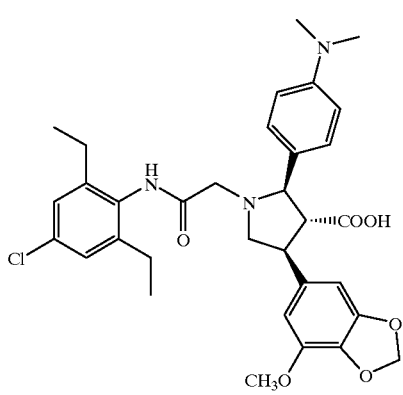 | 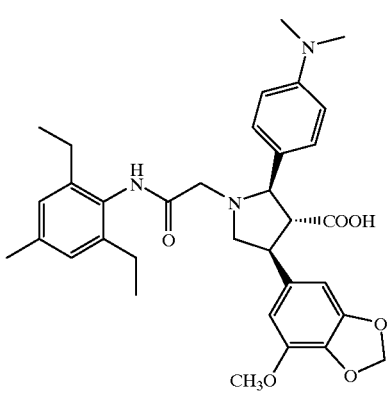 |
| 726 | 727 |
| 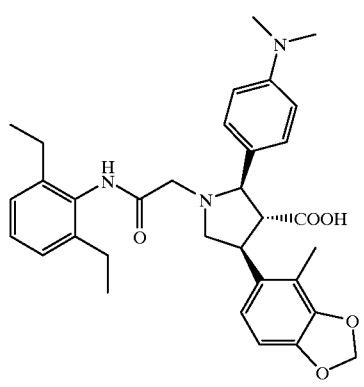 | 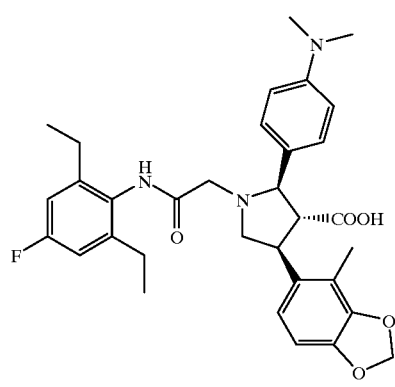 |
| 728 | 729 |
| 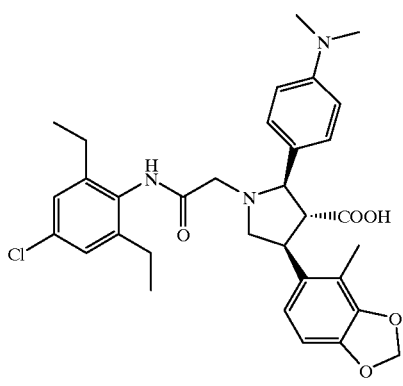 | 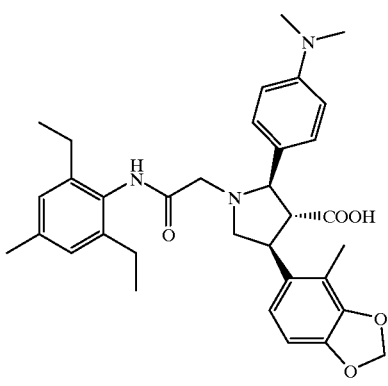 |

-continued
730
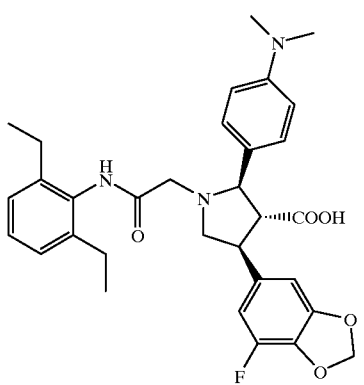
731
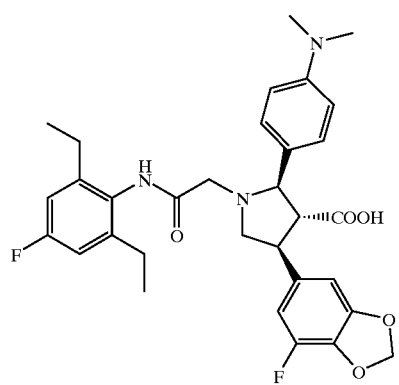
732
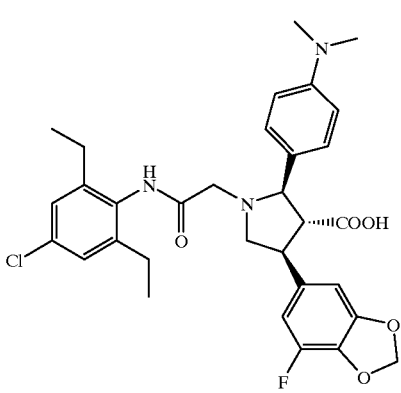
733
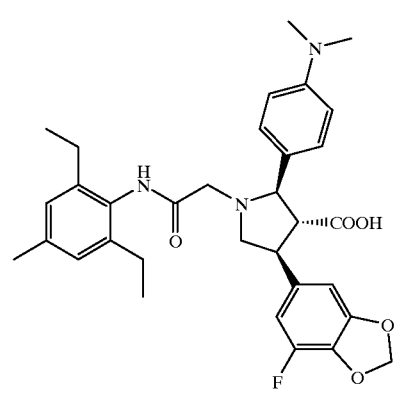
734
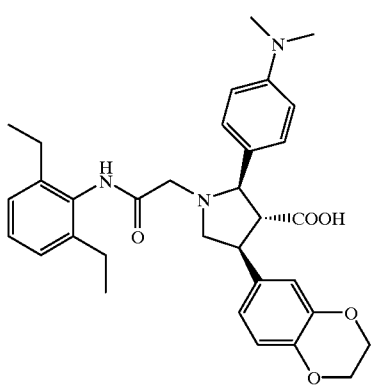
735
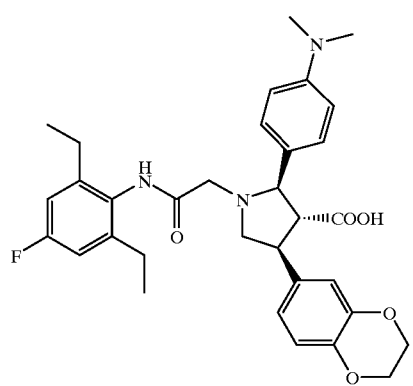
736
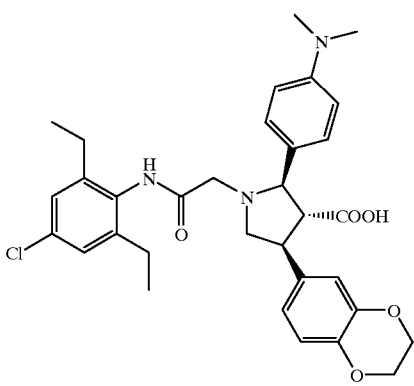
737
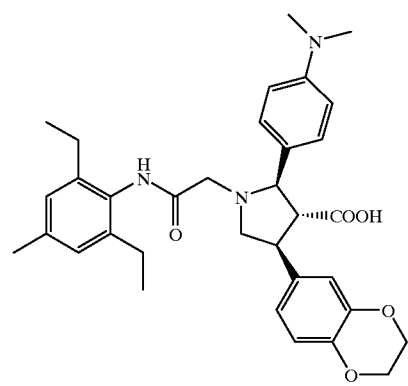

738
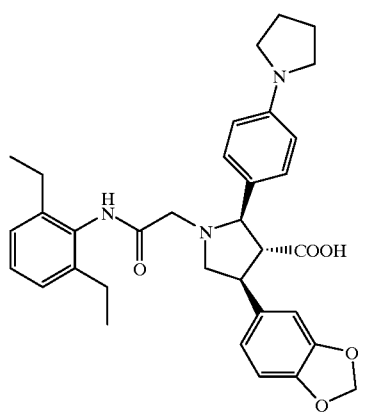
740
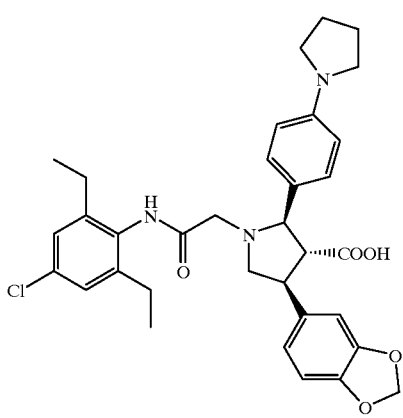
742
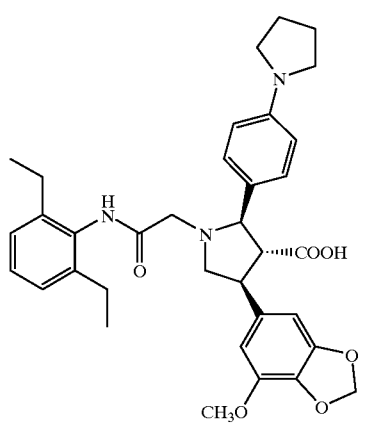
739
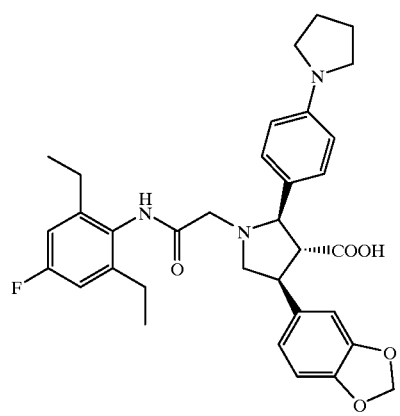
741
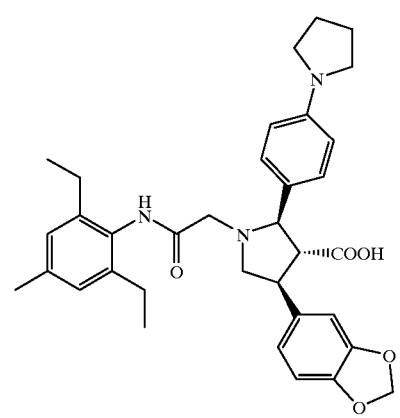
743
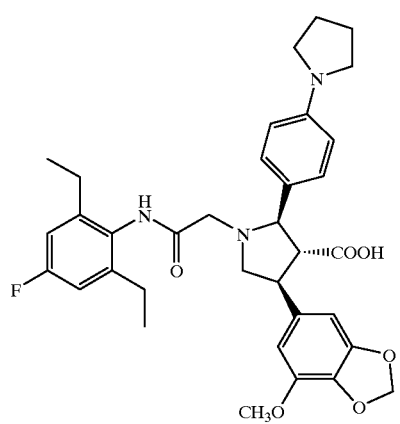

-continued
744
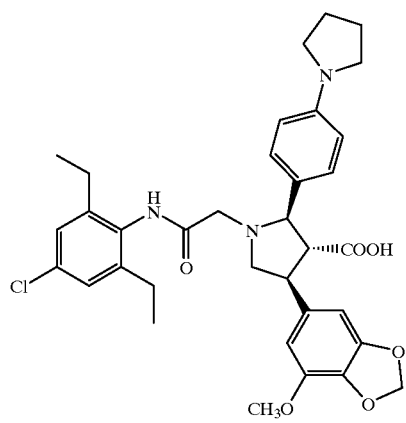
745
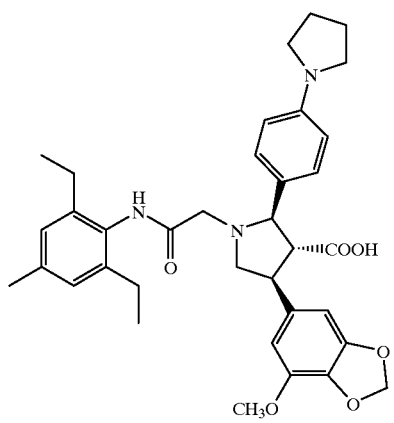
746
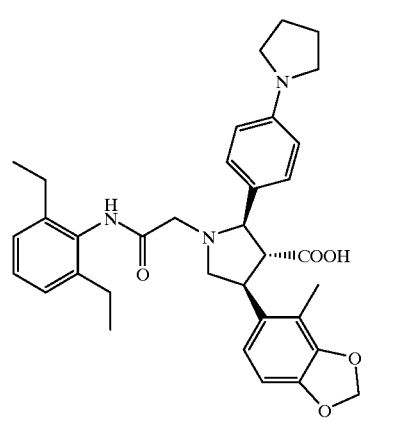
747
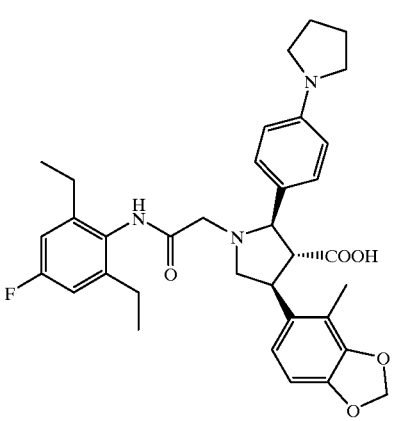
748
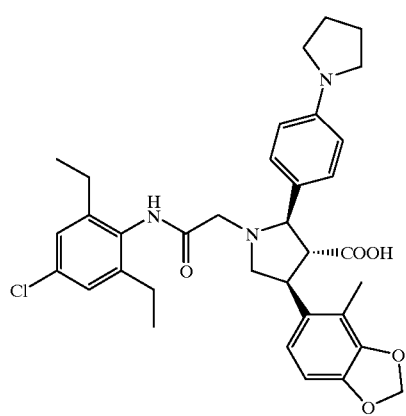
749
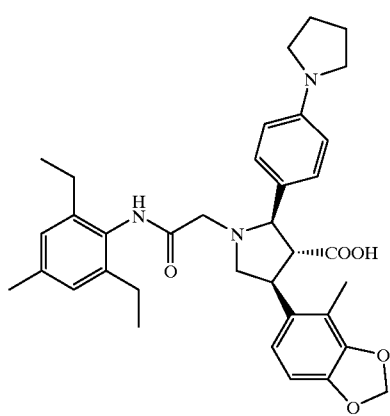

| 235 | 236 |
|---|---|
| 750 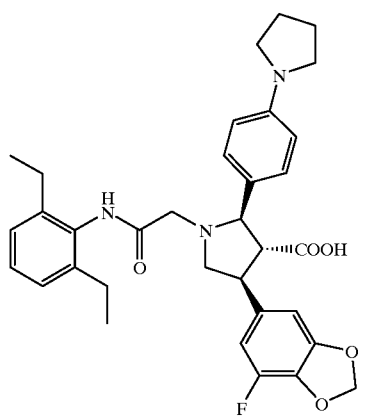 | 751 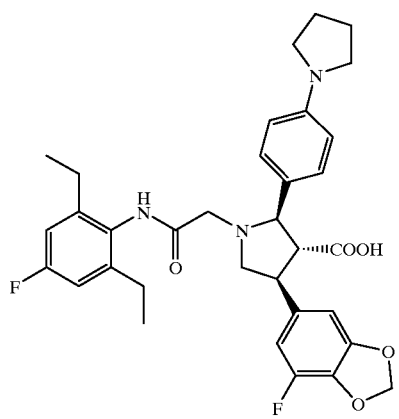 |
| 752 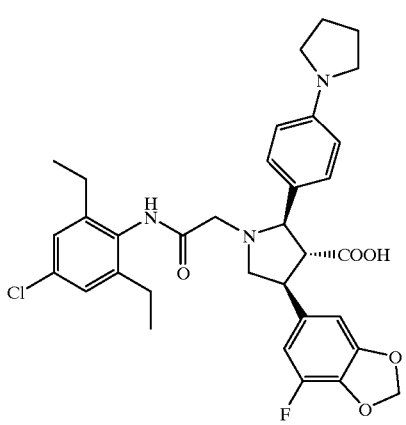 | 753 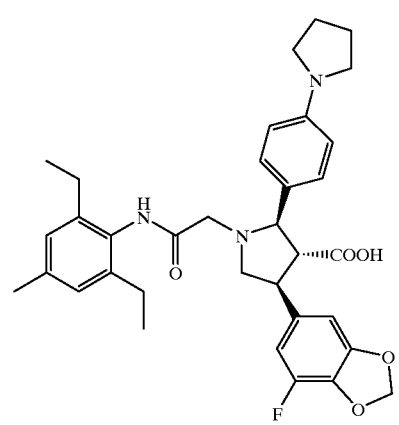 |
| 754 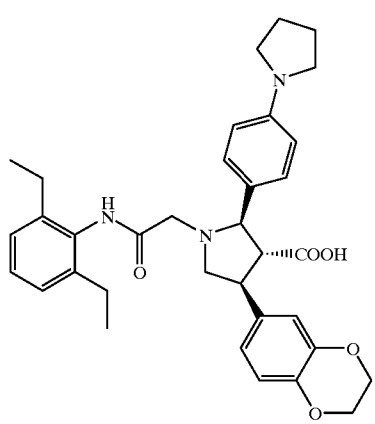 | 755 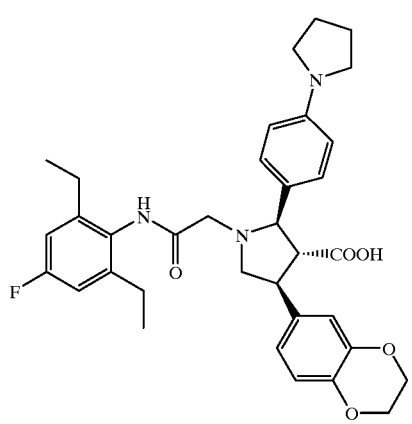 |

-continued
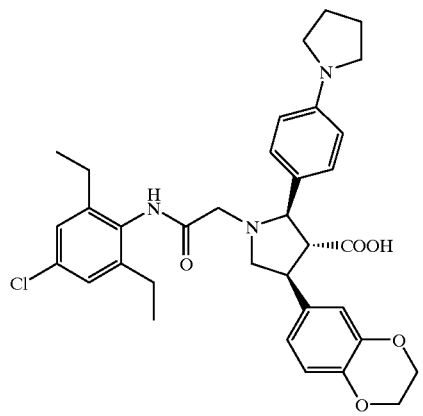
756
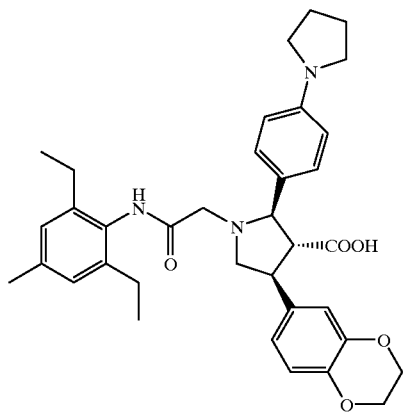
757
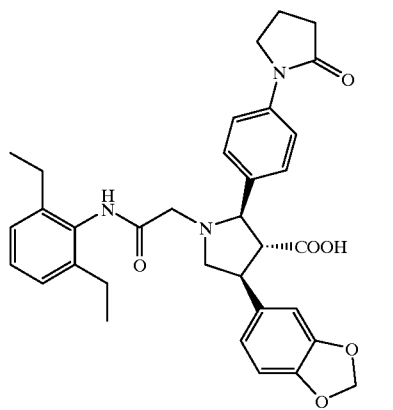
758
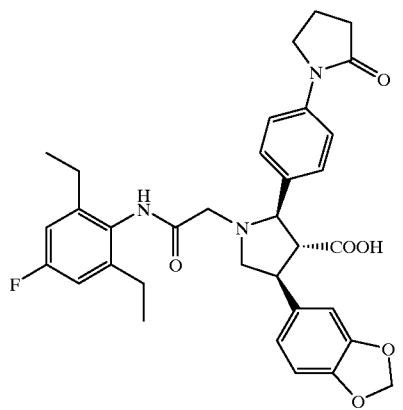
759
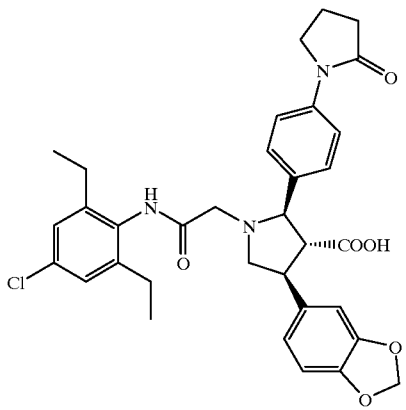
760
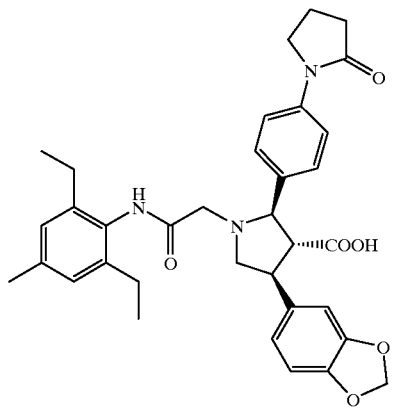
761

239 240
-continued
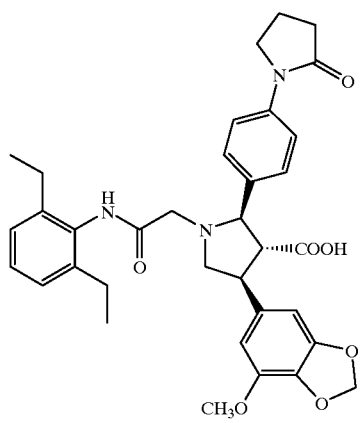
762
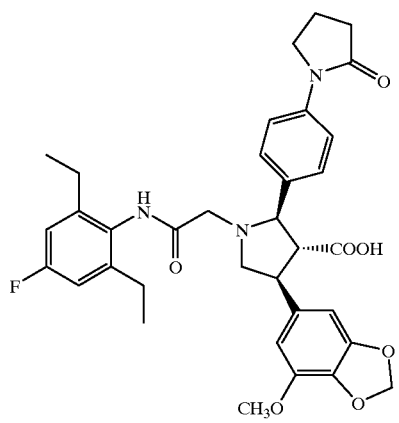
763
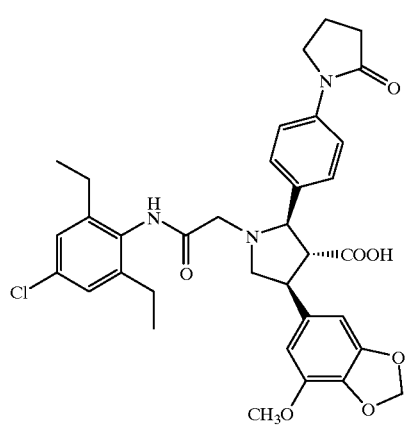
764
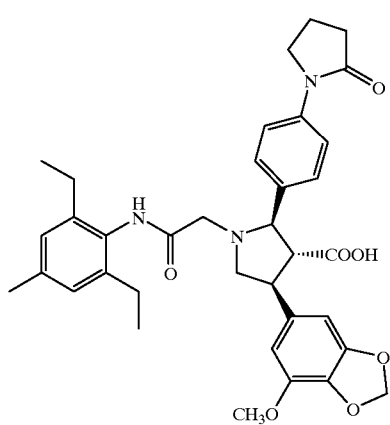
765
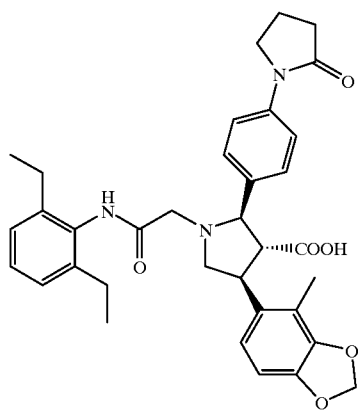
766
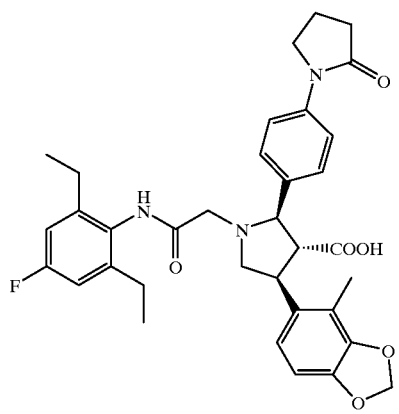
767

-continued
| 768 | 769 |
|---|---|
| 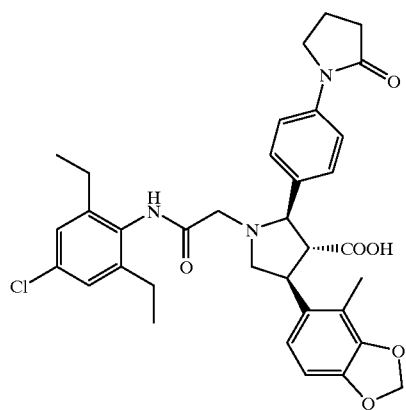 | 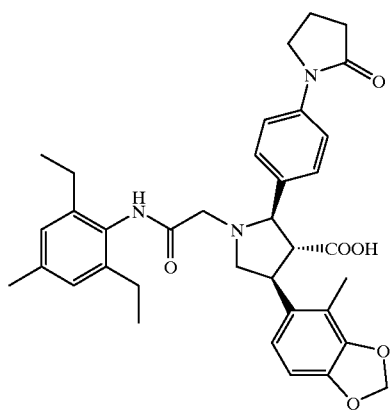 |
| 770 | 771 |
| 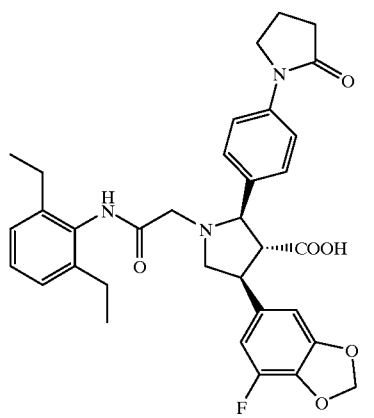 | 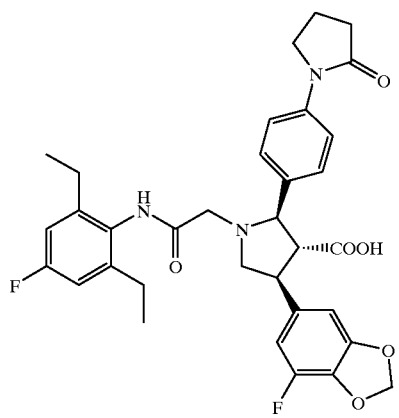 |
| 772 | 773 |
| 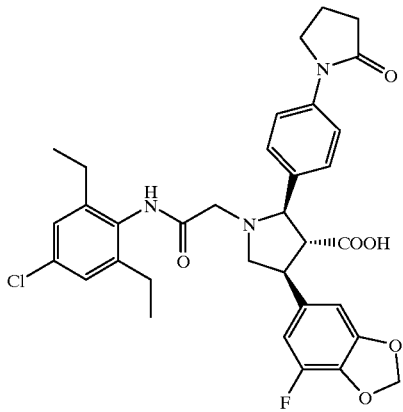 | 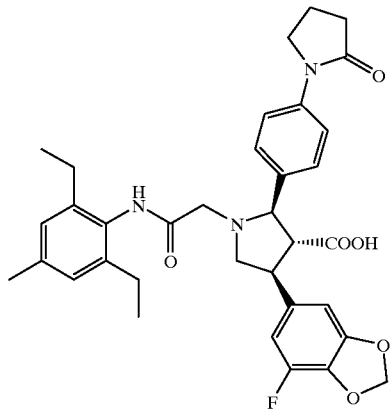 |

-continued
774
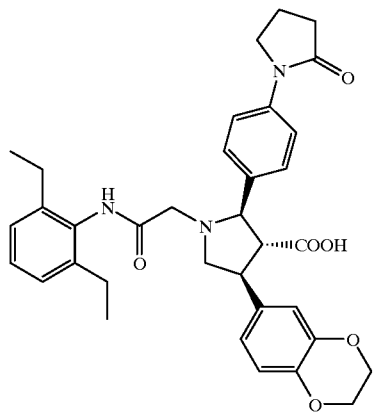
775
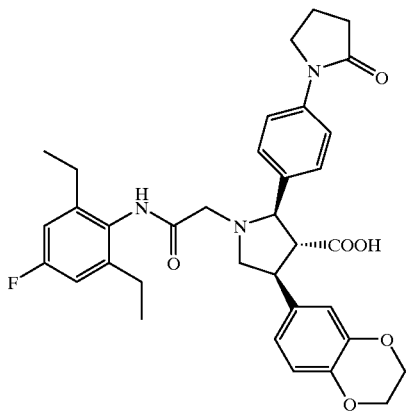
776
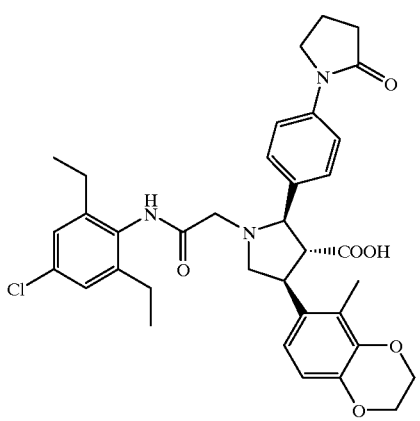
777
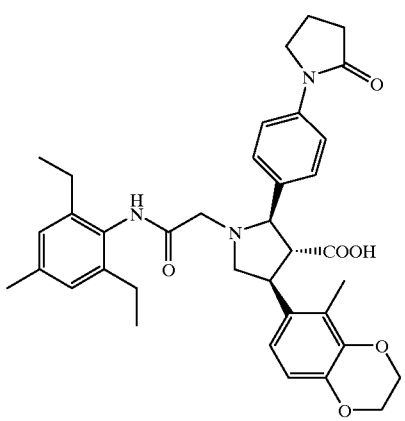
778
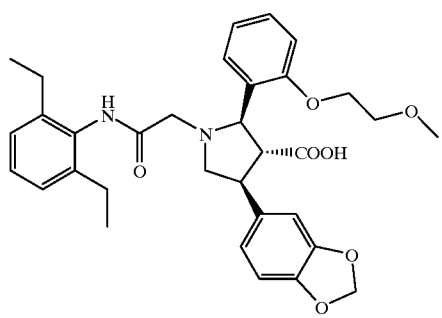
779
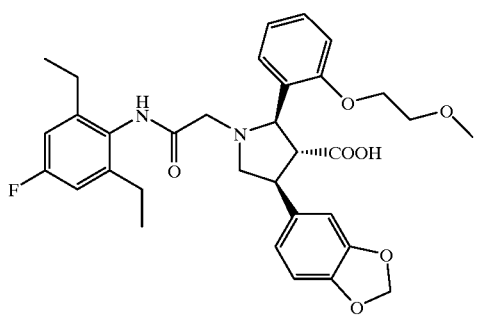
780
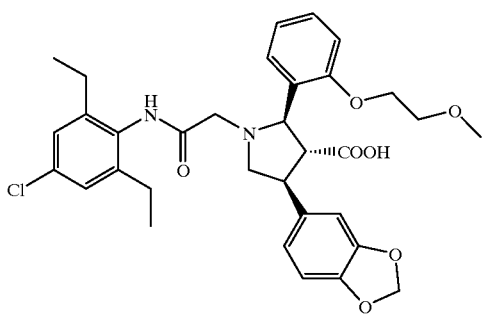
781
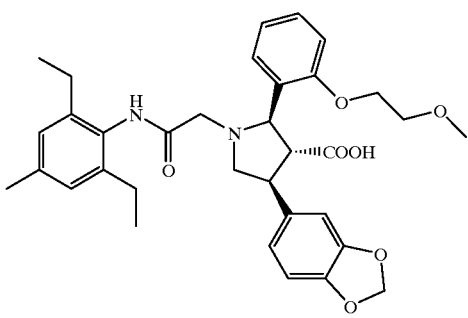

245
246
-continued
782 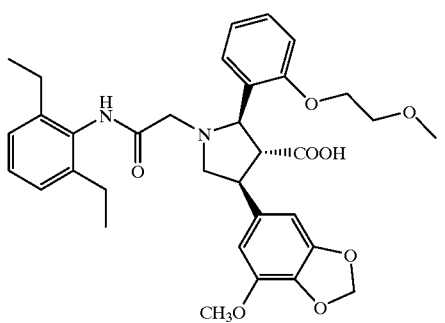
783 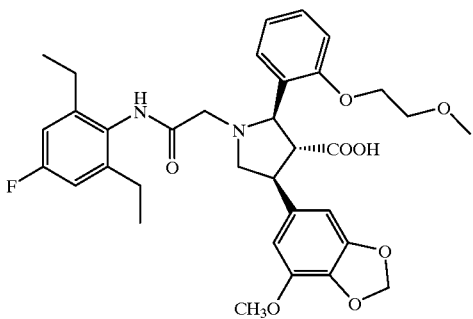
784 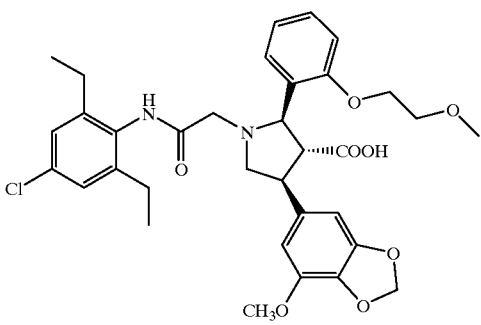
785 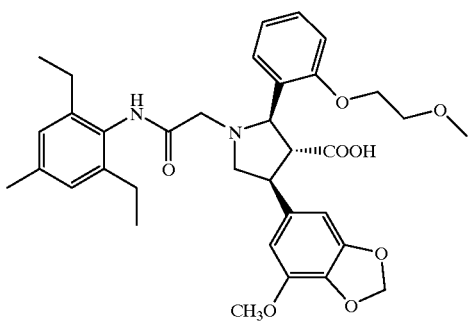
786 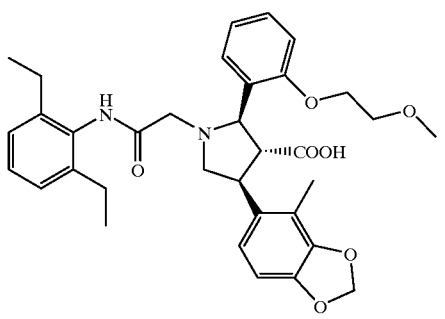
787 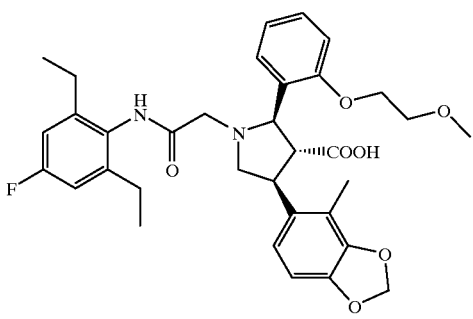
788 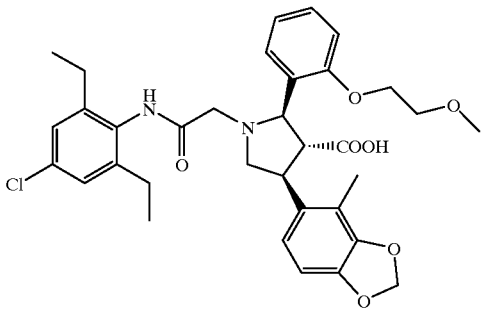
789 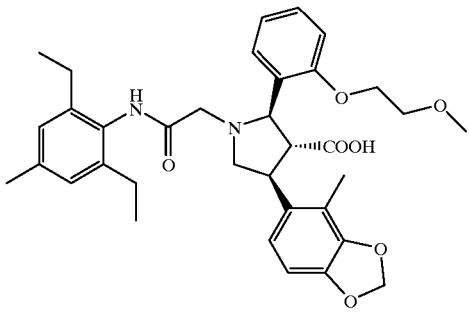
790 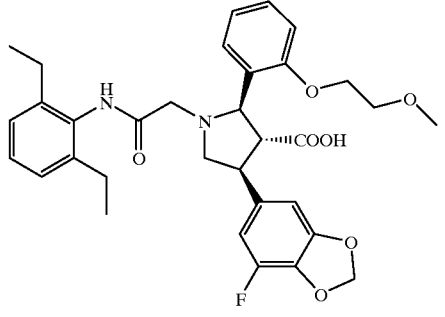
791 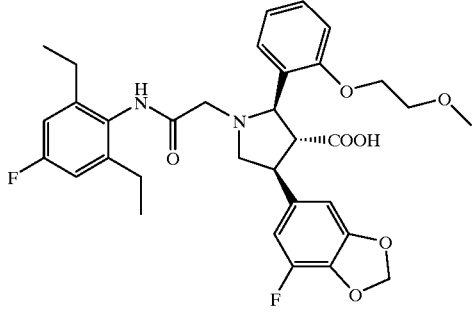

247                                    248
-continued
792                                            793
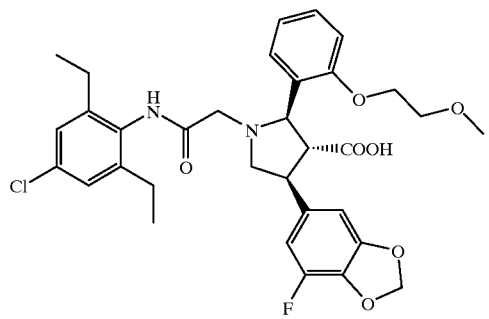                          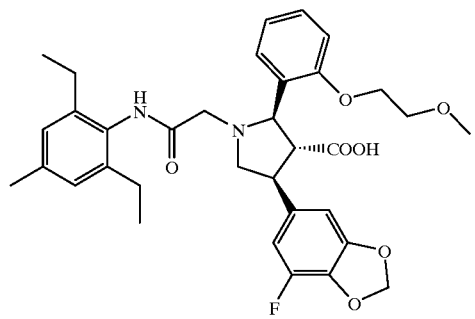
794                                            795
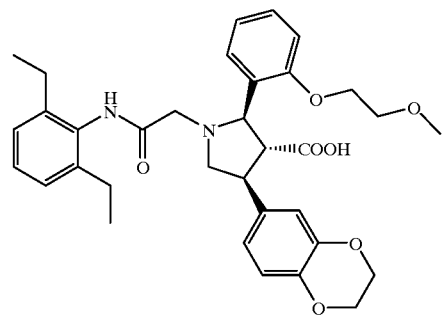                          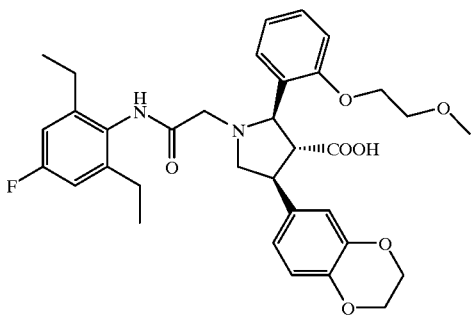
796                                            797
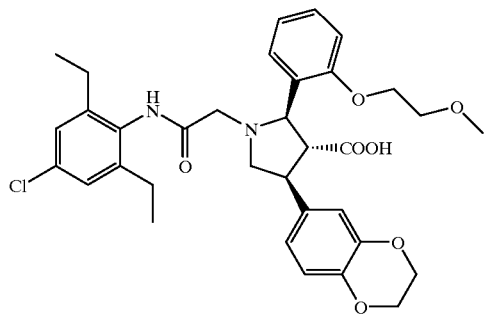                          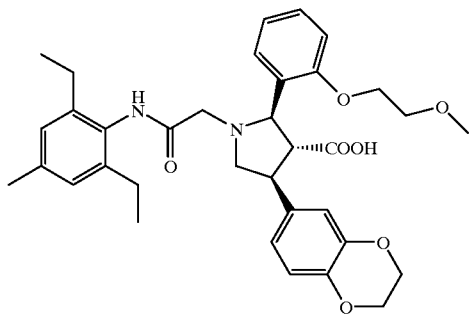
798                                            799
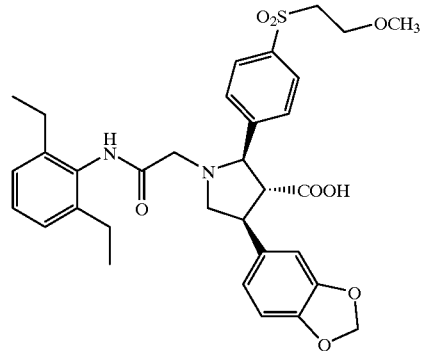                          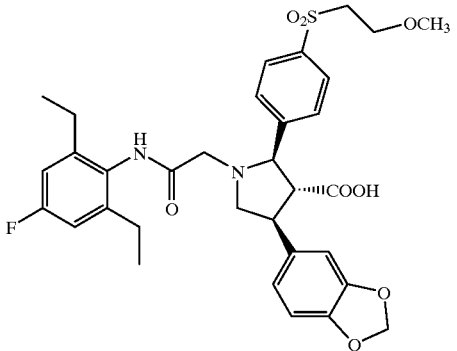

-continued
| 249 | 250 |
|---|---|
| 800 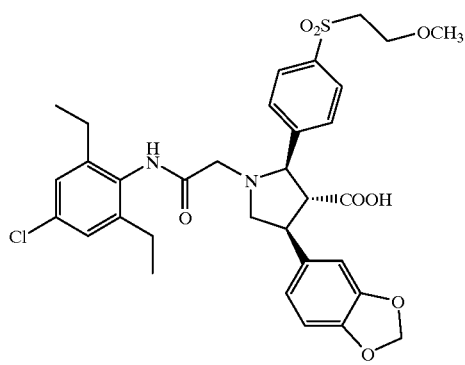 | 801 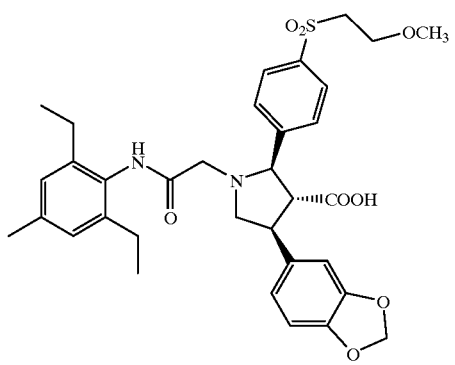 |
| 802 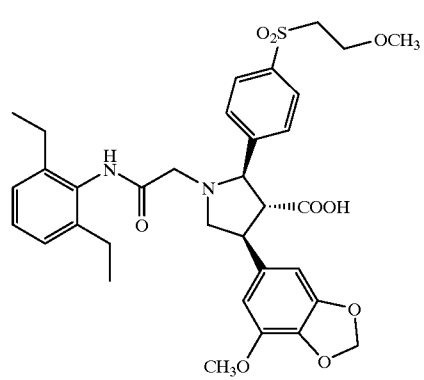 | 803 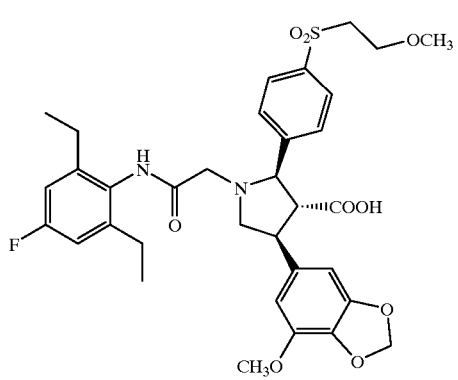 |
| 804 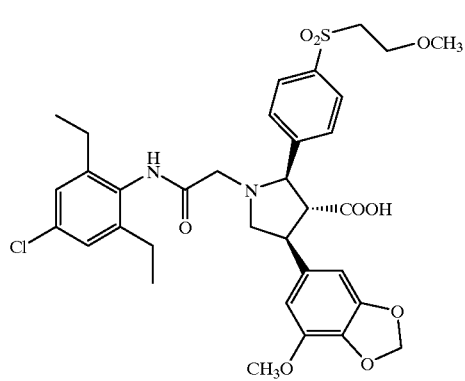 | 805 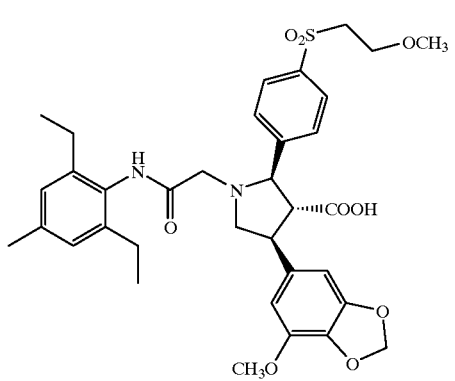 |
| 806 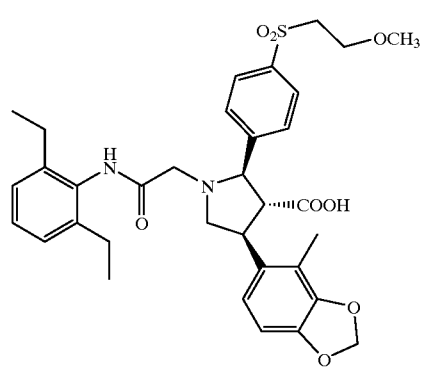 | 807 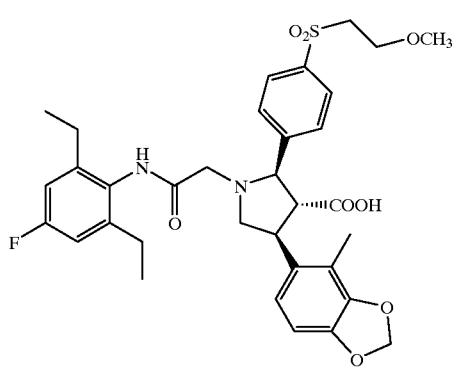 |

251
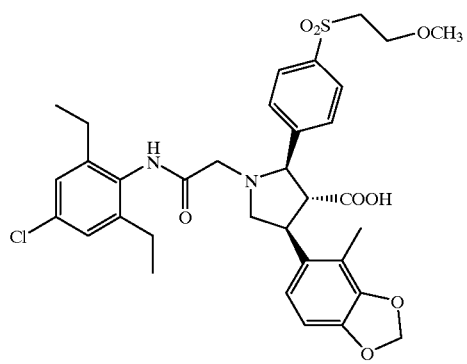
808
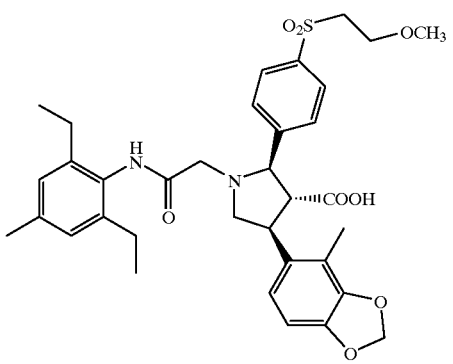
809
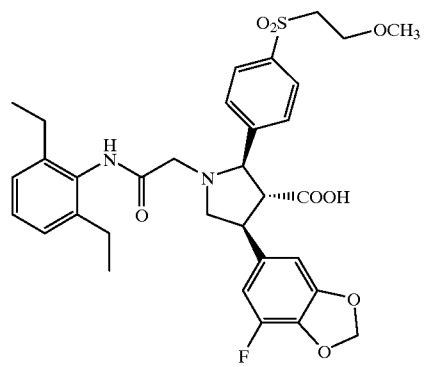
810
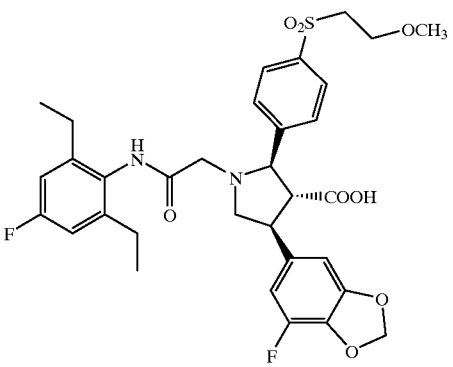
811
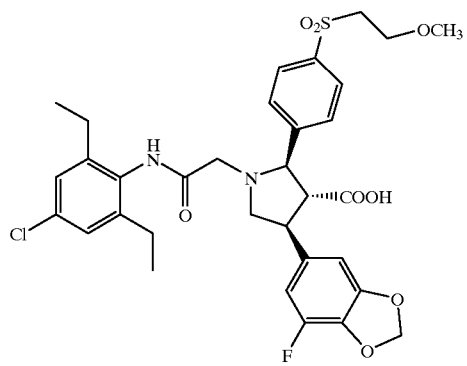
812
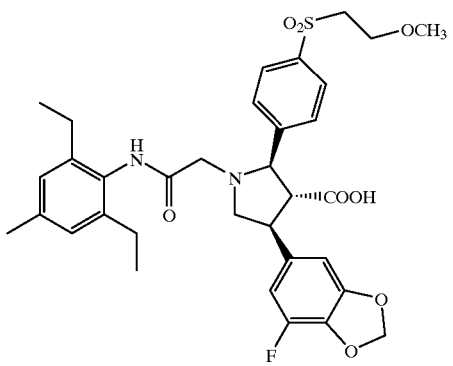
813
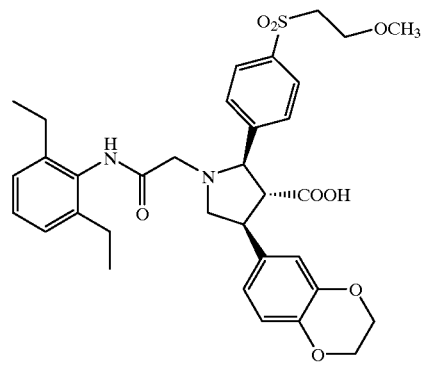
814
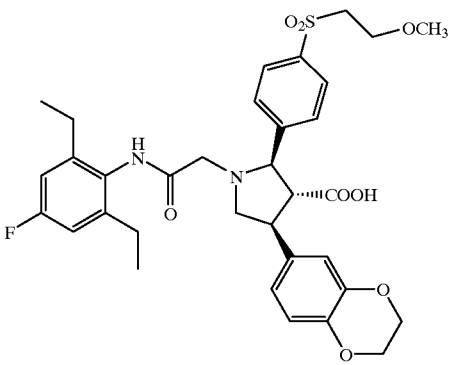
815

253 254
-continued
816 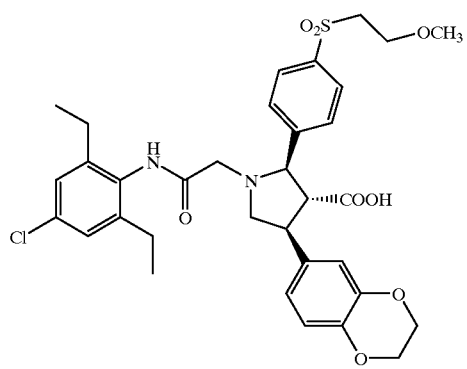 817 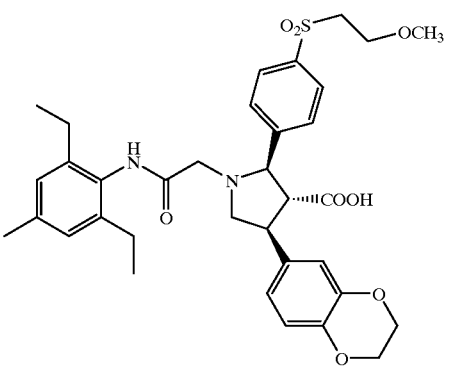
818 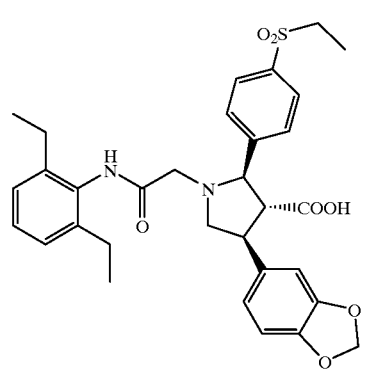 819 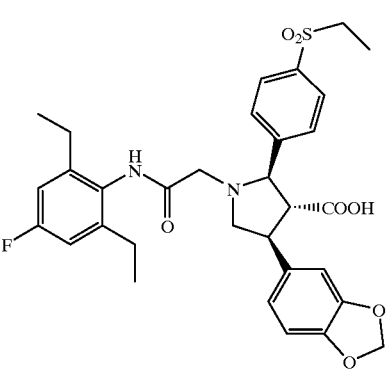
820 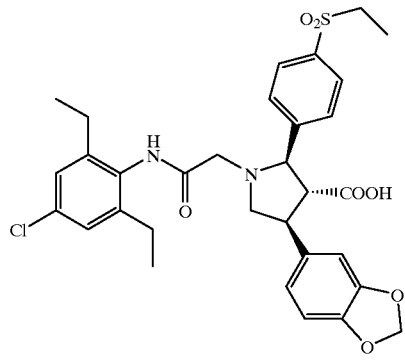 821 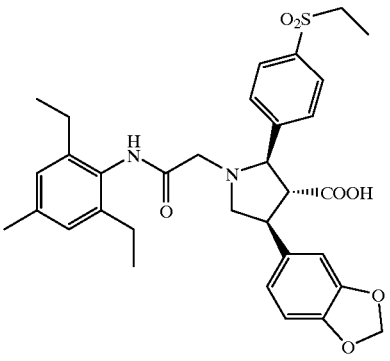
822 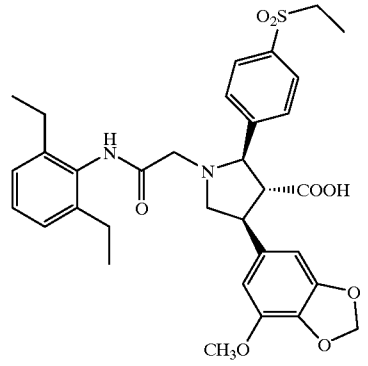 823 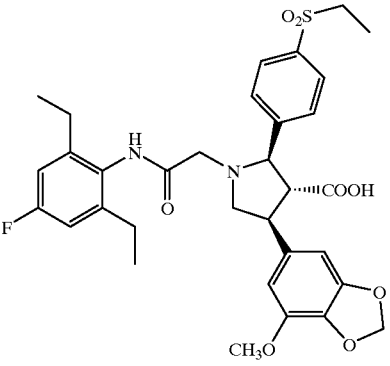

-continued
| 255 | 256 |
|---|---|
| 824 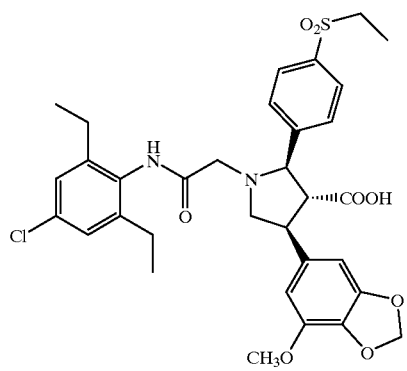 | 825 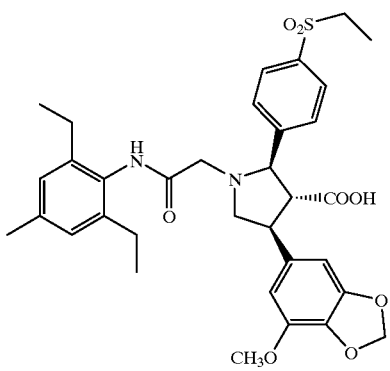 |
| 826 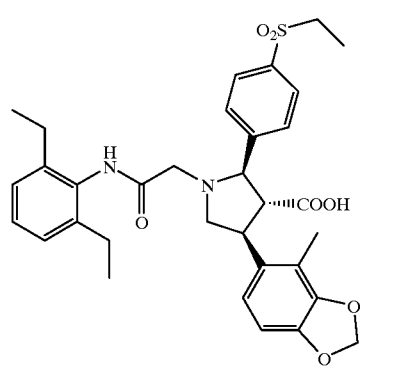 | 827 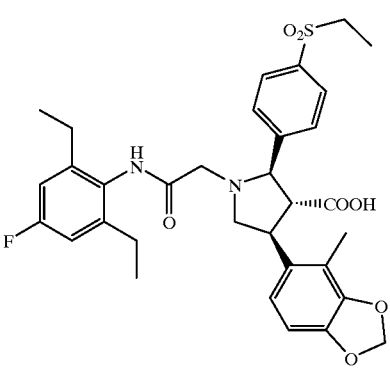 |
| 828 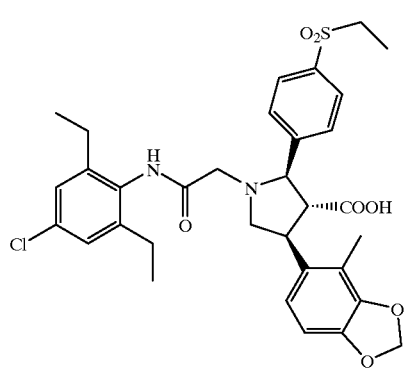 | 829 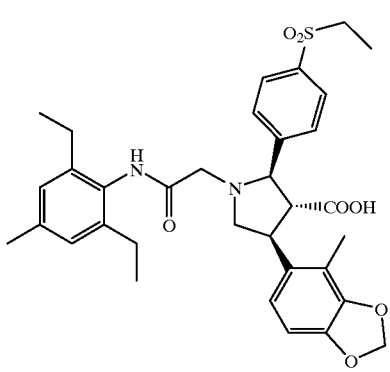 |
| 830 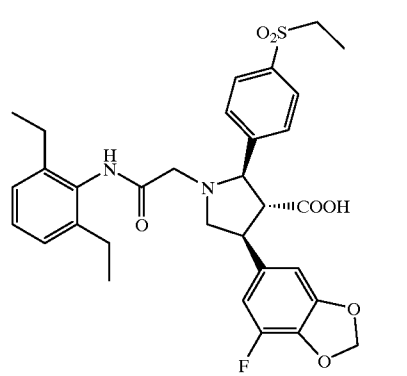 | 831 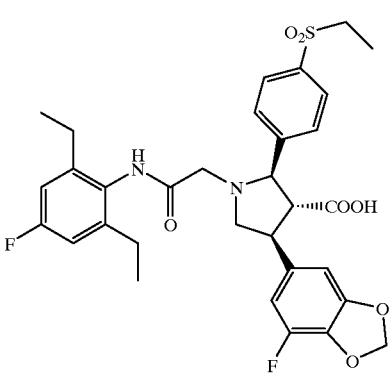 |

-continued
| 257 | 258 |
|---|---|
| 832 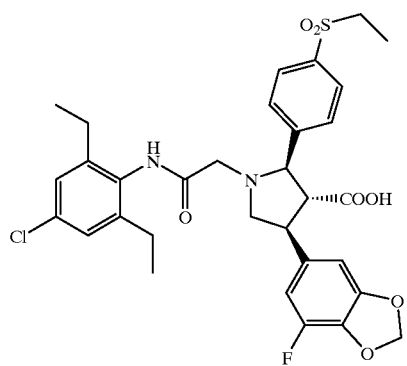 | 833 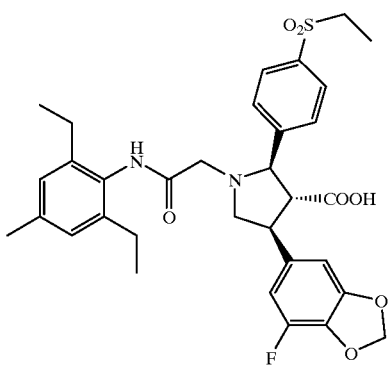 |
| 834 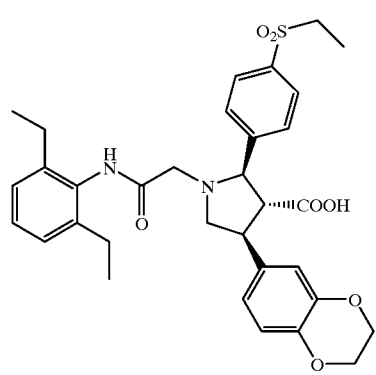 | 835 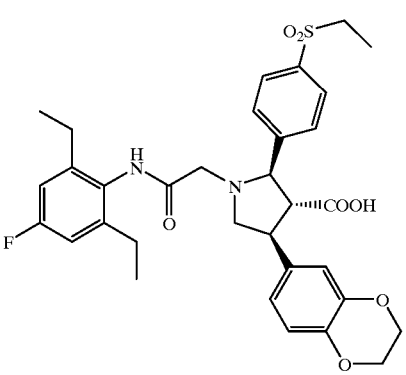 |
| 836 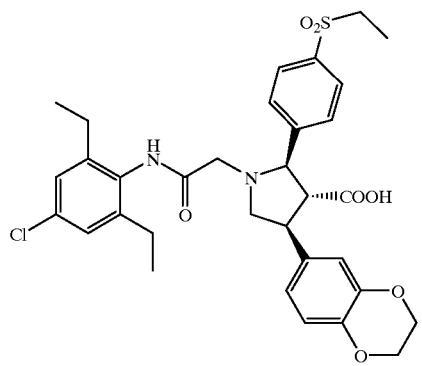 | 837 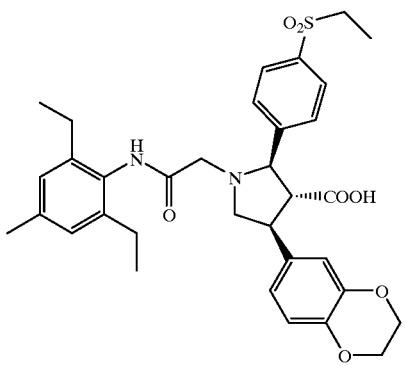 |
| 838 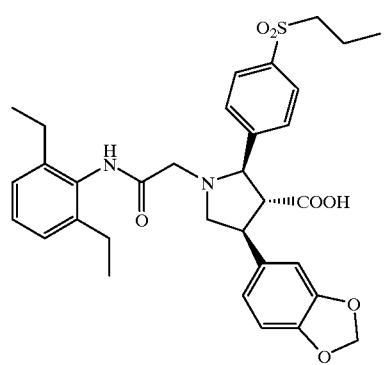 | 839 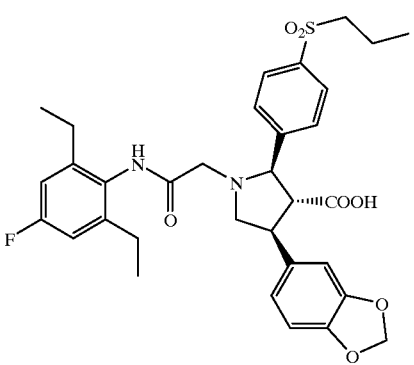 |

259 260
-continued
840 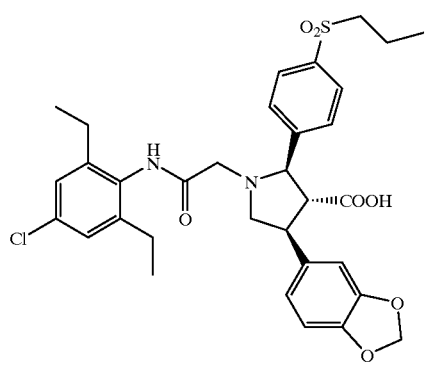 841 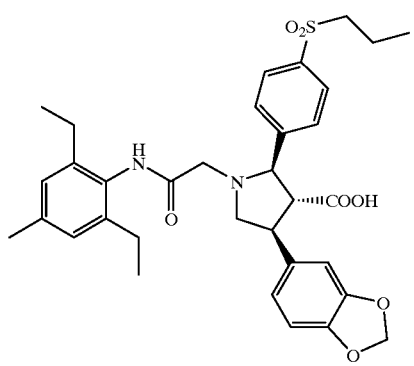
842 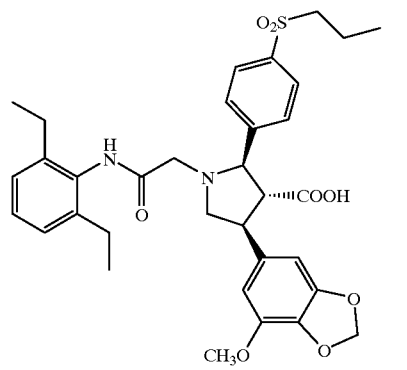 843 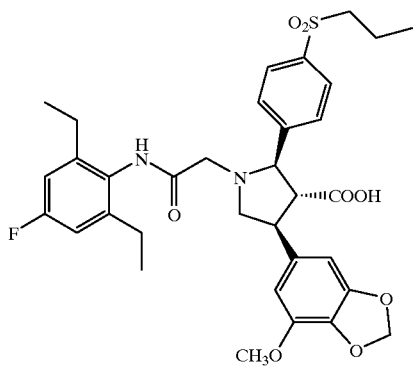
844 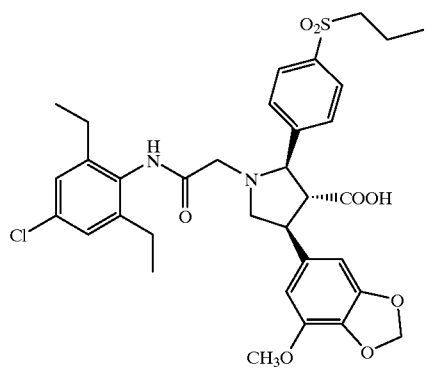 845 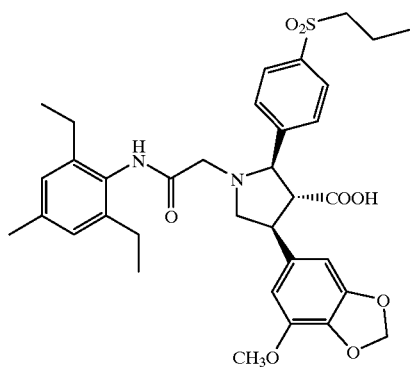
846 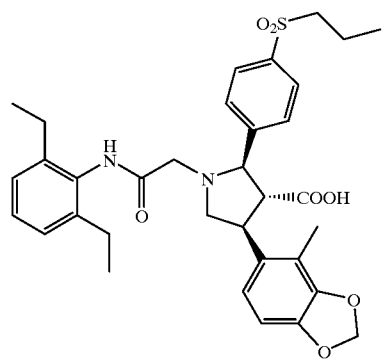 847 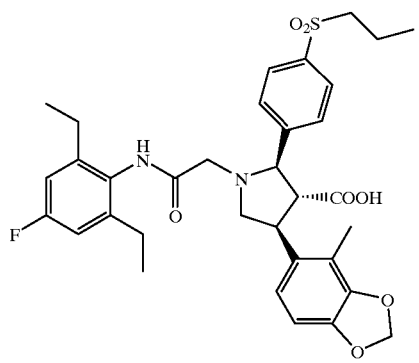

-continued
| 848 | 849 |
|---|---|
| 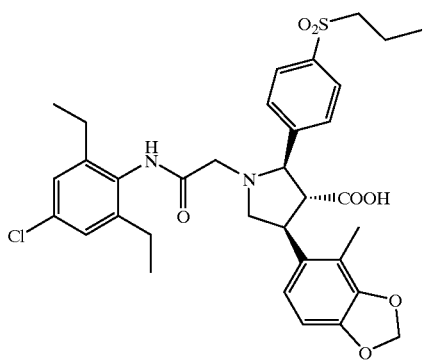 | 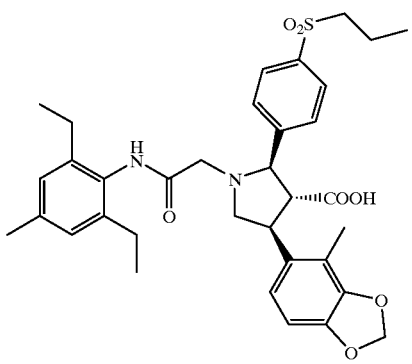 |
| 850 | 851 |
| 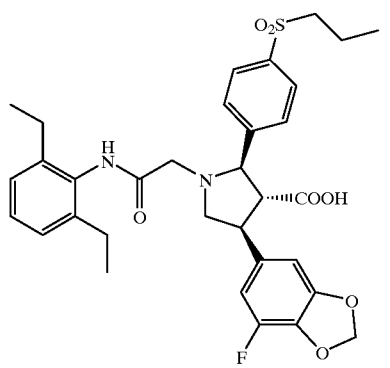 | 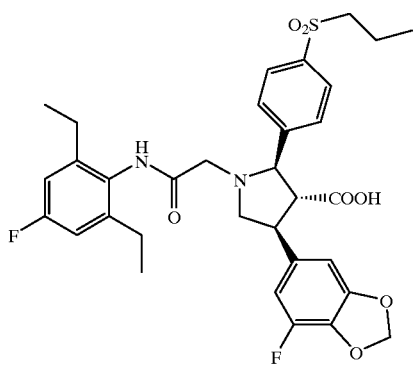 |
| 852 | 853 |
| 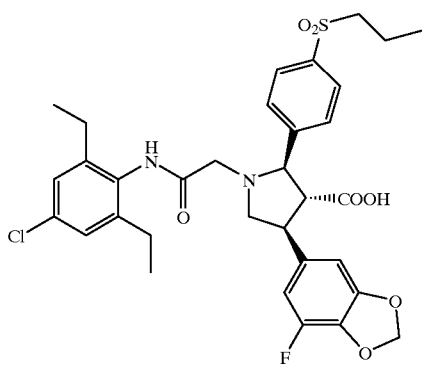 | 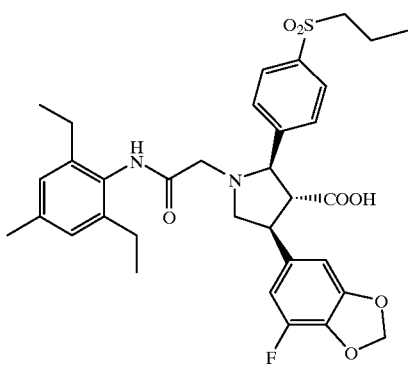 |
| 854 | 855 |
| 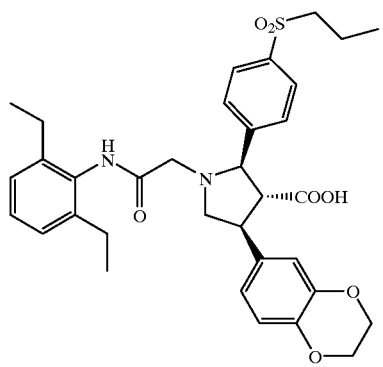 | 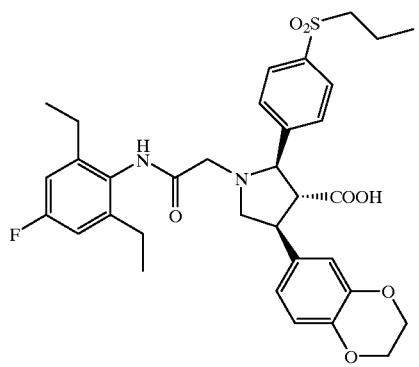 |

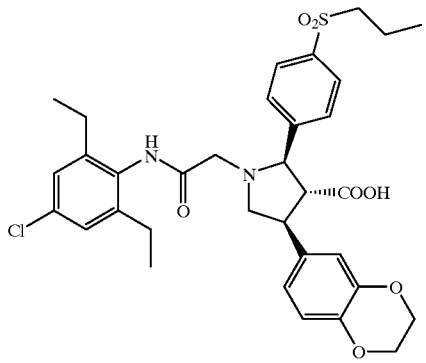

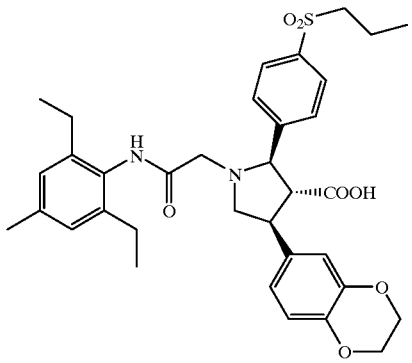

EXAMPLE 858 trans,trans-2-(4-Methoxy)phenyl-4-(1,3-benzodioxol-5-yl)-1-((N-2,6-diethylphenyl)aminocarbonyl)amino-pyrrolidine3-carboxylic acid

Example 858A

Ethyl trans,trans-2-(4-methoxy)phenyl-4-(1,3-benzodioxol-5-yl)-1-amino-pyrrolidine-3-carboxylate To a solution of 1.00 g (2.71 mmol) ethyl trans,trans-2-(4-methoxy)phenyl-4-(1,3-benzodioxol-5-yl)-1-pyrrolidine-3-carboxylate in 6 mL of acetonitrile was added a solution of 1.18 g (10.4 mmol) of hydroxylamine—O-sulfonic acid in 2 mL of $H_2O$. The homogeneous reaction mixture warmed spontaneously, and was stirred for 20 minutes, then concentrated in vacuo. The residue was dissolved in 15 mL of ethyl acetate and extracted with 0.7M $NaHCO_3$ solution (2×25 mL), then brine (1×10 mL), dried over $MgSO_4$, filtered, and concentrated to a thick oil. This consisted of a mixture of the starting pyrrolidine and the corresponding 1-aminopyrrolidine. To a solution of 892 mg (2.2 mmol) of this oil in 10 mL of ethyl acetate was added 700 mg (3.21 mmol) of di-tertbutoxycarbonic anhydride. The mixture was stirred at ambient temperature for 30 min, then concentrated in vacuo. Silica gel chromatography, eluting with 30% EtOAc/Hex, gave 360 mg of ethyl trans,trans-2-(4-methoxy) phenyl-4-(1,3-benzodioxol-5-yl)-1-(tert-butoxycarbonyl) amino-pyrrolidine-3-carboxylate as a colorless oil. The desired product was slightly more polar than the tertbutoxycarbonylpyrrolidine. To 360 mg (0.768 mmol) of the Boc hydazine was added 2 mL of trifluoroacetic acid. After stirring for 2 h at ambient temperature, the solvent was removed in vacuo. The residue was taken up in 10 mL of 0.6M $NaHCO_3$ solution and extracted with ethyl acetate (3×3 mL). The combined ethyl acetate layers were back extracted with brine (1×3 mL), dried over $MgSO_4$, filtered, and concentrated to 249 mg of a nearly colorless oil.

Example 858B trans,trans-2-(4-Methoxy)phenyl-4-(1,3-benzodioxol-5-yl)-1-((N-2,6-diethylphenyl)aminocarbonyl)amino-pyrrolidine3-carboxylic acid To an ice cooled solution of 100 mg (0.670 mmol) of 2,6-diethylaniline in 2 mL of THF and 0.4 mL of N,N-diisopropyl—N-ethylamine was added 66 mg (0.223 mmol) of triphosgene. The suspension was stirred at 0° C. for 10 min, then a solution of 249 mg (0.645 mmol) of ethyl trans,trans-2-(4-methoxy) phenyl-4-(1,3-benzodioxol-5-yl)-1-amino-pyrrolidine-3-carboxylate in 2 mL of THF was added. The mixture was stirred for 1.5 h, then a 20 mL of 0.6M $NaHCO_3$ solution was added. The suspension was extracted with ethyl acetate (3×5 mL), dried over $MgSO_4$, filtered, and concentrated to an oil which began to crystallize. This was taken up in a small amount of ethyl acetate, allowed to crystallize, and filtered to give 108 mg (30% from the hydrazine) of ethyl trans,trans-2-(4-Methoxy)phenyl-4-(1,3-benzodioxol-5-yl)-1-1-((N-2,6-diethylphenyl) aminocarbonyl) amino-pyrrolidine3-carboxylate. Hydrolysis of the ester was performed as described for other examples to give the title compound as a white solid. $^1H$ NMR (300 MHz, D-DMSO) δ 1.00 (t, J=7.4, 6H), 2.33 (br t, J=7.0 Hz, 4H), 2.90 (t, J=9.9 Hz, 1H), 3.38-3.50 (m, 2H), 3.59 (m, 1H), 3.75 (s, 3H), 4.11 (d, J=10.3 Hz,1H), 5.98 (d, J=0.7 Hz,1H), 5.99 (d, J=1.1 Hz,1H), 6.82 (m, 2H), 6.89 (d, J=8.4 Hz, 2H), 7.03 (d, J=7.0 Hz, 2H), 7.12 (m,1H), 7.33 (d, J=1.5 Hz,1H), 7.38 (s,1H), 7.53 (d, J=8.8 Hz, 2H), 8.02 (s, 1H), 12.3 (s, 1H); MS (CDI, m/z) 532 (MH$^+$). Anal. Calcd for $C_{30}H_{33}N_3O_6$: C, 67.78, H, 6.26, N, 7.90. Found: C, 67.71, H, 6.42, N, 7.82.

EXAMPLE 859

[2R,3S,4S]-2[4-(2-methoxyethoxy)phenyl]-4-(1,3-benzodioxol-5-yl)-1-(2,6-diethylphenylaminocarbonylmethyl)-pyrrolidine-3-carboxylic acid

Example 859A

Ethyl [2R,3S,4S]-2[4-(2-methoxyethoxy)phenyl]-4-(1,3-benzodioxol-5-yl)- pyrrolidine-3-carboxylate Ethyl trans,trans-2[4-(2-methoxyethoxy)]-4-(1,3-benzodioxol-5-yl)-pyrrolidine-3-carboxylate, from example 30, was reacted with di-tert-butyl dicarbonate, and the resulting product was hydrolyzed with NaOH to give trans, trans -2-[4-(2-methoxyethyl)]-4-(1,3-benzodioxol-5-yl)-1-(tert-butyloxycarbonyl)-pyrrolidine-3-carboxylic acid. This acid was resolved by salt formation with R-(+)- alpha methyl benzylamine. The resolved salt was washed with aqueous HCl to remove the resolving agent, then heated with HCl in ethanol at 70 degrees C. for 18 hours to produce ethyl [2R,3S,4S]-2[4-(2-methoxyethoxy)]-4-(1,3-benzodioxol-5-yl)-pyrrolidine-3-carboxylate, which was purified by chromatography on silica gel, eluting with ethyl acetate.

Example 859B

[2R,3S,4S]-2[4-(2-methoxyethoxy)phenyl]-4-(1,3-benzodioxol-5-yl)-1-(2,6-diethylphenylaminocarbonylmethyl)-pyrrolidine-3-carboxylic acid The title compound was prepared as described in Example 30, employing the compound of Example 859A as starting material. $^1$H NMR (300 MHz, CDCl$_3$) δ 1.08 (t, J=7 Hz, 6H), 2.43 (q, J=7 Hz, 4H), 3.00 (d, J=11 Hz, 1H), 3.05-3.15 (m, 2H), 3.44 (s, 3H), 3.46 (d, J=11 Hz, 1H), 3.45-3.55 (m, 1H), 3.65-3.75 (m, 1H), 3.75-3.80 (m, 2H), 3.93 (d, J=7 Hz,1H), 4.12-4.17 (m, 2H), 5.94 (dd, J=2 Hz, 4 Hz, 2H), 6.75 (d, J=8 Hz, 1H), 6.82 (dd, J=2 Hz, 9 Hz, 1H), 6.87 (d, J=2 Hz, 1H), 6.95 (d, J=8 Hz, 1H), 7.10 (d, J=6 Hz, 2H), 7.19-7.24 (m, 1H), 7.37 (d, d=8 Hz, 2H), 8.29 (s, 1H).

EXAMPLE 860 trans,trans-2-(4-(2-Ethoxyethoxy))4-( 1,3-benzodioxol-5-yl)- 1-(2,6-diethylphenylaminocarbonylmethyl)-pyrrolidine-3-carboxylic acid The title compound was prepared by the procedures described in Example 30. $^1$H NMR (300 MHz, CD$_3$OD) δ 1.09 (t, J=7 Hz, 6H), 1.23 (t, J=7 Hz, 3H), 2.47 (q, J=7 Hz, 4H), 3.4-3.55 (broad, 2H), 3.62 (q, J=7 Hz, 2H), 3.6-3.9 (broad, 4H), 3.82 (m, 2H), 4.16 (m, 2H), 4.4 (broad, 1H), 5.93 (dd, J=1 Hz,2 Hz, 2H), 6.77 (d, J=8 Hz, 1H), 6.90 (dd, J=2 Hz, 8 Hz, 1H), 7.04 (m, 3H), 7.12 (m, 2H), 7.22 (dd, J=7 Hz,9 Hz, 2H), 7.44 (m, 2H). MS (ESI+) m/e 589 (M+H$^+$). Anal. Calc for C$_{34}$H$_{40}$N$_2$O$_7$.0.5TFA: C, 65.11, H, 6.32, N 4.34. Found: C, 64.81, H, 6.36, N, 4.25.

EXAMPLE 861 trans,trans-2-(4-(2-Isopropoxyethoxy))-4-( 1,3-benzodioxol-5-yl)-1-(2,6-diethylphenylaminocarbonylmethyl)-pyrrolidine-3-carboxylic acid The title compound was prepared by the procedures described in Example 30. $^1$H NMR (300 MHz, CD$_3$OD) δ 1.10 (t, J=7 Hz, 6H), 1.18 (2, J=7 Hz, 6H), 2.47 (q, J=7 Hz, 4H), 3.4-3.55 (broad, 2H), 3.6-3.9 (broad, 4H), 3.75 (hept, 1H, J=7 Hz), 3.82 (m, 2H), 4.17 (m, 2H), 4.4-4.5 (broad, 1H), 5.93 (broad s, 2H), 6.78 (d, J=8 Hz, 1H), 6.90 (dd, J=2 Hz, 8 Hz, 1H), 7.05 (m, 3H), 7.12 (m, 2H), 7.20 (dd, J=7 Hz,9 Hz, 2H), 7.56 (m, 2H). MS (ESI+) m/e 603 (M+H$^+$). Anal. Calc for C$_{35}$H$_{42}$N$_2$O$_7$.0.6TFA: C, 64.79, H, 6.40, N, 4.17. Found: C, 64.40, H, 6.53, N, 4.20.

EXAMPLE 862 trans,trans-2-(4-(2-Propoxy))-4-(1,4-benzodioxan-6-yl)-1-(2,6-diethylphenylaminocarbonylmethyl)-pyrrolidine-3-carboxylic acid The title compound was prepared by the procedures described in Example 1. $^1$H NMR (300 MHz, CD$_3$OD) δ 1.06 (t, J=7 Hz, 3H), 1.09 (t, J=7 Hz, 6H), 1.81 (m, 2H), 2.46 (q, J=7 Hz, 4H), 3.3 (m, 2H), 3.4-3.5 (broad, 2H), 3.6-3.9 (broad, 4H), 3.95 (t, J=6 Hz, 2H), 4.22 (s, 4H), 4.4 (broad, 1H), 6.80 (d, J=8 Hz, 1H), 6.92 (dd, J=2 Hz, 8 Hz., 1H), 6.99 (m, 3H), 7.13 (m, 2H), 7.22 (dd, J=7 Hz,9 Hz, 2H), 7.44 (m, 2H). MS (ESI+) m/e 573 (M+H$^+$), 595 (M+Na$^+$). Anal. Calc for C$_{34}$H$_{48}$N$_2$O$_6$.0.6TFA: C, 65.95, H, 6.38, N 4.37. Found: C, 65.83, H, 6.40, N, 4.31.

EXAMPLE 863 trans,trans-2[(4-butoxyphenyl)]-4-(1,3-benzodioxol-5-yl)-1-(2,6-diethylphenylaminocarbonylmethyl)-pyrrolidine-3-carboxylic acid The title compound was prepared by using the method of example 30 by substituting 1-bromobutane for 1-bromo-2-methoxyethane. $^1$H NMR (300 MHz, CDCl$_3$) δ 0.99 (t, J=7 Hz, 3H), 1.08 (t, J=7 Hz, 6H), 1.42-1.57 (m, 2H), 1.73-1.82 (m, 2H), 2.42 (q, J=7 Hz, 4H), 3.00 (d, J=11 Hz, 1H), 3.05-3.15 (m, 2H), 3.46 (d, J=11 Hz, 1H), 3.50-3.55 (m, 1H), 3.65-3.75 (m, 1H), 3.93-4.00 (m, 3H), 5.94 (dd, J=2 Hz, 4 Hz, 2H), 6.75 (d, J=8 Hz, 1H), 6.82 (dd, J=2 Hz, 9 Hz, 1H), 6.87 (d, J=2 Hz, 1H), 6.93 (d, J=8 Hz, 1H), 7.10 (d, J=7 Hz, 2H), 7.19-7.24 (m, 1H), 7.37 (d, H=8 Hz, 2H), 8.30 (s, 1H). MS (APCl+) m/e 573 (M+H$^+$). Anal. Calc for C$_{34}$H$_{40}$N$_2$O$_6$: C, 71,31H, 7.04 N, 4.89. Found: C, 71.05 H,7.09 N, 4.83

EXAMPLE 864 trans,trans-2[4-{(2-methoxyethoxy)ethoxy}phenyl]-4-(1,3-benzodioxol-5-yl)-1-(2,6-diethylphenylaminocarbonylmethyl)-pyrrolidine-3-carboxylic acid The title compound was prepared by using the method of example 30 by substituting 1-bromo-2-(2-methoxyethoxy) ethane for 1-bromo-2-methoxyethane. $^1$H NMR (300 MHz, CDCl$_3$) δ 1.08 (t, J=7 Hz, 6H), 2.43 (q, J=7 Hz, 4H), 3.00 (d, J=11 Hz,1H), 3.05-3.15 (m, 2H), 3.40 (s, 3H), 3.46 (d, J=1 Hz, 1H), 3.44-3.55 (m, 1H), 3.57-3.62 (m, 2H), 3.65-3.75 (m, 1H), 3.70-3.75 (m, 1H), 3.88 (t, J=6 Hz, 2H), 3.93 (d, J=7 Hz, 1H), 4.15 (t, J=7 Hz, 2H), 5.94 (dd, J=2 Hz, 4 Hz, 2H), 6.75 (d, J=8 Hz,1H), 6.82 (dd, J=2 Hz, 9 Hz, 1H), 6.87 (d, J=2 Hz, 1H), 6.93 (d, J=8 Hz, 1H), 7.10 (d, J=7 Hz, 2H), 7.19-7.24 (m, 1H), 7.37 (d, H=8 Hz, 2H), 8.30 (s, 1H). MS (APCI+) m/e 619 (M+H$^+$). Anal. Calc for C$_{35}$H$_{42}$N$_2$O$_8$: C, 67.94 H, 6.84 N, 4.53. Found: C, 67.49 H, 6.90 N, 4.41.

EXAMPLE 865 trans,trans-2[(3-propoxyphenyl)]-4-(1,3-benzodioxol-5-yl)-1-(2,6-diethylphenylaminocarbonylmethyl)-pyrrolidine-3-carboxylic acid The title compound was prepared by using the method of example 30 by substituting 1-bromopropane for 1-bromo-2-methoxyethane and methyl 3-hyroxybenzoate for ethyl 4-hyroxybenzoate. $^1$H NMR (300 MHz, CDCl$_3$) δ 1.02 (t, J=7 Hz, 3H), 1.08 (t, J=7 Hz, 6H), 1.75-1.87 (m, 2H), 2.43 (q, J=7 Hz, 4H), 3.02 (d, J=11 Hz,1H), 3.09-3.20 (m, 3H), 3.48-3.56 (m, 2H), 3.65-3.75 (M, 1H), 3.90 (t, J=7 Hz, 2H), 3.98 (d, J=8 Hz, 1H), 5.94 (dd, J=2 Hz, 4 Hz, 2H), 6.75 (d, J=8 Hz, 1H), 6.80-6.89 (m, 3H), 6.98-7.05 (m, 2H), 7.10 (d, J=8 Hz, 2H), 7.19-7.32 (m, 2H), 8.30 (s, 1H). MS (APCl+) m/e 559 (M+H$^+$). Anal. Calc for C$_{33}$H$_{38}$N$_2$O$_6$: C, 70.94 H, 6.86 N, 5.01. Found: C, 70.65 H, 6.63 N, 4.92.

EXAMPLE 866 trans,trans-2-(4-(2-methoxy)ethyl)phenyl-4-(1,3-benzodioxol-5-yl)-1-((N-2,6-diethylphenyl)aminocarbonyl)methyl-pyrrolidine-3-carboxylic acid

Example 866A 4-(2-methoxy)ethylbenzoic acid

To a 3-necked 50 mL flask fitted with two septa and a nitrogen balloon was added 800 mg (20 mmol) of 60% NaH dispersed in mineral oil. The oil was removed by washing and decanting with hexanes (3×5 mL), using a pipette and keeping a positive pressure of $N_2$ over the flask. Next, 5 mL of THF was added, the suspension was cooled with an ice bath, then a solution of 2.01 g (10.0 mmol) of 4-bromophenethanol in 5 mL of THF was added via cannula. The ice bath was removed, and the mixture was stirred for 10 min, then 700 mL (11 mmol) of iodomethane was added. The mixture was stirred at ambient temperature for 1 h, then 1 mL of $H_2O$ was added to quench the excess NaH. The reaction was poured into 50 mL of $H_2O$, then extracted with diethyl ether (3×20 mL). The combined ether layers were back extracted with brine (1×20 mL), dried over $MgSO_4$, filtered, and concentrated to 2.08 g (97%) of a colorless oil. To a solution of 1.03 g (4.78 mmol) of the above 4-(2-methoxy)ethylbromobenzene in 10 mL of THF was added 400 mg of magnesium turnings, and a crystal of $I_2$. The mixture was heated to reflux under $N_2$ for 5 min, then cooled to ambient temperature. The Grignard reagent was transferred via syringe to a 50 mL 3-necked flask under $N_2$. A balloon of $CO_2$ was opened over the reaction, and the red color quickly faded to yellow. After stirring for 1 h at ambient temperature, the reaction was concentrated in vacuo. The residue was taken up in 20 mL of $H_2O$ and acidified with 12M HCl to pH=1, then extracted with diethyl ether (3×10 mL). The combined ether layers were back extracted with 2M NaOH (3×5 mL), then the combined NaOH layers were extracted with diethyl ether (2×5 mL). The basic layers were treated with 12M HCl until pH=1, then the product was extracted with ethyl acetate (2×5 mL). The combined ethyl acetate layers were back extracted with brine (1×5 mL), dried over $MgSO_4$, filtered, and concentrated to 427 mg (50%) of 4-(2-methoxy)ethylbenzoic acid as a yellow solid. The yellow impurity did not interfere with any subsequent reactions.

Example 866B trans,trans-2-(4-(2-methoxy)ethyl)phenyl-4-(1,3-benzodioxol-5-yl)-1-((N-2,6-diethylphenyl)aminocarbonyl)methyl-pyrrolidine-3-carboxylic acid Prepared according to the procedures described in Example 1. $^1$H NMR (300 MHz, $d_6$-DMSO) δ 1.00 (t, J=7.5 Hz, 6H), 2.40 (q, J=7.5 Hz, 4H), 2,66 (t, J=8.3 Hz, 1H), 2.79 (t, J=6.8 Hz, 2H), 2.87 (d, J=1 5.6 Hz, 1H), 3.00 (t, J=9.2 Hz, 1H), 3.20 (d, J=1 5.9 Hz, 1H), 3.24 (s, 3H), 3.42-3.47 (m, 1H), 3.53 (t, J=6.9 Hz, 1H), 3.60 (m, 1H), 3.91 (d, J=9.5 Hz, 1H), 5.94 (s, 2H), 6.76 (d, J=7.8 Hz, 1H), 6.84 (dd, J=1.4 Hz, 8.1 Hz, 1H), 7.08 (d, J=7.5 Hz, 2H), 7.17 (d, J=6.4 Hz, 3H), 7.22 (d, J=1.4 Hz,1H), 7.51 (d, J=8.1 Hz, 2H), 9.21 (s, 1H); MS (CDl m/z) 559 (MH$^+$); Anal. Calcd for $C_{33}H_{38}N_2O_6$·0.20 $H_3PO_4$. C, 68.54, H, 6.73, N, 4.84. Found C, 68.28, H, 6.46, N, 4.82.

EXAMPLE 867 trans,trans-2[3-(2-methoxyethoxy)phenyl]-4-(1,3-benzodioxol-5-yl)-1-(2,6-diethylphenylaminocarbonylmethyl)-pyrrolidine-3-carboxylic acid The title compound was prepared by using the method of example 30 by substituting methyl 3-hydroxybenzoate for methyl 4-hyroxybenzoate. 1H NMR (300 MHz, $CDCl_3$) δ 1.08 (t, J=7 Hz, 6H), 2.43 (q, J=7 Hz, 4H), 3.00-3.20 (m, 3H), 3.42 (s, 3H), 3.50 (d, J=11 Hz, 1H), 3.53-3.59 (m, 1H), 3.65-3.75 (m, 1H), 3.75 (t, J=6 Hz, 2H), 3.98 (d, J=8 Hz, 1H), 4.11 (t, J=6 Hz, 2H), 5.94 (dd, J=2 Hz, 4 Hz, 2H), 6.75 (d, J=8 Hz, 1H), 6.80-6.89 (m, 3H), 7.05-7.10 (m, 2H), 7.10 (d, J=8 Hz, 2H), 7.19-7.32 (m, 2H), 8.30 (s, 1H). MS (APCl+) m/e 575 (M+H$^+$) Anal. Calc for C33H38N207: C, 68.97 H, 6.67 N, 4.87. Found: C, 68.78 H, 6.84 N, 4.72.

EXAMPLE 868 trans,trans-2[(2-methyl-4-propoxyphenyl)1-4-(1,3-benzodioxol-5-yl)-1-(2,6-diethylphenylaminocarbonylmethyl)-pyrrolidine-3-carboxylic acid Example 868A Ethyl (4-propoxy-2-methylbenzoyl) acetate 4-Hydroxy-2-methylacetophenone was reacted with 1-bromopropane and potassium carbonate in dimethylformamide to give 4-propoxy-2-methylacetophenone. This compound was reacted with diethyl carbonate, using the method described in example 15B to provide the title compound.

Example 868B trans,trans-2[(2-methyl-4-propoxyphenyl)]-4-(1,3-benzodioxol-5-yl)-1-(2,6-diethylphenylaminocarbonylmethyl)-pyrrolidine-3-carboxylic acid Prepared using the procedures described in Example 30, employing the compound of Example 868A as starting material. 1H NMR (300 MHz, $CDCl_3$) δ 1.02 (t, J=7 Hz, 3H), 1.08 (t, J=7 Hz, 6H), 1.75-1.85 (m, 2H), 2.33 (s, 3H), 2.40-2.48 (q, J=7 Hz, 4H), 2.98 (d, J=1 Hz, 1H), 3.06-3.18 (m, 2H), 3.39 (d, J=1 Hz, 1H), 3.50-3.58 (m, 1H), 3.65-3.75 (m, 1H), 3.90 (t, J=7 Hz, 2H), 4.28 (d, J=8 Hz, 1H), 5.94 (dd, J=2 Hz, 4 Hz, 2H), 6.70-6.88 (m, 5H), 7.08-7.25 (m, 3H), 7.48 (d, J=8 Hz, 1H), 8.28 (s, 1H). MS (APCl+) m/e 773 (M+H$^+$). Anal. Calc for $C_{34}H_{40}N_2O_6$: C, 70.56 H, 7.79 N, 4.33. Found: C, 70.16 H, 7.70 N, 4.26.

EXAMPLE 869 trans,trans-2-(4-(3-methoxy)propyl)phenyl-4-(1,3-benzodioxol-5-yl)-1-((N-2,6-diethylphenyl)aminocarbonyl)methyl-pyrrolidine-3-carboxylic acid Example 869A 4-(3-methoxy)propylbenzoic acid To a mixture of 10.0 g (46.5 mmol) of methyl 4-bromobenzoate, 325 mg (1.45 mmol) of palladium(II) acetate, 15.1 g (51.0 mmol) of tetrabutylammonium chloride, and 13.7 g (140 mmol) of potassium acetate was added 200 mL of DMF. The mixture was degassed and back filled with $N_2$ twice, then 10 mL of allyl methyl ether was added. The reaction was stirred at 50° C. for 6 h, then at ambient temperature for 66 h. The reaction was monitored by TLC (20% ethyl acetate/hexanes). Additional Pd catalyst: (319 mg) was added after this time, as some bromoester remained. After heating at 50° C. under $N_2$ for 2 h, the reaction was poured into 1 L of water, and this suspension was divided into two portions for ease of handling. Each was extracted with diethyl ether (3×100 mL), then each set of ether layers was back extracted with water (1× 100 mL), saturated aq. $NaHCO_3$ solution (1×100 mL), and brine (1×100 mL), dried over $MgSO_4$, filtered and concentrated in vacuo. The combined crude yield of methyl 4-(3-methoxy- 1-propenyl)benzoate and methyl 4-(3-methoxy-2-propenyl) benzoate was 9.17 g. To a mixture of 8.57 g (41.6 mmol) of the above and 400 mg of 10% Pd-C was added 75 mL of THF. The mixture was stirred at ambient temperature under 1 atm of $H_2$ for 2 h, then the catalyst was filtered away, and the solvent was removed in vacuo. Purification via a 15% ethyl acetate/hexanes column gave 3.35 g (39%) of methyl 4-(3-methoxypropyl)benzoate as a colorless oil. This material was combined with 20 mL of 1.39M NaOH in 5:1 ethanol:$H_2O$. The reaction was heated at reflux for 30 min, then concentrated in vacuo. The residue was taken up in 25 mL of $H_2O$, then 40 mL of 1M HCl was added. The mixture was extracted with diethyl ether (3×25 mL), then the combined ether layers were back extracted with brine (1×25 mL), dried over $MgSO_4$, filtered, and concentrated in vacuo to 3.03 g (97%) of 4-(3-methoxy)propylbenzoic acid as a white solid.

EXAMPLE 869 trans trans-2-(4-(3-methoxy)propyl)phenyl-4-(1,3-benzodioxol-5-yl)-1-((N-2,6-diethylphenyl) aminocarbonyl)methyl-pyrrolidine-3-carboxylic acid Prepared according to the procedures of Example 1. $^1H$ NMR (300 MHz, $d_6$-DMSO) δ 1.00 (t, J=7.5 Hz, 6H), 1.80 (m, 2), 2.41 (q, J=7.5 Hz, 4H), 2,62 (t, J=7.7 Hz, 2H), 2.86 (t, J=9.7 Hz, 1H), 2.93 (d, J=15.8 Hz,1H), 3.11 (t, J=9.6 Hz,1H), 3.18 (d, J=16.2 Hz,1H), 3.23 (s, 3H), 3.31-3.40 (m, 2H), 3.50 (m, 1H), 3.53 (m, 1H), 3.95 (d, J=9.9 Hz, H), 5.98 (s, 2H), 6.80 (dd, J=1.5 Hz, 8.1 Hz, 1H), 6.85 (dd, J=1.5 Hz, 8.1 Hz, 1H), 7.10 (d, J=7.0 Hz, 2H), 7.18 (m, 3H), 7.28 (d, J=1.5 Hz, 1H), 7.53 (d, J=8.1 Hz, 1H), 9.28 (s, 1H); MS (CDl m/z) 571 (MH+); Anal. Calcd for $C_{34}H_{40}N_2O_6 \cdot 0.05H_3PO_4$: C, 70.70, H, 7.00, N, 4.85. Found: C, 70.68, H, 6.91, N, 4.62.

As an indication that the compounds described herein act through binding to endothelin receptors, the compounds have been evaluated for their ability to displace endothelin from its receptor.

Binding Assay $ET_B$ Receptor
Preparation of membranes from Porcine cerebellum

Porcine cerebellum was homogenized in 25 volumes (w/v) of 10 mM Hepes (pH 7.4) containing 0.25M sucrose and protease inhibitors (3 mM EDTA, 0.1 mM PMSF, and 5 μg/ml Pepstatin A) by 3–10 sec polytron at 13,500 rpm with 10 sec intervals. The mixture was centrifuged at 1000×g for 10 min. The supernatant was collected and centrifuged at 30,000×g for 30 min. The precipitate was resuspended in Buffer A (20 mM Tris, 100 mM NaCl, 10 mM $MgCl_2$, pH 7.4) containing the aforementioned protease inhibitors and centrifuged again. The final pellet was resuspended in Buffer A containing protease inhibitors and stored at $-80°$ C. until used. Protein content was determined by the Bio-Rad dye-binding protein assay.

[$^{125}I$]ET-3 binding to membranes

Binding assays were performed in 96-well microtiter plates pretreated with 0.1% BSA. Membranes prepared from cells were diluted 100 fold in Buffer B (20 mM Tris, 100 mM NaCl, 10 mM $MgCl_2$, pH 7.4, with 0.2% BSA, 0.1 mM PMSF, 5 μg/mL Pepstatin A, 0.025% bacitracin, and 3 mM EDTA) to a final concentration of 0.2 mg/mL of protein. In competition studies, membranes (0.02 mg) were incubated with 0.1 nM of [$^{125}I$]ET-3 in Buffer B (final volume: 0.2 mL) in the presence of increasing concentrations of unlabeled ET-3 or a test compound for 4 hours at 25° C. After incubation, unbound ligands were separated from bound ligarids by a vacuum filtration method using glass-fiber filter strips in PHD cell harvesters (Cambridge Technology, Inc., MA), followed by washing the filter strips with saline (1 mL) for three times. Nonspecific binding was determined in the presence of 1 μM ET-1. The data are shown in Table 1. The per cent inhibition at a concentration of 1 μM is shown. The data show that the compounds of the invention bind to the endothelin receptor.

TABLE 1

Binding Data

| Example | % Inhibition of $ET_B$ at 1 μM | Example | % Inhibition of $ET_B$ at 1 μM |
|---|---|---|---|
| 1 | 96.4 | 2 | 91.5 |
| 3 | 82.1 | 4 | 94.0 |
| 5 | 96.5 | 6 | 92.9 |
| 7 | 94.5 | 8 | 93.6 |
| 9 | 94.8 | 10 | 95.2 |
| 11 | 96.0 | 12 | 96.7 |
| 13 | 91.3 | 14 | 96.6 |
| 15 | 93.4 | 16 | 92.3 |
| 17 | 97.1 | 18 | 94.9 |
| 19 | 94.9 | 20 | 95.5 |
| 21 | 97.1 | 22 | 95.3 |
| 23 | 99.1 | 24 | 93.3 |
| 25 | 95.7 | 26 | 98.0 |
| 27 | 98.8 | 28 | 97.2 |
| 29 | 94.7 | 30 | 97.4 |
| 858 | 98.3 | 859 | 95.6 |
| 860 | 93.0 | 861 | 96.7 |
| 862 | 92.8 | 863 | 92.7 |
| 864 | 96.3 | 865 | 92.1 |
| 866 | 92.0 | 867 | 93.5 |
| 868 | 96.1 | 869 | 98.9 |

The ability of the compounds of the invention to lower blood pressure can be demonstrated according to the methods described in Matsumura, et al., Eur. J. Pharmacol. 185 103 (1990) and Takata, et al., Clin. Exp. Pharmacol. Physiol. 10 131 (1983).

The ability of the compounds of the invention to treat congestive heart failure can be demonstrated according to the method described in Margulies, et al., Circulation 82 2226 (1990).

The ability of the compounds of the invention to treat myocardial ischemia can be demonstrated according to the method described in Watanabe, et al., Nature 344 114 (1990).

The ability of the compounds of the invention to treat coronary angina can be demonstrated according to the method described in Heistad, et al., Circ. Res. 54 711 (1984).

The ability of the compounds of the invention to treat cerebral vasospasm can be demonstrated according to the methods described in Nakagomi, et al., J. Neurosurg. 66 915 (1987) or Matsumura, et al., Life Sci. 49 841–848 (1991).

The ability of the compounds of the invention to treat cerebral ischemia can be demonstrated according to the method described in Hara et al., European. J. Pharmacol. 197: 75–82, (1991).

The ability of the compounds of the invention to treat acute renal failure can be demonstrated according to the method described in Kon, et al., J. Clin. Invest. 83 1762 (1989).

The ability of the compounds of the invention to treat chronic renal failure can be demonstrated according to the method described in Benigni, et al., Kidney Int. 44 440–444 (1993).

The ability of the compounds of the invention to treat gastric ulceration can be demonstrated according to the method described in Wallace, et al., Am. J. Physiol. 256 G661 (1989).

The ability of the compounds of the invention to treat cyclosporin-induced nephrotoxicity can be demonstrated according to the method described in Kon, et al., Kidney Int. 37 1487 (1990).

The ability of the compounds of the invention to treat endotoxin-induced toxicity (shock) can be demonstrated according to the method described in Takahashi, et al., Clinical Sci. 79 619 (1990).

The ability of the compounds of the invention to treat asthma can be demonstrated according to the method described in Potvin and Varma, Can. J. Physiol. and Pharmacol. 67 1213 (1989).

The ability of the compounds of the invention to treat transplant-induced atherosclerosis can be demonstrated according to the method described in Foegh, et al., Atherosclerosis 78 229–236 (1989).

The ability of the compounds of the invention to treat atherosclerosis can be demonstrated according to the methods described in Bobik, at al., Am. J. Physiol. 258 C408 (1990) and Chobanian, et al., Hypertension 15 327 (1990).

The ability of the compounds of the invention to treat LPL-related lipoprotein disorders can be demonstrated according to the method described in Ishida, et al., Biochem. Pharmacol. 44 1431–1436 (1992).

The ability of the compounds of the invention to treat proliferative diseases can be demonstrated according to the methods described in Bunchman ET and CA Brookshire, Transplantation Proceed. 23 967–968 (1991); Yamagishi, et al., Biochem. Biophys. Res. Comm. 191 840–846 (1993); and Shichiri, et al., J. Clin. Invest. 87 1867–1871 (1991). Proliferative diseases include smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, scieroderma, prostatic hyperplasia, cardiac hyperplasia, restenosis following arterial injury or other pathologic stenosis of blood vessels.

The ability of the compounds of the invention to treat acute or chronic pulmonary hypertension can be demonstrated according to the method described in Bonvallet et al., Am. J. Physiol. 266 H1327 (1994). Pulmonary hypertension can be associated with congestive heart failure, mitral valve stenosis, emphysema, lung fibrosis, chronic obstructive pulmonary disease (COPD), acute repiratory distress syndrome (ARDS), altitude sickness, chemical exposure, or may be idiopathic.

The ability of the compounds of the invention to treat plaletet aggregation, and thrombosis, can be demonstrated according to the method described in McMurdo et al. Eu. J. Pharmacol. 259 51 (1994).

The ability of the compounds of the invention to treat cancers can be demonstrated according to the method described in Shichiri, et al., J. Clin. Invest. 87 1867 (1991).

The ability of the compounds of the invention to treat adenocarcinoma can be demonstrated according to the method described in Nelson, et al., Nature Medicine, 1, (9), 944 (1995).

The ability of the compounds of the invention to treat IL-2 (and other cytokine) mediated cardiotoxicity and vascular permeability disorders can be demonstrated according to the method described in Klemm et al., Proc. Nat. Acad. Sci. 92 2691 (1995).

The ability of the compounds of the invention to treat nociception can be demonstrated according to the method described in Yamamoto et al., J. Pharmacol. Exp. Therap. 271 156 (1994).

The ability of the compounds of the invention to treat colitis can be demonstrated according to the method described in Hogaboam et al (EUR. J. Pharmacol. 1996, 309, 261–269).

The ability of the compounds of the invention to treat ischemia-repurfusion injury in kidney transplantation can be demonstrated according to the method described in Aktan et al (Transplant Int 1996, 9, 201–207).

The ability of the compounds of the invention to treat angina, pulmonary hypertension, Raynaud's disease, and migraine can be demonstrated according to the method described in Ferro and Webb (Drugs 1996, 51, 12–27).

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting the carboxylic acid function with a suitable base such as the hydroxide, carbonate or bicarbonate of a pharmaceutically acceptable metal cation or with ammonia, or an organic primary, secondary or tertiary amine. Such pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds of the invention are useful for antagonizing endothelin in a human or other mammal. In addition, the compounds of the present invention are useful (in a human or other mammal) for the treatment of hypertension, acute or chronic pulmonary hypertension, Raynaud's disease, congestive heart failure, myocardial ischemia, reperfusion injury, coronary angina, cerebral ischemia, cerebral vasospasm, chronic or acute renal failure, non-steroidal antiinflammatory drug induced gastric ulceration, cyclosporin induced nephrotoxicity, endotoxin-induced toxicity, asthma, fibrotic or proliferative diseases, including smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, scieroderma, prostatic hyperplasia, cardiac hyperplasia, restenosis following arterial injury or other pathologic stenosis of blood vessels, LPL-related lipoprotein disorders, transplantation-induced atherosclerosis or atherosclerosis in general, platelet aggregation, thrombosis, cancers, adenocarcinoma, IL-2 and other cytokine mediated cardiotoxicity and permeability disorders, colitis, migraine, and nociception.

Total daily dose administered to a host in single or divided doses may be in amounts, for example, from 0.001 to 1000 mg/kg body weight daily and more usually 0.1 to 100 mg/kg for oral administration or 0.01 to 10 mg/kg for parenteral administration. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be formulated according to the known art. The title compound was prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capabale of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

A representative solid dosage form, for example, a tablet or a capsule, comprises:

| | |
|---|---|
| Compound of the invention: | 35% w/w |
| Starch, Pregelatinized, NF | 50% w/w |
| Microcrystalline Cellulose, NF | 10% w/w |
| Talc, Powder, USP | 5% w/w |

While the compounds of the invention can be administered as the sole active pharmaceutical agent, they can also be used in combination with one or more cardiovascular agents independently selected from diuretics, adrenergic blocking agents, vasodilators, calcium channel blockers, renin inhibitors, angiotensin converting enzyme (ACE) inhibitors, angiotensin II antagonists, potassium channel activators and other cardiovascular agents.

Representative diuretics include hydrochlorothiazide, chlorothiazide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hydralazine, minoxidil, diazoxide, nitroprusside and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative renin inhibitors include enalkiren, zankiren, RO 42-5892, PD-134672 and the like or a pharmaceutically acceptable salt thereof.

Representative angiotensin II antagonists include DUP 753, A-81988 and the like.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

The compounds of the invention and the cardiovascular agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds, processes, compositions and methods. Variations and changes which are obvious to one skilled in the art are intended to be within the scope and nature of the invention which are defined in the appended claims.

What is claimed is:

1. A compound of the formula:

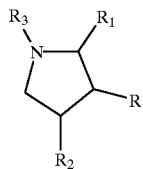

wherein

R is —(CH$_2$)$_m$-W wherein m is an integer from 0 to 6 and W is (a) —C(O)$_2$—G wherein G is hydrogen or a carboxy protecting group, (b) —PO$_3$H$_2$, (c) —P(O)(OH)E wherein E is hydrogen, loweralkyl or arylalkyl, (d) —CN, (e) —C(O)NHR$_{17}$ wherein R$_{17}$ is loweralkyl, (f) alkylaminocarbonyl, (g) dialkylaminocarbonyl, (h) tetrazolyl, (i) hydroxy, (j) alkoxy, (k) sulfonamido, (l) —C(O)NHS(O)$_2$R$_{16}$ wherein R$_{16}$ is loweralkyl, haloalkyl, aryl or dialkylamino, (m) —S(O)$_2$NHC(O)R$_{16}$ wherein R$_{16}$ is defined as above, (n) 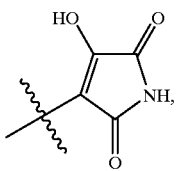

(o) 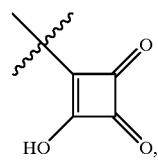

(p) 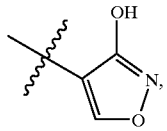

(q) 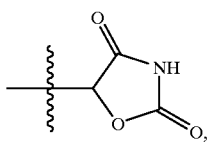

(r) 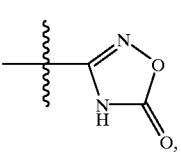

(s) 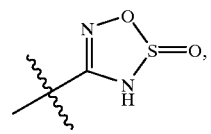

(t) 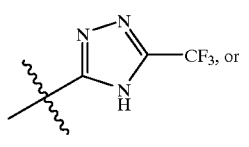

(u) 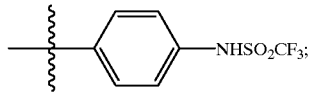

R$_1$ and R$_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, heterocyclic, (heterocyclic)alkyl and (R$_{aa}$)(R$_{bb}$)N—R$_{cc}$- wherein R$_{aa}$ is aryl or arylalkyl, R$_{bb}$ is hydrogen or alkanoyl and R$_{cc}$ is alkylene, with the proviso that one or both of $R_1$ and $R_2$ is other than hydrogen; with the proviso that heterocyclic is not morpholine or pyrazole $R_3$ is $R_4$—C(O)—$R_5$— or $R_6$—S(O)$_2$—$R_7$— wherein $R_5$ is (i) a covalent bond, (ii) alkylene, (iii) alkenylene, (iv) —N($R_{20}$)—$R_8$— or —$R_{8a}$—N($R_{20}$)—$R_8$— wherein $R_8$ and $R_{8a}$ are independently selected from the group consisting of alkylene and alkenylene and $R_{20}$ is hydrogen, loweralkyl, alkenyl, haloalkyl, alkoxyalkyl, haloalkoxyalkyl, cylcoalkyl or cycloalkylalkyl or (v) —O—$R_9$— or —$R_{9a}$—O—$R_9$— wherein $R_9$ and $R_{9a}$ are independently selected from alkylene;

$R_7$ is (i) a covalent bond, (ii) alkylene, (iii) alkenylene or (iv) —N($R_{21}$)—$R_{10}$— or —$R_{10a}$—N($R_{21}$)—$R_{10}$— wherein $R_{10}$ and $R_{10a}$ are independently selected from the group consisting of alkylene and alkenylene and $R_{21}$ is hydrogen, loweralkyl, alkenyl, haloalkyl, alkoxyalkyl, haloalkoxyalkyl, aryl or arylalkyl;

wherein $R_4$ and $R_6$ are (i)

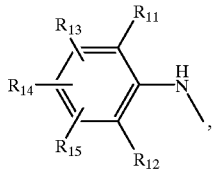

wherein $R_{11}$ and $R_{12}$ are independently selected from the group consisting of loweralkyl, cyano, alkoxy, halo, haloalkyl, and phenyl, and $R_{13}$, $R_{14}$, and $R_{15}$ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano with the proviso that heterocyclic is not morpholine or pyrazole or (ii) heterocyclic(amino), with the proviso that when R is —C(O)$_2$—G and G is hydrogen, then $R_1$ is not arylalkoxyalkyl or a pharmaceutically acceptable salt thereof.

2. The compound according to claim 1 wherein $R_3$ is $R_4$—C(O)—$R_5$— wherein $R_4$ is as defined therein and $R_5$ is alkylene or $R_3$ is $R_6$—S(O)$_2$—$R_7$— wherein $R_7$ is alkylene and $R_6$ is as defined therein.

3. The compound according to claim 1 wherein
R is —C(O)$_2$—G wherein G is hydrogen or a carboxy protecting group or R is tetrazolyl or R is —C(O)—NHS(O)$_2$R$_{16}$ wherein $R_{16}$ is loweralkyl, haloalkyl or aryl, $R_1$ and $R_2$ are independently selected from (i) loweralkyl, (ii) cycloalkyl, (iii) substituted or unsubstituted aryl and (iv) substituted or unsubstituted heterocyclic, with the proviso that heterocyclic is not morpholine or pyrazole and $R_3$ is $R_4$—C(O)—$R_5$— wherein $R_4$ is as defined therein and $R_5$ is alkylene or $R_3$ is $R_6$—S(O)$_2$—$R_7$— wherein $R_7$ is alkylene and $R_6$ is as defined therein.

4. The compound according to claim 1 wherein
R is —C(O)$_2$—G wherein G is hydrogen or a carboxy protecting group, tetrazolyl or —C(O)—NHS(O)$_2$R$_{16}$ wherein $R_{16}$ is loweralkyl, haloalkyl or aryl, $R_1$ is (i) alkoxyalkyl, (ii) cycloalkyl, (iii) phenyl, (iv) pyridyl, (v) furanyl or (vi) substituted or unsubstituted 4-methoxyphenyl, 4-fluorophenyl, 3-fluorophenyl, 4-ethoxyphenyl, 4-propoxyphenyl, 4-isopropoxyphenyl, 4-trifluoromethylphenyl, 4-pentafluoroethylphenyl, 2-fluoro-4-ethoxyphenyl, 3-fluoro-4-methoxyphenyl, 3-fluoro-4-ethoxyphenyl, 3-fluoro-4-propoxyphenyl, 3-methoxy-4-propoxyphenyl, 2-fluorophenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofuranyl, 4-methoxyphenyl, dimethoxyphenyl, fluorophenyl or difluorophenyl and $R_3$ is $R_4$—C(O)—$R_5$— wherein $R_4$ is as defined therein and $R_5$ is alkylene or $R_3$ is $R_6$—S(O)$_2$—$R_7$— wherein $R_7$ is alkylene and $R_6$ is as defined therein.

5. The compound according to claim 1 wherein
R is —C(O)$_2$—G wherein G is hydrogen or a carboxy protecting group, tetrazolyl or —C(O)—NHS(O)$_2$R$_{16}$ wherein $R_{16}$ is loweralkyl, haloalkyl or aryl, $R_1$ is selected from the group consisting of (i) alkoxyalkyl, (ii) cycloalkyl, (iii) phenyl, (iv) pyridyl, (v) furanyl or (vi) substituted or unsubstituted 4-methoxyphenyl, 4-fluorophenyl, 3-fluorophenyl, 4-ethoxyphenyl, 4-propoxyphenyl,4-isopropxyphenyl, 4-trifluoromethylphenyl, 4-pentafluoroethylphenyl, 2-fluoro-4-ethoxyphenyl, 3-fluoro-4-methoxyphenyl, 3-fluoro-4-ethoxyphenyl, 3-fluoro-4-propoxyphenyl, 3-methoxy-4-propoxyphenyl, 2-fluorophenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl,1,4-benzodioxanyl or dihydrobenzofuranyl wherein the substituent is selected from alkoxy, alkoxyalkoxy and carboxyalkoxy, $R_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl and $R_3$ is $R_4$—C(O)—$R_5$— wherein $R_4$ is as defined therein and $R_5$ is alkylene.

6. The compound according to claim 1 wherein
R is —C(O)$_2$—G wherein G is hydrogen or a carboxy protecting group, tetrazolyl or —C(O)—NHS(O)$_2$R$_{16}$ wherein $R_{16}$ is loweralkyl or haloalkyl, $R_1$ is substituted or unsubstituted 4-methoxyphenyl, 4-fluorophenyl, 2-fluorophenyl, 4-ethoxyphenyl, 4-propoxyphenyl, 4-isopropoxyphenyl, 3-fluoro-4-methoxyphenyl, 3-fluoro-4-ethoxyphenyl, 2-fluoro-4-ethoxyphenyl, 3-fluoro-4- propoxyphenyl, 3-methoxy-4-propoxyphenyl, 4-trifluoromethylphenyl, 4-pentafluoroethylphenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and $R_3$ is $R_4$—C(O)—$R_5$— wherein $R_4$ is as defined therein and $R_5$ is alkylene.

7. The compound according to claim 1 wherein

R is —C(O)$_2$—G wherein G is hydrogen or a carboxy protecting group, $R_1$ is substituted or unsubstituted 4-methoxyphenyl, 4-fluorophenyl, 2-fluorophenyl, 3-fluoro-4-ethoxyphenyl, 3-fluoro-4-methoxyphenyl, 4-ethoxyphenyl, 4-propoxyphenyl, 4-isopropoxyphenyl, 3-fluoro-4-propoxyphenyl, 3-methoxy-4-propoxyphenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and $R_3$ is $R_4$—C(O)—$R_5$— wherein $R_4$ is

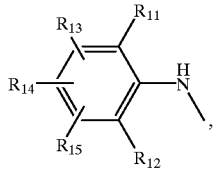

wherein $R_{11}$ and $R_{12}$ are independently selected from the group consisting of loweralkyl and $R_{13}$, $R_{14}$, and $R_{15}$ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano with the proviso that heterocyclic is not morpholine or pyrazole and $R_5$ is alkylene.

8. The compound according to claim 1 wherein

R is —C(O)$_2$—G wherein G is hydrogen or a carboxy protecting group, $R_1$ is substituted or unsubstituted 4-methoxyphenyl, 4-fluorophenyl, 2-fluorophenyl, 3-fluoro-4-ethoxyphenyl, 3-fluoro-4-methoxyphenyl, 4-ethoxyphenyl, 4-propoxyphenyl, 4-isopropoxyphenyl, 2-fluoro-4-ethoxyphenyl, 3-fluoro-4-propoxyphenyl, 3-methoxy-4-propoxyphenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and $R_3$ is $R_4$—C(O)—$R_5$— wherein $R_4$ is

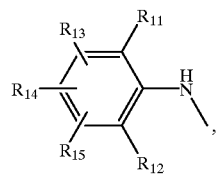

wherein $R_{11}$ and $R_{12}$ are independently selected from the group consisting of loweralkyl, alkoxy and halo, and $R_{13}$, $R_{14}$, and $R_{15}$ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano, with the proviso that heterocyclic is not morpholine or pyrazole and $R_5$ is alkylene.

9. The compound according to claim 1 wherein

R is —C(O)$_2$—G wherein G is hydrogen or a carboxy protecting group, $R_1$ is substituted or unsubstituted 4-methoxyphenyl, 4-fluorophenyl, 2-fluorophenyl, 3-fluoro-4-ethoxyphenyl, 3-fluoro-4-methoxyphenyl, 4-ethoxyphenyl, 4-propoxyphenyl, 4-isopropoxyphenyl, 2-fluoro-4-ethoxyphenyl, 3-fluoro-4-propoxyphenyl, 3-methoxy-4-propoxyphenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and $R_3$ is $R_4$—C(O)—$R_5$— wherein $R_4$ is

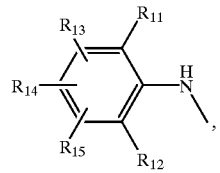

wherein $R_{11}$ and $R_{12}$ are independently selected from the group consisting of methyl, ethyl, and isopropyl, and $R_{13}$, $R_{14}$, and $R_{15}$ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano and $R_5$ is alkylene.

10. The compound according to claim 1 wherein

R is —C(O)$_2$—G wherein G is hydrogen or a carboxy protecting group, $R_1$ is substituted or unsubstituted 4-methoxyphenyl, 4-fluorophenyl, 2-fluorophenyl, 3-fluoro-4-ethoxyphenyl, 3-fluoro-4-methoxyphenyl, 4-ethoxyphenyl, 4-propoxyphenyl, 4-isopropoxyphenyl, 2-fluoro-4-ethoxyphenyl, 3-fluoro-4-propoxyphenyl, 3-methoxy-4-propoxyphenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and $R_3$ is $R_4$—C(O)—$R_5$— wherein $R_4$ is

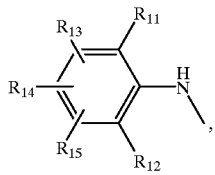

wherein $R_{11}$ and $R_{12}$ are independently selected from the group consisting of methyl, ethyl, and isopropyl, and $R_{13}$, $R_{14}$, and $R_{15}$ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano with the proviso that heterocyclic is not morpholine or pyrazole and $R_5$ is methylene.

11. The compound according to claim 1 of the formula:

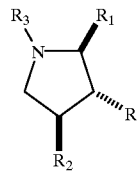

wherein

R is —(CH$_2$)$_m$-W wherein m is an integer from 0 to 6 and W is (a) —C(O)$_2$—G wherein G is hydrogen or a carboxy protecting group, (b) —PO$_3$H$_2$, (c) —P(O)(OH)E wherein E is hydrogen, loweralkyl or arylalkyl, (d) —CN, (e) —C(O)NHR$_{17}$ wherein R$_{17}$ is loweralkyl, (f) alkylaminocarbonyl, (g) dialkylaminocarbonyl, (h) tetrazolyl, (i) hydroxy, (j) alkoxy, (k) sulfonamido, (l) —C(O)NHS(O)$_2$R$_{16}$ wherein R$_{16}$ is loweralkyl, haloalkyl, aryl or dialkylamino, (m) —S(O)$_2$NHC(O)R$_{16}$ wherein R$_{16}$ is defined as above, (n)

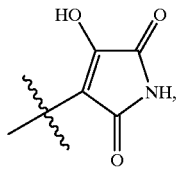

(o)

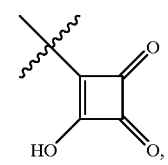

(p)

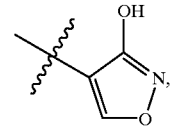

(q)

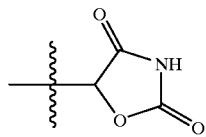

(r)

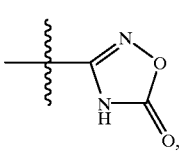

(s)

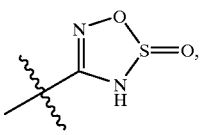

(t)

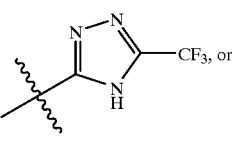

(u)

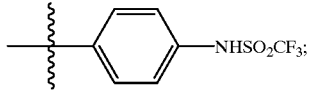

$R_1$ an $R_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, heterocyclic, (heterocyclic)alkyl with the proviso that heterocyclic is not morpholine or pyrazole and $(R_{aa})(R_{bb})N\text{—}R_{cc}\text{—}$ wherein $R_{aa}$ is aryl or arylalkyl, $R_{bb}$ is hydrogen or alkanoyl and $R_{cc}$ is alkylene, with the proviso that one or both of $R_1$ and $R_2$ is other than hydrogen;

$R_3$ is $R_4\text{—}C(O)\text{—}R_5\text{—}$ or $R_6\text{—}S(O)_2\text{—}R_7\text{—}$ wherein $R_5$ is (i) a covalent bond, (ii) alkylene, (iii) alkenylene, (iv) $\text{—}N(R_{20})\text{—}R_8\text{—}$ or $\text{—}R_{8a}\text{—}N(R_{20})\text{—}R_8\text{—}$ wherein $R_8$ and $R_{8a}$ are independently selected from the group consisting of alkylene and alkenylene and $R_{20}$ is hydrogen, loweralkyl, alkenyl, haloalkyl, alkoxyalkyl, haloalkoxyalkyl, cylcoalkyl or cycloalkylalkyl or (v) $\text{—}O\text{—}R_9\text{—}$ or $\text{—}R_{9a}\text{—}O\text{—}R_9\text{—}$ wherein $R_9$ and $R_{9a}$ are independently selected from alkylene;

$R_7$ is (i) a covalent bond, (ii) alkylene, (iii) alkenylene or (iv) $\text{—}N(R_{21})\text{—}R_{10}\text{—}$ or $\text{—}R_{10a}\text{—}N(R_{21})\text{—}R_{10}\text{—}$ wherein $R_{10}$ and $R_{10a}$ are independently selected from the group consisting of alkylene and alkenylene and $R_{21}$ is hydrogen, loweralkyl, alkenyl, haloalkyl, alkoxyalkyl, haloalkoxyalkyl, aryl or arylalkyl; wherein $R_4$ and $R_6$ are (i)

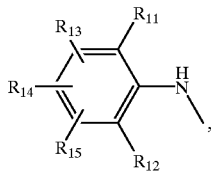

wherein $R_{11}$ and $R_{12}$ are independently selected from the group consisting of loweralkyl, cyano, halo, alkoxy, haloalkyl and phenyl and $R_{13}$, $R_{14}$, $R_{15}$ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano; with the proviso that heterocyclic is not morpholine or pyrazole or (ii) heterocyclic(amino), or a pharmaceutically acceptable salt thereof.

12. The compound according to claim 11 wherein $R_3$ is $R_4\text{—}C(O)\text{—}R_5\text{—}$ wherein $R_4$ is as defined therein and $R_5$ is alkylene or $R_3$ is $R_6\text{—}S(O)_2\text{—}R_7\text{—}$ wherein $R_7$ is alkylene and $R_6$ is as defined therein.

13. The compound according to claim 11 wherein R is $\text{—}C(O)_2\text{—}G$ wherein G is hydrogen or a carboxy protecting group or R is tetrazolyl or R is $\text{—}C(O)\text{—}NHS(O)_2R_{16}$ wherein $R_{16}$ is loweralkyl, haloalkyl or aryl, $R_1$ and $R_2$ are independently selected from (i) loweralkyl, (ii) cycloalkyl, (iii) substituted or unsubstituted aryl and (iv) substituted or unsubstituted heterocyclic, with the proviso that heterocyclic is not morpholine or pyrazole and $R_3$ is $R_4\text{—}C(O)\text{—}R_5\text{—}$ wherein $R_4$ is as defined therein and $R_5$ is alkylene or $R_3$ is $R_6\text{—}S(O)_2\text{—}R_7\text{—}$ wherein $R_7$ is alkylene and $R_6$ is as defined therein.

14. The compound according to claim 11 wherein R is $\text{—}C(O)_2\text{—}G$ wherein G is hydrogen or a carboxy protecting group, tetrazolyl or $\text{—}C(O)\text{—}NHS(O)_2R_{16}$ wherein $R_{16}$ is loweralkyl, haloalkyl or aryl, $R_1$ is (i) alkoxyalkyl, (ii) cycloalkyl, (iii) phenyl, (iv) pyridyl, (v) furanyl or (vi) substituted or unsubstituted 4-methoxyphenyl, 4-fluorophenyl, 3-fluorophenyl, 4-ethoxyphenyl, 4-propoxyphenyl, 4-isopropoxyphenyl, 4-trifluoromethylphenyl, 4-pentafluoroethylphenyl, 2-fluoro-4-ethoxyphenyl, 3-fluoro-4-methoxyphenyl, 3-fluoro-4-ethoxyphenyl, 3-fluoro-4-propoxyphenyl, 3-methoxy-4-propoxyphenyl, 2-fluorophenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofuranyl, 4-methoxyphenyl, dimethoxyphenyl, fluorophenyl or difluorophenyl and $R_3$ is $R_4\text{—}C(O)\text{—}R_5\text{—}$ wherein $R_4$ is as defined therein and $R_5$ is alkylene or $R_3$ is $R_6\text{—}S(O)_2\text{—}R_7\text{—}$ wherein $R_7$ is alkylene and $R_6$ is as defined therein.

15. The compound according to claim 11 wherein R is $\text{—}C(O)_2\text{—}G$ wherein G is hydrogen or a carboxy protecting group, tetrazolyl or $\text{—}C(O)\text{—}NHS(O)_2R_{16}$ wherein $R_{16}$ is loweralkyl, haloalkyl or aryl, $R_1$ is selected from the group consisting of (i) alkoxyalkyl, (ii) cycloalkyl, (iii) phenyl, (iv) pyridyl, (v) furanyl or (vi) substituted or unsubstituted 4-methoxyphenyl, 4-fluorophenyl, 3-fluorophenyl, 4-ethoxyphenyl, 4-propoxyphenyl,4-isopropoxyphenyl, 4-trifluoromethylphenyl, 4-pentafluoroethylphenyl, 2-fluoro-4-ethoxyphenyl, 3-fluoro-4-methoxyphenyl, 3-fluoro-4-ethoxyphenyl, 3-fluoro-4-propoxyphenyl, 3-methoxy-4-propoxyphenyl, 2-fluorophenyl, 4-methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl and $R_3$ is $R_4\text{—}C(O)\text{—}R_5\text{—}$ wherein $R_4$ is as defined therein and $R_3$ is alkylene.

16. The compound according to claim 11 wherein R is $\text{—}C(O)_2\text{—}G$ wherein G is hydrogen or a carboxy protecting group, tetrazolyl or $\text{—}C(O)\text{—}NHS(O)_2R_{16}$ wherein $R_{16}$ is loweralkyl or haloalkyl, $R_1$ is substituted or unsubstituted 4-methoxyphenyl, 4-fluorophenyl, 2-fluorophenyl, 4-ethoxyphenyl, 4-propoxyphenyl, 4-isopropoxyphenyl, 3-fluoro-4-methoxyphenyl, 3-fluoro-4-ethoxyphenyl, 2-fluoro-4-ethoxyphenyl, 3-fluoro-4-propoxyphenyl, 3-methoxy-4-propoxyphenyl, 4-trifluoromethylphenyl, 4-pentafluoroethylphenyl, 4-methoxymethoxyphenyl, 4-(2-methoxyethoxy)phenyl, 4-(2-ethoxyethoxy) phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy,

285

R₂ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and R₃ is R₄—C(O)—R₅— wherein R₄ is as defined therein and R₅ is alkylene.

17. The compound according to claim 11 wherein

R is —C(O)₂—G wherein G is hydrogen or a carboxy protecting group,

R₁ is substituted or unsubstituted 4-methoxyphenyl, 4-fluorophenyl, 2-fluorophenyl, 3-fluoro-4-ethoxyphenyl, 3-fluoro-4-methoxyphenyl, 4-ethoxyphenyl, 4-propoxyphenyl, 4-isopropoxyphenyl, 3-fluoro-4-propoxyphenyl, 3-methoxy-4-propoxyphenyl, 4methoxymethoxyphenyl, 4-(2-methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, R₂ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and R₃ is R₄—C(O)—R₅— wherein R₄ is

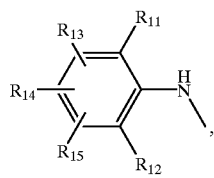

wherein R₁₁ and R₁₂ are independently selected from the group consisting of loweralkyl and R₁₃, R₁₄, and R₁₅ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano with the proviso that heterocyclic is not morpholine or pyrazole and R₅ is alkylene.

18. The compound according to claim 11 wherein

R is —C(O)₂—G wherein G is hydrogen or a carboxy protecting group,

R₁ is substituted or unsubstituted 4-methoxyphenyl, 4-fluorophenyl, 2-fluorophenyl, 3-fluoro-4-ethoxyphenyl, 3-fluoro-4-methoxyphenyl, 4-ethoxyphenyl, 4-propoxyphenyl, 4-isopropoxyphenyl, 2-fluoro-4-ethoxyphenyl, 3-fluoro-4-propoxyphenyl, 3-methoxy-4-propoxyphenyl, 4-methoxymethoxyphenyl, 4-(2-methoxyethoxy)phenyl, 4-(2-ethoxyethoxy)phenyl, 4-(2-isopropoxyethoxyphenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, R₂ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and

286

R₃ is R₄—C(O)—R₅— wherein R₄ is

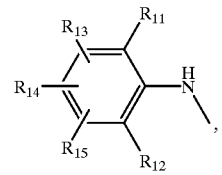

wherein R₁₁ and R₁₂ are independently selected from the group consisting of loweralkyl, alkoxy and halo, and R₁₃, R₁₄, and R₁₅ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano, with the proviso that heterocyclic is not morpholine or pyrazole and R₅ is alkylene.

19. The compound according to claim 11 wherein

R is —C(O)₂—G wherein G is hydrogen or a carboxy protecting group,

R₁ is substituted or unsubstituted 4-methoxyphenyl, 4-fluorophenyl, 2-fluorophenyl, 3-fluoro-4-ethoxyphenyl, 3-fluoro-4-methoxyphenyl, 4-ethoxyphenyl, 4-propoxyphenyl, 4-isopropoxyphenyl, 2-fluoro-4-ethoxyphenyl, 3-fluoro-4-propoxyphenyl, 3-methoxy-4-propoxyphenyl, 4-methoxymethoxyphenyl, 4-(2 methoxyethoxy)phenyl, 4-(2-ethoxyethoxy)phenyl, 4-(2 isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, R₂ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and R₃ is R₄—C(O)—R₅— wherein R₄ is

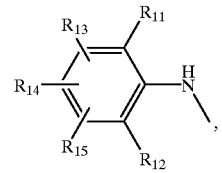

wherein R₁₁ and R₁₂ are independently selected from the group consisting of methyl, ethyl, and isopropyl, and R₁₃, R₁₄, and R₁₅ are independently selected from the group consisting of hydrogen, loweralkyl, hydroxy, amino, alkoxy, aryl, heterocyclic, halo, carboxy, nitro, alkylsulfonyl, arylsulfonyl, thioalkoxy, thioaryloxy, or cyano with the proviso that heterocyclic is not morpholine or pyrazole and R₅ is alkylene.

20. The compound according to claim 11 wherein

R is —C(O)₂—G wherein G is hydrogen or a carboxy protecting group,

R₁ is substituted or unsubstituted 4-methoxyphenyl, 4-fluorophenyl, 2-fluorophenyl, 3-fluoro-4-ethoxyphenyl, 3-fluoro-4-methoxyphenyl, 4-ethoxyphenyl, 4-propoxyphenyl, 4-isopropoxyphenyl, 2-fluoro-4-ethoxyphenyl, 3-fluoro-4-propoxyphenyl, 3-methoxy-4-propoxyphenyl, 4-methoxymethoxyphenyl, 4-(2- methoxyethoxy)phenyl, 4-(2-ethoxyethoxy)phenyl, 4-(2-isopropoxyethoxy)phenyl, 4-hydroxyphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 7-methoxy-1,3-benzodioxolyl, 1,4-benzodioxanyl, dihydrobenzofuranyl, benzofuranyl, 4-methoxyphenyl, dimethoxyphenyl, fluorophenyl or difluorophenyl and $R_3$ is $R_4$—C(O)—$R_5$— wherein $R_4$ is

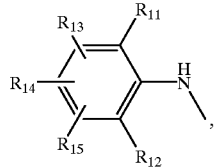

wherein $R_{11}$ and $R_{12}$ are independently selected from the group consisting of methyl, ethyl, and isopropyl, and $R_{13}$, $R_{14}$, and $R_{15}$ are independently selected from the group consisting of hydrogen, loweralkyl, hydroxy, amino, alkoxy, aryl, heterocyclic, halo, carboxy, nitro, or cyano with the proviso that heterocyclic is not morpholine or pyrazole and $R_5$ is methylene.

21. A compound selected from the group consisting of
trans,trans-2-(4-Methoxyphenyl)-4-(1,3-benzodioxol-5-yl)-1-((2,6-diethyl)phenylaminocarbonylmethyl)-pyrrolidine-3-carboxylic acid;

trans,trans-2-(4-Propoxyphenyl)-4-(1,3-benzodioxol-5-yl)-1-((2,6-diethyl)phenylaminocarbonylmethyl)-pyrrolidine-3-carboxylic acid;

trans,trans-2-(3-Fluoro-4-methoxyphenyl)-4-(1,3-benzodioxol-5-yl)-1-((2,6-diethyl) phenylaminocarbonylmethyl)-pyrrolidine-3-carboxylic acid;

trans,trans-2-(3-Fluoro-4-ethoxyphenyl)-4-(1,3-benzodioxol-5-yl)-1-((2,6-diethyl) phenylaminocarbonylmethyl)-pyrrolidine-3-carboxylic acid;

trans,trans-2-(3-Fluoro-4-methoxyphenyl)-4-(7-methoxy-1,3-benzodioxol-5-yl)-1-((2,6-diethyl) phenylaminocarbonylmethyl)-pyrrolidine-3-carboxylic acid;

trans,trans-2-(3-methoxy-4-propoxyphenyl)-4-(1,3-benzodioxol-5-yl)-1-((2,6-diethyl) phenylaminocarbonylmethyl)-pyrrolidine-3-carboxylic acid;

trans,trans-2-(4-ethoxyphenyl)-4-(1,3-benzodioxol-5-yl)-1-((2,6-15 diethyl)phenylaminocarbonylmethyl)-pyrrolidine-3-carboxylic acid;

trans,trans-2-(4-propoxyphenyl)-4-(7-methoxy-1,3-benzodioxol-5-yl)-1-((2,6-diethyl) phenylaminocarbonylmethyl)-pyrrolidine-3-carboxylic acid trans,trans-2-(3-methoxy-4-propoxyphenyl)-4-(7-methoxy-1,3-benzodioxol-5-yl)-1-(2,6-diethyl) phenylaminocarbonylmethyl)-pyrrolidine-3-carboxylic acid;

[2R,3R,4S]2-(4-Methoxyphenyl)-4-(1,3-benzodioxol-5-yl)-1-(N-((2,6-diethyl)phenylaminocarbonylmethyl)-pyrrolidine-3-carboxylic acid,

[2R,3R,4S]2-(4-Propoxyphenyl)-4-(1,3-benzodioxol-5-yl)-1-(N-(2,6-diethyl)phenylaminocarbonylmethyl)-pyrrolidine-3-carboxylic acid;

and (2R,3R,4S)-2-(4-ethoxyphenyl)-4-(1,3-benzodioxol-5-yl)-1-(2,6-diethyl)phenylaminocarbonylmethyl)-pyrrolidine-3-carboxylic acid, trans,trans-2-(4-isopropoxyphenyl)-4-(1,3-benzodioxol-5-yl)-1-(2,6-diethylphenylaminocarbonylmethyl)-pyrrolidine-3-carboxylic acid, trans,trans-2-(2-fluoro-4-propoxyphenyl)-4- (1,3-benzodioxol-5-yl)-1-(2,6-diethylphenylaminocarbonylmethyl)-pyrrolidine-3-carboxylic acid, trans,trans-2-(4- (2-Methoxyethoxy)phenyl)-4-(1,3-benzodioxol-5-yl)-1-(2,6-diethylphenylaminocarbonylmethyl)-pyrrolidine-3-carboxylic acid, trans,trans-2-(4-(2-Ethoxyethoxy)phenyl)-4-(1,3-benzodioxol-5-yl)-1-(2,6-diethylphenylaminocarbonylmethyl)-pyrrolidine-3-carboxylic acid,

[2R,3R,4S]-2-(4-(2-Methoxyethoxy)phenyl)-4-(1,3-benzodioxol-5-yl)-1-(2,6-diethylphenylaminocarbonylmethyl)-pyrrolidine-3-carboxylic acid,

[2R,3R,4S]-2-(4-(2-Ethoxyethoxy)phenyl)-4-(1,3-benzodioxol-5-yl)-1-(2,6-diethylphenylaminocarbonylmethyl)-pyrrolidine-3-carboxylic acid, and trans,trans-2-(4-(2-isopropoxyethoxy)phenyl)-4-(1,3-benzodioxol-5-yl)-1-(2,6-diethylphenylaminocarbonylmethyl)-pyrrolidine-3-carboxylic acid, or a pharmaceutically acceptable salt thereof.

22. A compound of claim 21 wherein said compound is trans,trans-2-(4-Propoxyphenyl)-4-(1,3-benzodioxol-5-yl)-1-((2,6-diethyl)phenylaminocarbonylmethyl)-pyrrolidine-3-carboxylic acid; or a pharmaceutically acceptable salt thereof.

23. A compound of claim 21 wherein said compound is [2R,3R,4S]2-(4-Methoxyphenyl)-4-(1,3-benzodioxol-5-yl)-1-(N-((2,6-diethyl)phenylaminocarbonylmethyl)-pyrrolidine-3-carboxylic acid, or a pharmaceutically acceptable salt thereof.

24. A compound of claim 21 wherein said compound is [2R,3R,4S]2-(4-Propoxyphenyl)-4-(1,3-benzodioxol-5-yl)-1-(N-((2,6-diethyl)phenylaminocarbonylmethyl)-pyrrolidine- 3-carboxylic acid, or a pharmaceutically acceptable salt thereof.

25. A compound of claim 21 wherein said compound is (2R,3R,4S)-2-(4-ethoxyphenyl)-4-(1,3-benzodioxol-5-yl)-1-((2,6-diethyl)phenylaminocarbonylmethyl)-pyrrolidine-3-carboxylic acid, or a pharmaceutically acceptable salt thereof.

26. A compound of claim 21 wherein said compound is trans,trans-2-(4-(2-Methoxyethoxy)phenyl)-4-(1,3-benzodioxol-5-yl)-1-(2,6-diethylphenylaminocarbonylmethyl)-pyrrolidine-3-carboxylic acid, or a pharmaceutically acceptable salt thereof.

27. A pharmaceutical composition for antagonizing endothelin comprising a therapeutically effective amount of the compound of claim 1 and a pharmaceutically acceptable carrier.

28. A pharmaceutical composition for antagonizing endothelin comprising a therapeutically effective amount of the compound of claim 11 and a pharmaceutically acceptable carrier.

29. A method for antagonizing endothelin comprising administering to a mammal in need of such treatment a therapeutically effective amount of a compound of claim 1.

30. A method for antagonizing endothelin comprising administering to a mammal in need of such treatment a therapeutically effective amount of a compound of claim 11.

31. A method for treating hypertension, congestive heart failure, restenosis following arterial injury, cerebral or myocardial ischemia or atherosclerosis comprising administering to a mammal in need of such treatment a therapeutically effective amount of a compound of claim 1.

32. A method for treating hypertension, congestive heart failure, restenosis following arterial injury, cerebral or myocardial ischemia or atherosclerosis comprising administering to a mammal in need of such treatment a therapeutically effective amount of a compound of claim 11.

33. A method for treating coronary angina, cerebral vasospasm, acute and chronic pulmonary hypertension, acute and chronic renal failure, gastric ulceration, cyclosporin-induced nephrotoxicity, endotoxin-induced toxicity, asthma, LPL-related lipoprotein disorders, fibrotic or proliferative diseases, platelet aggregation, thrombosis, IL-2 mediated cardiotoxicity, nociception, colitis, vascular permeability disorders, ischemia-repurfusion injury, systemic sclerosis, liver cirrhosis, adult respiratory distress syndrome, idiopathic cardiomyopathy, lupus erythematosus, diabetic retinopathy or other retinopathies, psoriasis, schleroderma, prostatic hyperplasia, cardiac hyperplasia, Raynaud's disease, cancers, adenocarcinomas, angina, transplant-induced artherosclerosis, and migraine comprising administering to a mammal in need of such treatment a therapeutically effective amount of a compound of claim 1.

34. A method for treating coronary angina, cerebral vasospasm, acute and chronic pulmonary hypertension, acute and chronic renal failure, gastric ulceration, cyclosporin-induced nephrotoxicity, endotoxin-induced toxicity, asthma, LPL-related lipoprotein disorders, fibrotic or proliferative diseases, platelet aggregation, thrombosis, IL-2 mediated cardiotoxicity, nociception, colitis, vascular permeability disorders, ischemia-repurfusion injury, systemic sclerosis, liver cirrhosis, adult respiratory distress syndrome, idiopathic cardiomyopathy, lupus Erythematosus, diabetic retinopathy or other retinopathies, psoriasis, schleroderma, prostatic hyperplasia, cardiac hyperplasia, Raynaud's disease, cancers, adenocarcinomas, angina, transplant-induced arterosclerosis, and migraine comprising administering to a mammal in need of such treatment a therapeutically effective amount of a compound of claim 11.

35. A method for treating hypertension, congestive heart failure, restenosis following arterial injury, cerebral or myocardial ischemia or atherosclerosis comprising administering to a mammal in need of such treatment a therapeutically effective amount of a compound of claim 1 in combination with one or more cardiovascular agents.

36. A method for treating hypertension, congestive heart failure, restenosis following arterial injury, cerebral or myocardial ischemia or atherosclerosis comprising administering to a mammal in need of such treatment a therapeutically effective amount of a compound of claim 11 in combination with one or more cardiovascular agents.

* * * * *

UNITED STATES PATENT AND TRADEMARK OFFICE
CERTIFICATE OF CORRECTION

PATENT NO.   : 6,124,341                              Page 1 of 1
DATED        : September 26, 2000
INVENTOR(S)  : Andrew S. Tasker et al.

It is certified that error appears in the above-identified patent and that said Letters Patent is hereby corrected as shown below:

Column 280,
Line 56, replace "or cyano and $R_5$ is alkylene." with
-- or cyano with the proviso that heterocyclic is not morpholine or pyrazole and $R_5$ is alkylene. --

Signed and Sealed this

Thirteenth Day of August, 2002

*Attest:*

*Attesting Officer*

JAMES E. ROGAN
*Director of the United States Patent and Trademark Office*